(12) United States Patent
Kofoed

(10) Patent No.: US 10,392,428 B2
(45) Date of Patent: Aug. 27, 2019

(54) GLP-1 DERIVATIVES AND USES THEREOF

(71) Applicant: Novo Nordisk A/S, Bagsvaerd (DK)

(72) Inventor: Jacob Kofoed, Vaerloese (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 15/534,644

(22) PCT Filed: Dec. 17, 2015

(86) PCT No.: PCT/EP2015/080165
§ 371 (c)(1),
(2) Date: Jun. 9, 2017

(87) PCT Pub. No.: WO2016/097108
PCT Pub. Date: Jun. 23, 2016

(65) Prior Publication Data
US 2018/0258153 A1    Sep. 13, 2018

(30) Foreign Application Priority Data
Dec. 17, 2014 (EP) .................................... 14198589

(51) Int. Cl.
*A61P 3/04* (2006.01)
*A61P 3/10* (2006.01)
*A61K 38/00* (2006.01)
*C07K 14/605* (2006.01)

(52) U.S. Cl.
CPC .............. *C07K 14/605* (2013.01); *A61P 3/04* (2018.01); *A61P 3/10* (2018.01); *A61K 38/00* (2013.01)

(58) Field of Classification Search
CPC ... A61K 38/00; A61P 3/04; A61P 3/10; C07K 14/605
See application file for complete search history.

(56) References Cited

U.S. PATENT DOCUMENTS

| | | | |
|---|---|---|---|
| 9,006,178 B2 | 4/2015 | Kofoed et al. | |
| 10,195,255 B2 * | 2/2019 | Reedtz-Runge | A61K 38/26 |
| 2006/0014241 A1 | 1/2006 | Glaesner et al. | |
| 2008/0207507 A1 | 8/2008 | Lau et al. | |
| 2010/0261637 A1 | 10/2010 | Spetzler et al. | |
| 2011/0166321 A1 | 7/2011 | Garibay et al. | |
| 2013/0116173 A1 | 5/2013 | DiMarchi et al. | |
| 2013/0143798 A1 | 6/2013 | Lau et al. | |
| 2013/0244931 A1 | 9/2013 | Lau et al. | |
| 2013/0288958 A1 | 10/2013 | Lau et al. | |
| 2013/0288960 A1 | 10/2013 | Madsen et al. | |
| 2014/0088005 A1 | 3/2014 | Wieczorek et al. | |
| 2014/0179899 A1 | 6/2014 | Garibay et al. | |
| 2016/0143998 A1 | 5/2016 | Reedtz-Runge et al. | |
| 2017/0320927 A1 | 11/2017 | Sauerberg et al. | |

FOREIGN PATENT DOCUMENTS

| | | |
|---|---|---|
| EP | 1060191 A1 | 12/2000 |
| WO | 200055119 A1 | 9/2000 |
| WO | 200135988 A1 | 5/2001 |
| WO | 0215981 A1 | 2/2002 |
| WO | 2004/093823 A2 | 11/2004 |
| WO | 2005/027978 A2 | 3/2005 |
| WO | 2006/037810 | 4/2006 |
| WO | 2006097537 A2 | 9/2006 |
| WO | 2006124529 A1 | 11/2006 |
| WO | 2009/030771 A1 | 3/2009 |
| WO | 2009030738 A1 | 3/2009 |
| WO | 2010/142665 A1 | 12/2010 |
| WO | 2011/080103 A1 | 7/2011 |
| WO | 2012/012352 A2 | 1/2012 |
| WO | 2012062803 A1 | 5/2012 |
| WO | 2012140117 A1 | 10/2012 |
| WO | 2012177929 A2 | 12/2012 |
| WO | 2013/167454 A1 | 11/2013 |
| WO | 2014202727 A1 | 12/2014 |
| WO | 2015000942 A1 | 1/2015 |

OTHER PUBLICATIONS

Deacon, C F et al., "Dipeptidyl Peptidase IV Resistant Analouges of Glucagon-Like Peptide-1 Which Have Extended Metabolic Stability and Improved Biological Activity," Diabetologia, 1998, vol. 41, pp. 271-278.

Knudsen L. B. et al., Potent Derivatives of Glucagon-like Peptide-1 with Pharmacokinetic Properties Suitable for Once Daily Administration, Journal of Medical Chemistry, 2000, vol. 43, No. 9, 1664-1669.

\* cited by examiner

*Primary Examiner* — Marcela M Cordero Garcia
(74) *Attorney, Agent, or Firm* — Jianjie Hu

(57) ABSTRACT

The invention relates to a derivative of a GLP-1 analog of a general Formula I, which derivative comprises a side chain attached to a Lys residue at position 34, 35, 36, 37, 38, or 39 of the GLP-1 analog. The side chain comprises a Branched linker, a $1^{st}$ and a $2^{nd}$ Protractor and a Pre-linker. The Branched linker is connected to the Lys residue of the GLP-1 analog via the Pre-linker and to the $1^{st}$ and the $2^{nd}$ Protractor via a $1^{st}$ and $2^{nd}$ Post-linker, respectively. The Branched linker may, e.g., be a tri-radical of Lys. The $1^{st}$ and the $2^{nd}$ Protractor is C20 diacid. Various linker elements may be used in the Prelinker as well as the two Post-linkers. The invention also relates to novel GLP-analogs, novel side chain intermediates and their manufacture and use to prepare derivatives of biologically active peptides and proteins, as well as pharmaceutical compositions and medical uses of the analogs and derivatives. The derivatives have very long half-lives while maintaining a satisfactory potency, which makes them potentially suitable for once-monthly administration.

11 Claims, 3 Drawing Sheets
Specification includes a Sequence Listing.

GLP-1 DERIVATIVES AND USES THEREOF

CROSS-REFERENCE TO RELATED APPLICATIONS

This application is a 35 U.S.C. § 371 National Stage application of International Application PCT/EP2015/080165 (WO 2016/097108), filed Dec. 17, 2015, which claims priority to European Patent Application No. 14198589.5, filed Dec. 17, 2014; the contents of all above-named applications are incorporated herein by reference.

TECHNICAL FIELD

The present invention relates to derivatives of analogues of glucagon-like peptide 1 (GLP-1), more in particular to GLP-1 derivatives with a branched acylation, and their pharmaceutical use.

INCORPORATION-BY-REFERENCE OF THE SEQUENCE LISTING

The instant application contains a Sequence Listing which has been submitted in ASCII format via EFS-Web and is hereby incorporated by reference in its entirety. Said ASCII copy, created on Jun. 7, 2017, is named 140100US01_SequenceListing_ST25.txt and is 7 kilobytes in size.

BACKGROUND

WO 2005/027978 A2 discloses a number of GLP-1 derivatives including some with a branched acylation of C12 or C14 fatty acids.

Patent application no. PCT/EP2014/062952 which was filed 19 Jun. 2014 and claims a first priority date of 20 Jun. 2013 (WO 2014/202727 A1, publication date 24 Dec. 2014) discloses a number of GLP-1 derivatives with branched acylation.

SUMMARY

Semaglutide is a GLP-1 derivative for once weekly administration which is under development by Novo Nordisk A/S. This compound is disclosed in WO 2006/097537 A2, Example 4.

The invention relates to novel GLP-1 derivatives which have potential for once-monthly administration.

In one aspect the invention relates to a derivative of a GLP-1 analogue which is acylated at a Lys residue corresponding to position 34, 35, 36, 37, 38, or 39 of human native GLP-1(7-37) with two acyl chains, via one and the same Branched linker. The Branched linker is a tri-radical of an amino acid having a C1-C5 alkyl side chain with a terminal amino group, such as lysine. Each of the acyl chains is made up of two long fatty diacids, connected to the Branched linker via a so-called Post-linker. The Branched linker is connected to the $Lys^{34}$, $Lys^{35}$, $Lys^{36}$, $Lys^{37}$, $Lys^{38}$, or $Lys^{39}$ residue of the GLP-1 analogue via a so-called Pre-linker. Each of the Pre-linker and the two Post-linkers comprises a —CO group and an —NH group. They may, e.g., include one or more of a number of linker elements which are disclosed in the present application.

In a second aspect the invention relates to novel GLP-1 analogues which comprise the following changes when compared to GLP-1(7-37) (SEQ ID NO: 1): (7Imp, 8Aib, 22E, 26R, 34R, 38G), (7Imp, 8Aib, 22E, 26R, 34R, 39K), (7Imp, 8Aib, 22E, 26R, 34R, 38G, 39K), or (8Aib, 22E, 26R, 34R, 35K); such as the analogue of SEQ ID NO: 3. Also SEQ ID NO: 5, SEQ ID NO: 6, and SEQ ID NO: 9 are novel GLP-1 analogues of the invention. These analogues are novel peptide intermediates of the GLP-1 derivatives of the invention.

In a third aspect the invention relates to novel side chain intermediate products relating to the GLP-1 derivatives of the invention. These compounds are defined by formula II (see FIG. 2), wherein q is an integer in the range of 0-5, w is an integer in the range of 0-5, with the provisos that when w is 0 q is an integer in the range of 1-5, and when q is 0 w is an integer in the range of 1-5; $R_1$, is —OH or a suitable activation group; $R_2$ is —COOH or a suitable protective group for —COOH; and each of the Pre-linker, the $1^{st}$ Post-linker, and the $2^{nd}$ Post-linker comprises a —CO group and an —NH group. The $R_1$ group may for example be —OPfp or a similar leaving group forming an active ester together with the —CO group of the Pre-linker. The $R_2$ group may for example be —COOtBu or similar protective groups for a —COOH group.

In a fourth aspect the invention relates to pharmaceutical compositions comprising such derivatives or analogues and pharmaceutically acceptable excipients, as well as the medical use thereof.

The amino acid sequence of native human GLP-1(7-37) is included in the sequence listing as SEQ ID NO: 1. SEQ ID NO's 2-3 and 5-9 are specific GLP-1 analogues of the GLP-1 derivatives of the invention, and SEQ ID NO: 4 is a GLP-1 analogue which is incorporated in two comparative compounds.

The derivatives of the invention have very long half-lives and still a very good potency.

BRIEF DESCRIPTION OF DRAWINGS

The structure of the derivatives of the invention is explained in more detail in the drawings, where.

DESCRIPTION

In what follows, Greek letters may be represented by their symbol or the corresponding written name, for example: α=alpha; β=beta; ε=epsilon; γ=gamma; δ=delta; ω=omega; etc. Also, the Greek letter of μ may be represented by "u", e.g. in μl=ul, or in μM=uM.

An asterisk (*) or a waved line in a chemical formula designates i) a point of attachment, ii) a radical, and/or iii) an unshared electron.

In its first aspect the invention relates to a derivative of a GLP-1 analogue of the general Formula I:

(SEQ ID NO: 10)
Xaa$_7$-Xaa$_8$-Glu-Gly-Thr-Xaa$_{12}$-Thr-Ser-Asp-Xaa$_{16}$-Ser-

Xaa$_{18}$-Xaa$_{19}$-Xaa$_{20}$-Glu-Xaa$_{22}$-Xaa$_{23}$-Ala-Xaa$_{25}$-Xaa$_{26}$-Xaa$_{27}$-

-continued
Phe-Ile-Xaa30-Xaa31-Leu-Xaa33-Xaa34-Xaa35-Xaa36-Xaa37-Xaa38-Xaa39, wherein Xaa7 is L-histidine, (S)-2-Hydroxy-3-(1H-imidazol-4-yl)-propionic acid, D-histidine, deamino-histidine, homohistidine, N°-acetyl-histidine, N°-formyl-histidine, N°-methyl-histidine, 3-pyridylalanine, 2-pyridylalanine, or 4-pyridylalanine; Xaa8 is Ala, Gly, Ser, Aib, (1-aminocyclopropyl) carboxylic acid, or (1-aminocyclobutyl) carboxylic acid; Xaa12 is Phe or Leu; Xaa16 is Val or Leu; Xaa18 is Ser, Val, Arg, or Leu; Xaa19 is Tyr or Gln; Xaa20 is Leu or Met; Xaa22 is Gly or Glu; Xaa23 is Gin, Glu, or Arg; Xaa25 is Ala or Val; Xaa26 is Arg; Xaa27 is Glu or Leu; Xaa30 is Ala, Glu, or Arg; Xaa31 is Trp or His; Xaa33 is Val; Xaa34 is Lys, Arg, His, Asn, or Gin; Xaa35 is Lys, Gly, or Ala; Xaa36 is Lys, Arg, or Gly; Xaa37 is Gly, Pro, or Lys; Xaa38 is Lys, Gly, or absent; Xaa39 is Lys or absent; wherein at least one of Xaa34, Xaa35, Xaa36, Xaa37, Xaa38, and Xaa39 is Lys; which derivative comprises a side chain that is attached to the Lys residue of Xaa34, Xaa35, Xaa36, Xaa37, Xaa38, or Xaa39, which side chain comprises: (i) a Branched linker of Chem. 11:

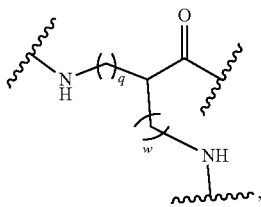

Chem. 11 wherein q is an integer in the range of 0-5, w is an integer in the range of 0-5, and with the provisos that when w is 0 q is an integer in the range of 1-5, and when q is 0 w is an integer in the range of 1-5; and (ii) a 1st and a 2nd Protractor of Chem. 12:

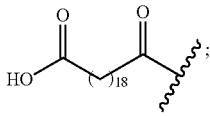

Chem. 12 wherein the Branched linker is connected a) at its —CO end to the epsilon amino group of the Lys residue of Xaa34, Xaa35, Xaa36, Xaa37, Xaa38, or Xaa39, via a Pre-linker, and b) at each of its two —NH ends to the —CO end of each of the 1st and 2nd Protractor, respectively, via a 1st and a 2nd Post-linker, respectively; wherein each of the Pre-linker, the 1st Post-linker, and the 2nd Post-linker comprises a —CO group and an —NH group; or a pharmaceutically acceptable salt, amide, or ester thereof.

In its second aspect the invention relates to novel GLP-1 analogues which comprise the following changes when compared to GLP-1(7-37) (SEQ ID NO: 1): (7Imp, 8Aib, 22E, 26R, 34R, 38G), (7Imp, 8Aib, 22E, 26R, 34R, 39K), or (7Imp, 8Aib, 22E, 26R, 34R, 38G, 39K), or (8Aib, 22E, 26R, 34R, 35K); or a pharmaceutically acceptable salt, amide, or ester thereof.

Figure 1:
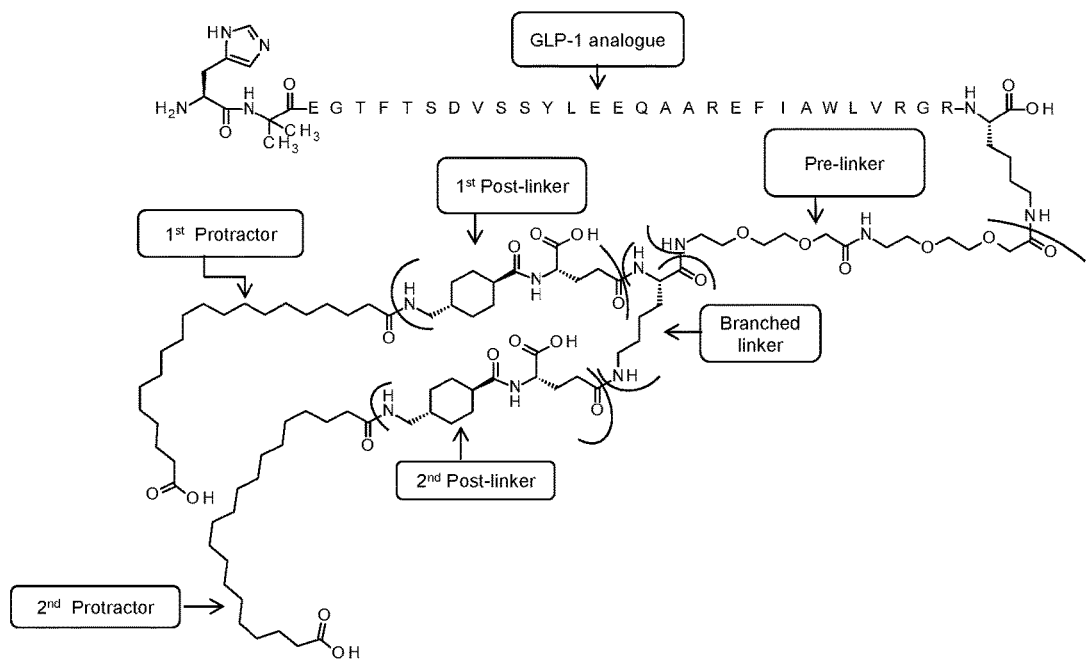
FIG. 1 shows the structure of the derivative of Example 11 with added boxes and lines showing the terminology used herein for the various parts of the molecule.
Figure 2:
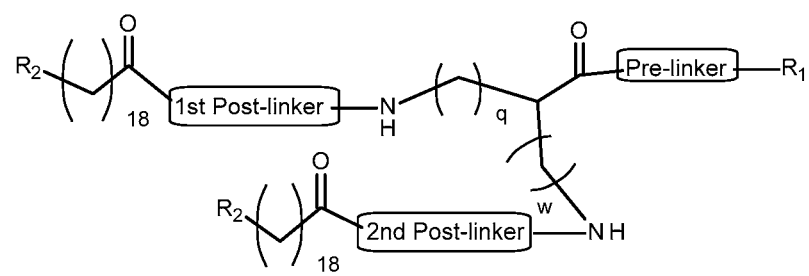
FIG. 2 shows a formula to define novel side chain intermediate products relating to the GLP-1 derivatives of the invention.

In its third aspect the invention relates to a compound of formula II (see FIG. 2), wherein q is an integer in the range of 0-5, w is an integer in the range of 0-5, with the provisos that when w is 0 q is an integer in the range of 1-5, and when q is 0 w is an integer in the range of 1-5; $R_1$ is —OH or a suitable activation group; $R_2$ is —COOH or a suitable protective group for —COOH; and each of the Pre-linker, the 1st Post-linker, and the 2nd Post-linker comprises a —CO group and an —NH group; or a pharmaceutically acceptable salt, amide, or ester thereof. The invention also relates to the manufacture of this compound, and its use for attachment to a biologically active peptide or protein.

In its fourth aspect the invention relates to a pharmaceutical composition comprising a derivative or an analogue of the invention, and a pharmaceutically acceptable excipient; and the use of a derivative or analogue of the invention as a medicament, in particular for use in (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C; (ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes; (iii) improving β-cell function, such as decreasing β-cell apoptosis, increasing β-cell function and/or β-cell mass, and/or for restoring glucose sensitivity to β-cells; (iv) prevention and/or treatment of cognitive disorders and/or neurodegenerative disorders, such as Alzheimer's disease, Parkinson's disease, and/or multiple sclerosis; (v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence; (vi) prevention and/or treatment of diabetic complications, such as angiopathy; neuropathy, including peripheral neuropathy; nephropathy; and/or retinopathy; (vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo; (viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure; (ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus; (x) prevention and/or treatment of critical illness, such as treatment of a critically ill patient, a critical illness poly-nephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness; (xi) prevention and/or treatment of polycystic ovary syndrome (PCOS); (xii) prevention and/or treatment of cerebral disease, such as cerebral ischemia, cerebral haemorrhage, and/or traumatic brain injury; (xiii) prevention and/or treatment of sleep apnoea; and/or (xiv) prevention and/or treatment of abuse, such as alcohol abuse and/or drug abuse.

The invention also relates to GLP-1 derivatives, GLP-1 analogues, side chain intermediate products and pharmaceutical compositions and uses as disclosed herein, wherein open ended terms like "comprises" and "comprising" used for defining these inventions are replaced with closed terms such as "consists of", "consisting of", and the like.

GLP-1 Receptor Agonist

A receptor agonist may be defined as an analogue that binds to a receptor and elicits a response typical of the natural ligand. A full agonist may be defined as one that elicits a response of the same magnitude as the natural ligand (see e.g. "Principles of Biochemistry", A L Lehninger, D L Nelson, M M Cox, Second Edition, Worth Publishers, 1993, page 763).

Thus, for example, a "GLP-1 receptor agonist" may be defined as a compound which is capable of binding to the GLP-1 receptor and capable of activating it. And a "full" GLP-1 receptor agonist may be defined as a GLP-1 receptor agonist which is capable of eliciting a magnitude of GLP-1 receptor response that is similar to native GLP-1.

Structural Features
GLP-1 Analogues

The term "GLP-1 analogue" as used herein refers to an analogue (or variant) of the human glucagon-like peptide-1 (GLP-1(7-37)), the sequence of which is included in the sequence listing as SEQ ID NO: 1. The peptide having the sequence of SEQ ID NO: 1 may also be designated "native" GLP-1.

The GLP-1 analogue incorporated in the GLP-1 derivative of the invention may be defined by the following formula I:

Xaa$_7$-Xaa$_8$-Glu-Gly-Thr-Xaa$_{12}$-Thr-Ser-Asp-Xaa$_{16}$-Ser-Xaa$_{18}$-Xaa$_{19}$-Xaa$_{20}$-Glu-Xaa$_{22}$-Xaa$_{23}$-Ala-Xaa$_{25}$-Xaa$_{26}$-Xaa$_{27}$-Phe-Ile-Xaa$_{30}$-Xaa$_{31}$-Leu-Xaa$_{33}$-Xaa$_{34}$-Xaa$_{35}$-Xaa$_{36}$-Xaa$_{37}$-Xaa$_{38}$-Xaa$_{39}$ (SEQ ID NO: 10), wherein Xaa$_7$ is L-histidine, (S)-2-Hydroxy-3-(1H-imidazol-4-yl)-propionic acid, D-histidine, deamino-histidine, homohistidine, N$^α$-acetyl-histidine, N$^α$-formyl-histidine, N$^α$-methyl-histidine, 3-pyridylalanine, 2-pyridylalanine, or 4-pyridylalanine; Xaa$_8$ is Ala, Gly, Ser, Aib, (1-aminocyclopropyl) carboxylic acid, or (1-aminocyclobutyl) carboxylic acid; Xaa$_{12}$ is Phe or Leu; Xaa$_{16}$ is Val or Leu; Xaa$_{18}$ is Ser, Val, Arg, or Leu; Xaa$_{19}$ is Tyr or Gln; Xaa$_{20}$ is Leu or Met; Xaa$_{22}$ is Gly or Glu; Xaa$_{23}$ is Gln, Glu, or Arg; Xaa$_{25}$ is Ala or Val; Xaa$_{26}$ is Arg; Xaa$_{27}$ is Glu or Leu; Xaa$_{30}$ is Ala, Glu, or Arg; Xaa$_{31}$ is Trp or His; Xaa$_{33}$ is Val; Xaa$_{34}$ is Lys, Arg, His, Asn, or Gln; Xaa$_{35}$ is Lys, Gly, or Ala; Xaa$_{36}$ is Lys, Arg, or Gly; Xaa$_{37}$ is Gly, Pro, or Lys; Xaa$_{38}$ is Lys, Gly, or absent; Xaa$_{39}$ is Lys or absent; wherein at least one of Xaa$_{34}$, Xaa$_{35}$, Xaa$_{36}$, Xaa$_{37}$, Xaa$_{38}$, and Xaa$_{39}$ is Lys.

In this formula, the numbering of the amino acid residues follows the established practice in the art for native GLP-1, namely that the first (N-terminal) amino acid residue is numbered or accorded position no. 7, and the subsequent amino acid residues downstream towards the C-terminus are numbered 8, 9, 10, and so on, until the last (C-terminal) amino acid residue. In native GLP-1 the C-terminal amino acid residue is Gly, with number 37. However, as it appears from the above formula, in the peptide of Formula I the C-terminal amino acid may be Xaa$_{37}$, Xaa$_{38}$, or Xaa$_{39}$, i.e. have number 37, 38, or 39, respectively. GLP-1 analogues of the invention where the C-terminal amino acid Xaa$_{38}$ is present may be said to comprise an addition (or extension) of one amino acid, as compared to native GLP-1. Likewise, GLP-1 analogues of the invention where the C-terminal amino acid is Xaa$_{39}$ may be said to comprise an addition of two amino acids (namely Xaa$_{38}$ and Xaa$_{39}$), as compared to native GLP-1.

The numbering is done differently in the sequence listing, where the first amino acid residue of SEQ ID NO: 1 (His) is assigned no. 1, and the last (Gly) no. 31. However, herein we follow the established numbering practice in the art, as explained above.

Each of the GLP-1 analogues of the derivatives of the invention may be described by reference to i) the number of the amino acid residue in native GLP-1(7-37) which corresponds to the amino acid residue which is changed (i.e., the corresponding position in native GLP-1), and to ii) the actual change.

In other words, the GLP-1 analogue of the invention may be described by reference to the native GLP-1(7-37) peptide, namely as a variant thereof in which a number of amino acid residues have been changed when compared to native GLP-1(7-37) (SEQ ID NO: 1). These changes may represent, independently, one or more amino acid substitutions, additions, and/or deletions.

The following are non-limiting examples of suitable analogue nomenclature.

The GLP-1 analogue incorporated in the derivative of Example 1 herein may be referred to as (8Aib, 22E, 26R, 34R, 37K) GLP-1(7-37). When this Example 1 analogue is aligned with native GLP-1, the amino acid at the position in the analogue which corresponds, according to the alignment, to position 8 in native GLP-1 is Aib, the amino acid at the position in the analogue which corresponds to position 22 in native GLP-1 is E, the amino acid at the position in the analogue which corresponds to position 26 in native GLP-1 is R, the amino acid at the position in the analogue which corresponds to position 34 in native GLP-1 is R, and the amino acid at the position in the analogue which corresponds to position 37 in native GLP-1 is K. All other amino acids in this analogue are identical to the corresponding amino acid in native GLP-1.

As another example the GLP-1 analogue which is incorporated in the derivative of Example 7 herein may be referred to as (7Imp, 8Aib, 22E, 26R, 34R, 38G, 39K) GLP-1(7-37). When this Example 10 analogue is aligned with native GLP-1, the amino acid at the position in the analogue which corresponds, according to the alignment, to position 7 is deamino-His, the amino acid at the position in the analogue which corresponds to position 8 in native GLP-1 is Aib, the amino acid at the position in the analogue which corresponds to position 22 in native GLP-1 is E, the amino acid at the position in the analogue which corresponds to position 26 in native GLP-1 is R, the amino acid at the position in the analogue which corresponds to position 34 in native GLP-1 is R, and then the Example 7 analogue includes a C-terminal addition (or extension) of the dipeptide G-K, which for the present purposes is said to correspond to positions 38-39, respectively, in native GLP-1. Each of the other amino acids in this analogue is identical to the corresponding amino acid in native GLP-1.

The general formula I is to be understood in a similar manner.

Analogues "comprising" certain specified changes may comprise further changes, when compared to SEQ ID NO: 1. In a particular embodiment, the analogue "has" the specified changes, or "is" the specified analogue, in which cases there are no further changes, when compared to SEQ ID NO: 1.

As is apparent from above, amino acid residues may be identified by their full name, their one-letter code, and/or their three-letter code. These three ways are fully equivalent.

The expressions "a position equivalent to" or "corresponding position" may be used to characterise the site of change in a variant GLP-1(7-37) sequence by reference to a reference sequence such as native GLP-1(7-37) (SEQ ID NO: 1). Equivalent or corresponding positions, as well as the number of changes, are easily deduced, e.g. by simple handwriting and eyeballing (visual inspection); and/or a standard protein or peptide alignment program may be used, such as "align" which is based on a Needleman-Wunsch algorithm. This algorithm is described in Needleman, S. B. and Wunsch, C. D., (1970), Journal of Molecular Biology, 48: 443-453, and the align program by Myers and W. Miller in "Optimal Alignments in Linear Space" CABIOS (computer applications in the biosciences) (1988) 4:11-17. For the alignment, the default scoring matrix BLOSUM62 and the default identity matrix may be used, and the penalty for the first residue in a gap may be set at −12, or preferably at −10, and the penalties for additional residues in a gap at −2, or preferably at −0.5.

An example of such alignment is inserted below, in which sequence no. "1" is native GLP-1 of SEQ ID NO: 1, and sequence no. "2" is the analogue (7Imp, 8Aib, 22E, 26R, 34R, 38G, 39K) thereof (SEQ ID NO: 3):

```
# ========================================

# Aligned_sequences: 2
# 1: 1
# 2: 2
# Matrix: EBLOSUM62
# Gap_penalty: 10.0
# Extend_penalty: 0.5

# Length: 33
# Identity:    26/33 (78.8%)
# Similarity:  28/33 (84.8%)
# Gaps:         2/33 (6.1%)
# Score: 134.0

# ========================================

1      1  HAEGTFTSDVSSYLEGQAAKEFIAWLVKGRG--      31
          ..|||||||||||||.|||:|||||||:|||
2      1  XXEGTFTSDVSSYLEEQAAREFIAWLVRGRGGK     33
```

When 6 is added to the position numbers shown in this alignment (e.g. to "1" and "31" in sequence 1, and to "1" and "32" in sequence 2) one gets the position numbering as used herein. For example, in sequence 1 (which is identical to SEQ ID NO: 1), the N-terminal amino acid (H) has position number 7, and the C-terminal amino acid (G) has number 37. Regarding sequence 2, the N-terminal amino acid (Imp) has number 7 and the C-terminal amino acid (K) has number 39.

In case specific amino acid residues or the like with no one-letter codon (such as Imp and Aib) are included in the sequence these may, for alignment purposes, be replaced with, e.g., X, as shown in the above alignment. If desired, X can later be manually corrected.

The following are non-limiting examples of what can be inferred from the above alignment:

As one example it can be inferred that sequence 2 has 7 amino acid changes as compared to sequence 1 (namely at all those positions where a full stop ("."), a colon (":"), or a horisontal hyphen ("-") is shown in the alignment).

As another example it can be inferred that, e.g., sequence no. 2 comprises 39K, since it has a K at the position which corresponds, according to the alignment, to position 39 in the reference sequence (sequence 1, SEQ ID NO: 1).

And similarly all other changes in sequence 2 as compared to sequence 1 can be deduced from the alignment.

In what follows, all amino acids of the GLP-1 analogue of the invention for which the optical isomer is not stated is to be understood to mean the L-isomer (unless otherwise specified).

Preferred GLP-1 analogues of the invention, and for incorporation in the GLP-1 derivatives of the invention, are disclosed in the sections headed PARTICULAR EMBODIMENTS, ADDITIONAL PARTICULAR EMBODIMENTS, and STILL FURTHER PARTICULAR EMBODIMENTS.

GLP-1 Derivatives

The term "derivative" as used herein in the context of a GLP-1 analogue means a chemically modified GLP-1 analogue, in which one or more substituents have been covalently attached to the analogue.

The GLP-1 derivative of the invention is a derivative of a GLP-1 analogue of Formula I, as defined in the above section headed GLP-1 analogues.

The GLP-1 derivative of the invention comprises a substituent in the form of a side chain that is attached to the Lys residue at position 34, 35, 36, 37, 38, or 39 of the GLP-1 analogue (i.e., to $Xaa_{34}$, $Xaa_{35}$, $Xaa_{36}$, $Xaa_{37}$, $Xaa_{38}$, or $Xaa_{39}$ in Formula I).

The side chain is capable of forming non-covalent complexes with albumin, thereby promoting the circulation of the derivative with the blood stream, and also having the effect of protracting the time of action of the derivative, due to the fact that the complex of the GLP-1-derivative and albumin is only slowly disintegrated to release the active pharmaceutical ingredient.

The side chain comprises a Branched linker of

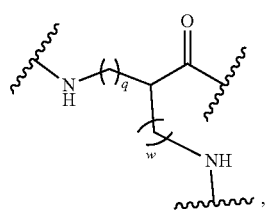

Chem. 11 wherein q is an integer in the range of 0-5, w is an integer in the range of 0-5, and with the provisos that when w is 0 q is an integer in the range of 1-5, and when q is 0 w is an integer in the range of 1-5.

In a particular embodiment where q is 4 and w is 0, the Branched linker may be referred to as a tri-radical of eps-Lys(Bis), of Chem. 11a:

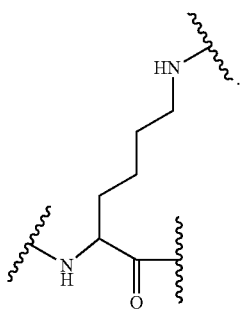

Chem. 11a

Also in another particular embodiment where q is 0 and w is 4, the Branched linker is a tri-radical of eps-Lys(Bis) of Chem. 11a.

The side chain also comprises a $1^{st}$ and a $2^{nd}$ Protractor of Chem. 12, which may be referred to as C20 diacid:

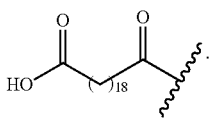

Chem. 12

The Branched linker is a tri-radical, thus it serves to provide a side chain with a two-leg structure. The —CO end of the Branched linker is covalently bound to the Lys residue at position 34, 35, 36, 37, 38, or 39 of the GLP-1 analogue via a so-called Pre-linker. At each of its two —NH ends the Branched linker is connected to the —CO end of each of the $1^{st}$ and $2^{nd}$ Protractor, respectively, via a $1^{st}$ and a $2^{nd}$ so-called Post-linker, respectively.

Each of the Pre-linker, the $1^{st}$ Post-linker, and the $2^{nd}$ Post-linker comprises a —CO group and an —NH group.

In some embodiments the —NH group of the Pre-linker is connected to the —CO group of the Branched linker, and the —CO group of the Pre-linker is connected to the epsilon amino group of the Lys residue of $Xaa_{34}$, $Xaa_{35}$, $Xaa_{36}$, $Xaa_{37}$, $Xaa_{38}$, or $Xaa_{39}$.

In some embodiments the —CO group of the $1^{st}$ Post-linker is connected to a $1^{st}$ —NH group of the Branched linker, and the —NH group of the $1^{st}$ Post-linker is connected to the —CO group of the $1^{st}$ Protractor.

In some embodiments the —CO group of the $2^{nd}$ Post-linker is connected to a $2^{nd}$ —NH group of the Branched linker, and the —NH group of the $2^{nd}$ Post-linker is connected to the —CO group of the $2^{nd}$ Protractor.

These linkers may, e.g., include one or more of the following linker elements: Linker element-1 of Chem. 1:

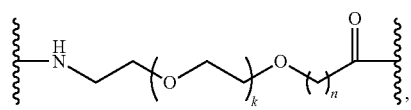

wherein k is an integer in the range of 1-19, and n is an integer in the range of 1-5.

Linker element-1 may form part of the Pre-linker, the $1^{st}$ Post-linker, and/or the $2^{nd}$ Post-linker.

For example, in the Pre-linker a number of t Linker element-1 structures may be juxtaposed (mutually connected, in a row), where t ranges from 1 to 8.

In particular embodiments, Linker element-1 represents the following structures: 8-amino-3,6-dioxaoctanoic acid, abbreviated Ado (when k=1, and n=1), dPEG6 (when k=5, and n=2), dPEG12 (when k=11, and n=2), or dPEG20 (when k=19, and n=2).

A number of additional linker elements may be incorporated in the derivatives of the invention (possibly in more copies), such as Linker element-2 (Chem. 2b, which in a particular embodiment, Chem. 2c, may also be referred to as epsilon Lys, abbreviated eps-Lys), Linker element-3 (Chem. 3, also referred to as gamma Glu, abbreviated gGlu), and/or Linker element-4 (Chem. 4, also referred to as tranexamic acid, abbreviated Trx):

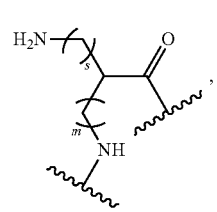

Chem. 2b where m is an integer in the range of 0-5, s is an integer in the range of 0-5, and with the provisos that when m is 0 s is an integer in the range of 1-5, and when s is 0 m is an integer in the range of 1-5;

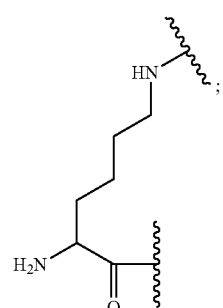

Chem. 2c

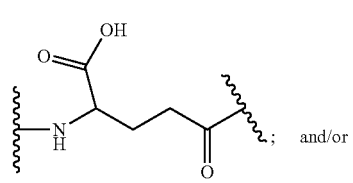

Chem. 3 and/or

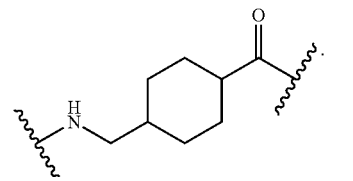

Chem. 4

In one particular embodiment none of the $1^{st}$ and the $2^{nd}$ Post-linker includes Linker element-1, as defined above.

Other preferred GLP-1 derivatives, e.g. some with particular combinations of linker elements in the various linker parts (Pre-linker, $1^{st}$ and $2^{nd}$ Post-linker), are disclosed in the sections headed PARTICULAR EMBODIMENTS, ADDITIONAL PARTICULAR EMBODIMENTS, and STILL FURTHER PARTICULAR EMBODIMENTS.

In a particular embodiment all connections between the various linker elements, the GLP-1 analogue, the 1$^{st}$ and 2$^{nd}$ Protractor and the Branched linker are amide bonds.

Each of the specific GLP-1 derivatives of Examples 1-22 are particularly preferred GLP-1 derivatives of the invention, together with their pharmaceutically acceptable salts, amides or esters.

As explained above, the side chain of the GLP-1 derivatives of the invention and the compounds of formula II (side chain intermediates) can be referred to as being branched, with two legs.

In a particular embodiment, the two legs are similar, preferably substantially identical, or, most preferably, identical.

In another particular embodiment, the 1$^{st}$ and the 2$^{nd}$ Protractor are similar, preferably substantially identical, or, most preferably, identical.

In a still further particular embodiment, the 1$^{st}$ and the 2$^{nd}$ Post-linker are similar, preferably substantially identical, or, most preferably identical.

The term "substantially identical" includes differences from identity which are due to formation of one or more esters and/or amides; preferably formation of one or more methyl esters, and simple amides; more preferably formation of no more than two methyl esters, and/or simple amides; or most preferably formation of no more than one methyl ester, and/or simple amide.

In the context of chemical compounds such as the Protractors and Post-linkers, similarity and/or identity may be determined using any suitable computer program and/or algorithm known in the art.

For example, the similarity of two Protractors, two Post-linkers, or of the two branches or legs in their entirety (consisting of Protractor plus Post-linker) may suitably be determined using molecular fingerprints, which refers to a mathematical method of representing a chemical structure (see e.g. Chemoinformatics: A textbook, Johann Gasteiger and Thomas Engel (Eds), Wiley-VCH Verlag, 2003).

Examples of suitable fingerprints include, without limitation, UNITY fingerprints, MDL fingerprints, and/or ECFP fingerprints, such as ECFP_6 fingerprints (ECFP stands for extended-connectivity fingerprints).

In particular embodiments, the two protracting moieties, the two linkers, and/or the two entire side chains are represented as a) ECFP_6 fingerprints; b) UNITY fingerprints; and/or c) MDL fingerprints.

The Tanimoto coefficient is preferably used for calculating the similarity of the two fingerprints, whether a), b), or c) is used.

In particular embodiments, whether a), b), or c) is used, the two protracting moieties, the two linkers, and/or the two entire side chains, respectively, have a similarity of at least 0.5 (50%); preferably at least 0.6 (60%); more preferably at least 0.7 (70%), or at least 0.8 (80%); even more preferably at least 0.9 (90%); or most preferably at least 0.99 (99%), such as a similarity of 1.0 (100%).

UNITY fingerprints may be calculated using the programme SYBYL (available from Tripos, 1699 South Hanley Road, St. Louis, Mo. 63144-2319 USA). ECFP_6 and MDL fingerprints may be calculated using the programme Pipeline Pilot (available from Accelrys Inc., 10188 Telesis Court, Suite 100, San Diego, Calif. 92121, USA).

For more details, see for example J. Chem. Inf. Model. 2008, 48, 542-549; J. Chem. Inf. Comput. Sci. 2004, 44, 170-178; J. Med. Chem. 2004, 47, 2743-2749; J. Chem. Inf. Model. 2010, 50, 742-754; as well as SciTegic Pipeline Pilot Chemistry Collection: Basic Chemistry User Guide, March 2008, SciTegic Pipeline Pilot Data Modeling Collection, 2008—both from Accelrys Software Inc., San Diego, US, and the guides http://www.tripos.com/tripos_resources/file-root/pdfs/Unity_111408.pdf, and http://www.tripos.com/data/SYBYL/SYBYL_072505.pdf.

An example of a similarity calculation is inserted below, in which a known entire side chain of a known GLP-1 derivative was compared with a methyl ester thereof:

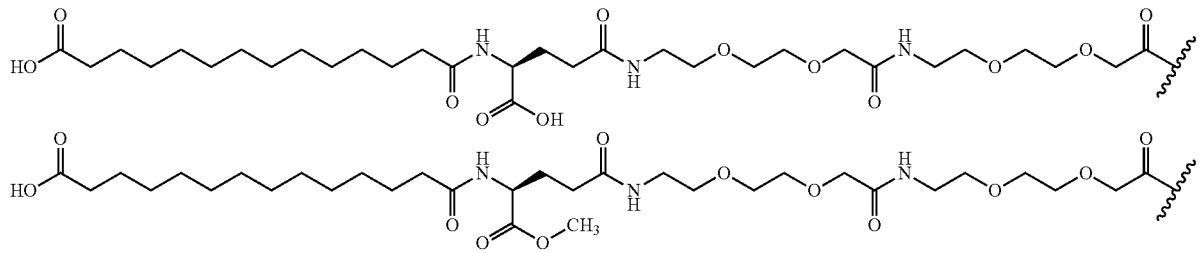

Using a) ECFP_6 fingerprints the similarity is 0.798, using b) UNITY fingerprints the similarity is 0.957; and using MDL fingerprints the similarity is 0.905.

In case of two identical side chains (albumin binding moieties) the derivative may be designated symmetrical.

In particular embodiments, the similarity coefficient is at least 0.80, preferably at least 0.85, more preferably at least 0.90, even more preferably at least 0.95, or most preferably at least 0.99.

The derivatives and compounds of formula II (side chain intermediates) of the invention may exist in different stereoisomeric forms having the same molecular formula and sequence of bonded atoms, but differing only in the three-dimensional orientation of their atoms in space. The stereoisomerism of the exemplified derivatives and compounds of formula II of the invention is indicated in the experimental section, in the names as well as the structures, using standard nomenclature. Unless otherwise stated the invention relates to all stereoisomeric forms of the claimed derivative/compound of formula II.

The concentration in plasma of the GLP-1 derivatives of the invention may be determined using any suitable method. For example, LC-MS (Liquid Chromatography Mass Spectroscopy) may be used, or immunoassays such as RIA (Radio Immuno Assay), ELISA (Enzyme-Linked Immuno Sorbent Assay), and LOCI (Luminescence Oxygen Channeling Immunoasssay). General protocols for suitable RIA and ELISA assays are found in, e.g., WO 2009/030738 on p. 116-118. A preferred assay is the LOCI assay, where LOCI refers to Luminescence Oxygen Channeling Immunoasssay, which is generally described for the determination of insulin by Poulsen and Jensen in Journal of Biomolecular Screening 2007, vol. 12, p. 240-247. The donor beads were coated with streptavidin, while acceptor beads were conjugated with a monoclonal antibody recognising a mid-/C-terminal epitope of the peptide. Another monoclonal antibody, specific for the N-terminus, was biotinylated. The three reactants were combined with the analyte and formed a two-sited immunocomplex. Illumination of the complex released singlet oxygen atoms from the donor beads, which were channelled into the acceptor beads and triggered chemiluminescence which was measured in an Envision plate reader. The amount of light was proportional to the concentration of the compound.

The GLP-1 derivatives and analogues of the invention have GLP-1 activity. This term refers to the ability to bind to the GLP-1 receptor and initiate a signal transduction pathway resulting in insulinotropic action or other physiological effects as is known in the art. For example, the analogues and derivatives of the invention can be tested for GLP-1 activity using the assays described in Examples 23, 24, 26, and/or 27 herein.

Side Chain Intermediate Products

The invention also relates to a compound of formula II (see FIG. 2), wherein q is an integer in the range of 0-5, w is an integer in the range of 0-5, with the provisos that when w is 0 q is an integer in the range of 1-5, and when q is 0 w is an integer in the range of 1-5; $R_1$ is —OH or a suitable activation group; $R_2$ is —COOH or a suitable protective group for —COOH; and each of the Pre-linker, the $1^{st}$ Post-linker, and the $2^{nd}$ Post-linker comprises a —CO group and an —NH group; or a pharmaceutically acceptable salt, amide, or ester thereof.

The compound of formula II includes in its structure the Branched linker of Chem. 11, as well as a $1^{st}$ and a $2^{nd}$ group —CO—$(CH_2)_{18}$—$R_2$, corresponding to the $1^{st}$ and the $2^{nd}$ Protractor, respectively, of Chem. 12.

In some embodiments the —NH group of the Pre-linker is connected to the —CO group of the Branched linker, and the —CO group of the Pre-linker is connected to $R_1$.

In some embodiments the —CO group of the $1^{st}$ Post-linker is connected to a $1^{st}$ —NH group of the Branched linker, and the —NH group of the $1^{st}$ Post-linker is connected to the —CO group of the $1^{st}$ group of —CO—$(CH_2)_{18}$—$R_2$.

In some embodiments the —CO group of the $2^{nd}$ Post-linker is connected to a $2^{nd}$ —NH group of the Branched linker, and the —NH group of the $2^{nd}$ Post-linker is connected to the —CO group of the $2^{nd}$ group of —CO—$(CH_2)_{18}$—$R_2$.

This compound is an intermediate product in the sense that it constitutes the non-peptide part (or the side chain part) of the GLP-1 derivative of the invention.

The side chain part of the GLP-1 derivatives of the invention can be prepared and attached to the peptide part thereof as described in the experimental part, stepwise directly on solid support during peptide synthesis.

Alternatively, the side chain part can be prepared directly on solid support and subsequently be attached to the peptide part using appropriate activation and protective groups.

As a non-limiting example the side-chain part of Chem. 54 of the derivative of Example 14 (Chem. 34) can be prepared on 2-chlorotrityl resin by coupling of Fmoc-8-amino-3,6-dioxaoctanoic acid (2 equivalents) in dichloromethane/N-methyl pyrrolidine (1:1) using diisopropylethylamine (6 equivalents) as the first residue. The resin is then washed with dichloromethane/methanol/diisopropylethylamine (85:10:5) twice, dichloromethane, N-methylpyrrolidone. The Fmoc group is then removed by treatment with 20% piperidine in N-methylpyrrolidine (two treatments each for four minutes). Subsequently the resin is washed with NMP, DCM three times each and another coupling of Fmoc-8-amino-3,6-dioxaoctanoic acid (8 equivalents) in N-methyl pyrrolidone using diisopropylcarbodiimide, collidine, and OxymaPure® (each 8 equivalents). Subsequently the resin is washed with NMP, DCM three times each and the Fmoc group removed as outlined above. The following building blocks can then be coupled using the repetitive cycle of coupling, washing, Fmoc removal and washing: Fmoc-Lys(Fmoc)-OH, Fmoc-8-amino-3,6-dioxaoctanoic acid, Fmoc-8-amino-3,6-dioxaoctanoic acid, Fmoc-8-amino-3,6-dioxaoctanoic acid, Fmoc-8-amino-3,6-dioxaoctanoic acid, Fmoc-Glu-OtBu, Fmoc-tranexamic acid, and icosanedioic acid mono-tert-butyl ester. The crude side-chain part can then be liberated from the resin using trifluoroethanol/dichloromethane (20:80) and concentrated to dryness in vacuo. If desired the side-chain part can be purified using flash chromatography as known in the art. The tert-butyl protected side chain part (1.25 equivalents) can then be activated for coupling to the peptide part of the Example 14 compound (1.0 equivalent) of interest by dissolving the side-chain part in dimethylformamide:tetrahydrofurane (1:1). Then O—(N-succinimidyl)-N,N,N',N'-tetramethyluronium tetrafluoroborate (1.4 equivalents) is added followed by diisopropylethylamide (2.5 equivalents) and stirring for 1 h. The peptide part (1.0 equivalent) is dissolved in 200 mM $Na_2CO_3$(aq)/tetrahydrofuran (5:2) pH 10.6. The above prepared OSuc ester of the side chain part is added dropwise to the dissolved peptide under stirring and the pH kept at 10.6-10.8 with 1N NaOH. Stands to react 1 h. The pH is lowered to the isoelectric point of the peptide-sidechain conjugate and the precipitate centrifuged down. The dried precipitate is treated with triflouroacetic acid/water (95:5) for 30 min, and poured into diethyl ether. The finalised product is isolated by centrifugation.

Alternatively, the side chain part can be prepared by solution phase chemistry and subsequently be attached to the peptide part using suitable activation and protective groups such as those discussed in the following.

Alternatively, the side chain part can be attached in several steps using suitable protective groups. As a non-limiting example, the Branched linker of Chem. 11, and the Pre-linker, linked together with amide bonds and suitable protective groups, can be attached to a lysine epsilon amino group of the peptide part by forming an amide bond, using a suitable activation group such as an active ester. Subsequently the $1^{st}$ and the $2^{nd}$ Post-linker and the $1^{st}$ and the $2^{nd}$ Protractor of Chem. 12, linked together with amide bonds and suitable protective groups, can be attached to the distal amino groups of the Branched linker of Chem. 11.

Non-limiting examples of $R_1$ functional groups are —OH and other suitable activation groups, for example, without limitation, activation groups in the form of suitable leaving groups, for example, without limitation, suitable leaving groups forming an active ester together with a carbonyl group (such as the proximal carbonyl group) of the Pre-linker, such as, without limitation:

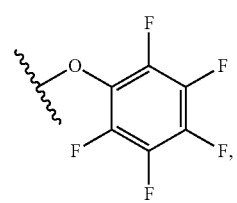

Chem. 81 which may also be designated —OPfp (2,3,4,5,6-pentafluorophenoxy),

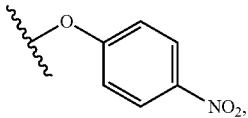

Chem. 82 which may also be designated —OPnp (4-nitrophenoxy), and

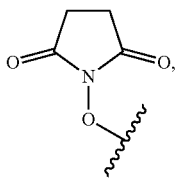

Chem. 83 which may also be designated —OSuc ((2,5-dioxopyrrolidin-1-yl)oxy), and the like. Other suitable activation groups may be selected, e.g., without limitation, according to the teaching of M. Bodanszky, "Principles of Peptide Synthesis", 2nd ed., Springer Verlag, 1993.

Non-limiting examples of $R_2$ functional groups are —COOH and suitable carboxylic acid protective groups, for example, without limitation, suitable non-reactive esters, such as, without limitation:

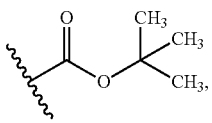

Chem. 84 which may also be designated —COOtBu (tert-butoxycarbonyl),

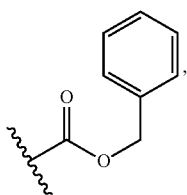

Chem. 85 which may also be designated —COOBz (benzyloxycarbonyl),

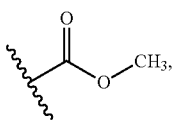

Chem. 86 which may also be designated —COOMe (methoxycarbonyl),

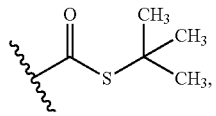

Chem. 87 which may also be designated —COSC(CH$_3$)$_3$ (tert-butylsulfanylcarbonyl),

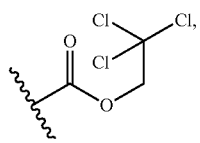

Chem. 88 which may also be designated —COCH$_2$CCl$_3$ (2,2,2-trichloroethoxycarbonyl), and the like.

Other suitable non-reactive esters and other carboxylic acid protective groups may be selected, e.g., without limitation, according to the teaching of P. G. M. Wuts, T. W. Greene, "Greene's Protective Groups in Organic Synthesis", 4th ed., John Wiley & Sons, Inc, 2007.

In some embodiments of the side chain intermediate compound of the invention the 1$^{st}$ and the 2$^{nd}$ Post-linker each comprises z times the Linker element-1 of Chem. 1, where z is 0 or an integer in the range of 1-4, and at least one further linker element selected from Linker element-3 of Chem. 3 and Linker element-4 of Chem. 4, wherein in Chem. 3 the free acid group (—COOH) is substituted with $R_3$, wherein $R_3$ is —COOH or a suitable protective group for a carboxylic acid group.

In some embodiments of the side chain intermediate compound of the invention the Pre-linker part thereof comprises at least one of Linker element-1 of Chem. 1 or at least one Linker element-2 of Chem. 2b, wherein in Chem. 2b the free amino group (—NH$_2$) is substituted with $R_5$, wherein $R_5$ is —NH$_2$ or a suitable protective group for an amino group.

Non-limiting examples of $R_3$ functional groups are —COOH and suitable protective groups for carboxylic acid groups, for example, without limitation, suitable ester groups, such as, without limitation, —COOtBu (Chem. 84), —COOBz (Chem. 85), —COOMe (Chem. 86), —COSC(CH$_3$)$_3$ (Chem. 87), and —COCH$_2$CCl$_3$ (Chem. 88), and the like. Other suitable esters and protective groups for carboxylic acid groups may be selected, e.g., without limitation, according to the teaching of P. G. M. Wuts, T. W. Greene, "Greene's Protective Groups in Organic Synthesis", 4th ed., John Wiley & Sons, Inc, 2007.

Non-limiting examples of $R_5$ functional groups are —NH$_2$ and suitable protective groups for amino groups, for example, without limitation, suitable carbamates, such as, without limitation:

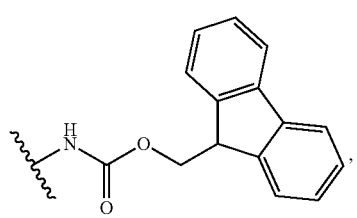

Chem. 89 which may also be designated as —NHFmoc (9H-fluoren-9-ylmethoxycarbonylamino),

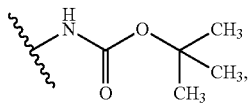

Chem. 90 which may also be designated as —NHBoc (tert-butoxycarbonylamino), and

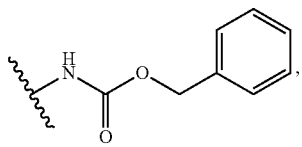

Chem. 91 which may also be designated as —NHCbz (benzyloxycarbonylamino), and the like. Other suitable carbamates and other protective groups for amino groups may be selected, e.g., without limitation, according to the teaching of P. G. M. Wuts, T. W. Greene, "Greene's Protective Groups in Organic Synthesis", 4th ed., John Wiley & Sons, Inc, 2007.

A number of particular side chain intermediate compounds of the invention are disclosed in the section headed PARTICULAR EMBODIMENTS.

Of particular interest are the side chain intermediate compounds of Chem. 50 to Chem. 64 listed in Table A below. Please note that Table A refers to Table B further below for definition of the structure of the $1^{st}$ Post-linker, the $2^{nd}$ Post-linker, and the Pre-linker. Table A also shows the Chem. no. of the particular GLP-1 derivative of the invention that incorporates the particular side chain intermediate compound of the invention.

TABLE A

Some specific side chain intermediate compounds of the invention

| Intermediate Chem. No. | Corresponding Derivative Chem. No. | $1^{st}$ Post-linker & $2^{nd}$ Post-linker | Pre-Linker |
|---|---|---|---|
| Chem. 50 | Chem. 22 | Chem. 67 | Chem. 76 |
|  | Chem. 27 |  |  |
| Chem. 51 | Chem. 35 | Chem. 67 | Chem. 77 |
| Chem. 52 | Chem. 21 | Chem. 67 | Chem. 75 |
| Chem. 53 | Chem. 42 | Chem. 68 | Chem. 80 |
| Chem. 54 | Chem. 34 | Chem. 69 | Chem. 76 |
| Chem. 55 | Chem. 41 | Chem. 66 | Chem. 77 |
| Chem. 56 | Chem. 29 | Chem. 65 | Chem. 70 |
| Chem. 57 | Chem. 31 | Chem. 65 | Chem. 76 |
| Chem. 58 | Chem. 30 | Chem. 65 | Chem. 71 |
| Chem. 59 | Chem. 26 | Chem. 65 | Chem. 77 |
|  | Chem. 28 |  |  |
| Chem. 60 | Chem. 32 | Chem. 65 | Chem. 78 |
|  | Chem. 36 |  |  |
|  | Chem. 37 |  |  |
|  | Chem. 38 |  |  |
|  | Chem. 39 |  |  |
|  | Chem. 40 |  |  |
| Chem. 61 | Chem. 33 | Chem. 65 | Chem. 79 |
| Chem. 62 | Chem. 24 | Chem. 65 | Chem. 73 |
| Chem. 63 | Chem. 25 | Chem. 65 | Chem. 74 |
| Chem. 64 | Chem. 23 | Chem. 65 | Chem. 72 |

TABLE B

Combinations of linker elements

| Linker-element | Designation | Structure |
|---|---|---|
| Chem. 65 | Trx-gGlu | 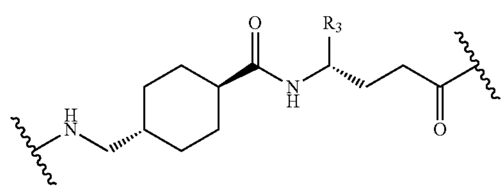 |
| Chem. 66 | Trx-gGlu-Ado | 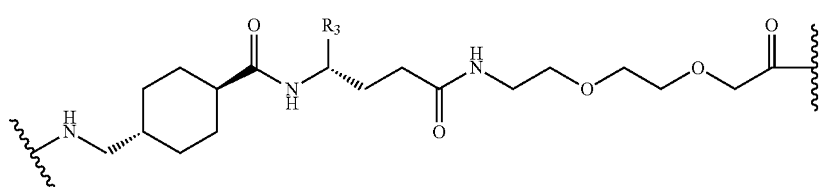 |
| Chem. 67 | Trx-gGlu-2xAdo | 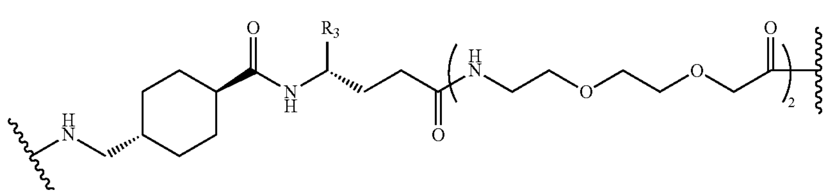 |

TABLE B-continued

Combinations of linker elements

| Linker-element | Designation | Structure |
| --- | --- | --- |
| Chem. 68 | Trx-gGlu-3xAdo | 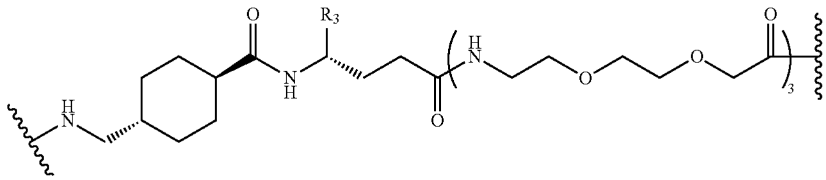 |
| Chem. 69 | Trx-gGlu-4xAdo | 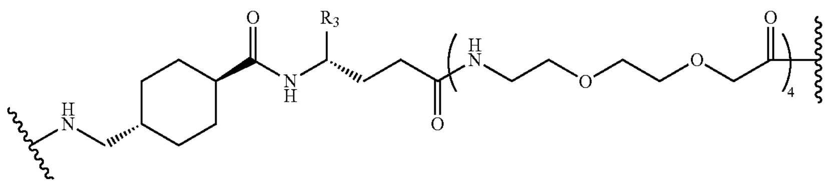 |
| Chem. 70 | 2xeps-Lys | 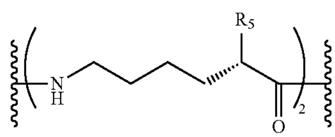 |
| Chem. 71 | 4xeps-Lys | 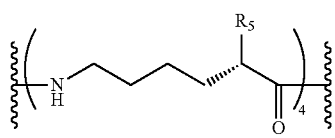 |
| Chem. 72 | dPEG6 | 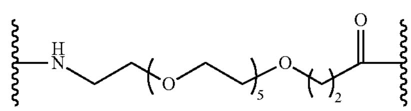 |
| Chem. 73 | dPEG12 | 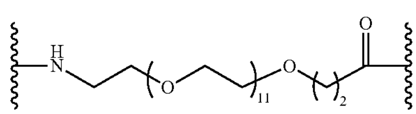 |
| Chem. 74 | dPEG20 | 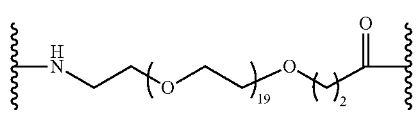 |
| Chem. 75 | Ado | 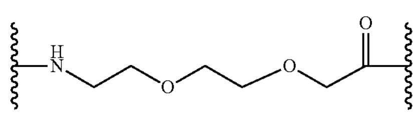 [SMILES: *NCCOCCOCC(*)=O] |
| Chem. 76 | 2xAdo | 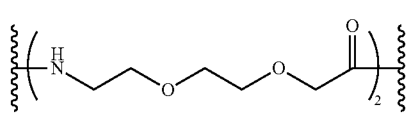 |
| Chem. 77 | 4xAdo | 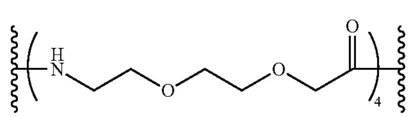 |
| Chem. 78 | 6xAdo | 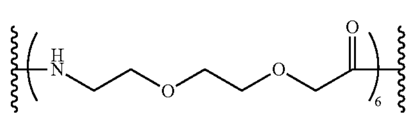 |

TABLE B-continued

Combinations of linker elements

| Linker-element | Designation | Structure |
|---|---|---|
| Chem. 79 | 8xAdo | (structure: [-NH-CH$_2$CH$_2$-O-CH$_2$CH$_2$-O-CH$_2$-C(=O)-]$_8$) |
| Chem. 80 | 3xAdo | (structure: [-NH-CH$_2$CH$_2$-O-CH$_2$CH$_2$-O-CH$_2$-C(=O)-]$_3$) |

The invention also relates to the preparation of the intermediate side chain compound of the invention as well as its use for attachment to a biologically active peptide or protein under the formation of a derivative thereof. Non-limiting examples of how this can be done are outlined above. Additional particular embodiments are disclosed in the section headed PARTICULAR EMBODIMENTS.

In some embodiments the intermediate side chain compound of the invention is capable of forming non-covalent complexes with albumin. In some embodiments, when attached to a biologically active peptide or protein this effect is carried over to the final peptide or protein derivative which accordingly exhibits a prolonged duration of action in vivo.

Pharmaceutically Acceptable Salt, Amide, or Ester

The derivatives, analogues, and side chain intermediate products of the invention may be in the form of a pharmaceutically acceptable salt, amide, or ester.

Salts are e.g. formed by a chemical reaction between a base and an acid, e.g.: $2NH_3 + H_2SO_4 \rightarrow (NH_4)_2SO_4$.

The salt may be a basic salt, an acid salt, or it may be neither nor (i.e. a neutral salt). Basic salts produce hydroxide ions and acid salts hydronium ions in water.

The salts of the derivatives of the invention may be formed with added cations or anions between anionic or cationic groups, respectively. These groups may be situated in the peptide moiety, and/or in the side chain of the derivatives of the invention.

Non-limiting examples of anionic groups of the derivatives of the invention include free carboxylic groups in the side chain, if any, as well as in the peptide moiety. The peptide moiety often includes a free carboxylic acid group at the C-terminus, and it may also include free carboxylic groups at internal acid amino acid residues such as Asp and Glu.

Non-limiting examples of cationic groups in the peptide moiety include the free amino group at the N-terminus, if present, as well as any free amino group of internal basic amino acid residues such as His, Arg, and Lys.

The ester of the derivatives of the invention may, e.g., be formed by the reaction of a free carboxylic acid group with an alcohol or a phenol, which leads to replacement of at least one hydroxyl group by an alkoxy or aryloxy group The ester formation may involve the free carboxylic group at the C-terminus of the peptide, and/or any free carboxylic group in the side chain.

The amide of the derivatives of the invention may, e.g., be formed by the reaction of a free carboxylic acid group with an amine or a substituted amine, or by reaction of a free or substituted amino group with a carboxylic acid.

The amide formation may involve the free carboxylic group at the C-terminus of the peptide, any free carboxylic group in the side chain, the free amino group at the N-terminus of the peptide, and/or any free or substituted amino group of the peptide in the peptide and/or the side chain.

In a particular embodiment, the peptide or derivative is in the form of a pharmaceutically acceptable salt. In another particular embodiment, the derivative is in the form of a pharmaceutically acceptable amide, preferably with an amide group at the C-terminus of the peptide. In a still further particular embodiment, the peptide or derivative is in the form a pharmaceutically acceptable ester.

Functional Properties

In a particular embodiment the derivatives of the invention have a very long half-life and at the same time a very good potency in vitro and in vivo, which makes them potentially suitable for once-monthly administration.

Thus, in a first functional aspect, the derivatives of the invention have a good potency. Also, or alternatively, in a second aspect, they bind very well to the GLP-1 receptor, e.g. at a high concentration of albumin. Preferably they are full GLP-1 receptor agonists as is reflected by their ability to bind strongly to the GLP-1 receptor combined with the capacity to activate the receptor. Also, or alternatively, in a third functional aspect, they have improved pharmacokinetic properties.

Biological Activity—In Vitro Potency

The GLP-1 analogue of the derivative of the invention is one non-limiting example of a biologically active peptide or protein.

According to the first functional aspect, the derivatives of the invention, as well as the constituent GLP-1 analogues as such, are biologically active, or potent.

In a particular embodiment, potency and/or activity refers to in vitro potency, i.e. performance in a functional GLP-1 receptor assay, more in particular to the capability of activating the human GLP-1 receptor.

The in vitro potency may, e.g., be determined in a medium containing membranes expressing the human GLP-1 receptor, and/or in an assay with whole cells expressing the human GLP-1 receptor.

For example, the response of the human GLP-1 receptor may be measured in a reporter gene assay, e.g. in a stably transfected BHK cell line that expresses the human GLP-1 receptor and contains the DNA for the cAMP response element (CRE) coupled to a promoter and the gene for firefly luciferase (CRE luciferase). When cAMP is produced as a result of activation of the GLP-1 receptor this in turn results in the luciferase being expressed. Luciferase may be determined by adding luciferin, which by the enzyme is converted to oxyluciferin and produces bioluminescence, which is measured and is a measure of the in vitro potency. One non-limiting example of such an assay is described in Example 23.

The term half maximal effective concentration ($EC_{50}$) generally refers to the concentration which induces a response halfway between the baseline and maximum, by reference to the dose response curve. $EC_{50}$ is used as a measure of the potency of a compound and represents the concentration where 50% of its maximal effect is observed.

The in vitro potency of the derivatives of the invention may be determined as described above, and the $EC_{50}$ of the derivative in question determined. The lower the $EC_{50}$ value, the better the potency.

In a particular embodiment, the derivatives of the invention are very potent, despite the fact that they have very long half-lives. In a particular embodiment, the derivative of the invention has an in vitro potency determined using the method of Example 23 corresponding to an $EC_{50}$ at or below 300 pM.

Additional particular embodiments are disclosed in the section headed PARTICULAR EMBODIMENTS, ADDITIONAL PARTICULAR EMBODIMENTS, and STILL FURTHER PARTICULAR EMBODIMENTS.

Biological Activity—In Vivo Pharmacology

In another particular embodiment the derivatives of the invention as well as the constituent GLP-1 analogues as such are potent in vivo, which may be determined as is known in the art in any suitable animal model, as well as in clinical trials.

The Sprague Dawley rat is one example of a suitable animal model, and the acute effect on food intake and/or body weight may be determined in such rats in vivo, e.g. as described in Example 26. In a particular embodiment an acute effect of the derivatives of the invention on food intake and body weight is observed at 48 hours after administration.

The obese, diabetic mouse (db/db mice) is another example of a suitable animal model, and the acute effect on food intake and/or body weight may be determined in such mice in vivo, e.g. as described in Example 27. In a particular embodiment an acute effect of the derivatives of the invention on food intake and body weight is observed at 48 hours after administration.

Additional particular embodiments are disclosed in the section headed PARTICULAR EMBODIMENTS, ADDITIONAL PARTICULAR EMBODIMENTS, and STILL FURTHER PARTICULAR EMBODIMENTS.

Biological Activity—In Vitro Receptor Binding

According to the second functional aspect, the derivatives of the invention, as well as the constituent GLP-1 analogues as such bind very well to the GLP-1 receptor, e.g. at a high concentration of albumin. This may be determined as described in Example 24.

Generally, the binding to the GLP-1 receptor at low albumin concentration should be as good as possible, corresponding to a low $IC_{50}$ value.

The $IC_{50}$ value at high albumin concentration reflects the influence of serum albumin on the binding of the derivative to the GLP-1 receptor. As is known, the GLP-1 derivatives can bind to serum albumin and if this is the case then the $IC_{50}$ value at high serum albumin will be higher than the $IC_{50}$ value at low albumin. An increased $IC_{50}$ value at high serum albumin represents a reduced binding to the GLP-1 receptor caused by serum albumin binding competing with the binding to the GLP-1 receptor.

In a particular embodiment, the derivatives of the invention bind very well to the GLP-1 receptor at a low albumin concentration, but they also bind very well at a high albumin concentration.

As an example, in a particular embodiment, the GLP-1 receptor binding affinity ($IC_{50}$) of the derivatives of the invention in the presence of 2.0% HSA (high albumin) is at 400 nM or below.

Additional particular embodiments are disclosed in the section headed PARTICULAR EMBODIMENTS, ADDITIONAL PARTICULAR EMBODIMENTS, and STILL FURTHER PARTICULAR EMBODIMENTS.

Pharmacokinetics Profile

According to the third functional aspect, the derivatives of the invention have improved pharmacokinetic properties such as increased terminal half-life, and/or decreased clearance.

Increasing terminal half-life and/or decreasing of the clearance means that the compound in question is eliminated slower from the body. For the derivatives of the invention this entails an extended duration of pharmacological effect.

The pharmacokinetic properties of the derivatives of the invention may suitably be determined in-vivo in pharmacokinetic (PK) studies. Such studies are conducted to evaluate how pharmaceutical compounds are absorbed, distributed, and eliminated in the body, and how these processes affect the concentration of the compound in the body, over the course of time.

In the discovery and preclinical phase of pharmaceutical drug development, animal models such as the mouse, rat, monkey, dog, or pig, may be used to perform this characterisation. Any of these models can be used to test the pharmacokinetic properties of the derivatives of the invention.

In such studies, animals are typically administered with a single dose of the drug, either intravenously (i.v.), subcutaneously (s.c.), or orally (p.o.) in a relevant formulation. Blood samples are drawn at predefined time points after dosing, and samples are analysed for concentration of drug with a relevant quantitative assay. Based on these measurements, time-plasma concentration profiles for the compound of study are plotted and a so-called non-compartmental pharmacokinetic analysis of the data is performed.

For most compounds, the terminal part of the plasma-concentration profiles will be linear when drawn in a semi-logarithmic plot, reflecting that after the initial absorption and distribution, drug is removed from the body at a constant fractional rate. The rate (lambda Z or $\lambda_z$) is equal to minus the slope of the terminal part of the plot. From this rate, also a terminal half-life may be calculated, as $t\frac{1}{2}=\ln(2)/\lambda_z$ (see, e.g., Johan Gabrielsson and Daniel Weiner: Pharmacokinetics and Pharmacodynamic Data Analysis. Concepts & Applications, 3rd Ed., Swedish Pharmaceutical Press, Stockholm (2000)).

Clearance can be determined after i.v. administration and is defined as the dose (D) divided by area under the curve (AUC) on the plasma concentration versus time profile (Rowland, M and Tozer T N: Clinical Pharmacokinetics: Concepts and Applications, 3rd edition, 1995 Williams Wilkins).

The estimate of terminal half-life and/or clearance is relevant for evaluation of dosing regimens and an important parameter in drug development, in the evaluation of new drug compounds.

Pharmacokinetics Profile—Half Life In Vivo in Minipigs

According to the third functional aspect, the derivatives of the invention have improved pharmacokinetic properties.

In a particular embodiment, the pharmacokinetic properties may be determined as terminal half-life ($T_{1/2}$) in vivo in minipigs after i.v. administration, e.g. as described in Example 25 herein.

In a particular embodiment the derivatives of the invention have an excellent terminal half-life in minipigs which makes them suitable for once-monthly administration. In a particular embodiment, the terminal half-life of the derivatives of the invention in minipigs after i.v. administration is at least 100 hours.

Additional particular embodiments are disclosed in the sections headed PARTICULAR EMBODIMENTS, ADDITIONAL PARTICULAR EMBODIMENTS, and STILL FURTHER PARTICULAR EMBODIMENTS.

Production Processes

The production of peptides like GLP-1(7-37) and GLP-1 analogues is well known in the art.

The GLP-1 moiety of the derivatives of the invention (or fragments thereof) as well as the GLP-1 analogues of the invention may for instance be produced by classical peptide synthesis, e.g., solid phase peptide synthesis using t-Boc or Fmoc chemistry or other well established techniques, see, e.g., Greene and Wuts, "Protective Groups in Organic Synthesis", John Wiley & Sons, 1999, Florencio Zaragoza Dörwald, "Organic Synthesis on solid Phase", Wiley-VCH Verlag GmbH, 2000, and "Fmoc Solid Phase Peptide Synthesis", Edited by W. C. Chan and P. D. White, Oxford University Press, 2000.

Also, or alternatively, they may be produced by recombinant methods, viz. by culturing a host cell containing a DNA sequence encoding the analogue and capable of expressing the peptide in a suitable nutrient medium under conditions permitting the expression of the peptide. Non-limiting examples of host cells suitable for expression of these peptides are: *Escherichia coli, Saccharomyces cerevisiae*, as well as mammalian BHK or CHO cell lines.

Those derivatives of the invention which include non-natural amino acids and/or a covalently attached N-terminal mono- or dipeptide mimetic may e.g. be produced as described in the experimental part. Or see e.g., Hodgson et al: "The synthesis of peptides and proteins containing non-natural amino acids", Chemical Society Reviews, vol. 33, no. 7 (2004), p. 422-430; and WO 2009/083549 A1 entitled "Semi-recombinant preparation of GLP-1 analogues".

Specific examples of methods of preparing a number of the derivatives of the invention are included in the experimental part.

Pharmaceutical Compositions

The invention also relates to pharmaceutical compositions comprising a derivative of the invention or a pharmaceutically acceptable salt, amide, or ester thereof, and a pharmaceutically acceptable excipient. Such compositions may be prepared as is known in the art.

The term "excipient" broadly refers to any component other than the active therapeutic ingredient(s). The excipient may be an inert substance, an inactive substance, and/or a not medicinally active substance.

The excipient may serve various purposes, e.g. as a carrier, vehicle, diluent, tablet aid, and/or to improve administration, and/or absorption of the active substance.

The formulation of pharmaceutically active ingredients with various excipients is known in the art, see e.g. Remington: The Science and Practice of Pharmacy (e.g. 19th edition (1995), and any later editions).

Non-limiting examples of excipients are: Solvents, diluents, buffers, preservatives, tonicity regulating agents, chelating agents, and stabilisers.

Examples of formulations include liquid formulations, i.e. aqueous formulations comprising water. A liquid formulation may be a solution, or a suspension. An aqueous formulation typically comprises at least 50% w/w water, or at least 60%, 70%, 80%, or even at least 90% w/w of water.

Alternatively, a pharmaceutical composition may be a solid formulation, e.g. a freeze-dried or spray-dried composition, which may be used as is, or whereto the physician or the patient adds solvents, and/or diluents prior to use.

The pH in an aqueous formulation may be anything between pH 3 and pH 10, for example from about 7.0 to about 9.5; or from about 3.0 to about 7.0, such as from 7.0 to 9.5, or from 3.0 to 7.0.

A pharmaceutical composition may comprise a buffer. The buffer may e.g. be selected from sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid, and mixtures thereof.

A pharmaceutical composition may comprise a preservative. The preservative may e.g. be selected from phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol), and mixtures thereof. The preservative may be present in a concentration from 0.1 mg/ml to 20 mg/ml. A pharmaceutical composition may comprise an isotonic agent. The isotonic agent may e.g. be selected from a salt (e.g. sodium chloride), a sugar or sugar alcohol, an amino acid (e.g. glycine, histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), and mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alfa and beta HPCD, soluble starch, hydroxyethyl starch and carboxymethylcellulose-Na may be used. Sugar alcohol is defined as a C4-C8 hydrocarbon having at least one —OH group and includes, for example, mannitol, sorbitol, inositol, galactitol, dulcitol, xylitol, and arabitol. In one embodiment, the sugar alcohol additive is mannitol.

A pharmaceutical composition may comprise a chelating agent. The chelating agent may e.g. be selected from salts of ethylenediaminetetraacetic acid (EDTA), citric acid, and aspartic acid, and mixtures thereof.

A pharmaceutical composition may comprise a stabiliser. The stabiliser may e.g. be one or more oxidation inhibitors, aggregation inhibitors, surfactants, and/or one or more protease inhibitors. Non-limiting examples of these various kinds of stabilisers are disclosed in the following.

The term "aggregate formation" refers to a physical interaction between the polypeptide molecules resulting in formation of oligomers, which may remain soluble, or large visible aggregates that precipitate from the solution. Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

A pharmaceutical composition may comprise an amount of an amino acid base sufficient to decrease aggregate formation of the polypeptide during storage of the composition. The term "amino acid base" refers to one or more amino acids (such as methionine, histidine, imidazole, arginine, lysine, isoleucine, aspartic acid, tryptophan, threonine), or analogues thereof. Any amino acid may be present either in its free base form or in its salt form. Any stereoisomer (i.e., L, D, or a mixture thereof) of the amino acid base may be present.

Methionine (or other sulphuric amino acids or amino acid analogous) may be added to inhibit oxidation of methionine residues to methionine sulfoxide when the polypeptide acting as the therapeutic agent is a polypeptide comprising at least one methionine residue susceptible to such oxidation. Any stereoisomer of methionine (L or D) or combinations thereof can be used.

A pharmaceutical composition may comprise a stabiliser selected from high molecular weight polymers or low molecular compounds. The stabiliser may e.g. be selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). A pharmaceutical composition may comprise additional stabilising agents such as, but not limited to, methionine and EDTA, which protect the polypeptide against methionine oxidation, and a nonionic surfactant, which protects the polypeptide against aggregation associated with freeze-thawing or mechanical shearing.

A pharmaceutical composition may comprise one or more surfactants. The term "surfactant" refers to any molecules or ions that are comprised of a water-soluble (hydrophilic) part, and a fat-soluble (lipophilic) part. The surfactant may e.g. be selected from anionic surfactants, cationic surfactants, nonionic surfactants, and/or zwitterionic surfactants.

A pharmaceutical composition may comprise one or more protease inhibitors, such as, e.g., EDTA (ethylenediamine tetraacetic acid), and/or benzamidineHCl.

Additional, optional, ingredients of a pharmaceutical composition include, e.g., wetting agents, emulsifiers, antioxidants, bulking agents, metal ions, oily vehicles, proteins (e.g., human serum albumin, gelatine), and/or a zwitterion (e.g., an amino acid such as betaine, taurine, arginine, glycine, lysine and histidine).

Still further, a pharmaceutical composition may be formulated as is known in the art of oral formulations of insulinotropic compounds, e.g. using any one or more of the formulations described in WO 2008/145728.

An administered dose may contain from 0.1 mg-100 mg of the derivative, from 1-100 mg of the derivative, or from 1-50 mg of the derivative.

The derivative may be administered in the form of a pharmaceutical composition. It may be administered to a patient in need thereof at several sites, for example, at topical sites such as skin or mucosal sites; at sites which bypass absorption such as in an artery, in a vein, or in the heart; and at sites which involve absorption, such as in the skin, under the skin, in a muscle, or in the abdomen.

The route of administration may be, for example, lingual; sublingual; buccal; in the mouth; oral; in the stomach; in the intestine; nasal; pulmonary, such as through the bronchioles, the alveoli, or a combination thereof; parenteral, epidermal; dermal; transdermal; conjunctival; uretal; vaginal; rectal; and/or ocular. A composition may be an oral composition, and the route of administration is per oral.

A composition may be administered in several dosage forms, for example as a solution; a suspension; an emulsion; a microemulsion; multiple emulsions; a foam; a salve; a paste; a plaster; an ointment; a tablet; a coated tablet; a chewing gum; a rinse; a capsule such as hard or soft gelatine capsules; a suppositorium; a rectal capsule; drops; a gel; a spray; a powder; an aerosol; an inhalant; eye drops; an ophthalmic ointment; an ophthalmic rinse; a vaginal pessary; a vaginal ring; a vaginal ointment; an injection solution; an in situ transforming solution such as in situ gelling, setting, precipitating, and in situ crystallisation; an infusion solution; or as an implant.

A composition may be a tablet, optionally coated, a capsule, or a chewing gum.

A composition may further be compounded in a drug carrier or drug delivery system, e.g. in order to improve stability, bioavailability, and/or solubility. In a particular embodiment a composition may be attached to such system through covalent, hydrophobic, and/or electrostatic interactions. The purpose of such compounding may be, e.g., to decrease adverse effects, achieve chronotherapy, and/or increase patient compliance.

A composition may also be used in the formulation of controlled, sustained, protracting, retarded, and/or slow release drug delivery systems.

Parenteral administration may be performed by subcutaneous, intramuscular, intraperitoneal, or intravenous injection by means of a syringe, optionally a pen-like syringe, or by means of an infusion pump.

A composition may be administered nasally in the form of a solution, a suspension, or a powder; or it may be administered pulmonally in the form of a liquid or powder spray.

Transdermal administration is a still further option, e.g. by needle-free injection, from a patch such as an iontophoretic patch, or via a transmucosal route, e.g. buccally.

A composition may be a stabilised formulation. The term "stabilised formulation" refers to a formulation with increased physical and/or chemical stability, preferably both. In general, a formulation must be stable during use and storage (in compliance with recommended use and storage conditions) until the expiration date is reached.

The term "physical stability" refers to the tendency of the polypeptide to form biologically inactive and/or insoluble aggregates as a result of exposure to thermo-mechanical stress, and/or interaction with destabilising interfaces and surfaces (such as hydrophobic surfaces). The physical stability of an aqueous polypeptide formulation may be evaluated by means of visual inspection, and/or by turbidity measurements after exposure to mechanical/physical stress (e.g. agitation) at different temperatures for various time periods. Alternatively, the physical stability may be evaluated using a spectroscopic agent or probe of the conformational status of the polypeptide such as e.g. Thioflavin T or "hydrophobic patch" probes.

The term "chemical stability" refers to chemical (in particular covalent) changes in the polypeptide structure leading to formation of chemical degradation products potentially having a reduced biological potency, and/or increased immunogenic effect as compared to the intact polypeptide. The chemical stability can be evaluated by measuring the amount of chemical degradation products at various time-points after exposure to different environmental conditions, e.g. by SEC-HPLC, and/or RP-HPLC.

The treatment with a derivative according to the present invention may also be combined with one or more additional pharmacologically active substances, e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity. Examples of these pharmacologically active substances are: Insulin, sulphonylureas, biguanides, meglitinides, glucosidase inhibitors, glucagon agonists, glucagon antagonists, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents as HMG CoA inhibitors (statins), Gastric Inhibitory Polypeptides (GIP analogs), compounds lowering food intake, RXR agonists and agents acting on the ATP-dependent potassium channel of the β-cells; Cholestyramine, colestipol, clofibrate, gemfibrozil, lovastatin, pravastatin, simvastatin, probucol, dextrothyroxine, neteglinide, repaglinide; β-blockers such as alprenolol, atenolol, timolol, pindolol, propranolol and metoprolol, ACE (angiotensin converting enzyme) inhibitors such as benazepril, captopril, enalapril, fosinopril, lisinopril, alatriopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin; CART (cocaine amphetamine regulated transcript) agonists, NPY (neuropeptide Y) antagonists, PYY agonists, Y2 receptor agonists, Y4 receptor agonits, mixed Y2/Y4 receptor agonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, oxyntomodulin and analogues, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, fibroblast growth factor 21 (FGF-21), galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators, TR β agonists; histamine H3 antagonists, Gastric Inhibitory Polypeptide agonists or antagonists (GIP analogs), gastrin and gastrin analogs.

The treatment with a derivative according to this invention may also be combined with a surgery that influences the glucose levels, and/or lipid homeostasis such as gastric banding or gastric bypass.

Pharmaceutical Indications

The present invention also relates to a derivative of the invention, for use as a medicament.

In particular embodiments, the derivative of the invention may be used for the following medical treatments:

(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse.

In a particular embodiment the indication is selected from the group consisting of (i)-(xiv), such as indications (i)-(viii), (x)-(xiii), and/or (xiv), and relates in one way or the other to diabetes.

In another particular embodiment, the indication is selected from the group consisting of (i)-(iii) and (v)-(viii), such as indications (i), (ii), and/or (iii); or indication (v), indication (vi), indication (vii), and/or indication (viii).

In a still further particular embodiment, the indication is (i). In a further particular embodiment the indication is (v). In a still further particular embodiment the indication is (viii).

The following indications are particularly preferred: Type 2 diabetes, and/or obesity.

In some embodiments the invention relates to a method for weight management. In some embodiments the invention relates to a method for reduction of appetite. In some embodiments the invention relates to a method for reduction of food intake.

Generally, all subjects suffering from obesity are also considered to be suffering from overweight. In some embodiments the invention relates to a method for treatment or prevention of obesity. In some embodiments the invention relates to use of the derivative or analogue of the invention for treatment or prevention of obesity. In some embodiments the subject suffering from obesity is human, such as an adult human or a paediatric human (including infants, children, and adolescents). Body mass index (BMI) is a measure of body fat based on height and weight. The formula for calculation is BMI=weight in kilograms/height in meters$^2$. A human subject suffering from obesity may have a BMI of ≥30; this subject may also be referred to as obese. In some embodiments the human subject suffering from obesity may have a BMI of ≥35 or a BMI in the range of ≥30 to <40. In some embodiments the obesity is severe obesity or morbid obesity, wherein the human subject may have a BMI of ≥40.

In some embodiments the invention relates to a method for treatment or prevention of overweight, optionally in the presence of at least one weight-related comorbidity. In some embodiments the invention relates to use of the derivative or analogue of the invention for treatment or prevention of overweight, optionally in the presence of at least one weight-related comorbidity. In some embodiments the subject suffering from overweight is human, such an adult human or a paediatric human (including infants, children, and adolescents). In some embodiments a human subject suffering from overweight may have a BMI of ≥25, such as a BMI of ≥27. In some embodiments a human subject suffering from overweight has a BMI in the range of 25 to <30 or in the range of 27 to <30. In some embodiments the weight-related comorbidity is selected from the group consisting of hypertension, diabetes (such as type 2 diabetes), dyslipidaemia, high cholesterol, and obstructive sleep apnoea.

In some embodiments the invention relates to a method for reduction of body weight. In some embodiments the invention relates to use of the derivative or analogue of the invention for reduction of body weight. A human to be subjected to reduction of body weight according to the present invention may have a BMI of ≥25, such as a BMI of ≥27 or a BMI of ≥30. In some embodiments the human to be subjected to reduction of body weight according to the present invention may have a BMI of ≥35 or a BMI of ≥40. The term "reduction of body weight" may include treatment or prevention of obesity and/or overweight.

PARTICULAR EMBODIMENTS

The following are particular embodiments of the invention:

1. A derivative of a GLP-1 analogue of the general Formula I:

(SEQ ID NO: 10)
Xaa$_7$-Xaa$_8$-Glu-Gly-Thr-Xaa$_{12}$-Thr-Ser-Asp-Xaa$_{16}$-Ser-
Xaa$_{18}$-Xaa$_{19}$-Xaa$_{20}$-Glu-Xaa$_{22}$-Xaa$_{23}$-Ala-Xaa$_{25}$-Xaa$_{26}$-Xaa$_{27}$-
Phe-Ile-Xaa$_{30}$-Xaa$_{31}$-Leu-Xaa$_{33}$-Xaa$_{34}$-Xaa$_{35}$-Xaa$_{36}$-Xaa$_{37}$-
Xaa$_{38}$-Xaa$_{39}$, wherein
Xaa$_7$ is L-histidine, (S)-2-Hydroxy-3-(1H-imidazol-4-yl)-propionic acid, D-histidine, deamino-histidine, homohistidine, N$^\alpha$-acetyl-histidine, N$^\alpha$-formyl-histidine, N$^\alpha$-methyl-histidine, 3-pyridylalanine, 2-pyridylalanine, or 4-pyridylalanine;
Xaa$_8$ is Ala, Gly, Ser, Aib, (1-aminocyclopropyl) carboxylic acid, or (1-aminocyclobutyl) carboxylic acid;
Xaa$_{12}$ is Phe or Leu;
Xaa$_{16}$ is Val or Leu;
Xaa$_{18}$ is Ser, Val, Arg, or Leu;
Xaa$_{19}$ is Tyr or Gln;
Xaa$_{20}$ is Leu or Met;
Xaa$_{22}$ is Gly or Glu;
Xaa$_{23}$ is Gln, Glu, or Arg;
Xaa$_{25}$ is Ala or Val;
Xaa$_{26}$ is Arg;
Xaa$_{27}$ is Glu or Leu;
Xaa$_{30}$ is Ala, Glu, or Arg;
Xaa$_{31}$ is Trp or His;
Xaa$_{33}$ is Val;
Xaa$_{34}$ is Lys, Arg, His, Asn, or Gln;
Xaa$_{35}$ is Lys, Gly or Ala;
Xaa$_{36}$ is Lys, Arg or Gly;
Xaa$_{37}$ is Gly, Pro, or Lys;
Xaa$_{38}$ is Lys, Gly, or absent;
Xaa$_{39}$ is Lys or absent;
wherein at least one of Xaa$_{34}$, Xaa$_{35}$, Xaa$_{36}$, Xaa$_{37}$, Xaa$_{38}$, and Xaa$_{39}$ is Lys;
which derivative comprises a side chain that is attached to the Lys residue of Xaa$_{34}$, Xaa$_{35}$, Xaa$_{36}$, Xaa$_{37}$, Xaa$_{38}$, or Xaa$_{39}$,
which side chain comprises:
(i) a Branched linker of Chem. 11

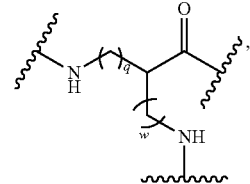

Chem. 11 wherein
q is an integer in the range of 0-5,
w is an integer in the range of 0-5,
with the provisos that when w is 0 q is an integer in the range of 1-5, and when q is 0 w is an integer in the range of 1-5; and (ii) a 1st and a 2nd Protractor of Chem. 12:

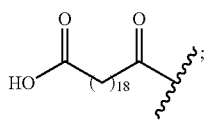
Chem. 12 wherein the Branched linker is connected
   a) at its —CO end to the epsilon amino group of the Lys residue of $Xaa_{34}$, $Xaa_{35}$, $Xaa_{36}$, $Xaa_{37}$, $Xaa_{38}$, or $Xaa_{39}$, via a Pre-linker, and
   b) at each of its two —NH ends to the —CO end of each of the 1st and 2nd Protractor, respectively, via a 1st and a 2nd Post-linker, respectively;
wherein each of the Pre-linker, the 1st Post-linker, and the 2nd Post-linker comprises a —CO group and an —NH group;
or a pharmaceutically acceptable salt, amide, or ester thereof.

2. The derivative of embodiment 1, wherein when $Xaa_{38}$ is absent $Xaa_{39}$ is also absent.

3. The derivative of any of embodiments 1-2, wherein $Xaa_7$ is L-histidine, or deamino-histidine; $Xaa_8$ is Aib; $Xaa_{12}$ is Phe; $Xaa_{16}$ is Val; $Xaa_{18}$ is Ser; $Xaa_{19}$ is Tyr; $Xaa_{20}$ is Leu; $Xaa_{22}$ is Gly or Glu; $Xaa_{23}$ is Gln; $Xaa_{25}$ is Ala; $Xaa_{26}$ is Arg; $Xaa_{27}$ is Glu; $Xaa_{30}$ is Ala; $Xaa_{31}$ is Trp; $Xaa_{33}$ is Val; $Xaa_{34}$ is Lys or Arg; $Xaa_{35}$ is Lys or Gly; $Xaa_{36}$ is Lys or Arg; $Xaa_{37}$ is Gly or Lys; $Xaa_{38}$ is Lys, Gly, or absent; $Xaa_{39}$ is Lys or absent; and wherein at least one of $Xaa_{34}$, $Xaa_{35}$, $Xaa_{36}$, $Xaa_{37}$, $Xaa_{38}$, and $Xaa_{39}$ is Lys.

4. The derivative of any of embodiments 1-3, wherein the GLP-1 analogue has a maximum of 10 amino acid changes as compared to the sequence of GLP-1(7-37) (SEQ ID NO: 1).

5. The derivative of any of embodiments 1-4, wherein the GLP-1 analogue has a maximum of 9 amino acid changes as compared to the sequence of GLP-1(7-37) (SEQ ID NO: 1).

6. The derivative of any of embodiments 1-5, wherein the GLP-1 analogue has a maximum of 8 amino acid changes as compared to the sequence of GLP-1(7-37) (SEQ ID NO: 1).

7. The derivative of any of embodiments 1-6, wherein the GLP-1 analogue has a maximum of 7 amino acid changes as compared to the sequence of GLP-1(7-37) (SEQ ID NO: 1).

8. The derivative of any of embodiments 1-7, wherein the GLP-1 analogue has a maximum of 6 amino acid changes as compared to the sequence of GLP-1(7-37) (SEQ ID NO: 1).

9. The derivative of any of embodiments 1-8, wherein the GLP-1 analogue has a maximum of 5 amino acid changes as compared to the sequence of GLP-1(7-37) (SEQ ID NO: 1).

10. The derivative of any of embodiments 1-9, wherein the GLP-1 analogue has a maximum of 4 amino acid changes as compared to the sequence of GLP-1(7-37) (SEQ ID NO: 1).

11. The derivative of any of embodiments 1-10, wherein the GLP-1 analogue has a maximum of 3 amino acid changes as compared to the sequence of GLP-1(7-37) (SEQ ID NO: 1).

12. The derivative of any of embodiments 1-11, wherein the GLP-1 analogue has a maximum of 2 amino acid changes as compared to the sequence of GLP-1(7-37) (SEQ ID NO: 1).

13. The derivative of any of embodiments 1-12, wherein the GLP-1 analogue has a maximum of 1 change as compared to the sequence of GLP-1(7-37) (SEQ ID NO: 1).

14. The derivative of any of embodiments 1-13, wherein the GLP-1 analogue has at least 1 amino acid change as compared to the sequence of GLP-1(7-37) (SEQ ID NO: 1).

15. The derivative of any of embodiments 1-14, wherein the GLP-1 analogue has at least 2 amino acid changes as compared to the sequence of GLP-1(7-37) (SEQ ID NO: 1).

16. The derivative of any of embodiments 1-15, wherein the GLP-1 analogue has at least 3 amino acid changes as compared to the sequence of GLP-1(7-37) (SEQ ID NO: 1).

17. The derivative of any of embodiments 1-16, wherein the GLP-1 analogue has at least 4 amino acid changes as compared to the sequence of GLP-1(7-37) (SEQ ID NO: 1).

18. The derivative of any of embodiments 1-17, wherein the GLP-1 analogue has at least 5 amino acid changes as compared to the sequence of GLP-1(7-37) (SEQ ID NO: 1).

19. The derivative of any of embodiments 1-18, wherein the GLP-1 analogue has at least 6 amino acid changes as compared to the sequence of GLP-1(7-37) (SEQ ID NO: 1).

20. The derivative of any of embodiments 1-19, wherein the GLP-1 analogue has at least 7 amino acid changes as compared to the sequence of GLP-1(7-37) (SEQ ID NO: 1).

21. The derivative of any of embodiments 1-20, wherein the number of amino acid changes as compared to GLP-1(7-37) (SEQ ID NO: 1) is identified by handwriting and visual inspection.

22. The derivative of any of embodiments 1-21, wherein the number of amino acid changes as compared to GLP-1(7-37) (SEQ ID NO: 1) is identified by by use of a standard protein or peptide alignment program.

23. The derivative of embodiment 22, wherein the alignment program is a Needleman-Wunsch alignment.

24. The derivative of any of embodiments 22-23, wherein the default scoring matrix and the default identity matrix is used.

25. The derivative of any of embodiments 22-24, wherein the scoring matrix is BLOSUM62.

26. The derivative of any of embodiments 22-25, wherein the penalty for the first residue in a gap is −10 (minus ten).

27. The derivative of any of embodiments 22-26, wherein the penalties for additional residues in a gap is −0.5 (minus point five).

28. The derivative of any of embodiments 1-27, wherein one of $Xaa_{34}$, $Xaa_{35}$, $Xaa_{36}$, $Xaa_{37}$, $Xaa_{38}$, and $Xaa_{39}$ is Lys.

29. The derivative of any of embodiments 1-28, wherein the GLP-1 analogue is selected from the peptides of SEQ ID NO: 2, SEQ ID NO: 3, SEQ ID NO: 5, SEQ ID NO: 6, SEQ ID NO: 7, SEQ ID NO: 8, and SEQ ID NO: 9.

30. The derivative of any of embodiments 1-29, wherein the side chain is attached to the Lys residue of $Xaa_{34}$.

31. The derivative of any of embodiments 1-29, wherein the side chain is attached to the Lys residue of $Xaa_{35}$.

32. The derivative of any of embodiments 1-29, wherein the side chain is attached to the Lys residue of $Xaa_{36}$.

33. The derivative of any of embodiments 1-29, wherein the side chain is attached to the Lys residue of $Xaa_{37}$.

34. The derivative of any of embodiments 1-29, wherein the side chain is attached to the Lys residue of $Xaa_{38}$.

35. The derivative of any of embodiments 1-29, wherein the side chain is attached to the Lys residue of $Xaa_{39}$.

36. The derivative of any of embodiments 1-35, wherein in Chem. 11 q is 4 and w is 0.

37. The derivative of any of embodiments 1-35, wherein in Chem. 11 q is 0 and w is 4.

38. The derivative of any of embodiments 1-37, wherein Chem. 11 is represented by

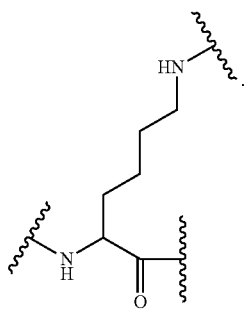

Chem. 11a

39. The derivative of any of embodiments 1-38, wherein Chem. 11 or Chem. 11a, respectively, is a bis-amino tri-radical of lysine.
40. The derivative of any of embodiments 1-39, wherein Chem. 11 or Chem. 11a, respectively, is eps-Lys(Bis).
41. The derivative of any of embodiments 1-39, wherein Chem. 11 or Chem. 11a, respectively, is in the L-form.
42. The derivative of any of embodiments 1-41, wherein the Pre-linker comprises
at least one Linker element-1 of Chem. 1:

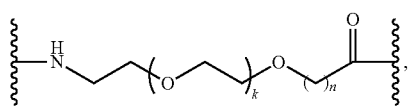

Chem. 1 wherein k is an integer in the range of 1-19, and n is an integer in the range of 1-5; or
at least one Linker element-2 of Chem. 2b:

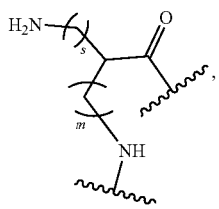

Chem. 2b wherein m is an integer in the range of 0-5, s is an integer in the range of 0-5, and with the provisos that when m is 0 s is an integer in the range of 1-5, and when s is 0 m is an integer in the range of 1-5.
43. The derivative of any of embodiments 1-42, wherein the Pre-linker comprises t times Linker element-1.
44. The derivative of embodiment 43, wherein t is an integer in the range of 1-8.
45. The derivative of embodiment 43, wherein t is 1.
46. The derivative of embodiment 43, wherein t is 2.
47. The derivative of embodiment 43, wherein t is 3.
48. The derivative of embodiment 43, wherein t is 4.
49. The derivative of embodiment 43, wherein t is 6.
50. The derivative of embodiment 43, wherein t is 8.
51. The derivative of any of embodiments 42-50, wherein k is 1, 5, 11, or 19.
52. The derivative of any of embodiments 42-51, wherein n is 1 or 2.
53. The derivative of any of embodiments 42-52, wherein k is 1 and n is 1.
54. The derivative of any of embodiments 42-52, wherein k is 5 and n is 2.
55. The derivative of any of embodiments 42-52, wherein k is 11 and n is 2.
56. The derivative of any of embodiments 42-52, wherein k is 19 and n is 2.
57. The derivative of any of embodiments 42-56, wherein when t is other than 1 the t times Linker element-1 are juxtaposed, where juxtaposed means mutually connected, via amide bonds.
58. The derivative of any of embodiments 42-57, wherein when t is other than 1 the t times Linker element-1 are arranged in a row, one after the other, mutually connected via amide bonds.
59. The derivative of any of embodiments 1-58, wherein the Pre-linker consists of one Linker element-1 of Chem. 1 where k is 1 and n is 1, and wherein the Pre-linker is connected at its —NH end to the —CO end of the Branched linker, and at its —CO end to the epsilon amino group of the Lys residue of $Xaa_{34}$, $Xaa_{35}$, $Xaa_{36}$, $Xaa_{37}$, $Xaa_{38}$, or $Xaa_{39}$.
60. The derivative of any of embodiments 1-58, wherein the Pre-linker consists of two times Linker element-1 of Chem. 1 where k is 1 and n is 1, interconnected via amide bonds, and wherein the Pre-linker is connected at its —NH end to the —CO end of the Branched linker, and at its —CO end to the epsilon amino group of the Lys residue of $Xaa_{34}$, $Xaa_{35}$, $Xaa_{36}$, $Xaa_{37}$, $Xaa_{38}$, or $Xaa_{39}$.
61. The derivative of any of embodiments 1-58, wherein the Pre-linker consists of three times Linker element-1 of Chem. 1 where k is 1 and n is 1, interconnected via amide bonds, and wherein the Pre-linker is connected at its —NH end to the —CO end of the Branched linker, and at its —CO end to the epsilon amino group of the Lys residue of $Xaa_{34}$, $Xaa_{35}$, $Xaa_{36}$, $Xaa_{37}$, $Xaa_{38}$, or $Xaa_{39}$.
62. The derivative of any of embodiments 1-58, wherein the Pre-linker consists of four times Linker element-1 of Chem. 1 where k is 1 and n is 1, interconnected via amide bonds, and wherein the Pre-linker is connected at its —NH end to the —CO end of the Branched linker, and at its —CO end to the epsilon amino group of the Lys residue of $Xaa_{34}$, $Xaa_{35}$, $Xaa_{36}$, $Xaa_{37}$, $Xaa_{38}$, or $Xaa_{39}$.
63. The derivative of any of embodiments 1-58, wherein the Pre-linker consists of six times Linker element-1 of Chem. 1 where k is 1 and n is 1, interconnected via amide bonds, and wherein the Pre-linker is connected at its —NH end to the —CO end of the Branched linker, and at its —CO end to the epsilon amino group of the Lys residue of $Xaa_{34}$, $Xaa_{35}$, $Xaa_{36}$, $Xaa_{37}$, $Xaa_{38}$, or $Xaa_{39}$.
64. The derivative of any of embodiments 1-58, wherein the Pre-linker consists of eight times Linker element-1 of Chem. 1 where k is 1 and n is 1, interconnected via amide bonds, and wherein the Pre-linker is connected at its —NH end to the —CO end of the Branched linker, and at its —CO end to the epsilon amino group of the Lys residue of $Xaa_{34}$, $Xaa_{35}$, $Xaa_{36}$, $Xaa_{37}$, $Xaa_{38}$, or $Xaa_{39}$.
65. The derivative of any of embodiments 1-58, wherein the Pre-linker consists of one Linker element-1 of Chem. 1 where k is 5 and n is 2, and wherein the Pre-linker is connected at its —NH end to the —CO end of the Branched linker, and at its —CO end to the epsilon amino group of the Lys residue of $Xaa_{34}$, $Xaa_{35}$, $Xaa_{36}$, $Xaa_{37}$, $Xaa_{38}$, or $Xaa_{39}$.
66. The derivative of any of embodiments 1-58, wherein the Pre-linker consists of one Linker element-1 of Chem. 1 where k is 11 and n is 2, and wherein the Pre-linker is connected at its —NH end to the —CO end of the Branched linker, and at its —CO end to the epsilon amino group of the Lys residue of $Xaa_{34}$, $Xaa_{35}$, $Xaa_{36}$, $Xaa_{37}$, $Xaa_{38}$, or $Xaa_{39}$.

67. The derivative of any of embodiments 1-58, wherein the Pre-linker consists of one Linker element-1 of Chem. 1 where k is 19 and n is 2, and wherein the Pre-linker is connected at its —NH end to the —CO end of the Branched linker, and at its —CO end to the epsilon amino group of the Lys residue of $Xaa_{34}$, $Xaa_{35}$, $Xaa_{36}$, $Xaa_{37}$, $Xaa_{38}$, or $Xaa_{39}$.

68. The derivative of any of embodiments 1-42, wherein the Pre-linker comprises Linker element-2.

69. The derivative of any of embodiments 1-42 and 68, wherein the Pre-linker comprises two or four times Linker element-2.

70. The derivative of any of embodiments 1-42 and 68-69, wherein the Pre-linker comprises two times Linker element-2.

71. The derivative of any of embodiments 1-42 and 68-69, wherein the Pre-linker comprises four times Linker element-2.

72. The derivative of any of embodiments 42, and 68-71, wherein m is 4 and s is 0.

73. The derivative of any of embodiments 42, and 68-71, wherein m is 0 and s is 4.

74. The derivative of any of embodiments 42, and 68-73, wherein Chem. 2b is represented by Chem. 2c:

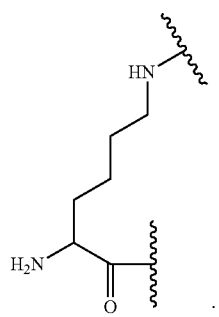

Chem. 2c

75. The derivative of any of embodiments 42, and 68-74, wherein each of Chem. 2b, or Chem. 2c, respectively, represents a di-radical of lysine.

76. The derivative of any of embodiments 42, and 68-75, wherein Chem. 2b, or Chem. 2c, respectively, represents eps-Lys.

77. The derivative of any of embodiments 42, and 68-76, wherein Chem. 2b, or Chem. 2c, respectively, is in the L-form.

78. The derivative of any of embodiments 69-77, wherein the two or four times Linker element-2, respectively, are juxtaposed, where juxtaposed means mutually connected, via amide bonds.

79. The derivative of any of embodiments 69-78, wherein the two or four times Linker element-2, respectively, are arranged in a row, one after the other, mutually connected via amide bonds.

80. The derivative of any of embodiments 1-42, and 68-79, wherein the Pre-linker consists of two times Linker element-2 of Chem. 2c, interconnected via amide bonds, and wherein the Pre-linker is connected at its —NH end to the —CO end of the Branched linker, and at its —CO end to the epsilon amino group of the Lys residue of $Xaa_{34}$, $Xaa_{35}$, $Xaa_{36}$, $Xaa_{37}$, $Xaa_{38}$, or $Xaa_{39}$.

81. The derivative of any of embodiments 1-42, and 68-79, wherein the Pre-linker consists of four times Linker element-2 of Chem. 2c, interconnected via amide bonds, and wherein the Pre-linker is connected at its —NH end to the —CO end of the Branched linker, and at its —CO end to the epsilon amino group of the Lys residue of $Xaa_{34}$, $Xaa_{35}$, $Xaa_{36}$, $Xaa_{37}$, $Xaa_{38}$, or $Xaa_{39}$.

82. The derivative of any of embodiments 1-81, wherein each of the $1^{st}$ and the $2^{nd}$ Post-linker comprises a Linker element-3 of Chem. 3:

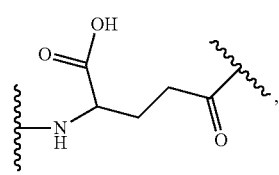

Chem. 3 and/or
a Linker element-4 of Chem. 4:

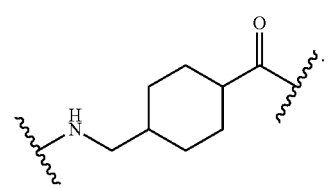

Chem. 4

83. The derivative of any of embodiments 1-82, wherein each of the $1^{st}$ and the $2^{nd}$ Post-linker comprises a Linker element-3 of Chem. 3:

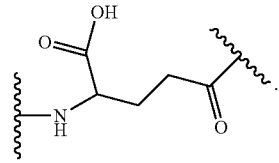

Chem. 3

84. The derivative of any of embodiments 82-83, wherein Chem. 3 is a di-radical of Glu.

85. The derivative of any of embodiments 82-84, wherein Chem. 3 is a di-radical of gGlu.

86. The derivative of any of embodiments 82-85, wherein Chem. 3 is a di-radical of L-gGlu.

87. The derivative of any of embodiments 1-86, wherein each of the $1^{st}$ and the $2^{nd}$ Post-linker comprises a Linker element-4 of Chem. 4:

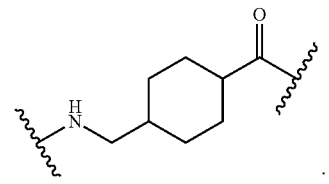

Chem. 4

88. The derivative of any of embodiments 82 and 87, wherein Chem. 4 is a di-radical of tranexamic acid.

89. The derivative of any of embodiments 82, and 87-88, wherein Chem. 4 is a di-radical of trans-4-(aminomethyl)cyclohexanecarboxylic acid.
90. The derivative of any of embodiments 1-89, wherein each of the $1^{st}$ and the $2^{nd}$ Post-linker comprises at least one Linker element-1 of Chem. 1:

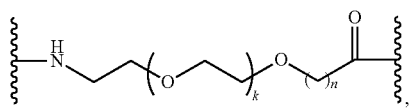

Chem. 1 wherein k is an integer in the range of 1-19, and n is an integer in the range of 1-5.
91. The derivative of embodiment 90, wherein each of the $1^{st}$ and the $2^{nd}$ Post-linker comprises one, two, three, or four times Linker element-1.
92. The derivative of any of embodiments 90-91, wherein each of the $1^{st}$ and the $2^{nd}$ Post-linker comprises one Linker element-1.
93. The derivative of any of embodiments 90-91, wherein each of the $1^{st}$ and the $2^{nd}$ Post-linker comprises two times Linker element-1.
94. The derivative of any of embodiments 90-91, wherein each of the $1^{st}$ and the $2^{nd}$ Post-linker comprises three times Linker element-1.
95. The derivative of any of embodiments 90-91, wherein each of the $1^{st}$ and the $2^{nd}$ Post-linker comprises four times Linker element-1.
96. The derivative of any of embodiments 90-95, wherein k is 1.
97. The derivative of any of embodiments 90-96, wherein n is 1.
98. The derivative of any of embodiments 90-97, wherein k is 1 and n is 1.
99. The derivative of any of embodiments 90-98, wherein if it includes more than one Linker element-1 these are juxtaposed, where juxtaposed means mutually connected, via amide bonds.
100. The derivative of any of embodiments 90-99, wherein if it includes more than one Linker element-1 these are arranged in a row, one after the other, mutually connected via amide bonds.
101. The derivative of any of embodiments 1-89, wherein none of the $1^{st}$ Post-linker and the $2^{nd}$ Post-Linker includes a Linker element-1 of Chem. 1:

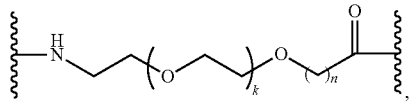

Chem. 1 wherein k is an integer in the range of 1-19, and n is an integer in the range of 1-5.
102. The derivative of any of embodiments 1-89, wherein each of the $1^{st}$ and $2^{nd}$ Post-linker optionally includes a Linker element-1, as defined in any of embodiments 90-100.
103. The derivative of any of embodiments 1-89, wherein each of the $1^{st}$ and $2^{nd}$ Post-linker further includes a Linker element-1, as defined in any of embodiments 90-100.

104. The derivative of any of embodiments 1-103, wherein each of the $1^{st}$ and the $2^{nd}$ Post-linker includes exactly one Linker element-3 and exactly one Linker element-4.
105. The derivative of any of embodiments 1-104, wherein each of the $1^{st}$ and the $2^{nd}$ Post-linker includes just one Linker element-3 and just one Linker element-4.
106. The derivative of any of embodiments 1-105, wherein each of the $1^{st}$ and $2^{nd}$ Post-linker consists of one Linker element-4, and one Linker element-3, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.
107. The derivative of any of embodiments 1-105, wherein each of the $1^{st}$ and $2^{nd}$ Post-linker consists of one Linker element-4, one Linker element-3, and one Linker element-1 where k is 1 and n is 1, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.
108. The derivative of any of embodiments 1-105, wherein each of the $1^{st}$ and $2^{nd}$ Post-linker consists of one Linker element-4, one Linker element-3, and two times Linker element-1 where k is 1 and n is 1, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.
109. The derivative of any of embodiments 1-105, wherein each of the $1^{st}$ and $2^{nd}$ Post-linker consists of one Linker element-4, one Linker element-3, and three times Linker element-1 where k is 1 and n is 1, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.
110. The derivative of any of embodiments 1-105, wherein each of the $1^{st}$ and $2^{nd}$ Post-linker consists of one Linker element-4, one Linker element-3, and four times Linker element-1 where k is 1 and n is 1, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.
111. The derivative of any of embodiments 1-110, wherein the Branched linker is connected, via amide bonds,
   a) at its —CO end to the epsilon amino group of the Lys residue of $Xaa_{34}$, $Xaa_{35}$, $Xaa_{36}$, $Xaa_{37}$, $Xaa_{38}$, or $Xaa_{39}$, via the Pre-linker, and
   b) at each of its two —N ends to the —CO end of each of the $1^{st}$ and $2^{nd}$ Protractor, respectively, via a $1^{st}$ and a $2^{nd}$ Post-linker, respectively.
112. The derivative of any of embodiments 1-111, wherein one of $Xaa_{37}$ and $Xaa_{39}$ is Lys;
   which derivative comprises a side chain that is attached to the Lys residue of $Xaa_{37}$ or $Xaa_{39}$, which side chain comprises:
(i) a Branched linker of Chem. 11a

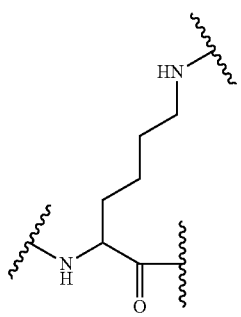

Chem. 11a (ii) a 1$^{st}$ and a 2$^{nd}$ Protractor of Chem. 12:

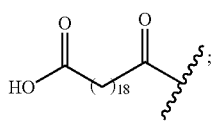

Chem. 12 wherein the Branched linker is connected
  a) at its —CO end to the epsilon amino group of the Lys residue of Xaa$_{37}$ or Xaa$_{39}$, via a Pre-linker, and
  b) at each of its two —NH ends to the —CO end of each of the 1$^{st}$ and 2$^{nd}$ Protractor, respectively, via a 1$^{st}$ and a 2$^{nd}$ Post-linker, respectively;
wherein each of the Pre-linker, the 1$^{st}$ Post-linker, and the 2$^{nd}$ Post-linker comprises at least one Linker element-1 of Chem. 1:

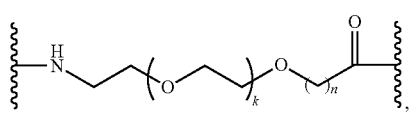

Chem. 1 wherein k is 1 and n is 1;
or a pharmaceutically acceptable salt, amide, or ester thereof.

113. The derivative of any of embodiments 1-112, wherein one of Xaa$_{37}$ and Xaa$_{39}$ is Lys;
  which derivative comprises a side chain that is attached to the Lys residue of Xaa$_{37}$ or Xaa$_{39}$, which side chain consists of:
(i) a Branched linker of Chem. 11a

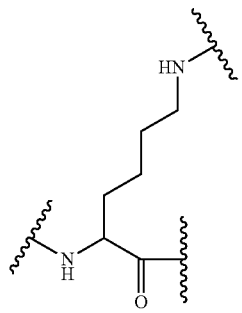

Chem. 11a (ii) a 1$^{st}$ and a 2$^{nd}$ Protractor of Chem. 12:

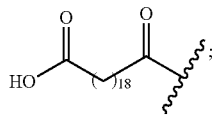

Chem. 12 wherein the Branched linker is connected
  a) at its —CO end to the epsilon amino group of the Lys residue of Xaa$_{37}$ or Xaa$_{39}$, via a Pre-linker, and
  b) at each of its two —NH ends to the —CO end of each of the 1$^{st}$ and 2$^{nd}$ Protractor, respectively, via a 1$^{st}$ and a 2$^{nd}$ Post-linker, respectively;
wherein each of the Pre-linker, the 1$^{st}$ Post-linker, and the 2$^{nd}$ Post-linker comprises one, two, three or four times the Linker element-1 of Chem. 1:

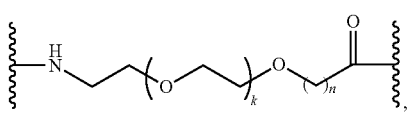

Chem. 1 wherein k is 1and n is 1, and if more than one Linker element-1 are included these are mutually connected via amide bonds;
or a pharmaceutically acceptable salt, amide, or ester thereof.

114. The derivative of any of embodiments 1-113, wherein the GLP-1 analogue has the following changes as compared to SEQ ID NO: 1: (8Aib, 22E, 26R, 34R), and in addition either (i) 37K or (ii) (38G and 39K), and optionally in addition (iii) 7Imp.

115. The derivative of any of embodiments 1-114, wherein the GLP-1 analogue has the sequence of any of SEQ ID NOs: 2 or 3.

116. The derivative of any of embodiments 1-115, wherein each of the 1$^{st}$ and 2$^{nd}$ Post-linker comprises one Linker element-3 of Chem. 3, which is a di-radical of gGlu, preferably in the L-form.

117. The derivative of any of embodiments 1-116, wherein each of the 1$^{st}$ and 2$^{nd}$ Post-linker comprises one Linker element-4 of Chem. 4, which is a di-radical of tranexamic acid, preferably trans-4-(aminomethyl)cyclohexanecarboxylic acid.

118. The derivative of any of embodiments 1-117, which is selected from Chem. 21, Chem. 22, Chem. 27, Chem. 34, Chem. 35, Chem. 41, and Chem. 42; or a pharmaceutically acceptable salt, amide, or ester thereof.

119. A GLP-1 derivative, preferably the derivative of any of embodiments 1-118, which is selected from Chem. 21, Chem. 22, Chem. 23, Chem. 24, Chem. 25, Chem. 26, Chem. 27, Chem. 28, Chem. 29, Chem. 30, Chem. 31, Chem. 32, Chem. 33, Chem. 34, Chem. 35, Chem. 36, Chem. 37, Chem. 38, Chem. 39, Chem. 40, Chem. 41, and Chem. 42; or a pharmaceutically acceptable salt, amide, or ester thereof.

120. A GLP-1 derivative, preferably the derivative of any of embodiments 1-119, which is selected from the compounds of Examples 1-22, or a pharmaceutically acceptable salt, amide, or ester thereof.

121. A GLP-1 analogue which comprises the following changes when compared to GLP-1(7-37) (SEQ ID NO: 1): (7Imp, 8Aib, 22E, 26R, 34R, 38G), (7Imp, 8Aib, 22E, 26R, 34R, 39K), (7Imp, 8Aib, 22E, 26R, 34R, 38G, 39K), or (8Aib, 22E, 26R, 34R, 35K); or a pharmaceutically acceptable salt, amide, or ester thereof.

122. The GLP-1 analogue of embodiment 121, which is selected from SEQ ID NO: 3, SEQ ID NO: 5, SEQ ID NO: 6, and SEQ ID NO: 9; or a pharmaceutically acceptable salt, amide, or ester thereof.

123. The GLP-1 analogue of any of embodiments 121-122 which is an intermediate of the GLP-1 derivative of any of embodiments 1-120.

124. A compound of formula II (see FIG. 2), wherein
q is an integer in the range of 0-5,
w is an integer in the range of 0-5,
with the provisos that when w is 0 q is an integer in the range of 1-5, and when q is 0 w is an integer in the range of 1-5;
$R_1$ is —OH or a suitable activation group;
$R_2$ is —COOH or a suitable protective group for —COOH; and
each of the Pre-linker, the $1^{st}$ Post-linker, and the $2^{nd}$ Post-linker comprises a —CO group and an —NH group;
or a pharmaceutically acceptable salt, amide, or ester thereof.

125. The compound of embodiment 124, wherein q is 4 and w is 0.

126. The compound of embodiment 124, wherein q is 0 and w is 4.

Figure 3A:
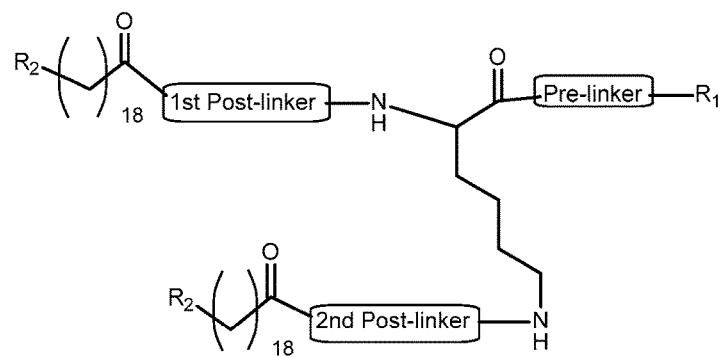
FIG. 3 A-B shows a formula to define novel side chain intermediate products relating to the GLP-1 derivatives of the invention, respectively.

127. The compound of any of embodiments 124-127, which has formula II' (see FIG. 3A).

Figure 3B:
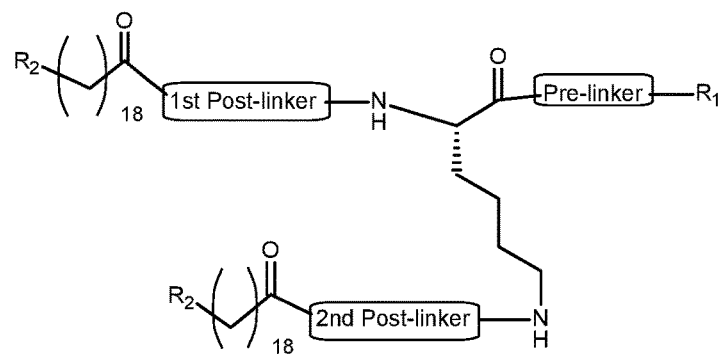

128. The compound of any of embodiments 124-127, which has formula II" (see FIG. 3B).

129. The compound of any of embodiments 124-128, wherein $R_1$ is —OH or a suitable leaving group.

130. The compound of any of embodiments 124-129, wherein $R_1$ is —OH.

131. The compound of any of embodiments 124-129, wherein $R_1$ is a suitable leaving group forming an active ester together with a carbonyl group.

132. The compound of any of embodiments 124-129 and 131, wherein $R_1$ is selected from Chem. 81 (—OPfp), Chem. 82 (OPnp), and Chem. 83 (OSuc).

133. The compound of any of embodiments 124-132, wherein $R_2$ is —COOH.

134. The compound of any of embodiments 124-132, wherein $R_2$ is a suitable protective group for —COOH.

135. The compound of any of embodiments 124-132 and 134, wherein the protective group for —COOH is a suitable non-reactive ester.

136. The compound of embodiment 135, wherein the non-reactive ester is selected from Chem. 84 (—COOtBu), Chem. 85 (—COOBz), Chem. 86 (—COOMe), Chem. 87 (—COCH$_2$CCl$_3$), and Chem. 88 (—COCH$_2$CCl$_3$).

137. The compound of any of embodiments 124-136, wherein the Pre-linker comprises
at least one Linker element-1 of Chem. 1:

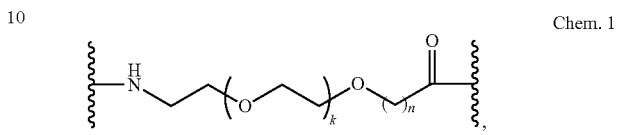

Chem. 1 wherein k is an integer in the range of 1-19, and n is an integer in the range of 1-5; or
at least one Linker element-1 of Chem. 1:

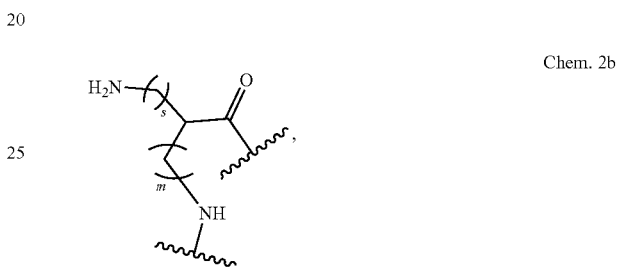

Chem. 2b wherein m is an integer in the range of 0-5, s is an integer in the range of 0-5, and with the provisos that when m is 0 s is an integer in the range of 1-5, and when s is 0 m is an integer in the range of 1-5, and wherein the free amino group (—NH$_2$) is substituted with $R_5$, wherein $R_5$ is —NH$_2$ or a suitable protective group for an amino group.

138. The compound of any of embodiments 124-137, wherein the Pre-linker comprises t times Linker element-1.

139. The compound of embodiment 138, wherein t is an integer in the range of 1-8.

140. The compound of embodiment 138, wherein t is 1.

141. The compound of embodiment 138, wherein t is 2.

142. The compound of embodiment 138, wherein t is 3.

143. The compound of embodiment 138, wherein t is 4.

144. The compound of embodiment 138, wherein t is 6.

145. The compound of embodiment 138, wherein t is 8.

146. The compound of any of embodiments 137-145, wherein k is 1, 5, 11, or 19.

147. The compound of any of embodiments 137-146, wherein n is 1 or 2.

148. The compound of any of embodiments 137-147, wherein k is 1 and n is 1.

149. The compound of any of embodiments 137-147, wherein k is 5 and n is 2.

150. The compound of any of embodiments 137-147, wherein k is 11 and n is 2.

151. The compound of any of embodiments 137-147, wherein k is 19 and n is 2.

152. The compound of any of embodiments 137-151, wherein when t is other than 1 the t times Linker element-1 are juxtaposed, where juxtaposed means mutually connected, via amide bonds.

153. The compound of any of embodiments 137-152, wherein when t is other than 1 the t times Linker element-1 are arranged in a row, one after the other, mutually connected via amide bonds.

154. The compound of any of embodiments 124-153, wherein the Pre-linker consists of one Linker element-1 of Chem. 1 where k is 1 and n is 1.

155. The compound of any of embodiments 124-153, wherein the Pre-linker consists of two times Linker element-1 of Chem. 1 where k is 1 and n is 1.

156. The compound of any of embodiments 124-153, wherein the Pre-linker consists of three times Linker element-1 of Chem. 1 where k is 1 and n is 1.

157. The compound of any of embodiments 124-153, wherein the Pre-linker consists of four times Linker element-1 of Chem. 1 where k is 1 and n is 1.

158. The compound of any of embodiments 124-153, wherein the Pre-linker consists of six times Linker element-1 of Chem. 1 where k is 1 and n is 1.

159. The compound of any of embodiments 124-153, wherein the Pre-linker consists of eight times Linker element-1 of Chem. 1 where k is 1 and n is 1.

160. The compound of any of embodiments 124-153, wherein the Pre-linker consists of one Linker element-1 of Chem. 1 where k is 5 and n is 2.

161. The compound of any of embodiments 124-153, wherein the Pre-linker consists of one Linker element-1 of Chem. 1 where k is 11 and n is 2.

162. The compound of any of embodiments 124-153, wherein the Pre-linker consists of one Linker element-1 of Chem. 1 where k is 19 and n is 2.

163. The compound of embodiment 137, wherein the Pre-linker comprises Linker element-2 as defined in embodiment 137.

164. The compound of embodiment 163, wherein the Pre-linker comprises two or four times Linker element-2 as defined in embodiment 137.

165. The compound of any of embodiments 163-164, wherein the Pre-linker comprises two times Linker element-2 as defined in embodiment 137.

166. The compound of any of embodiments 163-164, wherein the Pre-linker comprises four times Linker element-2 as defined in embodiment 137.

167. The compound of any of embodiments 137 and 163-166, wherein m is 4 and s is 0.

168. The compound of any of embodiments 137 and 163-166, wherein m is 0 and s is 4.

169. The compound of any of embodiments 137 and 163-168, wherein Chem. 2b is represented by Chem. 2c:

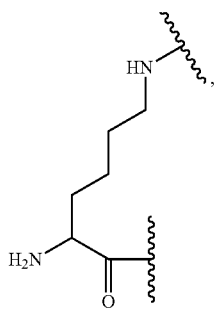

Chem. 2c wherein the free amino group (—NH$_2$) is substituted with R$_5$, wherein R$_5$ is —NH$_2$ or a suitable protective group for an amino group.

170. The compound of any of embodiments 137 and 163-169, wherein R$_5$ is —NH$_2$ 171. The compound of any of embodiments 137 and 163-169, wherein R$_5$ is a suitable protective group for an amino group.

172. The compound of any of embodiments 137, 163-169 and 171, wherein R$_5$ is a suitable carbamate.

173. The compound of any of embodiments 137, 163-169 and 171-172, wherein R$_5$ is selected from Chem. 89 (—NHFmoc), Chem. 90 (—NHBoc), and Chem. 91 (—NHCbz).

174. The compound of any of embodiments 137 and 163-173, wherein each of Chem. 2b, or Chem. 2c, respectively, represents a di-radical of lysine.

175. The compound of any of embodiments 137 and 163-174, wherein each of Chem. 2b, or Chem. 2c, respectively, represents eps-Lys.

176. The compound of any of embodiments 137 and 163-175, wherein each of Chem. 2b, or Chem. 2c, respectively, is in the L-form.

177. The compound of any of embodiments 137 and 163-176, wherein the two or four times Linker element-2 as defined in any of these embodiments, respectively, are juxtaposed, where juxtaposed means mutually connected, via amide bonds.

178. The compound of any of embodiments 137 and 163-177, wherein the two or four times Linker element-2 as defined in any of these embodiments, respectively, are arranged in a row, one after the other, mutually connected via amide bonds.

179. The compound of any of embodiments 137 and 163-178, wherein the Pre-linker consists of two times Linker element-2 of Chem. 2c as defined in any of these embodiments, interconnected via amide bonds.

180. The compound of any of embodiments 137 and 163-178, wherein the Pre-linker consists of four times Linker element-2 of Chem. 2c as defined in any of these embodiments, interconnected via amide bonds.

181. The compound of any of embodiments 124-180, wherein each of the 1$^{st}$ and the 2$^{nd}$ Post-linker comprises a Linker element-3 of Chem. 3, and/or a Linker element-4 of Chem. 4; wherein in Chem. 3 the free acid group (—COOH) is substituted with R$_3$, wherein R$_3$ is —COOH or a suitable protective group for a carboxylic acid group.

182. The compound of any of embodiments 124-181, wherein each of the 1$^{st}$ and the 2$^{nd}$ Post-linker comprises a Linker element-3 of Chem. 3 wherein the free acid group is substituted with R$_3$, wherein R$_3$ is —COOH or a suitable protective group for a carboxylic acid group.

183. The compound of any of embodiments 181-182, wherein R$_3$ is —COOH.

184. The compound of any of embodiments 181-182, wherein R$_3$ is a suitable protective group for a carboxylic acid group.

185. The compound of any of embodiments 181-182 and 184, wherein R$_3$ is a suitable ester group.

186. The compound of any of embodiments 181-182 and 184-185, wherein R$_3$ is selected from —COOtBu (Chem. 84), —COOBz (Chem. 85), —COOMe (Chem. 86), —COSC(CH$_3$)$_3$ (Chem. 87), and —COCH$_2$CCl$_3$ (Chem. 88).

187. The compound of any of embodiments 181-186, wherein Linker element-3 as defined in any of these embodiments is in the L-form.

188. The compound of any of embodiments 124-187, wherein each of the 1$^{st}$ and the 2$^{nd}$ Post-linker comprises a Linker element-4 of Chem. 4.

189. The compound of embodiment 188, wherein Linker element-4 is a di-radical of trans-4-(aminomethyl)cyclohexanecarboxylic acid.
190. The compound of any of embodiments 124-189, wherein each of the $1^{st}$ and the $2^{nd}$ Post-linker comprises at least one Linker element-1 of Chem. 1:

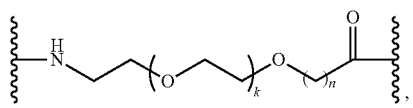

Chem. 1 wherein k is an integer in the range of 1-19, and n is an integer in the range of 1-5.
191. The compound of embodiment 190, wherein each of the $1^{st}$ and the $2^{nd}$ Post-linker comprises one, two, three, or four times Linker element-1.
192. The compound of any of embodiments 190-191, wherein each of the $1^{st}$ and the $2^{nd}$ Post-linker comprises one Linker element-1.
193. The compound of any of embodiments 190-191, wherein each of the $1^{st}$ and the $2^{nd}$ Post-linker comprises two times Linker element-1.
194. The compound of any of embodiments 190-191, wherein each of the $1^{st}$ and the $2^{nd}$ Post-linker comprises three times Linker element-1.
195. The compound of any of embodiments 190-191, wherein each of the $1^{st}$ and the $2^{nd}$ Post-linker comprises four times Linker element-1.
196. The compound of any of embodiments 190-195, wherein k is 1.
197. The compound of any of embodiments 190-196, wherein n is 1.
198. The compound of any of embodiments 190-197, wherein k is 1 and n is 1.
199. The compound of any of embodiments 190-198, wherein if it includes more than one Linker element-1 these are juxtaposed, where juxtaposed means mutually connected, via amide bonds.
200. The compound of any of embodiments 190-199, wherein if it includes more than one Linker element-1 these are arranged in a row, one after the other, mutually connected via amide bonds.
201. The compound of any of embodiments 124-189, wherein none of the $1^{st}$ Post-linker and the $2^{nd}$ Post-Linker includes a Linker element-1 of Chem. 1:

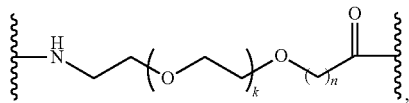

Chem. 1 wherein k is an integer in the range of 1-19, and n is an integer in the range of 1-5.
202. The compound of any of embodiments 124-201, which optionally includes a Linker element-1, as defined in any of embodiments 190-201.
203. The compound of any of embodiments 124-202, which further includes a Linker element-1, as defined in any of embodiments 190-201.
204. The compound of any of embodiments 124-203, wherein each of the $1^{st}$ and the $2^{nd}$ Post-linker includes exactly one Linker element-4 and exactly one Linker element-3 of Chem. 3 wherein the free acid group (—COOH) is substituted with $R_3$, wherein $R_3$ is defined as in any of embodiments 181-187.
205. The compound of any of embodiments 124-204, wherein each of the $1^{st}$ and the $2^{nd}$ Post-linker includes just one Linker element-4 and just one Linker element-3 of Chem. 3 wherein the free acid group (—COOH) is substituted with $R_3$, wherein $R_3$ is defined as in any of embodiments 181-187.
206. A compound selected from Chem. 50, Chem. 51, Chem. 52, Chem. 53, Chem. 54, Chem. 55, Chem. 56, Chem. 57, Chem. 58, Chem. 59, Chem. 60, Chem. 61, Chem. 62, Chem. 63, and Chem. 64; or a pharmaceutically acceptable salt, amide, or ester thereof.
207. The compound of embodiment 206, wherein the various Chem. nos. are defined in Tables A and B in the description.
208. The compound of any of embodiments 206 and 207, which is a compound of any of embodiments 124-205.
209. The compound of any of embodiments 124-208, which is an intermediate of the GLP-1 derivative of any of embodiments 1-120.
210. Use of the compound of any of embodiments 124-209 for attachment to a biologically active peptide or protein under the formation of a derivative thereof.
211. The use of embodiment 210 which has the effect of prolonging the duration of action and/or improving the pharmacokinetic properties in vivo of the derivative as compared to that of the biologically active peptide or protein, in any relevant animal model.
212. The use of any of embodiments 210-211, wherein the compound is attached to a Lys residue of the biologically active peptide or protein, under the formation of an amide bond between the epsilon amino group of the Lys residue and the —CO group of the Pre-linker.
213. The use of any of embodiments 210-212, wherein the biologically active peptide or protein is GLP-1(7-37) (SEQ ID NO: 1) or an analogue thereof, preferably an analogue as defined in any of embodiments 1-29.
214. A method of preparing a derivative of a biologically active peptide or protein which method comprises attaching a compound as defined in any of embodiments 124-209 to the biologically active peptide or protein.
215. The method of embodiment 214 which comprises the step of synthesising the compound, e.g. on solid support or by solution phase chemistry.
216. The method of any of embodiments 214-215, which comprises the step of attaching the compound to the biologically active peptide or protein, e.g. using appropriate activation and protective groups.
217. The method of any of embodiments 214-216, wherein the derivative has an improved duration of action and/or improved pharmacokinetic properties in vivo as compared to that of the biologically active peptide or protein, in any relevant animal model.
218. The method of any of embodiments 214-217, wherein the compound is attached to a Lys residue of the biologically active peptide or protein, under the formation of an amide bond between the epsilon amino group of the Lys residue and the —CO group of the Pre-linker.
219. The method of any of embodiments 214-218, wherein the biologically active peptide or protein is GLP-1(7-37) (SEQ ID NO: 1) or an analogue thereof, preferably an analogue as defined in any of embodiments 1-29.

220. A method of preparing a compound according to any of embodiments 124-209, which is conducted on solid support or by solution phase chemistry.
221. The method of embodiment 220 which is conducted on solid support.
222. The method of any of embodiments 220-221, wherein appropriate activation and protective groups are used.
223. The method of any of embodiments 220-222, wherein the compound is prepared on a suitable resin.
224. The method of any of embodiments 220-223, wherein an appropriately protected reagent dissolved in a suitable solvent is coupled to the resin.
225. The method of any of embodiments 220-224, wherein the protection is removed by appropriate treatment and one or more subsequent corresponding coupling and de-protecting steps are performed, with resin washing step(s) in between.
226. The method of any of embodiments 220-225, wherein a repetitive cycle of coupling, washing, protection removal, and washing is performed.
227. The method of any of embodiments 220-226, which results in the crude compound of any of embodiments 124-209.
228. The method of any of embodiments 220-227, wherein the compound is liberated from the resin using a suitable reagent.
229. The method of any of embodiments 220-228, wherein the compound is concentrated, e.g. concentrated to dryness in vacuo.
230. The method of any of embodiments 220-229, wherein the compound is purified, e.g. using flash chromatography.
231. The method of any of embodiments 220-230, wherein the compound is activated for coupling to a biologically active peptide or protein.
232. The method of any of embodiments 220-231, wherein the activated compound is dissolved in a suitable solvent.
233. The method of any of embodiments 220-232, wherein the biologically active peptide or protein is dissolved in a suitable solvent.
234. The method of any of embodiments 220-233, wherein the activated compound is added drop wise to the dissolved peptide or protein under stirring at a suitable pH for a suitable time and then left for a suitable time for the reaction to occur.
235. The method of any of embodiments 220-234, wherein after the attachment reaction the pH is changed to the isoelectric point of the resulting derivative (peptide-sidechain conjugate) and the precipitated derivative is isolated, e.g. by centrifugation.
236. The method of any of embodiments 220-235, wherein the precipitate is washed in one or more additional steps with a suitable washing medium and then isolated, e.g. by centrifugation.
237. A method of preparing a compound according to any of embodiments 124-209, wherein the compound is prepared by solution phase chemistry.
238. The method of embodiment 237, wherein the compound is attached to a biologically active peptide or protein using suitable activation and protective groups.
239. The method of any of embodiments 237-238, wherein for attachment of the thus prepared compound to the peptide or protein one or more steps of any of embodiments 228-236 are applied.
240. The derivative or analogue of any of embodiments 1-123, which is a GLP-1 receptor agonist.
241. The derivative or analogue of any of embodiments 1-123 and 240, which is a full GLP-1 receptor agonist.
242. The derivative or analogue of any of embodiments 1-123 and 240-241, which is biologically active in vitro.
243. The derivative or analogue of any of embodiments 1-123 and 240-242, which is potent in vitro.
244. The derivative or analogue of any of embodiments 1-123 and 240-243, which is capable of activating the human GLP-1 receptor.
245. The derivative or analogue of any of embodiments 1-123 and 240-244, which is capable of activating the human GLP-1 receptor in an assay with whole cells expressing the human GLP-1 receptor, wherein the assay is performed in the absence of HSA (0% HSA).
246. The derivative or analogue of any of embodiments 1-123 and 240-245, where the response of the human GLP-1 receptor is measured in a reporter gene assay, such as the assay of Example 23.
247. The derivative or analogue of any of embodiments 240-246, wherein the GLP-1 receptor agonism, the in vitro biological activity, the in vitro potency, or the capability of activating the human GLP-1 receptor, respectively, is determined essentially as described in Example 23.
248. The derivative or analogue of any of embodiments 1-123 and 240-247, which has an in vitro potency corresponding to an $EC_{50}$ of 300 pM or below.
249. The derivative or analogue of any of embodiments 1-123 and 240-248, which has an in vitro potency corresponding to an $EC_{50}$ of 200 pM or below.
250. The derivative or analogue of any of embodiments 1-123 and 240-249, which has an in vitro potency corresponding to an $EC_{50}$ of 150 pM or below.
251. The derivative or analogue of any of embodiments 1-123 and 240-250, which has an in vitro potency corresponding to an $EC_{50}$ of 125 pM or below.
252. The derivative or analogue of any of embodiments 1-123 and 240-251, which has an in vitro potency corresponding to an $EC_{50}$ of 100 pM or below.
253. The derivative or analogue of any of embodiments 1-123 and 240-252, which has an in vitro potency corresponding to an $EC_{50}$ of 75 pM or below.
254. The derivative or analogue of any of embodiments 1-123 and 240-253, which has an in vitro potency corresponding to an $EC_{50}$ of 50 pM or below.
255. The derivative or analogue of any of embodiments 1-123 and 240-254, which has an in vitro potency corresponding to an $EC_{50}$ of 25 pM or below.
256. The derivative or analogue of any of embodiments 1-123 and 240-255, which has an in vitro potency corresponding to an $EC_{50}$ of 20 pM or below.
257. The derivative or analogue of any of embodiments 248-256, wherein the $EC_{50}$ is determined essentially as described in Example 23.
258. The derivative or analogue of any of embodiments 1-123 and 240-257, which has an in vitro potency corresponding to an $EC_{50}$ of less than 30 times the $EC_{50}$ of semaglutide, wherein the $EC_{50}$ of semaglutide is determined in the same way as the $EC_{50}$ of the derivative.
259. The derivative or analogue of any of embodiments 1-123 and 240-258, which has an in vitro potency corresponding to an $EC_{50}$ of less than 25 times the $EC_{50}$ of semaglutide, wherein the $EC_{50}$ of semaglutide is determined in the same way as the $EC_{50}$ of the derivative.
260. The derivative or analogue of any of embodiments 1-123 and 240-259, which has an in vitro potency corresponding to an $EC_{50}$ of less than 20 times the $EC_{50}$ of semaglutide, wherein the $EC_{50}$ of semaglutide is determined in the same way as the $EC_{50}$ of the derivative.

261. The derivative or analogue of any of embodiments 1-123 and 240-260, which has an in vitro potency corresponding to an $EC_{50}$ of less than 15 times the $EC_{50}$ of semaglutide, wherein the $EC_{50}$ of semaglutide is determined in the same way as the $EC_{50}$ of the derivative.
262. The derivative or analogue of any of embodiments 1-123 and 240-261, which has an in vitro potency corresponding to an $EC_{50}$ of less than 10 times the $EC_{50}$ of semaglutide, wherein the $EC_{50}$ of semaglutide is determined in the same way as the $EC_{50}$ of the derivative.
263. The derivative or analogue of any of embodiments 1-123 and 240-262, which has an in vitro potency corresponding to an $EC_{50}$ of less than 5 times the $EC_{50}$ of semaglutide, wherein the $EC_{50}$ of semaglutide is determined in the same way as the $EC_{50}$ of the derivative.
264. The derivative or analogue of any of embodiments 1-123 and 240-263, which has an in vitro potency corresponding to an $EC_{50}$ of less than 3 times the $EC_{50}$ of semaglutide, wherein the $EC_{50}$ of semaglutide is determined in the same way as the $EC_{50}$ of the derivative.
265. The derivative or analogue of any of embodiments 258-264, wherein the $EC_{50}$ is determined essentially as described in Example 23.
266. The derivative or analogue of any of embodiments 1-123 and 240-265, which is capable of binding to the GLP-1 receptor.
267. The derivative or analogue of any of embodiments 1-123 and 240-266, which is capable of binding to the GLP-1 receptor at a low concentration of HSA (max. 0.001% final assay concentration).
268. The derivative or analogue of any of embodiments 1-123 and 240-267, which is capable of binding to the GLP-1 receptor at a high concentration of HSA (2.0% final assay concentration).
269. The derivative or analogue of any of embodiments 266-268, wherein the binding to the human GLP-1 receptor is measured in a competitive binding assay, such as the assay of Example 24.
270. The derivative or analogue of any of embodiments 266-269, wherein the binding to the human GLP-1 receptor in vitro is determined essentially as described in Example 24.
271. The derivative or analogue of any of embodiments 1-123 and 240-270, which at a low concentration of HSA is capable of binding to the human GLP-1 receptor with an $IC_{50}$ of 20.0 nM or below.
272. The derivative or analogue of any of embodiments 1-123 and 240-271, which at a low concentration of HSA is capable of binding to the human GLP-1 receptor with an $IC_{50}$ of 5.0 nM or below.
273. The derivative or analogue of any of embodiments 1-123 and 240-272, which at a low concentration of HSA is capable of binding to the human GLP-1 receptor with an $IC_{50}$ of 3.0 nM or below.
274. The derivative or analogue of any of embodiments 1-123 and 240-273, which at a low concentration of HSA is capable of binding to the human GLP-1 receptor with an $IC_{50}$ of 2.0 nM or below.
275. The derivative or analogue of any of embodiments 1-123 and 240-274, which at a low concentration of HSA is capable of binding to the human GLP-1 receptor with an $IC_{50}$ of 1.0 nM or below.
276. The derivative or analogue of any of embodiments 1-123 and 240-275, which at a low concentration of HSA is capable of binding to the human GLP-1 receptor with an $IC_{50}$ of 0.50 nM or below.
277. The derivative or analogue of any of embodiments 1-123 and 240-276, which at a low concentration of HSA is capable of binding to the human GLP-1 receptor with an $IC_{50}$ of 0.30 nM or below.
278. The derivative or analogue of any of embodiments 271-277, wherein the $IC_{50}$ is determined essentially as described in Example 24, in a reaction with max. 0.001% HSA (final assay concentration).
279. The derivative or analogue of any of embodiments 1-123 and 240-278, which at a low concentration of HSA is capable of binding to the human GLP-1 receptor with an $IC_{50}$ of less than 35 times the $IC_{50}$ of semaglutide, wherein the $IC_{50}$ of semaglutide is determined in the same way as the $IC_{50}$ of the derivative.
280. The derivative or analogue of any of embodiments 1-123 and 240-279, which at a low concentration of HSA is capable of binding to the human GLP-1 receptor with an $IC_{50}$ of less than 20 times the $IC_{50}$ of semaglutide, wherein the $IC_{50}$ of semaglutide is determined in the same way as the $IC_{50}$ of the derivative.
281. The derivative or analogue of any of embodiments 1-123 and 240-280, which at a low concentration of HSA is capable of binding to the human GLP-1 receptor with an $IC_{50}$ of less than 8 times the $IC_{50}$ of semaglutide, wherein the $IC_{50}$ of semaglutide is determined in the same way as the $IC_{50}$ of the derivative.
282. The derivative or analogue of any of embodiments 1-123 and 240-281, which at a low concentration of HSA is capable of binding to the human GLP-1 receptor with an $IC_{50}$ of less than 4 times the $IC_{50}$ of semaglutide, wherein the $IC_{50}$ of semaglutide is determined in the same way as the $IC_{50}$ of the derivative.
283. The derivative or analogue of any of embodiments 1-123 and 240-282, which at a low concentration of HSA is capable of binding to the human GLP-1 receptor with an $IC_{50}$ of less than 3 times the $IC_{50}$ of semaglutide, wherein the $IC_{50}$ of semaglutide is determined in the same way as the $IC_{50}$ of the derivative.
284. The derivative or analogue of any of embodiments 1-123 and 240-283, which at a low concentration of HSA is capable of binding to the human GLP-1 receptor with an $IC_{50}$ of less than 2 times the $IC_{50}$ of semaglutide, wherein the $IC_{50}$ of semaglutide is determined in the same way as the $IC_{50}$ of the derivative.
285. The derivative or analogue of any of embodiments 1-123 and 240-284, which at a low concentration of HSA is capable of binding to the human GLP-1 receptor with an $IC_{50}$ of less than the $IC_{50}$ of semaglutide, wherein the $IC_{50}$ of semaglutide is determined in the same way as the $IC_{50}$ of the derivative.
286. The derivative or analogue of any of embodiments 1-123 and 240-285, which at a low concentration of HSA is capable of binding to the human GLP-1 receptor with an $IC_{50}$ of less than 0.50 times the $IC_{50}$ of semaglutide, wherein the $IC_{50}$ of semaglutide is determined in the same way as the $IC_{50}$ of the derivative.
287. The derivative or analogue of any of embodiments 279-286, wherein the $IC_{50}$ is determined essentially as described in Example 24, in a reaction with max. 0.001% HSA (final assay concentration).
288. The derivative or analogue of any of embodiments 1-123 and 240-287, which at 2.0% HSA (final assay concentration) is capable of binding to the human GLP-1 receptor with an $IC_{50}$ of 400 nM or below.
289. The derivative or analogue of any of embodiments 1-123 and 240-288, which at 2.0% HSA (final assay concentration) is capable of binding to the human GLP-1 receptor with an $IC_{50}$ of 150 nM or below.

290. The derivative or analogue of any of embodiments 1-123 and 240-289, which at 2.0% HSA (final assay concentration) is capable of binding to the human GLP-1 receptor with an $IC_{50}$ of 100 nM or below.

291. The derivative or analogue of any of embodiments 1-123 and 240-290, which at 2.0% HSA (final assay concentration) is capable of binding to the human GLP-1 receptor with an $IC_{50}$ of 75 nM or below.

292. The derivative or analogue of any of embodiments 1-123 and 240-291, which at 2.0% HSA (final assay concentration) is capable of binding to the human GLP-1 receptor with an $IC_{50}$ of 40 nM or below.

293. The derivative or analogue of any of embodiments 1-123 and 240-292, which at 2.0% HSA (final assay concentration) is capable of binding to the human GLP-1 receptor with an $IC_{50}$ of 20 nM or below.

294. The derivative or analogue of any of embodiments 288-293, wherein the $IC_{50}$ is determined essentially as described in Example 24, in a reaction with 2.0% HSA (final assay concentration).

295. The derivative or analogue of any of embodiments 1-123 and 240-294, which at 2.0% HSA (final assay concentration) is capable of binding to the human GLP-1 receptor with an $IC_{50}$ of less than the $IC_{50}$ of semaglutide, wherein the $IC_{50}$ of semaglutide is determined in the same way as the $IC_{50}$ of the derivative.

296. The derivative or analogue of any of embodiments 1-123 and 240-295, which at 2.0% HSA (final assay concentration) is capable of binding to the human GLP-1 receptor with an $IC_{50}$ of less than 0.5 times the $IC_{50}$ of semaglutide, wherein the $IC_{50}$ of semaglutide is determined in the same way as the $IC_{50}$ of the derivative.

297. The derivative or analogue of any of embodiments 1-123 and 240-296, which at 2.0% HSA (final assay concentration) is capable of binding to the human GLP-1 receptor with an $IC_{50}$ of less than 0.25 times the $IC_{50}$ of semaglutide, wherein the $IC_{50}$ of semaglutide is determined in the same way as the $IC_{50}$ of the derivative.

298. The derivative or analogue of any of embodiments 1-123 and 240-297, which at 2.0% HSA (final assay concentration) is capable of binding to the human GLP-1 receptor with an $IC_{50}$ of less than 0.10 times the $IC_{50}$ of semaglutide, wherein the $IC_{50}$ of semaglutide is determined in the same way as the $IC_{50}$ of the derivative.

299. The derivative or analogue of any of embodiments 1-123 and 240-298, which at 2.0% HSA (final assay concentration) is capable of binding to the human GLP-1 receptor with an $IC_{50}$ of less than 0.050 times the $IC_{50}$ of semaglutide, wherein the $IC_{50}$ of semaglutide is determined in the same way as the $IC_{50}$ of the derivative.

300. The derivative or analogue of any of embodiments 295-299, wherein the $IC_{50}$ is determined essentially as described in Example 24, in a reaction with 2.0% HSA (final assay concentration).

301. The derivative of any of embodiments 1-123 and 240-300, which has improved pharmacokinetic properties.

302. The derivative of any of embodiments 1-123 and 240-301, which has an increased half-life and/or a decreased clearance.

303. The derivative of any of embodiments 1-123 and 240-302, which is suitable for once-monthly administration.

304. The derivative of any of embodiments 1-123 and 240-303, for s.c. administration.

305. The derivative of any of embodiments 1-123 and 240-304, wherein the derivative is tested in vivo in pharmacokinetic (PK) studies.

306. The derivative of any of embodiments 1-123 and 240-305, wherein the derivative is tested in any suitable animal model, such as mouse, rat, monkey, dog, or pig.

307. The derivative of any of embodiments 1-123 and 240-306, which is compared with semaglutide.

308. The derivative of any of embodiments 1-123 and 240-307, which has an improved terminal half-life (T½) in vivo in minipigs after i.v. administration as compared to semaglutide.

309. The derivative of embodiment 308, wherein the terminal half-life is determined in vivo in minipigs after i.v. administration using any suitable study protocol, such as the one described in Example 25.

310. The derivative of any of embodiments 308-309, wherein the terminal half-life is determined in vivo in minipigs after i.v. administration, essentially as described in Example 25.

311. The derivative of any of embodiments 1-123 and 240-310, which has a terminal half-life (T½) in vivo in minipigs after i.v. administration of at least 100 hours.

312. The derivative of any of embodiments 1-123 and 240-311, which has a terminal half-life (T½) in vivo in minipigs after i.v. administration of at least 115 hours.

313. The derivative of any of embodiments 1-123 and 240-312, which has a terminal half-life (T½) in vivo in minipigs after i.v. administration of at least 130 hours.

314. The derivative of any of embodiments 1-123 and 240-313, which has a terminal half-life (T½) in vivo in minipigs after i.v. administration of at least 145 hours.

315. The derivative of any of embodiments 1-123 and 240-314, which has a terminal half-life (T½) in vivo in minipigs after i.v. administration of at least 155 hours.

316. The derivative of any of embodiments 1-123 and 240-315, which has a terminal half-life (T½) in vivo in minipigs after i.v. administration of at least 2.0 times the terminal half-life of semaglutide, determined in the same way.

317. The derivative of any of embodiments 1-123 and 240-316, which has a terminal half-life (T½) in vivo in minipigs after i.v. administration of at least 2.5 times the terminal half-life of semaglutide, determined in the same way.

318. The derivative of any of embodiments 1-123 and 240-317, which has a terminal half-life (T½) in vivo in minipigs after i.v. administration of at least 2.8 times the terminal half-life of semaglutide, determined in the same way.

319. The derivative of any of embodiments 311-318, wherein the terminal halt-life (T½) is determined essentially as described in Example 25.

320. The derivative of any of embodiments 1-123 and 240-319, which is potent in vivo.

321. The derivative of any of embodiments 1-123 and 240-320, which is potent in vivo when determined in any suitable animal model, such as mouse, rat, or pig.

322. The derivative of embodiment 321, wherein the animal model is Sprague Dawley rats.

323. The derivative of any of embodiments 1-123 and 240-322, wherein an acute effect on food intake is determined, wherein acute preferably refers to a single s.c. injection of a suitable concentration such as 50 nmol/kg or 100 nmol/kg of the derivative in question.

324. The derivative of any of embodiments 1-123 and 240-323, wherein an acute effect on body weight is determined, and wherein acute preferably refers to a single s.c. injection of 50 nmol/kg or 100 nmol/kg of the derivative in question.

325. The derivative of any of embodiments 1-123 and 240-324, wherein an acute effect on food intake and/or body weight is determined in vivo in Sprague Dawley rats using any suitable study protocol and methodology, e.g. as described in Example 26.

326. The derivative of any of embodiments 1-123 and 240-325 wherein an acute effect on food intake and/or body weight is determined in vivo in Sprague Dawley rats, essentially as described in Example 26.

327. The derivative of any of embodiments 323-326, wherein the acute effect is a change in food intake at 48 h of at least −10%, calculated as [[(food intake at 48 h)−(baseline food intake)]/(baseline food intake)]×100%], where baseline food intake refers to the level before the administration of any treatment.

328. The derivative of any of embodiments 323-327, wherein the acute effect is a change in food intake at 48 h of at least −25%, calculated as [[(food intake at 48 h)−(baseline food intake)]/(baseline food intake)]×100%], where baseline food intake refers to the level before the administration of any treatment.

329. The derivative of any of embodiments 323-328, wherein the acute effect is a change in food intake at 48 h of at least −50%, calculated as [[(food intake at 48 h)−(baseline food intake)]/(baseline food intake)]×100%], where baseline food intake refers to the level before the administration of any treatment.

330. The derivative of any of embodiments 323-329, wherein the acute effect is a change in food intake at 48 h of at least −74%, calculated as [[(food intake at 48 h)−(baseline food intake)]/(baseline food intake)]×100%], where baseline food intake refers to the level before the administration of any treatment.

331. The derivative of any of embodiments 323-330, wherein the acute effect is a change in body weight at 48 h of at least −1%, calculated as [[(body weight at 48 h)−(baseline body weight)]/(baseline body weight)]×100%], where baseline body weight refers to the level before the administration of any treatment.

332. The derivative of any of embodiments 323-331, wherein the acute effect is a change in body weight at 48 h of at least −5%, calculated as [[(body weight at 48 h)−(baseline body weight)]/(baseline body weight)]×100%], where baseline body weight refers to the level before the administration of any treatment.

333. The derivative of any of embodiments 323-332, wherein the acute effect is a change in body weight at 48 h of at least −8%, calculated as [[(body weight at 48 h)−(baseline body weight)]/(baseline body weight)]×100%], where baseline body weight refers to the level before the administration of any treatment.

334. The derivative of any of embodiments 323-333, wherein the acute effect is a change in body weight at 48 h of at least −10%, calculated as [[(body weight at 48 h)−(baseline body weight)]/(baseline body weight)]×100%], where baseline body weight refers to the level before the administration of any treatment.

335. The derivative of embodiment 321, wherein the animal model is db/db mouse.

336. The derivative of embodiment 335, wherein the blood glucose lowering effect is determined.

337. The derivative of any of embodiments 335-336, wherein the body weight lowering effect is determined.

338. The derivative of any of embodiments 1-123 and 240-337, wherein the blood glucose lowering effect and/or the body weight lowering effect is determined after a single s.c. injection of a suitable concentration of the GLP-1 derivative in question.

339. The derivative of any of embodiments 1-123 and 240-338, wherein the suitable concentration is 3 nmol/kg, 10 nmol/kg, or 30 nmol/kg.

340. The derivative of any of embodiments 335-339, wherein blood glucose lowering effect and/or body weight lowering effect is determined in vivo in db/db mouse using any suitable study protocol and methodology, e.g. as described in Example 27.

341. The derivative of any of embodiments 335-340, wherein the blood glucose lowering effect and/or the body weight lowering effect is determined in vivo in db/db mouse, essentially as described in Example 27.

342. The derivative of any of embodiments 335-341, which has the effect in vivo of reducing blood glucose after 48 hours, determined in a single-dose study in a db/db mouse model.

343. The derivative of any of embodiments 335-342, wherein the blood glucose is reduced by at least 2%, as compared to the blood glucose level before administration of the derivative.

344. The derivative of any of embodiments 335-343, wherein the blood glucose is reduced by at least 10%, as compared to the blood glucose level before administration of the derivative.

345. The derivative of any of embodiments 335-344, wherein the blood glucose is reduced by at least 20%, as compared to the blood glucose level before administration of the derivative.

346. The derivative of any of embodiments 335-345, wherein the blood glucose is reduced by at least 30%, as compared to the blood glucose level before administration of the derivative.

347. The derivative of any of embodiments 335-346, wherein the blood glucose is reduced by at least 40%, as compared to the blood glucose level before administration of the derivative.

348. The derivative of any of embodiments 335-347, which has the effect in vivo of reducing body weight after 48 hours, determined in a single-dose study in a db/db mouse model.

349. The derivative of any of embodiments 335-348, wherein the body weight is reduced by at least 1.0%, as compared to the body weight before administration of the derivative.

350. The derivative of any of embodiments 335-349, wherein the body weight is reduced by at least 2.0%, as compared to the body weight before administration of the derivative.

351. The derivative of any of embodiments 335-350, wherein the body weight is reduced by at least 3.0%, as compared to the body weight before administration of the derivative.

352. The derivative of any of embodiments 335-351, wherein the body weight is reduced by at least 4.0%, as compared to the body weight before administration of the derivative.

353. A pharmaceutical composition comprising a derivative or an analogue according to any of embodiments 1-123 and 240-352, and a pharmaceutically acceptable excipient.

354. A derivative or an analogue according to any of embodiments 1-123 and 240-352, for use as a medicament.

355. A derivative or an analogue according to any of embodiments 1-123 and 240-352, for use in (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis obliterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse.

356. Use of a derivative or an analogue according to any of embodiments 1-123 and 240-352, in the manufacture of a medicament for (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis obliterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse.

357. A method for (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety;

treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atherosclerosis oblitterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse;

wherein a pharmaceutically active amount of a derivative or an analogue according to any of embodiments 1-123 and 240-352, is administered.

Additional Particular Embodiments

The following are additional particular embodiments of the invention:

1. A derivative of a GLP-1 analogue of the general Formula I:

Formula I:
(SEQ ID NO: 10)
$Xaa_7$-$Xaa_8$-Glu-Gly-Thr-$Xaa_{12}$-Thr-Ser-Asp-$Xaa_{16}$-Ser- $Xaa_{18}$-$Xaa_{19}$-$Xaa_{20}$-Glu-$Xaa_{22}$-$Xaa_{23}$-Ala-$Xaa_{25}$-$Xaa_{26}$-$Xaa_{27}$-

Phe-Ile-$Xaa_{30}$-$Xaa_{31}$-Leu-$Xaa_{33}$-$Xaa_{34}$-$Xaa_{35}$-$Xaa_{36}$-$Xaa_{37}$-

$Xaa_{38}$-$Xaa_{39}$, wherein $Xaa_7$ is L-histidine, (S)-2-Hydroxy-3-(1H-imidazol-4-yl)-propionic acid, D-histidine, deamino-histidine, homohistidine, N°-acetyl-histidine, N°-formyl-histidine, N°-methyl-histidine, 3-pyridylalanine, 2-pyridylalanine, or 4-pyridylalanine;

$Xaa_8$ is Ala, Gly, Ser, Aib, (1-aminocyclopropyl) carboxylic acid, or (1-aminocyclobutyl) carboxylic acid;

$Xaa_{12}$ is Phe or Leu;

$Xaa_{16}$ is Val or Leu;

$Xaa_{18}$ is Ser, Val, Arg, or Leu;

$Xaa_{19}$ is Tyr or Gln;

$Xaa_{20}$ is Leu or Met;

$Xaa_{22}$ is Gly or Glu;

$Xaa_{23}$ is Gln, Glu, or Arg;

$Xaa_{25}$ is Ala or Val;

$Xaa_{26}$ is Arg;

$Xaa_{27}$ is Glu or Leu;

$Xaa_{30}$ is Ala, Glu, or Arg;

$Xaa_{31}$ is Trp or His;

Xaa$_{33}$ is Val;
Xaa$_{34}$ is Arg, His, Asn, or Gln;
Xaa$_{35}$ is Gly or Ala;
Xaa$_{36}$ is Arg or Gly;
Xaa$_{37}$ is Gly, Pro, or Lys;
Xaa$_{38}$ is Gly or absent;
Xaa$_{39}$ is Lys or absent;
wherein at least one of Xaa$_{37}$ and Xaa$_{39}$ is Lys;
which derivative comprises a side chain that is attached to the Lys residue of Xaa$_{37}$ or Xaa$_{39}$,
which side chain comprises:
(i) a Branched linker of formula Chem. 11

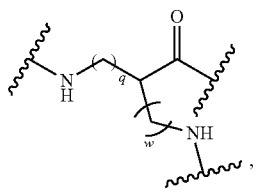

Chem. 11 wherein q is an integer in the range of 0-5,
wherein w is an integer in the range of 0-5,
with the provisos that when w is 0 q is an integer in the range of 1-5, and when q is 0 w is an integer in the range of 1-5; and
(ii) a 1$^{st}$ and a 2$^{nd}$ Protractor of Chem. 12:

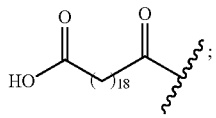

Chem. 12 wherein the Branched linker is connected
a) at its —CO end to the epsilon amino group of the Lys residue of Xaa$_{37}$ or Xaa$_{39}$, via a Pre-linker, and
b) at each of its two —NH ends to the —CO end of each of the 1$^{st}$ and 2$^{nd}$ Protractor, respectively, via a 1$^{st}$ and a 2$^{nd}$ Post-linker, respectively;
wherein each of the Pre-linker, the 1$^{st}$ Post-linker, and the 2$^{nd}$ Post-linker comprises a —CO group and an —NH group;
or a pharmaceutically acceptable salt, amide, or ester thereof.

2. The derivative of embodiment 1, wherein when Xaa$_{38}$ is absent Xaa$_{39}$ is also absent.
3. The derivative of any of embodiments 1-2, wherein Xaa$_7$ is L-histidine, or deamino-histidine; Xaa$_8$ is Aib; Xaa$_{12}$ is Phe; Xaa$_{16}$ is Val; Xaa$_{18}$ is Ser; Xaa$_{19}$ is Tyr; Xaa$_{20}$ is Leu; Xaa$_{22}$ is Glu; Xaa$_{23}$ is Gln; Xaa$_{25}$ is Ala; Xaa$_{26}$ is Arg; Xaa$_{27}$ is Glu; Xaa$_{30}$ is Ala; Xaa$_{31}$ is Trp; Xaa$_{33}$ is Val; Xaa$_{34}$ is Arg; Xaa$_{35}$ is Gly; Xaa$_{36}$ is Arg; Xaa$_{37}$ is Gly or Lys; Xaa$_{38}$ is Gly or absent; Xaa$_{39}$ is Lys or absent; and wherein at least one of Xaa$_{37}$ and Xaa$_{39}$ is Lys.
4. The derivative of any of embodiments 1-3, wherein one of Xaa$_{37}$ and Xaa$_{39}$ is Lys.
5. The derivative of any of embodiments 1-4, wherein the GLP-1 analogue is selected from the peptides of SEQ ID NO: 2 and SEQ ID NO: 3.
6. The derivative of any of embodiments 1-5, wherein the side chain is attached to the Lys residue of Xaa$_{37}$.
7. The derivative of any of embodiments 1-5, wherein the side chain is attached to the Lys residue of Xaa$_{39}$.
8. The derivative of any of embodiments 1-7, wherein in Chem. 11 q is 4 and w is 0.
9. The derivative of any of embodiments 1-7, wherein in Chem. 11 q is 0 and w is 4.
10. The derivative of any of embodiments 1-9, wherein Chem. 11 is represented by

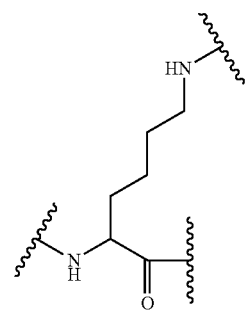

Chem. 11a

11. The derivative of any of embodiments 1-10, wherein Chem. 11 or Chem. 11a, respectively, is a bis-amino tri-radical of lysine.
12. The derivative of any of embodiments 1-11, wherein Chem. 11 or Chem. 11a, respectively, is eps-Lys(Bis).
13. The derivative of any of embodiments 1-11, wherein Chem. 11 or Chem. 11a, respectively, is in the L-form.
14. The derivative of any of embodiments 1-13, wherein the Pre-linker comprises
at least one Linker element-1 of Chem. 1:

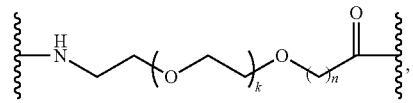

Chem. 1 wherein k is an integer in the range of 1-19, and n is an integer in the range of 1-5; or
at least one Linker element-2 of Chem. 2:

$*-NH-(CH_2)_m-CH[(CH_2)_s-NH_2]-CO-*$, such as

Chem. 2

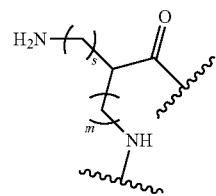

Chem. 2b wherein m is an integer in the range of 0-5, s is an integer in the range of 0-5, and with the provisos that when m is 0 s is an integer in the range of 1-5, and when s is 0 m is an integer in the range of 1-5.
15. The derivative of any of embodiments 1-14, wherein the Pre-linker comprises t times Linker element-1.
16. The derivative of embodiment 15, wherein t is an integer in the range of 1-8.

17. The derivative of embodiment 16, wherein t is 1.
18. The derivative of embodiment 16, wherein t is 2.
19. The derivative of embodiment 16, wherein t is 4.
20. The derivative of embodiment 16, wherein t is 6.
21. The derivative of embodiment 16, wherein t is 8.
22. The derivative of any of embodiments 14-21, wherein k is 1, 5, 11, or 19.
23. The derivative of any of embodiments 14-22, wherein n is 1 or 2.
24. The derivative of any of embodiments 14-23, wherein k is 1 and n is 1.
25. The derivative of any of embodiments 14-23, wherein k is 5 and n is 2.
26. The derivative of any of embodiments 14-23, wherein k is 11 and n is 2.
27. The derivative of any of embodiments 14-23, wherein k is 19 and n is 2.
28. The derivative of any of embodiments 14-27, wherein when t is other than 1 the t times Linker element-1 are juxtaposed, where juxtaposed means mutually connected, via amide bonds.
29. The derivative of any of embodiments 14-28, wherein when t is other than 1 the t times Linker element-1 are arranged in a row, one after the other, mutually connected via amide bonds.
30. The derivative of any of embodiments 1-29, wherein the Pre-linker consists of one Linker element-1 of Chem. 1 where k is 1 and n is 1, and wherein the Pre-linker is connected at its —NH end to the —CO end of the Branched linker, and at its —CO end to the epsilon amino group of the Lys residue of $Xaa_{37}$ or $Xaa_{39}$.
31. The derivative of any of embodiments 1-29, wherein the Pre-linker consists of two times Linker element-1 of Chem. 1 where k is 1 and n is 1, interconnected via amide bonds, and wherein the Pre-linker is connected at its —NH end to the —CO end of the Branched linker, and at its —CO end to the epsilon amino group of the Lys residue of $Xaa_{37}$ or $Xaa_{39}$.
32. The derivative of any of embodiments 1-29, wherein the Pre-linker consists of four times Linker element-1 of Chem. 1 where k is 1 and n is 1, interconnected via amide bonds, and wherein the Pre-linker is connected at its —NH end to the —CO end of the Branched linker, and at its —CO end to the epsilon amino group of the Lys residue of $Xaa_{37}$ or $Xaa_{39}$.
33. The derivative of any of embodiments 1-29, wherein the Pre-linker consists of six times Linker element-1 of Chem. 1 where k is 1 and n is 1, interconnected via amide bonds, and wherein the Pre-linker is connected at its —NH end to the —CO end of the Branched linker, and at its —CO end to the epsilon amino group of the Lys residue of $Xaa_{37}$ or $Xaa_{39}$.
34. The derivative of any of embodiments 1-29, wherein the Pre-linker consists of eight times Linker element-1 of Chem. 1 where k is 1 and n is 1, interconnected via amide bonds, and wherein the Pre-linker is connected at its —NH end to the —CO end of the Branched linker, and at its —CO end to the epsilon amino group of the Lys residue of $Xaa_{37}$ or $Xaa_{39}$.
35. The derivative of any of embodiments 1-29, wherein the Pre-linker consists of one Linker element-1 of Chem. 1 where k is 5 and n is 2, and wherein the Pre-linker is connected at its —NH end to the —CO end of the Branched linker, and at its —CO end to the epsilon amino group of the Lys residue of $Xaa_{37}$ or $Xaa_{39}$.
36. The derivative of any of embodiments 1-29, wherein the Pre-linker consists of one Linker element-1 of Chem. 1 where k is 11 and n is 2, and wherein the Pre-linker is connected at its —NH end to the —CO end of the Branched linker, and at its —CO end to the epsilon amino group of the Lys residue of $Xaa_{37}$ or $Xaa_{39}$.
37. The derivative of any of embodiments 1-29, wherein the Pre-linker consists of one Linker element-1 of Chem. 1 where k is 19 and n is 2, and wherein the Pre-linker is connected at its —NH end to the —CO end of the Branched linker, and at its —CO end to the epsilon amino group of the Lys residue of $Xaa_{37}$ or $Xaa_{39}$.
38. The derivative of any of embodiments 1-14, wherein the Pre-linker comprises two or four times Linker element-2 of Chem. 2 or Chem. 2b.
39. The derivative of embodiment 38, wherein the Pre-linker comprises two times Linker element-2.
40. The derivative of embodiment 38, wherein the Pre-linker comprises four times Linker element-2.
41. The derivative of any of embodiments 14, and 38-40, wherein m is 4 and s is 0.
42. The derivative of any of embodiments 14, and 38-40, wherein m is 0 and s is 4.
43. The derivative of any of embodiments 14, and 38-42, wherein Chem. 2 is represented by Chem. 2a or Chem. 2c:

Chem. 2a

\*——NH——$(CH_2)_4$——$CH(NH_2)$——CO——\*,   such as

Chem. 2c

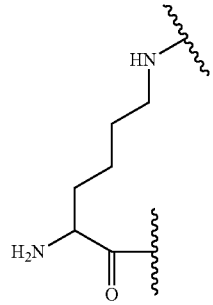

44. The derivative of any of embodiments 14, and 38-43, wherein Chem. 2, Chem. 2a, Chem. 2b, or Chem. 2c, respectively, is a di-radical of lysine.
45. The derivative of any of embodiments 14, and 38-44, wherein Chem. 2, Chem. 2a, Chem. 2b, or Chem. 2c, respectively, is eps-Lys.
46. The derivative of any of embodiments 14, and 38-45, wherein Chem. 2, Chem. 2a, Chem. 2b, or Chem. 2c, respectively, is in the L-form.
47. The derivative of any of embodiments 38-46, wherein the two or four times Linker element-2, respectively, are juxtaposed, where juxtaposed means mutually connected, via amide bonds.
48. The derivative of any of embodiments 38-47, wherein the two or four times Linker element-2, respectively, are arranged in a row, one after the other, mutually connected via amide bonds.
49. The derivative of any of embodiments 1-14, and 38-48, wherein the Pre-linker consists of two times Linker element-2 of Chem. 2a/2c, or Chem. 2/2b (where m is 4 and s is 0, or m is 0 and s is 4), respectively, interconnected via amide bonds, and wherein the Pre-linker is connected at its —NH end to the —CO end of the Branched linker, and at its —CO end to the epsilon amino group of the Lys residue of $Xaa_{37}$ or $Xaa_{39}$.

50. The derivative of any of embodiments 1-14, and 38-48, wherein the Pre-linker consists of four times Linker element-2 of Chem. 2a/2c, or Chem. 2/2b (where m is 4 and s is 0, or m is 0 and s is 4), respectively, interconnected via amide bonds, and wherein the Pre-linker is connected at its —NH end to the —CO end of the Branched linker, and at its —CO end to the epsilon amino group of the Lys residue of $Xaa_{37}$ or $Xaa_{39}$.

51. The derivative of any of embodiments 1-50, wherein each of the $1^{st}$ and the $2^{nd}$ Post-linker comprises a Linker element-3 of Chem. 3:

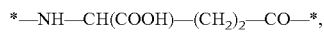
Chem. 3:

and/or
a Linker element-4 of Chem. 4:

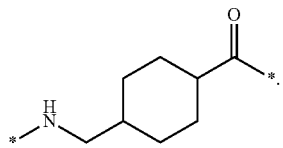
Chem. 4

52. The derivative of any of embodiments 1-51, wherein each of the $1^{st}$ and the $2^{nd}$ Post-linker comprises a Linker element-3 of formula Chem. 3:

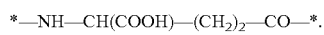
Chem. 3:

53. The derivative of any of embodiments 51-52, wherein Chem. 3 is a di-radical of Glu.
54. The derivative of any of embodiments 51-53, wherein Chem. 3 is a di-radical of gGlu.
55. The derivative of any of embodiments 51-54, wherein Chem. 3 is a di-radical of L-gGlu.
56. The derivative of any of embodiments 1-55, wherein each of the $1^{st}$ and the $2^{nd}$ Post-linker comprises a Linker element-4 of formula Chem. 4:

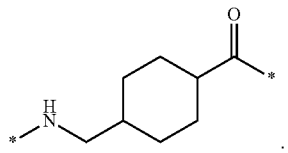
Chem. 4

57. The derivative of any of embodiments 51, and 56-57, wherein Chem. 4 is a di-radical of tranexamic acid.
58. The derivative of any of embodiments 51, and 56-58, wherein Chem. 4 is a di-radical of trans-4-(aminomethyl)cyclohexanecarboxylic acid.
59. The derivative of any of embodiments 1-57, wherein each of the $1^{st}$ and the $2^{nd}$ Post-linker comprises at least one Linker element-1 of formula Chem. 1:

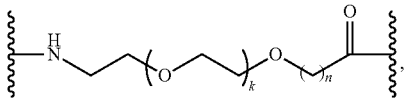
Chem. 1 wherein k is an integer in the range of 1-19, and n is an integer in the range of 1-5.

60. The derivative of embodiment 59, wherein each of the $1^{st}$ and the $2^{nd}$ Post-linker comprises two or four times Linker element-1.
61. The derivative of any of embodiments 59-60, wherein each of the $1^{st}$ and the $2^{nd}$ Post-linker comprises two times Linker element-1.
62. The derivative of any of embodiments 59-60, wherein each of the $1^{st}$ and the $2^{nd}$ Post-linker comprises four times Linker element-1.
63. The derivative of any of embodiments 59-62, wherein k is 1.
64. The derivative of any of embodiments 59-63, wherein n is 1.
65. The derivative of any of embodiments 59-64, wherein k is 1 and n is 1.
66. The derivative of any of embodiments 60-65, wherein the two or four times Linker element-1, respectively, are juxtaposed, where juxtaposed means mutually connected, via amide bonds.
67. The derivative of any of embodiments 60-66, wherein the two or four times Linker element-1 are arranged in a row, one after the other, mutually connected via amide bonds.
68. The derivative of any of embodiments 1-58, wherein none of the $1^{st}$ Post-linker and the $2^{nd}$ Post-Linker includes a Linker element-1 of Chem. 1:

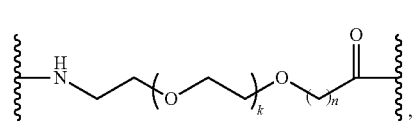
Chem. 1 wherein k is an integer in the range of 1-19, and n is an integer in the range of 1-5.

69. The derivative of any of embodiments 1-58, which optionally includes a Linker element-1, as defined in any of embodiments 59-67.
70. The derivative of any of embodiments 1-58, which further includes a Linker element-1, as defined in any of embodiments 59-67.
71. The derivative of any of embodiments 1-58, wherein each of the $1^{st}$ and the $2^{nd}$ Post-linker comprises exactly one Linker element-3 and exactly one Linker element-4.
72. The derivative of any of embodiments 1-58, wherein each of the $1^{st}$ and the $2^{nd}$ Post-linker includes just one Linker element-3 and just one Linker element-4.
73. The derivative of any of embodiments 1-58, 68, and 71-72, wherein each of the $1^{st}$ and $2^{nd}$ Post-linker consists of one Linker element-4, and one Linker element-3, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.
74. The derivative of any of embodiments 1-61, and 63-70, wherein each of the $1^{st}$ and $2^{nd}$ Post-linker consists of one Linker element-4, one Linker element-3, and two times Linker element-1 where k is 1 and n is 1, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.
75. The derivative of any of embodiments 1-60, and 62-70, wherein each of the $1^{st}$ and $2^{nd}$ Post-linker consists of one Linker element-4, one Linker element-3, and four times Linker element-1 where k is 1 and n is 1, interconnected via amide bonds and in the sequence indicated, and wherein each of the $1^{st}$ and the $2^{nd}$ Post-linker is connected at its —NH end to the —CO end of the $1^{st}$ and the $2^{nd}$ Protractor, respectively, and at its —CO end to each of the —NH ends of the Branched linker.

76. The derivative of any of embodiments 1-75, wherein the Branched linker is connected, via amide bonds,
   a) at its —CO end to the epsilon amino group of the Lys residue of $Xaa_{37}$ or $Xaa_{39}$, via the Pre-linker, and
   b) at each of its two —N ends to the —CO end of each of the $1^{st}$ and $2^{nd}$ Protractor, respectively, via a $1^{st}$ and a $2^{nd}$ Post-linker, respectively.

77. A GLP-1 derivative, preferably the derivative of any of embodiments 1-76, which is selected from Chem. 21, Chem. 22, Chem. 23, Chem. 24, Chem. 25, Chem. 26, Chem. 27, Chem. 28, Chem. 29, Chem. 30, Chem. 31, Chem. 32, Chem. 33, Chem. 34, and Chem. 35; or a pharmaceutically acceptable salt, amide, or ester thereof.

78. A GLP-1 derivative, preferably the derivative of any of embodiments 1-77, which is selected from the compounds of Examples 1-15, or a pharmaceutically acceptable salt, amide, or ester thereof.

79. A GLP-1 analogue which comprises the following changes when compared to GLP-1(7-37) (SEQ ID NO: 1): (7Imp, 8Aib, 22E, 26R, 34R, 38G), (7Imp, 8Aib, 22E, 26R, 34R, 39K), or (7Imp, 8Aib, 22E, 26R, 34R, 38G, 39K).

80. The GLP-1 analogue of embodiment 79, which is the following analogue of GLP-1(7-37) (SEQ ID NO: 1): (7Imp, 8Aib, 22E, 26R, 34R, 38G, 39K), or a pharmaceutically acceptable salt, amide, or ester thereof.

81. The GLP-1 analogue of any of embodiments 79-80, which is the peptide of SEQ ID NO: 3, or a pharmaceutically acceptable salt, amide, or ester thereof.

82. The derivative or analogue of any of embodiments 1-81, which is a GLP-1 receptor agonist.

83. The derivative or analogue of any of embodiments 1-82, which is a full GLP-1 receptor agonist.

84. The derivative or analogue of any of embodiments 1-83, which is biologically active in vitro.

85. The derivative or analogue of any of embodiments 1-84, which is potent in vitro.

86. The derivative or analogue of any of embodiments 1-85, which is capable of activating the human GLP-1 receptor.

87. The derivative or analogue of any of embodiments 1-86, which is capable of activating the human GLP-1 receptor in an assay with whole cells expressing the human GLP-1 receptor, wherein the assay is performed in the absence of HSA (0% HSA).

88. The derivative or analogue of any of embodiments 1-88, where the response of the human GLP-1 receptor is measured in a reporter gene assay, such as the assay of Example 23.

89. The derivative or analogue of any of embodiments 82-88, wherein the GLP-1 receptor agonism, the in vitro biological activity, the in vitro potency, or the capability of activating the human GLP-1 receptor, respectively, is determined essentially as described in Example 23.

90. The derivative or analogue of any of embodiments 1-89, which has an in vitro potency corresponding to an $EC_{50}$ of 300 pM or below.

91. The derivative or analogue of any of embodiments 1-90, which has an in vitro potency corresponding to an $EC_{50}$ of 200 pM or below.

92. The derivative or analogue of any of embodiments 1-91, which has an in vitro potency corresponding to an $EC_{50}$ of 150 pM or below.

93. The derivative or analogue of any of embodiments 1-92, which has an in vitro potency corresponding to an $EC_{50}$ of 125 pM or below.

94. The derivative or analogue of any of embodiments 1-93, which has an in vitro potency corresponding to an $EC_{50}$ of 100 pM or below.

95. The derivative or analogue of any of embodiments 1-94, which has an in vitro potency corresponding to an $EC_{50}$ of 75 pM or below.

96. The derivative or analogue of any of embodiments 1-95, which has an in vitro potency corresponding to an $EC_{50}$ of 50 pM or below.

97. The derivative or analogue of any of embodiments 1-96, which has an in vitro potency corresponding to an $EC_{50}$ of 25 pM or below.

98. The derivative or analogue of any of embodiments 1-97, which has an in vitro potency corresponding to an $EC_{50}$ of 20 pM or below.

99. The derivative or analogue of any of embodiments 90-98, wherein the $EC_{50}$ is determined essentially as described in Example 23.

100. The derivative or analogue of any of embodiments 1-99, which has an in vitro potency corresponding to an $EC_{50}$ of less than 30 times the $EC_{50}$ of semaglutide, wherein the $EC_{50}$ of semaglutide is determined in the same way as the $EC_{50}$ of the derivative.

101. The derivative or analogue of any of embodiments 1-100, which has an in vitro potency corresponding to an $EC_{50}$ of less than 25 times the $EC_{50}$ of semaglutide, wherein the $EC_{50}$ of semaglutide is determined in the same way as the $EC_{50}$ of the derivative.

102. The derivative or analogue of any of embodiments 1-101, which has an in vitro potency corresponding to an $EC_{50}$ of less than 20 times the $EC_{50}$ of semaglutide, wherein the $EC_{50}$ of semaglutide is determined in the same way as the $EC_{50}$ of the derivative.

103. The derivative or analogue of any of embodiments 1-102, which has an in vitro potency corresponding to an $EC_{50}$ of less than 15 times the $EC_{50}$ of semaglutide, wherein the $EC_{50}$ of semaglutide is determined in the same way as the $EC_{50}$ of the derivative.

104. The derivative or analogue of any of embodiments 1-103, which has an in vitro potency corresponding to an $EC_{50}$ of less than 10 times the $EC_{50}$ of semaglutide, wherein the $EC_{50}$ of semaglutide is determined in the same way as the $EC_{50}$ of the derivative.

105. The derivative or analogue of any of embodiments 1-104, which has an in vitro potency corresponding to an $EC_{50}$ of less than 5 times the $EC_{50}$ of semaglutide, wherein the $EC_{50}$ of semaglutide is determined in the same way as the $EC_{50}$ of the derivative.

106. The derivative or analogue of any of embodiments 1-105, which has an in vitro potency corresponding to an $EC_{50}$ of less than 3 times the $EC_{50}$ of semaglutide, wherein the $EC_{50}$ of semaglutide is determined in the same way as the $EC_{50}$ of the derivative.

107. The derivative or analogue of any of embodiments 100-106, wherein the $EC_{50}$ is determined essentially as described in Example 23.

108. The derivative or analogue of any of embodiments 1-107, which is capable of binding to the GLP-1 receptor.

109. The derivative or analogue of any of embodiments 1-108, which is capable of binding to the GLP-1 receptor at a low concentration of HSA (max. 0.001% final assay concentration).

110. The derivative or analogue of any of embodiments 1-109, which is capable of binding to the GLP-1 receptor at a high concentration of HSA (2.0% final assay concentration).

111. The derivative or analogue of any of embodiments 108-110, wherein the binding to the human GLP-1 receptor is measured in a competitive binding assay, such as the assay of Example 24.

112. The derivative or analogue of any of embodiments 108-111, wherein the binding to the human GLP-1 receptor in vitro is determined essentially as described in Example 24.

113. The derivative or analogue of any of embodiments 1-112, which at a low concentration of HSA is capable of binding to the human GLP-1 receptor with an $IC_{50}$ of 20.0 nM or below.

114. The derivative or analogue of any of embodiments 1-113, which at a low concentration of HSA is capable of binding to the human GLP-1 receptor with an $IC_{50}$ of 5.0 nM or below.

115. The derivative or analogue of any of embodiments 1-114, which at a low concentration of HSA is capable of binding to the human GLP-1 receptor with an $IC_{50}$ of 3.0 nM or below.

116. The derivative or analogue of any of embodiments 1-115, which at a low concentration of HSA is capable of binding to the human GLP-1 receptor with an $IC_{50}$ of 2.0 nM or below.

117. The derivative or analogue of any of embodiments 1-116, which at a low concentration of HSA is capable of binding to the human GLP-1 receptor with an $IC_{50}$ of 1.0 nM or below.

118. The derivative or analogue of any of embodiments 1-117, which at a low concentration of HSA is capable of binding to the human GLP-1 receptor with an $IC_{50}$ of 0.50 nM or below.

119. The derivative or analogue of any of embodiments 1-118, which at a low concentration of HSA is capable of binding to the human GLP-1 receptor with an $IC_{50}$ of 0.30 nM or below.

120. The derivative or analogue of any of embodiments 113-119, wherein the $IC_{50}$ is determined essentially as described in Example 24, in a reaction with max. 0.001% HSA (final assay concentration).

121. The derivative or analogue of any of embodiments 1-120, which at a low concentration of HSA is capable of binding to the human GLP-1 receptor with an $IC_{50}$ of less than 20 times the $IC_{50}$ of semaglutide, wherein the $IC_{50}$ of semaglutide is determined in the same way as the $IC_{50}$ of the derivative.

122. The derivative or analogue of any of embodiments 1-121, which at a low concentration of HSA is capable of binding to the human GLP-1 receptor with an $IC_{50}$ of less than 8 times the $IC_{50}$ of semaglutide, wherein the $IC_{50}$ of semaglutide is determined in the same way as the $IC_{50}$ of the derivative.

123. The derivative or analogue of any of embodiments 1-122, which at a low concentration of HSA is capable of binding to the human GLP-1 receptor with an $IC_{50}$ of less than 4 times the $IC_{50}$ of semaglutide, wherein the $IC_{50}$ of semaglutide is determined in the same way as the $IC_{50}$ of the derivative.

124. The derivative or analogue of any of embodiments 1-123, which at a low concentration of HSA is capable of binding to the human GLP-1 receptor with an $IC_{50}$ of less than 3 times the $IC_{50}$ of semaglutide, wherein the $IC_{50}$ of semaglutide is determined in the same way as the $IC_{50}$ of the derivative.

125. The derivative or analogue of any of embodiments 1-124, which at a low concentration of HSA is capable of binding to the human GLP-1 receptor with an $IC_{50}$ of less than 2 times the $IC_{50}$ of semaglutide, wherein the $IC_{50}$ of semaglutide is determined in the same way as the $IC_{50}$ of the derivative.

126. The derivative or analogue of any of embodiments 1-125, which at a low concentration of HSA is capable of binding to the human GLP-1 receptor with an $IC_{50}$ of less than the $IC_{50}$ of semaglutide, wherein the $IC_{50}$ of semaglutide is determined in the same way as the $IC_{50}$ of the derivative.

127. The derivative or analogue of any of embodiments 1-126, which at a low concentration of HSA is capable of binding to the human GLP-1 receptor with an $IC_{50}$ of less than 0.50 times the $IC_{50}$ of semaglutide, wherein the $IC_{50}$ of semaglutide is determined in the same way as the $IC_{50}$ of the derivative.

128. The derivative or analogue of any of embodiments 121-127, wherein the $IC_{50}$ is determined essentially as described in Example 24, in a reaction with max. 0.001% HSA (final assay concentration).

129. The derivative or analogue of any of embodiments 1-128, which at 2.0% HSA (final assay concentration) is capable of binding to the human GLP-1 receptor with an $IC_{50}$ of 400 nM or below.

130. The derivative or analogue of any of embodiments 1-129, which at 2.0% HSA (final assay concentration) is capable of binding to the human GLP-1 receptor with an $IC_{50}$ of 150 nM or below.

131. The derivative or analogue of any of embodiments 1-130, which at 2.0% HSA (final assay concentration) is capable of binding to the human GLP-1 receptor with an $IC_{50}$ of 100 nM or below.

132. The derivative or analogue of any of embodiments 1-131, which at 2.0% HSA (final assay concentration) is capable of binding to the human GLP-1 receptor with an $IC_{50}$ of 75 nM or below.

133. The derivative or analogue of any of embodiments 1-132, which at 2.0% HSA (final assay concentration) is capable of binding to the human GLP-1 receptor with an $IC_{50}$ of 40 nM or below.

134. The derivative or analogue of any of embodiments 1-133, which at 2.0% HSA (final assay concentration) is capable of binding to the human GLP-1 receptor with an $IC_{50}$ of 20 nM or below.

135. The derivative or analogue of any of embodiments 129-134, wherein the $IC_{50}$ is determined essentially as described in Example 24, in a reaction with 2.0% HSA (final assay concentration).

136. The derivative or analogue of any of embodiments 1-135, which at 2.0% HSA (final assay concentration) is capable of binding to the human GLP-1 receptor with an $IC_{50}$ of less than the $IC_{50}$ of semaglutide, wherein the $IC_{50}$ of semaglutide is determined in the same way as the $IC_{50}$ of the derivative.

137. The derivative or analogue of any of embodiments 1-136, which at 2.0% HSA (final assay concentration) is capable of binding to the human GLP-1 receptor with an $IC_{50}$ of less than 0.5 times the $IC_{50}$ of semaglutide, wherein the $IC_{50}$ of semaglutide is determined in the same way as the $IC_{50}$ of the derivative.

138. The derivative or analogue of any of embodiments 1-137, which at 2.0% HSA (final assay concentration) is capable of binding to the human GLP-1 receptor with an $IC_{50}$ of less than 0.25 times the $IC_{50}$ of semaglutide, wherein the $IC_{50}$ of semaglutide is determined in the same way as the $IC_{50}$ of the derivative.
139. The derivative or analogue of any of embodiments 1-138, which at 2.0% HSA (final assay concentration) is capable of binding to the human GLP-1 receptor with an $IC_{50}$ of less than 0.10 times the $IC_{50}$ of semaglutide, wherein the $IC_{50}$ of semaglutide is determined in the same way as the $IC_{50}$ of the derivative.
140. The derivative or analogue of any of embodiments 1-139, which at 2.0% HSA (final assay concentration) is capable of binding to the human GLP-1 receptor with an $IC_{50}$ of less than 0.050 times the $IC_{50}$ of semaglutide, wherein the $IC_{50}$ of semaglutide is determined in the same way as the $IC_{50}$ of the derivative.
141. The derivative or analogue of any of embodiments 136-140, wherein the $IC_{50}$ is determined essentially as described in Example 24, in a reaction with 2.0% HSA (final assay concentration).
142. The derivative of any of embodiments 1-141, which has improved pharmacokinetic properties.
43. The derivative of any of embodiments 1-142, which has an increased half-life and/or a decreased clearance.
144. The derivative of any of embodiments 1-143, which is suitable for once-monthly administration.
145. The derivative of any of embodiments 1-144, for s.c. administration.
146. The derivative of any of embodiments 1-145, wherein the derivative is tested in vivo in pharmacokinetic (PK) studies.
147. The derivative of any of embodiments 1-146, wherein the derivative is tested in any suitable animal model, such as mouse, rat, monkey, dog, or pig.
148. The derivative of any of embodiments 1-147, which is compared with semaglutide.
149. The derivative of any of embodiments 1-148, which has an improved terminal half-life (T½) in vivo in minipigs after i.v. administration as compared to semaglutide.
150. The derivative of embodiment 149, wherein the terminal half-life is determined in vivo in minipigs after i.v. administration using any suitable study protocol, such as the one described in Example 25.
151. The derivative of any of embodiments 149-150, wherein the terminal half-life is determined in vivo in minipigs after i.v. administration, essentially as described in Example 25.
152. The derivative of any of embodiments 1-151, which has a terminal half-life (T½) in vivo in minipigs after i.v. administration of at least 100 hours.
153. The derivative of any of embodiments 1-152, which has a terminal half-life (T½) in vivo in minipigs after i.v. administration of at least 115 hours.
154. The derivative of any of embodiments 1-153, which has a terminal half-life (T½) in vivo in minipigs after i.v. administration of at least 130 hours.
155. The derivative of any of embodiments 1-154, which has a terminal half-life (T½) in vivo in minipigs after i.v. administration of at least 145 hours.
156. The derivative of any of embodiments 1-155, which has a terminal half-life (T½) in vivo in minipigs after i.v. administration of at least 155 hours.
157. The derivative of any of embodiments 1-156, which has a terminal half-life (T½) in vivo in minipigs after i.v. administration of at least 2.0 times the terminal half-life of semaglutide, determined in the same way.
158. The derivative of any of embodiments 1-157, which has a terminal half-life (T½) in vivo in minipigs after i.v. administration of at least 2.5 times the terminal half-life of semaglutide, determined in the same way.
159. The derivative of any of embodiments 1-158, which has a terminal half-life (T½) in vivo in minipigs after i.v. administration of at least 2.8 times the terminal half-life of semaglutide, determined in the same way.
160. The derivative of any of embodiments 152-159, wherein the terminal halt-life (T½) is determined essentially as described in Example 25.
161. The derivative of any of embodiments 1-160, which is potent in vivo.
162. The derivative of any of embodiments 1-161, which is potent in vivo when determined in any suitable animal model, such as mouse, rat, or pig.
163. The derivative of embodiment 162, wherein the animal model is Sprague Dawley rats.
164. The derivative of any of embodiments 1-163, wherein an acute effect on food intake is determined, wherein acute preferably refers to a single s.c. injection of 100 nmol/kg of the derivative in question.
165. The derivative of any of embodiments 1-164, wherein an acute effect on body weight is determined, and wherein acute preferably refers to a single s.c. injection of 100 nmol/kg of the derivative in question.
166. The derivative of any of embodiments 1-165, wherein an acute effect on food intake and/or body weight is determined in vivo in Sprague Dawley rats using any suitable study protocol and methodology, e.g. as described in Example 26.
167. The derivative of any of embodiments 1-166 wherein an acute effect on food intake and/or body weight is determined in vivo in Sprague Dawley rats, essentially as described in Example 26.
168. The derivative of any of embodiments 164-167, wherein the acute effect is a change in food intake at 48 h of at least −25%, calculated as [[(food intake at 48 h)−(baseline food intake)]/(baseline food intake)]×100%], where baseline food intake refers to the level before the administration of any treatment.
169. The derivative of any of embodiments 164-168, wherein the acute effect is a change in food intake at 48 h of at least −50%, calculated as [[(food intake at 48 h)−(baseline food intake)]/(baseline food intake)]×100%], where baseline food intake refers to the level before the administration of any treatment.
170. The derivative of any of embodiments 164-169, wherein the acute effect is a change in food intake at 48 h of at least −74%, calculated as [[(food intake at 48 h)−(baseline food intake)]/(baseline food intake)]×100%], where baseline food intake refers to the level before the administration of any treatment.
171. The derivative of any of embodiments 164-170, wherein the acute effect is a change in body weight at 48 h of at least −5%, calculated as [[(body weight at 48 h)−(baseline body weight)]/(baseline body weight)]×100%], where baseline body weight refers to the level before the administration of any treatment.
172. The derivative of any of embodiments 164-171, wherein the acute effect is a change in body weight at 48 h of at least −8%, calculated as [[(body weight at 48 h)−(baseline body weight)]/(baseline body weight)]×100%], where baseline body weight refers to the level before the administration of any treatment.
173. The derivative of any of embodiments 164-172, wherein the acute effect is a change in body weight at 48 h of at least −10%, calculated as [[(body weight at 48 h)−(baseline body weight)]/(baseline body weight)]×100%], where baseline body weight refers to the level before the administration of any treatment.

174. The derivative of embodiment 162, wherein the animal model is db/db mouse.

175. The derivative of embodiment 174, wherein the blood glucose lowering effect is determined.

176. The derivative of any of embodiments 174-175, wherein the body weight lowering effect is determined.

177. The derivative of any of embodiments 174-176, wherein blood glucose lowering effect and/or body weight lowering effect is determined in vivo in db/db mouse using any suitable study protocol and methodology, e.g. as described in Example 27.

178. The derivative of any of embodiments 174-177, wherein the blood glucose lowering effect and/or the body weight lowering effect is determined in vivo in db/db mouse, essentially as described in Example 27.

179. The derivative of any of embodiments 174-178, which has the effect in vivo of reducing blood glucose after 48 hours, determined in a single-dose study in a db/db mouse model.

180. The derivative of any of embodiments 174-179, wherein the blood glucose is reduced by at least 2%, as compared to the blood glucose level before administration of the derivative.

181. The derivative of any of embodiments 174-180, wherein the blood glucose is reduced by at least 10%, as compared to the blood glucose level before administration of the derivative.

182. The derivative of any of embodiments 174-181, wherein the blood glucose is reduced by at least 20%, as compared to the blood glucose level before administration of the derivative.

183. The derivative of any of embodiments 174-182, wherein the blood glucose is reduced by at least 30%, as compared to the blood glucose level before administration of the derivative.

184. The derivative of any of embodiments 174-183, wherein the blood glucose is reduced by at least 40%, as compared to the blood glucose level before administration of the derivative.

185. The derivative of any of embodiments 174-184, which has the effect in vivo of reducing body weight after 48 hours, determined in a single-dose study in a db/db mouse model.

186. The derivative of any of embodiments 174-185, wherein the body weight is reduced by at least 1.0%, as compared to the body weight before administration of the derivative.

187. The derivative of any of embodiments 174-186, wherein the body weight is reduced by at least 2.0%, as compared to the body weight before administration of the derivative.

188. The derivative of any of embodiments 174-187, wherein the body weight is reduced by at least 3.0%, as compared to the body weight before administration of the derivative.

189. The derivative of any of embodiments 174-188, wherein the body weight is reduced by at least 4.0%, as compared to the body weight before administration of the derivative.

190. A pharmaceutical composition comprising a derivative or an analogue according to any of embodiments 1-189, and a pharmaceutically acceptable excipient.

191. A derivative or an analogue according to any of embodiments 1-189, for use as a medicament.

192. A derivative or an analogue according to any of embodiments 1-189, for use in (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse.

193. Use of a derivative or an analogue according to any of embodiments 1-189, in the manufacture of a medicament for (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse.

194. A method for (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse;

wherein a pharmaceutically active amount of a derivative or an analogue according to any of embodiments 1-189, is administered.

Still Further Particular Embodiments

The following are still further particular embodiments of the invention:

1. A derivative of a GLP-1 analogue of the general Formula I:

(SEQ ID NO: 10)
$Xaa_7$-$Xaa_8$-Glu-Gly-Thr-$Xaa_{12}$-Thr-Ser-Asp-$Xaa_{16}$-Ser-$Xaa_{18}$-$Xaa_{19}$-$Xaa_{20}$-Glu-$Xaa_{22}$-$Xaa_{23}$-Ala-$Xaa_{25}$-$Xaa_{26}$-$Xaa_{27}$-Phe-Ile-$Xaa_{30}$-$Xaa_{31}$-Leu-$Xaa_{33}$-$Xaa_{34}$-$Xaa_{35}$-$Xaa_{36}$-$Xaa_{37}$-$Xaa_{38}$-$Xaa_{39}$, wherein $Xaa_7$ is L-histidine, (S)-2-Hydroxy-3-(1H-imidazol-4-yl)-propionic acid, D-histidine, deamino-histidine, homohistidine, N°-acetyl-histidine, N°-formyl-histidine, N°-methyl-histidine, 3-pyridylalanine, 2-pyridylalanine, or 4-pyridylalanine;

$Xaa_8$ is Ala, Gly, Ser, Aib, (1-aminocyclopropyl) carboxylic acid, or (1-aminocyclobutyl) carboxylic acid;

$Xaa_{12}$ is Phe or Leu;

$Xaa_{16}$ is Val or Leu;

$Xaa_{18}$ is Ser, Val, Arg, or Leu;

$Xaa_{19}$ is Tyr or Gln;

$Xaa_{20}$ is Leu or Met;

$Xaa_{22}$ is Gly or Glu;

$Xaa_{23}$ is Gln, Glu, or Arg;

$Xaa_{25}$ is Ala or Val;

$Xaa_{26}$ is Arg;

$Xaa_{27}$ is Glu or Leu;

$Xaa_{30}$ is Ala, Glu, or Arg;

$Xaa_{31}$ is Trp or His;

$Xaa_{33}$ is Val;

$Xaa_{34}$ is Arg, His, Asn, or Gln;

$Xaa_{35}$ is Gly or Ala;

$Xaa_{36}$ is Arg or Gly;

$Xaa_{37}$ is Gly, Pro, or Lys;

$Xaa_{38}$ is Gly or absent;

$Xaa_{39}$ is Lys or absent;

wherein at least one of $Xaa_{37}$ and $Xaa_{39}$ is Lys;

which derivative comprises a side chain that is attached to the Lys residue of $Xaa_{37}$ or $Xaa_{39}$, which side chain comprises:

(i) a Branched linker of Chem. 11

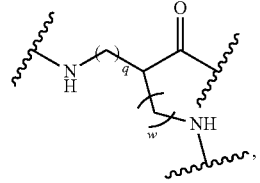

Chem. 11 wherein q is an integer in the range of 0-5, wherein w is an integer in the range of 0-5, with the provisos that when w is 0 q is an integer in the range of 1-5, and when q is 0 w is an integer in the range of 1-5; and (ii) a $1^{st}$ and a $2^{nd}$ Protractor of Chem. 12:

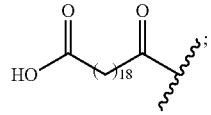

Chem. 12 wherein the Branched linker is connected a) at its —CO end to the epsilon amino group of the Lys residue of $Xaa_{37}$ or $Xaa_{39}$, via a Pre-linker, and b) at each of its two —NH ends to the —CO end of each of the $1^{st}$ and $2^{nd}$ Protractor, respectively, via a $1^{st}$ and a $2^{nd}$ Post-linker, respectively;

wherein each of the Pre-linker, the $1^{st}$ Post-linker, and the $2^{nd}$ Post-linker comprises a —CO group and an —NH group;

or a pharmaceutically acceptable salt, amide, or ester thereof.

2. The derivative of embodiment 1, wherein in Chem. 11 q is 4 and w is 0.

3. The derivative of any of embodiments 1-2, wherein the Pre-linker comprises at least one Linker element-1 of Chem. 1:

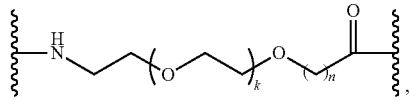

Chem. 1 wherein k is an integer in the range of 1-19, and n is an integer in the range of 1-5; or at least one Linker element-2 of Chem. 2:

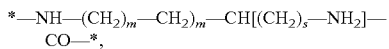

Chem. 2 where m is an integer in the range of 0-5, s is an integer in the range of 0-5, and with the provisos that when m is 0 s is an integer in the range of 1-5, and when s is 0 m is an integer in the range of 1-5.

4. The derivative of embodiment 3, wherein the Pre-linker comprises t times Linker element-1 of Chem. 1, wherein k is 5, 11, 19, or, preferably, 1, and n is 2 or, preferably, 1; and t is an integer in the range of 1-8.

5. The derivative of embodiment 3, wherein the Pre-linker comprises two or four times Linker element-2 of Chem. 2, wherein m is 4 and s is 0.

6. The derivative of any of embodiments 1-5, wherein each of the $1^{st}$ and the $2^{nd}$ Post-linker comprises a Linker element-3 and/or a Linker element-4, of formulas Chem. 3 and Chem. 4, respectively:

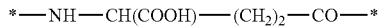

Chem. 3

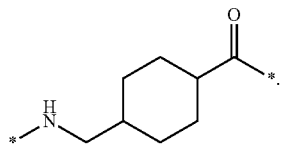

Chem. 4

7. The derivative of embodiment 6, wherein each of the $1^{st}$ and $2^{nd}$ Post-linker optionally includes a Linker element-1 of formula Chem. 1:

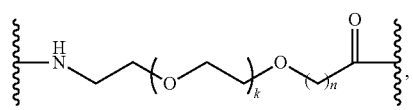

Chem. 1 wherein k is an integer in the range of 1-19, and n is an integer in the range of 1-5.

8. The derivative of embodiment 7, wherein each of the $1^{st}$ and $2^{nd}$ Post-linker includes a Linker element-1.

9. The derivative of any of embodiments 7-8, wherein in Chem. 1 k is 1 and n is 1.

10. The derivative of any of embodiments 7-9, wherein each of the $1^{st}$ and the $2^{nd}$ Post-linker comprises two or four times the Linker element-1 of Chem. 1, mutually connected via amide bonds.

11. The derivative of embodiment 6, wherein each of the $1^{st}$ and the $2^{nd}$ Post-linker consists of one Linker element-3 and one Linker element-4, of Chem. 3 and Chem. 4, respectively.

12. A GLP-1 derivative which is selected from Chem. 21, Chem. 22, Chem. 23, Chem. 24, Chem. 25, Chem. 26, Chem. 27, Chem. 28, Chem. 29, Chem. 30, Chem. 31, Chem. 32, Chem. 33, Chem. 34, and Chem. 35; or a pharmaceutically acceptable salt, amide, or ester thereof.

13. A pharmaceutical composition comprising a derivative according to any of embodiments 1-12, and a pharmaceutically acceptable excipient.

14. A derivative according to any of embodiments 1-12, for use as a medicament.

15. A derivative according to any of embodiments 1-12, for use in (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse.

In some embodiments the GLP-1 derivative of the invention is not selected from Chem. 21, Chem. 22, Chem. 23, Chem. 24, Chem. 25, Chem. 26, Chem. 27, Chem. 28, Chem. 29, Chem. 30, Chem. 31, Chem. 32, Chem. 33, Chem. 34, Chem. 35, Chem. 36, Chem. 37, Chem. 38, Chem. 39, Chem. 40, Chem. 41, and Chem. 42; and is also not a pharmaceutically acceptable salt, amide, or ester thereof.

In some embodiments the GLP-1 analogue of the invention is not selected from SEQ ID NO: 3, SEQ ID NO: 5, SEQ ID NO: 6, and SEQ ID NO: 9; and is also not a pharmaceutically acceptable salt, amide, or ester thereof.

In some embodiments the intermediate product of the invention is not selected from Chem. 50, Chem. 51, Chem. 52, Chem. 53, Chem. 54, Chem. 55, Chem. 56, Chem. 57, Chem. 58, Chem. 59, Chem. 60, Chem. 61, Chem. 62, Chem. 63, Chem. 64; and is also not a pharmaceutically acceptable salt, amide, or ester thereof.

EXAMPLES

This experimental part starts with a list of abbreviations, and is followed by a section including general methods for synthesising and characterising analogues and derivatives of the invention. Then follows a number of examples which relate to the preparation of specific GLP-1 derivatives, and at the end a number of examples have been included relating to the activity and properties of these analogues and derivatives (section headed pharmacological methods).

The examples serve to illustrate the invention.

LIST OF ABBREVIATIONS

Aib: α-aminoisobutyric acid (2-Aminoisobutyric acid)
AcOH: acetic acid
Ado: 8-amino-3,6-dioxaoctanoic acid
API: Active Pharmaceutical Ingredient
AUC: Area Under the Curve
BG: Blood Glucose
BHK Baby Hamster Kidney
BW: Body Weight
Boc: t-butyloxycarbonyl
Bom: benzyloxymethyl
BSA: Bovine serum albumin
BW: body weight
Bz: benzyl
C20 diacid: icosanedioic acid
CAS: Chemical Abstracts Service
Clt: 2-chlorotrityl
collidine: 2,4,6-trimethylpyridine
COOBz: benzyloxycarbonyl
COOMe: methoxycarbonyl
COOtBu: tert-butoxycarbonyl
DCM: dichloromethane
Dde: 1-(4,4-dimethyl-2,6-dioxocyclohexylidene)ethyl
DIC: diisopropylcarbodiimide
DIPEA: diisopropylethylamine
DMEM: Dulbecco's Modified Eagle's Medium (DMEM)
dPEG: discrete polyethylene glycol
EDTA: ethylenediaminetetraacetic acid
EGTA: ethylene glycol tetraacetic acid
FCS: Fetal Calf Serum
Fmoc: 9-fluorenylmethyloxycarbonyl
h: hours
HATU: (O-(7-azabenzotriazol-1-yl)-1,1,3,3-tetramethyluronium hexa fluorophosphate)
HBTU: (2-(1H-benzotriazol-1-yl-)-1,1,3,3 tetramethyluronium hexafluorophosphate)
HEPES: 4-(2-hydroxyethyl)-1-piperazineethanesulfonic acid
HFIP 1,1,1,3,3,3-hexafluoro-2-propanol or hexafluoroisopropanol
HOAt: 1-hydroxy-7-azabenzotriazole
HOBt: 1-hydroxybenzotriazole
HPLC: High Performance Liquid Chromatography
HSA: Human Serum Albumin
IBMX: 3-isobutyl-1-methylxanthine
Imp: Imidazopropionic acid (3-(Imidazol-5-yl)propanoic acid) (also called deamino-histidine, or deamino-His)
Inp: isonipecotic acid
i.v. intravenously
ivDde: 1-(4,4-dimethyl-2,6-dioxocyclohexylidene)-3-methylbutyl
IVGTT: Intravenous Glucose Tolerance Test
LCMS: Liquid Chromatography Mass Spectroscopy
LYD: Landrace Yorkshire Duroc
MALDI-MS: See MALDI-TOF MS
MALDI-TOF MS: Matrix-Assisted Laser Desorption/Ionisation Time of Flight Mass Spectroscopy
MeOH: methanol
Mmt: 4-methoxytrityl
Mtt: 4-methyltrityl
NHBoc: tert-butoxycarbonylamino
NHCbz: benzyloxycarbonylamino
NHFmoc: 9H-fluoren-9-ylmethoxycarbonylamino
NMP: N-methyl pyrrolidone
OBz: benzyloxy
OPfp: 2,3,4,5,6-pentafluorophenoxy
OPnp: 4-nitrophenoxy
OSuc: (2,5-dioxopyrrolidin-1-yl)oxy
OtBu: tert butyl ester
Oxyma Pure®: Cyano-hydroxyimino-acetic acid ethyl ester
Pbf: 2,2,4,6,7-pentamethyldihydrobenzofuran-5-sulfonyl
PBS: Phosphate Buffered Saline
PD: Pharmacodynamic
PEG: polyethylene glycol
Pen/Strep: Pencillin/Streptomycin
PK: Pharmacokinetic
PyBOP: benzotriazol-1-yl-oxytripyrrolidinophosphonium hexafluorophosphate
RP: Reverse Phase
RP-HPLC: Reverse Phase High Performance Liquid Chromatography
RT: Room Temperature
Rt: Retention time
s.c.: Subcutaneously
SD: Standard Deviation
SEC-HPLC: Size Exclusion High Performance Liquic Chromatography
SEM: Standard Error of Mean
SPA: Scintillation Proximity Assay
SPPS: Solid Phase Peptide Synthesis
tBu: tert. butyl
TFA: trifluoroacetic acid
TIS: triisopropylsilane
TLC: Thin Layer Chromatography Tos: tosylate (or pare-toluenesulfonyl)
Tris: tris(hydroxymethyl)aminomethane or 2-amino-2-hydroxymethyl-propane-1,3-diol
Trt: triphenylmethyl (trityl)
Trx: tranexamic acid (trans-4-(aminomethyl)cyclohexanecarboxylic acid)
UPLC: Ultra Performance Liquid Chromatography
Materials and Methods
Icosanedioic acid mono-tert-butyl ester
Fmoc-8-amino-3,6-dioxaoctanoic acid
17-(9-Fluorenylmethyloxycarbonyl-amino)-9-aza-3,6,12,15-tetraoxa-10-on-heptadecanoic acid
1-(9-Fluorenylmethyloxycarbonyl)amino-3,6,9,12,15,18-hexaoxahenicosan-21-oic acid
1-(9-Fluorenylmethyloxycarbonyl)amino-3,6,9,12,15,18,21,24,27,30,33,36-dodecaoxanonatriacontan-39-oic acid
alpha-Fmoc-amino-20(ethylene glycol)-omega-carboxylic acid
Fmoc-tranexamic acid
Boc-Lys(Fmoc)-OH
Fmoc-Lys(Fmoc)-OH
Fmoc-Glu-OtBu
Fmoc-Lys(Mtt)-Wang resin
Chemical Methods
This section is divided in two: Section A relating to general methods (of preparation (A1); and of detection and characterisation (A2)), and section B, in which the preparation and characterisation of a number of specific example compounds is described.

A. General Methods
A1. Methods of Preparation

This section relates to methods for solid phase peptide synthesis (SPPS methods, including methods for de-protection of amino acids, methods for cleaving the peptide from the resin, and for its purification), as well as methods for detecting and characterising the resulting peptide (LCMS, MALDI, and UPLC methods). The solid phase synthesis of peptides may in some cases be improved by the use of di-peptides protected on the di-peptide amide bond with a group that can be cleaved under acidic conditions such as, but not limited to, 2-Fmoc-oxy-4-methoxybenzyl, or 2,4,6-trimethoxybenzyl. In cases where a serine or a threonine is present in the peptide, pseudoproline di-peptides may be used (available from, e.g., Novabiochem, see also W. R. Sampson (1999), J. Pep. Sci., 5, 403). The Fmoc-protected amino acid derivatives used were the standard recommended: Fmoc-Ala-OH, Fmoc-Arg(Pbf)-OH, Fmoc-Asn(Trt)-OH, Fmoc-Asp(OtBu)-OH, Fmoc-Cys(Trt)-OH, Fmoc-Gln(Trt)-OH, Fmoc-Glu(OtBu)-OH, Fmoc-Gly-OH, Fmoc-His(Trt)-OH, Fmoc-Ile-OH, Fmoc-Leu-OH, Fmoc-Lys(Boc)-OH, Fmoc-Met-OH, Fmoc-Phe-OH, Fmoc-Pro-OH, Fmoc-Ser(tBu)-OH, Fmoc-Thr(tBu)-OH, Fmoc-Trp(Boc)-OH, Fmoc-Tyr(tBu)-OH, or, Fmoc-Val-OH etc. supplied from e.g. Anaspec, Bachem, Iris Biotech, or Novabiochem. Where nothing else is specified the natural L-form of the amino acids are used. The N-terminal amino acid was Boc protected at the alpha amino group (e.g. Boc-His(Boc)-OH, or Boc-His(Trt)-OH for peptides with His at the N-terminus). In case of modular side chain or albumin binding moiety attachment using SPPS the following suitably protected building blocks such as but not limited to Fmoc-8-amino-3,6-dioxaoctanoic acid, Fmoc-tranexamic acid, Fmoc-Glu-OtBu, and icosanedioic acid mono-tert-butyl ester were used. All operations stated below were performed at 250-μmol synthesis scale.

1. Synthesis of Resin Bound Protected Peptide Backbone
Method: SPPS_P

SPPS_P was performed on a Prelude Solid Phase Peptide Synthesizer from Protein Technologies (Tucson, Ariz. 85714 U.S.A.) at 250-μmol scale using six fold excess of Fmoc-amino acids (300 mM in NMP with 300 mM HOAt or Oxyma Pure®) relative to resin loading, e.g. low load Fmoc-Lys(Mtt)-Wang (0.35 mmol/g). Fmoc-deprotection was performed using 20% piperidine in NMP. Coupling was performed using 3:3:3:4 amino acid/(HOAt or Oxyma Pure®)/DIC/collidine in NMP. NMP and DCM top washes (7 ml, 0.5 min, 2×2 each) were performed between deprotection and coupling steps. Coupling times were generally 60 minutes. Some amino acids including, but not limited to Fmoc-Arg(Pbf)-OH, Fmoc-Aib-OH or Boc-His(Trt)-OH were "double coupled", meaning that after the first coupling (e.g. 60 min), the resin is drained and more reagents are added (amino acid, (HOAt or Oxyma Pure®), DIC, and collidine), and the mixture allowed to react again (e.g. 60 min).

Method: SPPS_L

SPPS_L was performed on a microwave-based Liberty peptide synthesiser from CEM Corp. (Matthews, N.C. 28106, U.S.A.) at 250-μmol or 100-μmol scale using six fold excess of Fmoc-amino acids (300 mM in NMP with 300 mM HOAt or Oxyma Pure®) relative to resin loading, e.g. low load Fmoc-Lys(Mtt)-Wang ? (0.35 mmol/g). Fmoc-deprotection was performed using 5% piperidine in NMP at up to 75° C. for 30 seconds where after the resin was drained and washed with NMP and the Fmoc-deprotection was repeated this time for 2 minutes at 75° C. Coupling was performed using 1:1:1 amino acid/(HOAt or Oxyma Pure®)/DIC in NMP. Coupling times and temperatures were generally 5 minutes at up to 75° C. Longer coupling times were used for larger scale reactions, for example 10 min. Histidine amino acids were double coupled at 50° C., or quadruple coupled if the previous amino acid was sterically hindered (e.g. Aib). Arginine amino acids were coupled at RT for 25 minutes and then heated to 75° C. for 5 min. Some amino acids such as but not limited to Aib, were "double coupled", meaning that after the first coupling (e.g. 5 min at 75° C.), the resin is drained and more reagents are added (amino acid, (HOAt or Oxyma Pure®) and DIC), and the mixture is heated again (e.g. 5 min at 75° C.). NMP washes (5×10 ml) were performed between deprotection and coupling steps.

2. Synthesis of Albumin Binder (Side Chain)

Icosanedioic acid mono-tert-butyl ester can be prepared as known in the art. For a method please refer to WO 2010102886 A1.

3. Attachment of Side Chains to Resin Bound Protected Peptide Backbone

When an acylation is present on a lysine side chain, the epsilon amino group of lysine to be acylated was protected with either Mtt, Mmt, Dde, ivDde, or Boc, depending on the route for attachment of the protracting moiety and linker. Dde- or ivDde-deprotection was performed with 2% hydrazine in NMP (2×20 ml, each 10 min) followed by NMP washings (4×20 ml). Mtt- or Mmt-deprotection was performed with 2% TFA and 2-3% TIS in DCM (5×20 ml, each 10 min) followed by DCM (2×20 ml), 10% MeOH and 5% DIPEA in DCM (2×20 ml) and NMP (4×20 ml) washings, or by treatment with hexafluoroisopropanol/DCM (75:25, 5×20 ml, each 10 min) followed by washings as above. In some cases the Mtt group was removed by automated steps on the Liberty peptide synthesiser. Mtt deprotection was performed with hexafluoroisopropanol or hexafluoroisopropanol/DCM (75:25) at room temperature for 30 min followed by washing with DCM (7 ml×5), followed by NMP washings (7 ml×5). The protracting moiety and/or linker can be attached to the peptide either by acylation of the resin bound peptide or by acylation in solution of the unprotected peptide. In case of attachment of the protracting moiety and/or linker to the protected peptidyl resin the attachment can be modular using SPPS and suitably protected building blocks.

Method: SC_P

The N-ε-lysine protection group was removed as described above and the chemical modification of the lysine was performed by one or more automated steps on the Prelude peptide synthesiser using suitably protected building blocks as described above. Double couplings were performed as described in SPPS_P with 3 hours per coupling.

Method: SC_L

The N-ε-lysine protection group was removed as described above and the chemical modification of the lysine was performed by one or more automated steps on the Liberty peptide synthesiser using suitably protected building blocks as described above. Double couplings were performed as described in SPPS_L.

Method: SC_M_1

The N-ε-lysine protection group was removed as described above and the chemical modification of the lysine was performed by one or more manual steps using suitably protected building blocks as described above. The SC_M_1 was performed at 500-μmol scale using four or six fold excess of Fmoc-amino acids (300 mM in NMP with 300 mM HOAt, Oxyma Pure®) relative to resin loading. Fmoc-deprotection was performed using 20% piperidine in NMP for 5 minutes at room temperature where after the resin was drained and washed with NMP and the Fmoc-deprotection was repeated this time for 15 minutes at room temperature. Coupling was performed using 1:1:1 amino acid/Oxyma Pure®)/DIC in NMP. Coupling times were generally 60 minutes at room temperature. Some building blocks were double coupled meaning that after the first coupling (e.g. 60 min), the resin is drained and more reagents are added (amino acid, (HOAt or Oxyma Pure®), DIC, and collidine), and the mixture allowed to react again (e.g. 60 min).

Method: SC_M2

Coupling of Fmoc-L-cysteic acid at 250 μmol or 500-μmol scale using two to four fold excess of the above acid dissolved DMF and the solution was mixed with PyBoP dissolved in NMP for 5 min. (300 mM in DMF with 300 mM PyBOP in NMP). The solution was added to the resin followed by addition of DIPEA (Acid/PyBOP/DIPEA (1:1:4). The resin was shaken for 2 hours. Double coupled.

Method: SC_M_3

Coupling of 16-Sulfo-hexadecanoic acid was performed at 250-μmol or 500-μmol scale using tree to four fold excess of the acid dissolved in boiling DMF followed by slowly cooling until 50° C. and addition of PyBoP dissolved in DMF (40 mM in DMF with 300 mM PyBOP) before adding the solution to the resin. Slowly addition of DIPEA (Acid/PyBOP/DIPEA (1:1:4). The resin was shaken for 2 hours. Double or triple coupled.

4. Cleavage of Resin Bound Peptide with or without Attached Side Chains and Purification Method: CP_M1

After synthesis the resin was washed with DCM, and the peptide was cleaved from the resin by a 2-3 hour treatment with TFA/TIS/water (95/2.5/2.5 or 92.5/5/2.5) followed by precipitation with diethylether. The peptide was dissolved in a suitable solvent (such as, e.g., 30% acetic acid) and purified by standard RP-HPLC on a C18, 5 μm column, using acetonitrile/water/TFA. The fractions were analysed by a combination of UPLC, MALDI and LCMS methods, and the appropriate fractions were pooled and lyophilised.

If desired the peptide counter ion can be exchanged to sodium using the methods known in the art. As an example approx. 2 g peptide was dissolved in 250 ml acetonitrile/water (50/50) and loaded onto a Waters X-Bridge C8, 5 μM, 50×250 mm column on a preparative RP-HPLC system. Following loading, the column was washed with water for 8 min at a flow rate of 60 ml/min and 0.01 N NaOH pH 11 at a flow rate of 60 ml/min for 2×8 min. The sodium salt of the peptide was eluted using an isocratic flow of water at 60 ml/min for 10 min followed by a linear gradient of 5% to 85% acetonitrile over 30 min.

A2. General Methods for Detection and Characterisation

1. LC-MS Methods

Method: LCMS01

LCMS01 was performed on a setup consisting of Waters Acquity UPLC system and LCT Premier XE mass spectrometer from Micromass. Eluents: A: 0.1% Formic acid in water; B: 0.1% Formic acid in acetonitrile. The analysis was performed at RT by injecting an appropriate volume of the sample (preferably 2-10 μl) onto the column which was eluted with a gradient of A and B. The UPLC conditions, detector settings and mass spectrometer settings were: Column: Waters Acquity UPLC BEH, C-18, 1.7 μm, 2.1 mm×50 mm. Gradient: Linear 5%-95% acetonitrile during 4.0 min (alternatively 8.0 min) at 0.4 ml/min. Detection: 214 nm (analogue output from TUV (Tunable UV detector)) MS ionisation mode: API-ES. Scan: 100-2000 amu (alternatively 500-2000 amu), step 0.1 amu.

Method: LCMS27

LCMS27 was performed on a setup consisting of Agilent 1290 infinity series UPLC system and Agilent Technologies LC/MSD TOF 6230 (G6230A). Eluents: A: 99.90% $H_2O$, 0.02% TFA; B: 99.90% $CH_3CN$, 0.02% TFA. The analysis was performed at RT by injecting an appropriate volume of the sample onto a an Eclipse $C18_+2.1×50$ mm 1.8 u column which was eluted with a linear gradient of 5% to 95% B with a run-time of 6 min: 0-4.5 min 5-95% B, 4.5-5.0 min 95% B, 5.0-5.5 min 95-5% B, 5.5-6.0 min 5% B, a flow rate of 0.40 ml/min, and a column temperature of 40° C. The ionisation method was Agilent Jet Stream source. The scanning range was as follows: m/z min. 100, m/z max. 3200. Linear reflector mode was used. Positive mode was used. Mass found is m/z of the compounds.

2. UPLC Method

Method: UPLC02

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 99.95% $H_2O$, 0.05% TFA; B: 99.95% $CH_3CN$, 0.05% TFA. The following linear gradient was used: 95% A, 5% B to 95% A, 5% B over 16 minutes at a flow-rate of 0.40 ml/min.

3. MALDI-MS Method

Method: MALDI01

Molecular weights were determined using matrix-assisted laser desorption and ionisation time-of-flight mass spectroscopy, recorded on a Microflex or Autoflex (Bruker). A matrix of alpha-cyano-4-hydroxy cinnamic acid was used.

B. Synthesis of Compounds of the Invention

Example 1

N{Epsilon-37}-[2-[2-[2-[[(2S)-2,6-bis[[2-[2-[2-[[2-[2-[2-[[(4S)-4-carboxy-4-[[4-[(19-carboxynonade-canoylamino)methyl]cyclohexanecarbonyl]amino]butanoyl]amino]ethoxy]ethoxy]acetyl]amino]ethoxy]ethoxy]acetyl]amino]hexanoyl]amino]ethoxy]ethoxy]acetyl]-[Aib8,Glu22,Arg26,Arg34,Lys37]-GLP-1-(7-37)-peptide Chem. 21

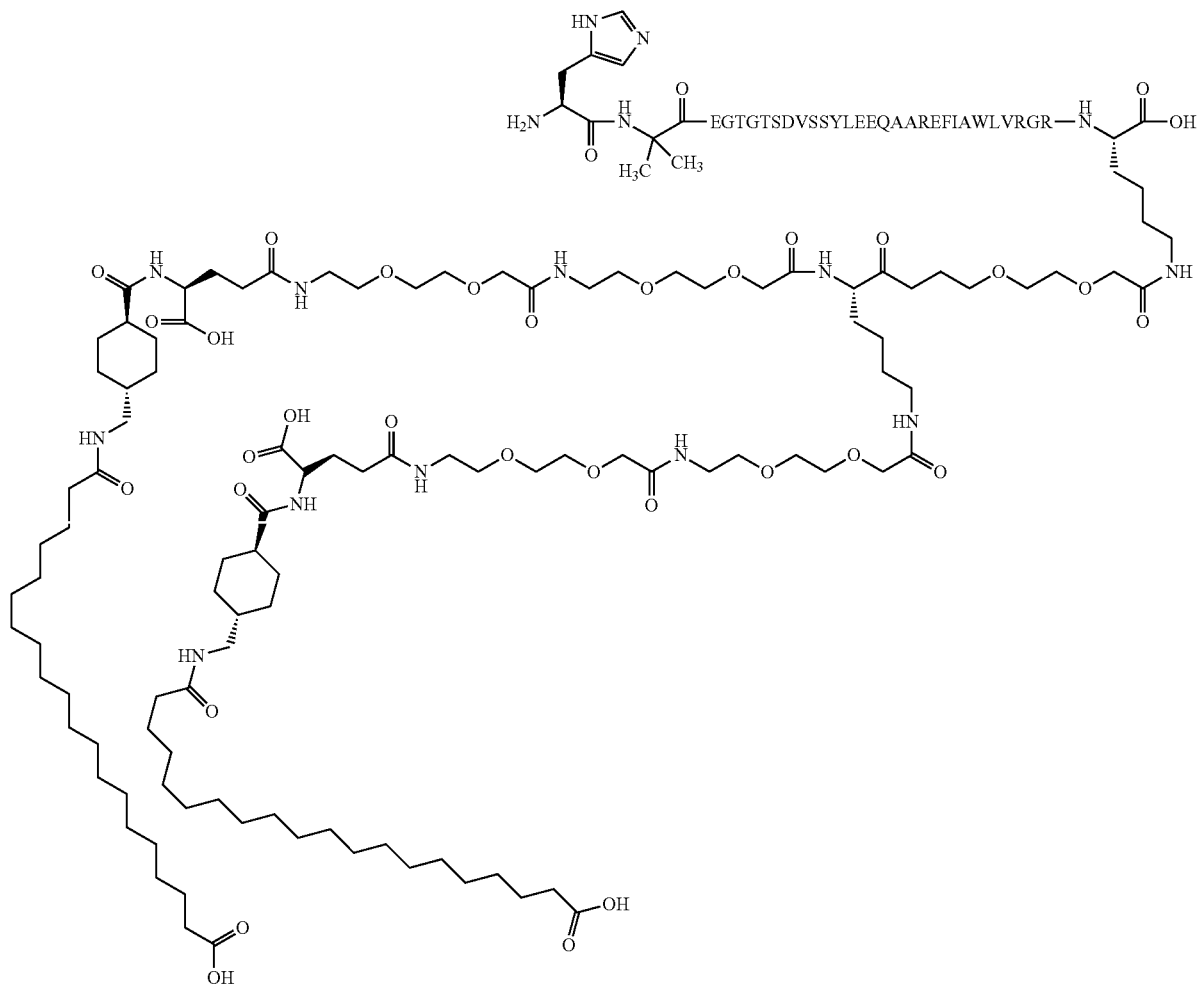

The peptide has SEQ ID NO: 2
Synthesis method: SPPS_P; SC_P; CP_M1
UPLC02: RT=11.2 min
MALDI01: m/z=5607.5

Example 2

N{Epsilon-37}-[2-[2-[2-[[2-[2-[2-[[(2S)-2,6-bis[[2-[2-[2-[[2-[2-[2-[[(4S)-4- carboxy-4-[[4-[(19-car-boxynonadecanoylamino)methyl]cyclohexanecarbonyl]amino]butanoyl]amino]ethoxy]ethoxy]acetyl]amino]ethoxy]ethoxy]acetyl]amino]hexanoyl]amino]ethoxy]ethoxy]acetyl]amino]ethoxy]ethoxy]acetyl]-[Aib8,Glu22,Arg26,Arg34,Lys37]-GLP-1-(7-37)-peptide Chem. 22
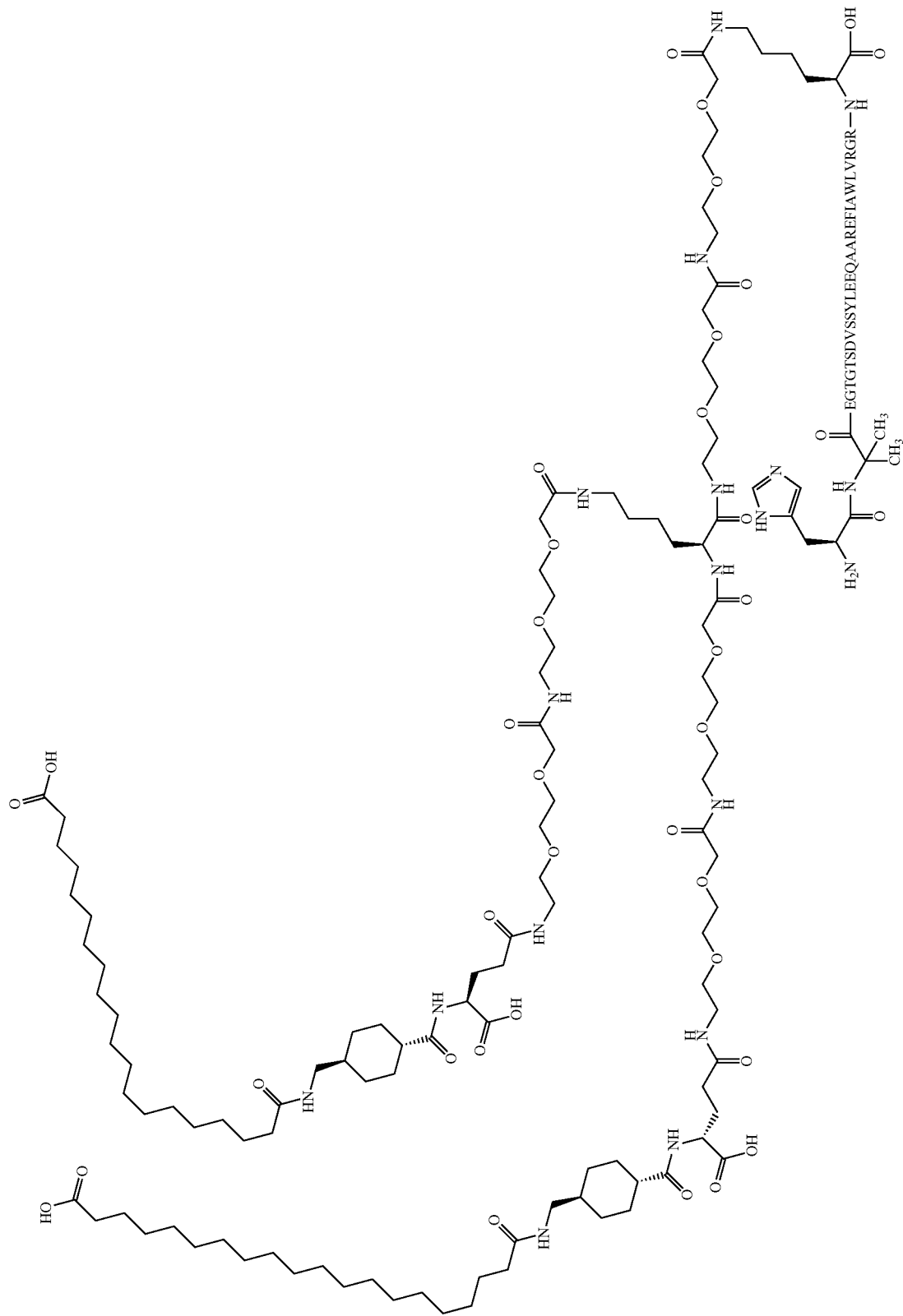

The peptide has SEQ ID NO: 2
Synthesis method: SPPS_P; SC_P; CP_M1
UPLC02: RT=11.3 min
LCMS01: RT=3.2 min, m/z: 1918 [M+3H]$^{3+}$, 1439 [M+4H]$^{4+}$ Example 3

N{Epsilon-37}-3-[2-[2-[2-[2-[2-[2-[[(2S)-2,6-bis[[(4S)-4-carboxy-4-[[4-[(19-carboxynonadecanoylamino)methyl]cyclohexanecarbonyl]amino]butanoyl]amino]hexanoyl]amino]ethoxy]ethoxy]ethoxy]ethoxy]ethoxy]ethoxy]propanoyl-[Aib8,Glu22,Arg26,Arg34,Lys37]-GLP-1-(7-37)-peptide Chem. 23

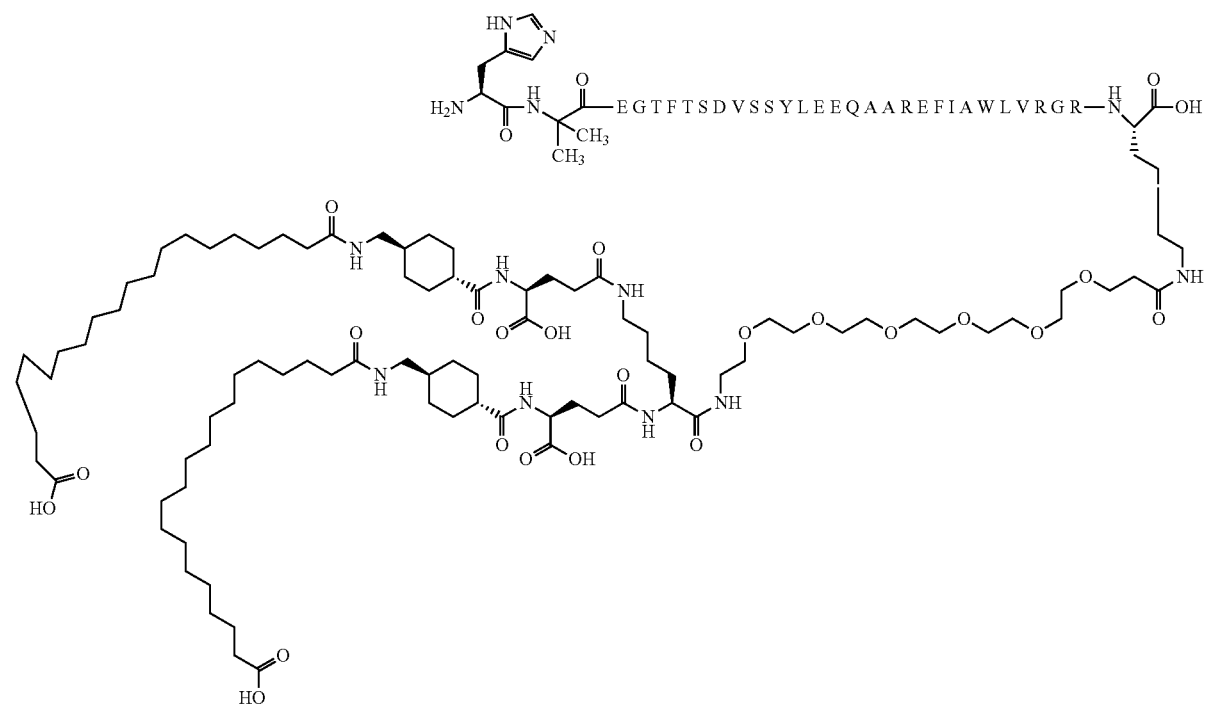

The peptide has SEQ ID NO: 2
Synthesis method: SPPS_P; SC_P; CP_M1
UPLC02: RT=11.6 min
LCMS01: RT=2.9 min, m/z: 1710 [M+3H]$^{3+}$, 1305 [M+4H]$^{4+}$, 1044 [M+5H]$^{5+}$

Example 4
N{Epsilon-37}-3-[2-[2-[2-[2-[2-[2-[2-[2-[2-[2-[2-[2-[[(2S)-2,6-bis[[(4S)-4- carboxy-4-[[4-[(19-carboxynonadecanoylamino)methyl]cyclohexanecarbonyl]amino]butanoyl]amino]hexanoyl]amino]ethoxy]ethoxy]ethoxy]ethoxy]ethoxy]ethoxy]ethoxy]ethoxy]ethoxy]ethoxy]ethoxy]propanoyl-[Aib8,Glu22,Arg26,Arg34,Lys37]-GLP-1-(7-37)-peptide
Chem. 24
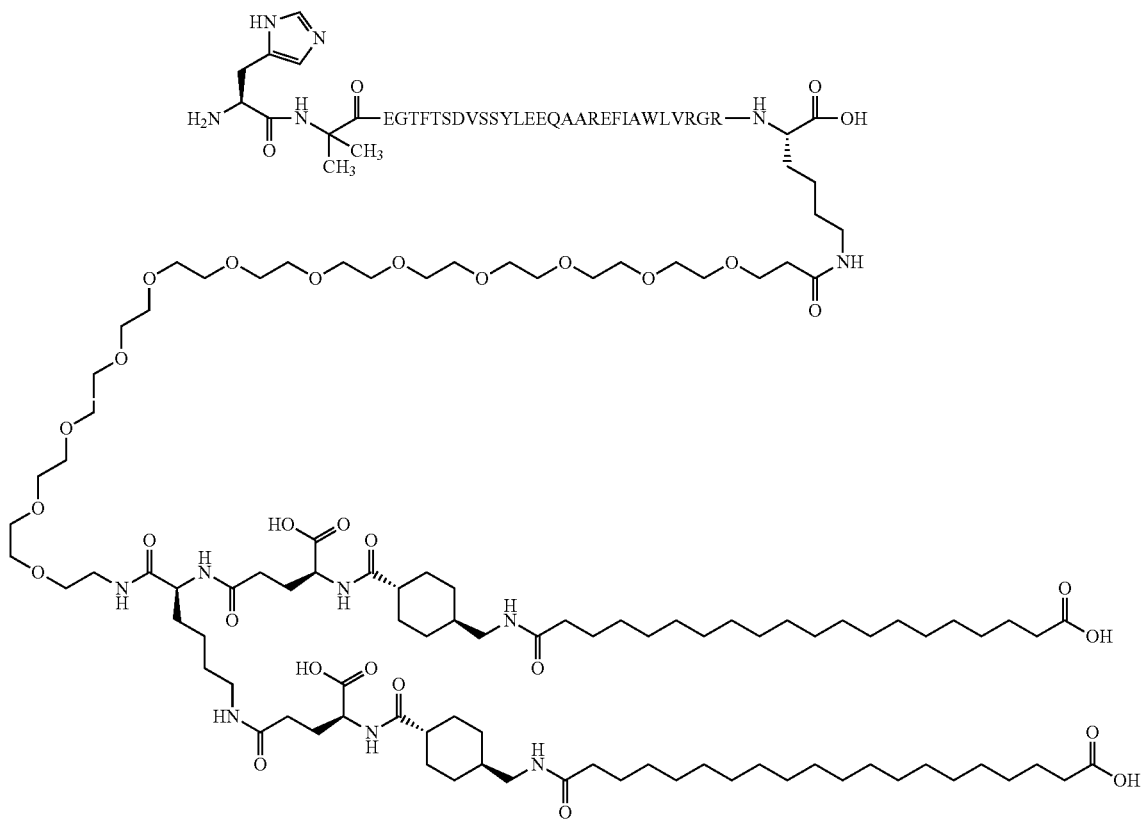
The peptide has SEQ ID NO: 2
Synthesis method: SPPS_P; SC_P; CP_M1
UPLC02: RT=11.6 min
LCMS01: RT=3.1 min, m/z: 1372 $[M+4H]^{4+}$, 1097 $[M+5H]^{5+}$

Example 5

N{Epsilon-37}-3-[2-[2-[2-[2-[2-[2-[2-[2-[2-[2-[2-[2-[2-[2-[2-[2-[2-[2-[2-[[(2S)-2,6-bis[[(4S)-4-carboxy-4-[[4-[(19-carboxynonadecanoylamino)methyl]cyclohexanecarbonyl]amino]butanoyl]amino]hexanoyl]amino]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]ethoxy]propanoyl-[Aib8,Glu22,Arg26,Arg24,Lys37]-GLP-1-(7-37)-peptide Chem. 25

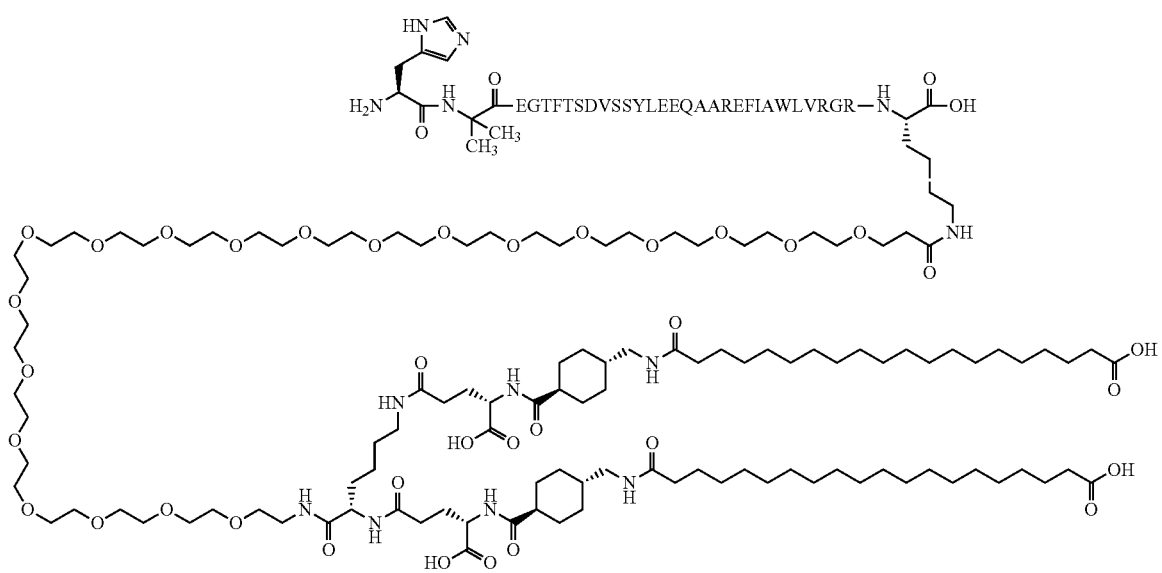

The peptide has SEQ ID NO: 2
Synthesis method: SPPS_P; SC_P; CP_M1
UPLC02: RT=11.9 min
LCMS01: RT=2.9 min, m/z: 1460 [M+4H]$^{4+}$, 1168 [M+5H]$^{5+}$

Example 6

[Imp7,Aib8,Glu22,Arg26,Arg34]-GLP-1-(7-37)-peptidyl-Gly-N{Epsilon}[2-[2-[2-[[2-[2-[2-[[2-[2-[2-[[2-[2-[2-[[(2S)-2,6-bis[[(4S)-4-carboxy-4-[[4-[(19-carboxynonadecanoylamino)methyl]cyclohexanecarbonyl]amino]butanoyl]amino]hexanoyl]amino]ethoxy]ethoxy]acetyl]amino]ethoxy]ethoxy]acetyl]amino]ethoxy]ethoxy]acetyl]amino]ethoxy]ethoxy]acetyl]Lys Chem. 26

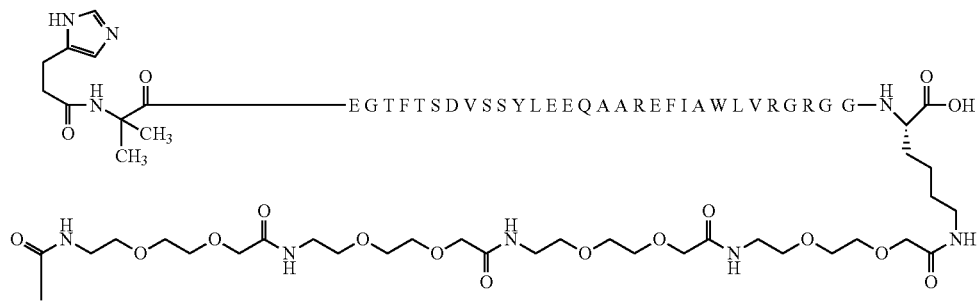

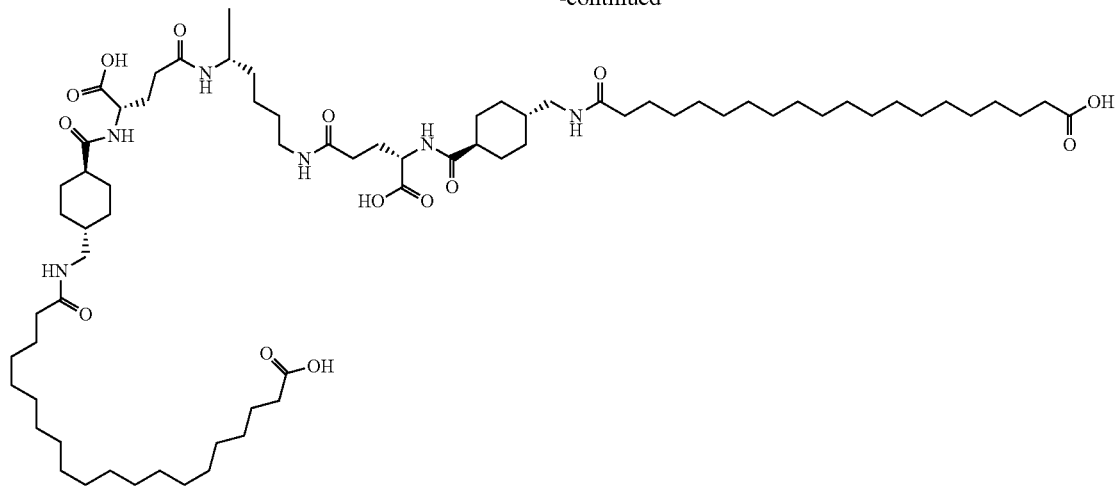

The peptide has SEQ ID NO: 3
Synthesis method: SPPS_P; SC_P; CP_M1
UPLC02: RT=12.1 min
LCMS01: RT=4.2 min, m/z: 1392 [M+4H]$^{4+}$, 1114 [M+5H]$^{5+}$ Example 7

[Imp7,Aib8,Glu22,Arg26,Arg34]-GLP-1-(7-37)-peptidyl-Gly-N{Epsilon}[2-[2-[2-[[2-[2-[2-[[(2S)-2,6-bis[[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]hexanoyl]amino]ethoxy]ethoxy]acetyl]amino]ethoxy]ethoxy]acetyl]Lys Chem. 27

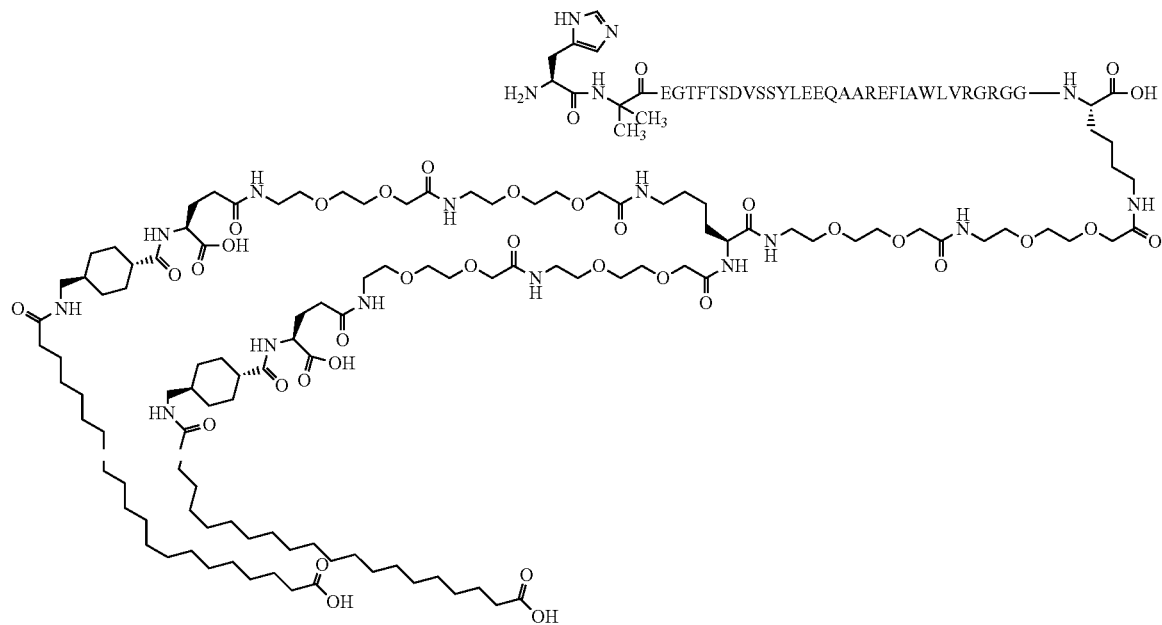

The peptide has SEQ ID NO: 3
Synthesis method: SPPS_P; SC_P; CP_M1
UPLC02: RT=11.6 min
LCMS01: RT=4.2 min, m/z: 1462 $[M+4H]^{4+}$, 1171 $[M+5H]^{5+}$ Example 8

N{Epsilon-37}-[2-[2-[2-[[2-[2-[2-[[2-[2-[2-[[2-[2-[2-[[(2S)-2,6-bis[[(4S)-4- carboxy-4-[[4-[(19-carboxynonadecanoylamino)methyl]cyclohexanecarbonyl]amino]butanoyl]amino]hexanoyl]amino]ethoxy]ethoxy]acetyl]amino]ethoxy]ethoxy]acetyl]amino]ethoxy]ethoxy]acetyl]amino]ethoxy]ethoxy]acetyl]-[Aib8,Glu22,Arg26,Arg34,Lys37]-GLP-1-(7-37)-peptide Chem. 28

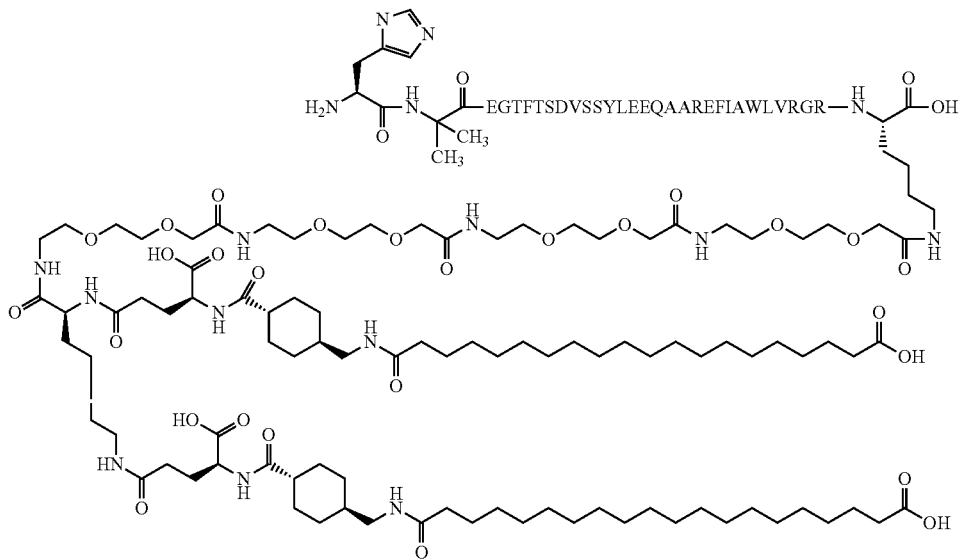

The peptide has SEQ ID NO: 2
Synthesis method: SPPS_P; SC_P; CP_M1
UPLC02: RT=11.5 min
LCMS01: RT=3.1 min, m/z: 1367 $[M+4H]^{4+}$, 1094 $[M+5H]^{5+}$

Example 9
N{Epsilon-37}-[(2S)-2-amino-6-[[(2S)-2-amino-6-[[(2S)-2,6-bis[[(4S)-4-carboxy-4-[[4-[(19-carboxynonadecanoylamino)methyl]cyclohexanecarbonyl]amino]butanoyl]amino]hexanoyl]amino]hexanoyl]amino]hexanoyl]-[Aib8,Glu22,Arg26,Arg34,Lys37]-GLP-1-(7-37)-peptide
Chem. 29
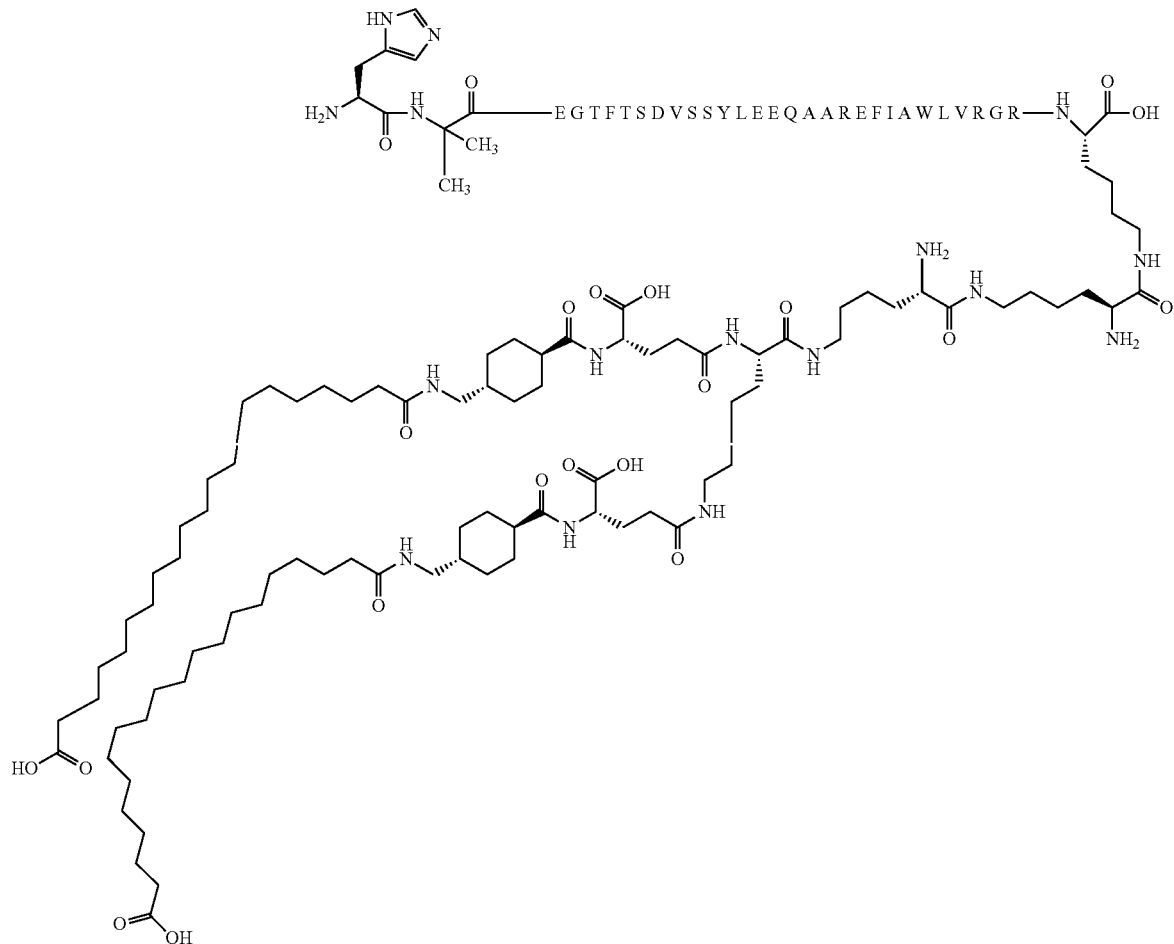
The peptide has SEQ ID NO: 2
Synthesis method: SPPS_P; SC_P; CP_M1
UPLC02: RT=11.4 min
LCMS01: RT=2.7 min, m/z: 1286 $[M+4H]^{4+}$, 1029 $[M+5H]^{5+}$ Example 10
N{Epsilon-37}-[(2S)-2-amino-6-[[(2S)-2-amino-6-[[(2S)-2-amino-6-[[(2S)-2-amino-6-[[(2S)-2,6-bis[[(4S)-4-carboxy-4-[[4-[(19-carboxynonadecanoylamino)methyl]cyclohexanecarbonyl]amino]butanoyl]amino]hexanoyl]amino]hexanoyl]amino]hexanoyl]amino]hexanoyl]amino]hexanoyl]-[Aib8,Glu22,Arg26,Arg34,Lys37]-GLP-1-(7-37)-peptide
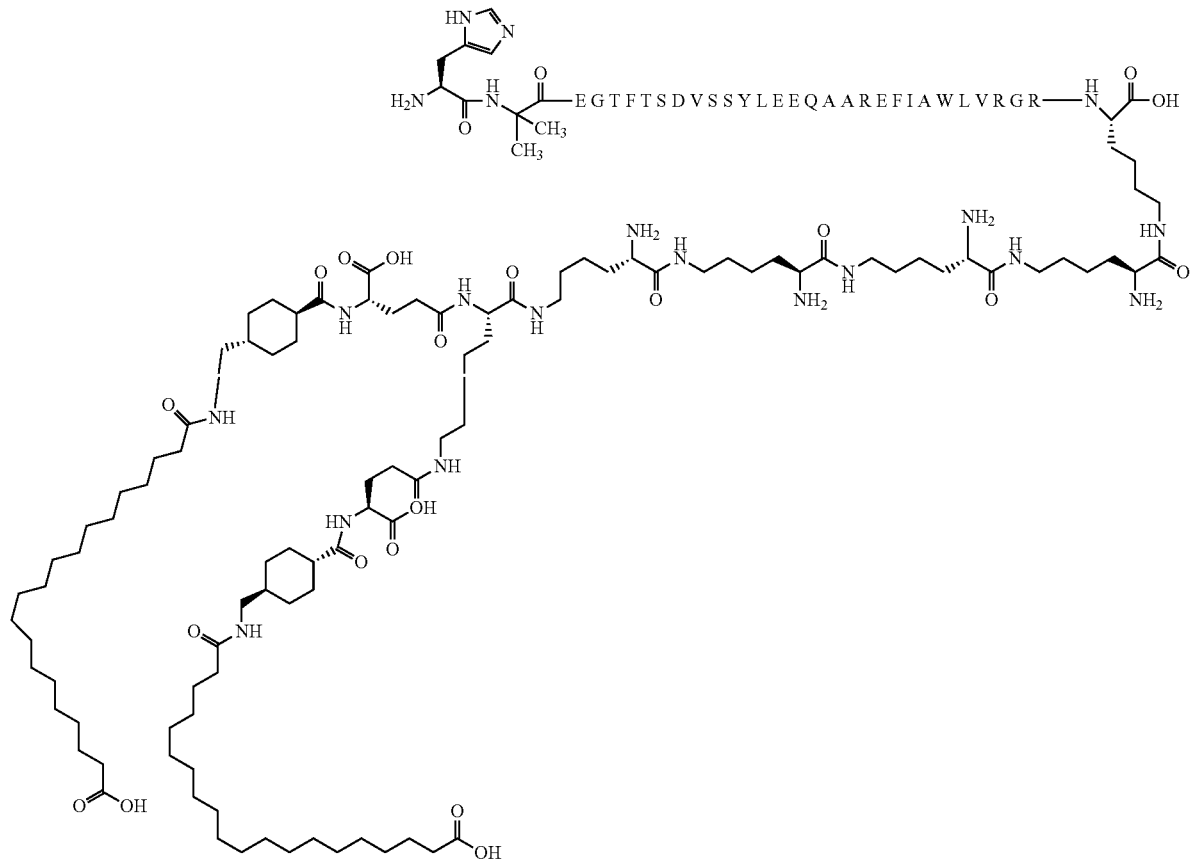
Chem. 30
The peptide has SEQ ID NO: 2
Synthesis method: SPPS_P; SC_P; CP_M1
UPLC02: RT=11.1 min
LCMS01: RT=2.5 min, m/z: 1350 [M+4H]$^{4+}$, 1080 [M+5H]$^{5+}$

Example 11
N{Epsilon-37}-[2-[2-[2-[[2-[2-[2-[[(2S)-2,6-bis
[[(4S)-4-carboxy-4-[[4-[(19-carboxynonadecanoy-
lamino)methyl]cyclohexanecarbonyl]amino]bu-
tanoyl]amino]hexanoyl]amino]ethoxy]ethoxy]acetyl]
amino]ethoxy]ethoxy]acetyl]-[Aib8,Glu22,Arg26,
Arg34,Lys37]-GLP-1-(7-37)-peptide
Chem. 31
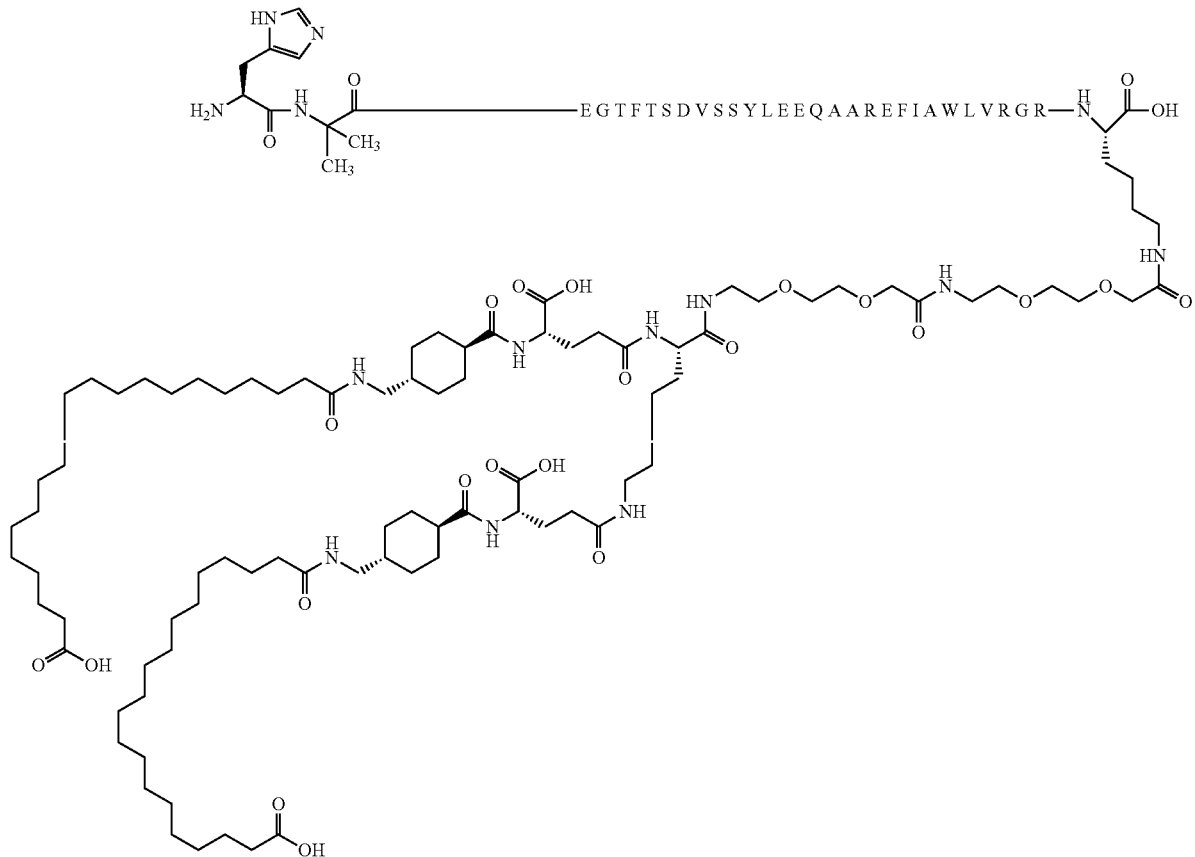
The peptide has SEQ ID NO: 2
Synthesis method: SPPS_P; SC_P; CP_M1
UPLC02: RT=11.7 min
LCMS01: RT=2.9 min, m/z: 1294 $[M+4H]^{4+}$, 1036 $[M+5H]^{5+}$

Example 12

N{Epsilon-37}-[2-[2-[2-[[2-[2-[2-[[2-[2-[2-[[2-[2-[2-[[2-[2-[2-[[2-[2-[[(2S)-2,6-bis[[(4S)-4-carboxy-4-[[4-[(19-carboxynonadecanoylamino)methyl]cyclohexanecarbonyl]amino]butanoyl]amino]hexanoyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]-[Aib8,Glu22,Arg26,Arg34,Lys37]-GLP-1-(7-37)-peptide Chem. 32

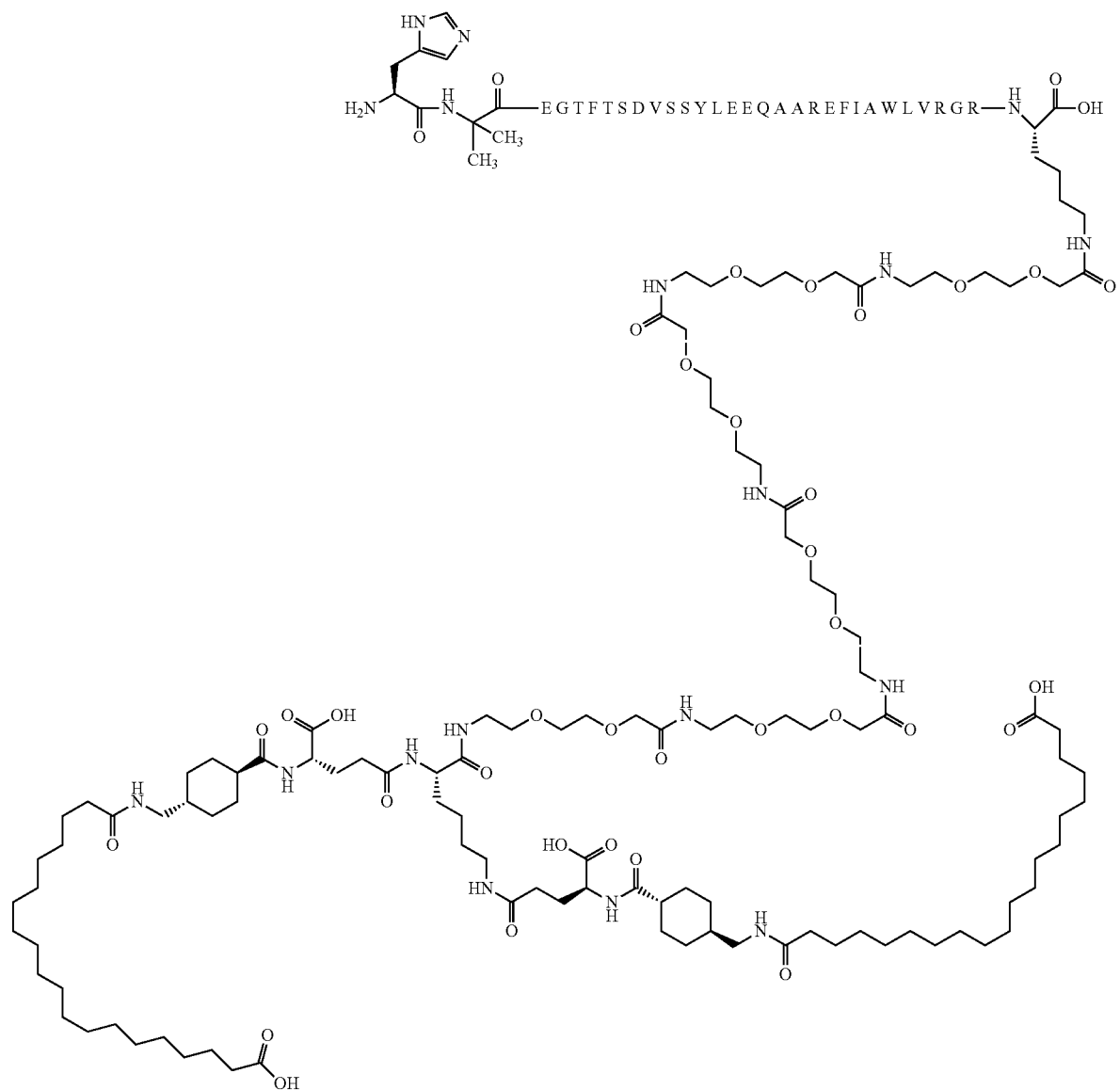

The peptide has SEQ ID NO: 2
Synthesis method: SPPS_P; SC_P; CP_M1
UPLC02: RT=12.0 min
LCMS01: RT=2.9 min, m/z: 1439 [M+4H]$^{4+}$, 1152 [M+5H]$^{5+}$

Example 13

N{Epsilon-37}-[2-[2-[2-[[2-[2-[2-[[2-[2-[2-[2-[2-[[2-[2-[2-[[2-[2-[2-[[2-[2-[2-[[2-[2-[2-[[(2S)-2,6-bis[[(4S)-4-carboxy-4-[[4-[(19-carboxynonadecanoylamino)methyl]cyclohexanecarbonyl]amino]butanoyl]amino]hexanoyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]-[Aib8,Glu22,Arg26,Arg34,Lys37]-GLP-1-(7-37)-peptide Chem. 33

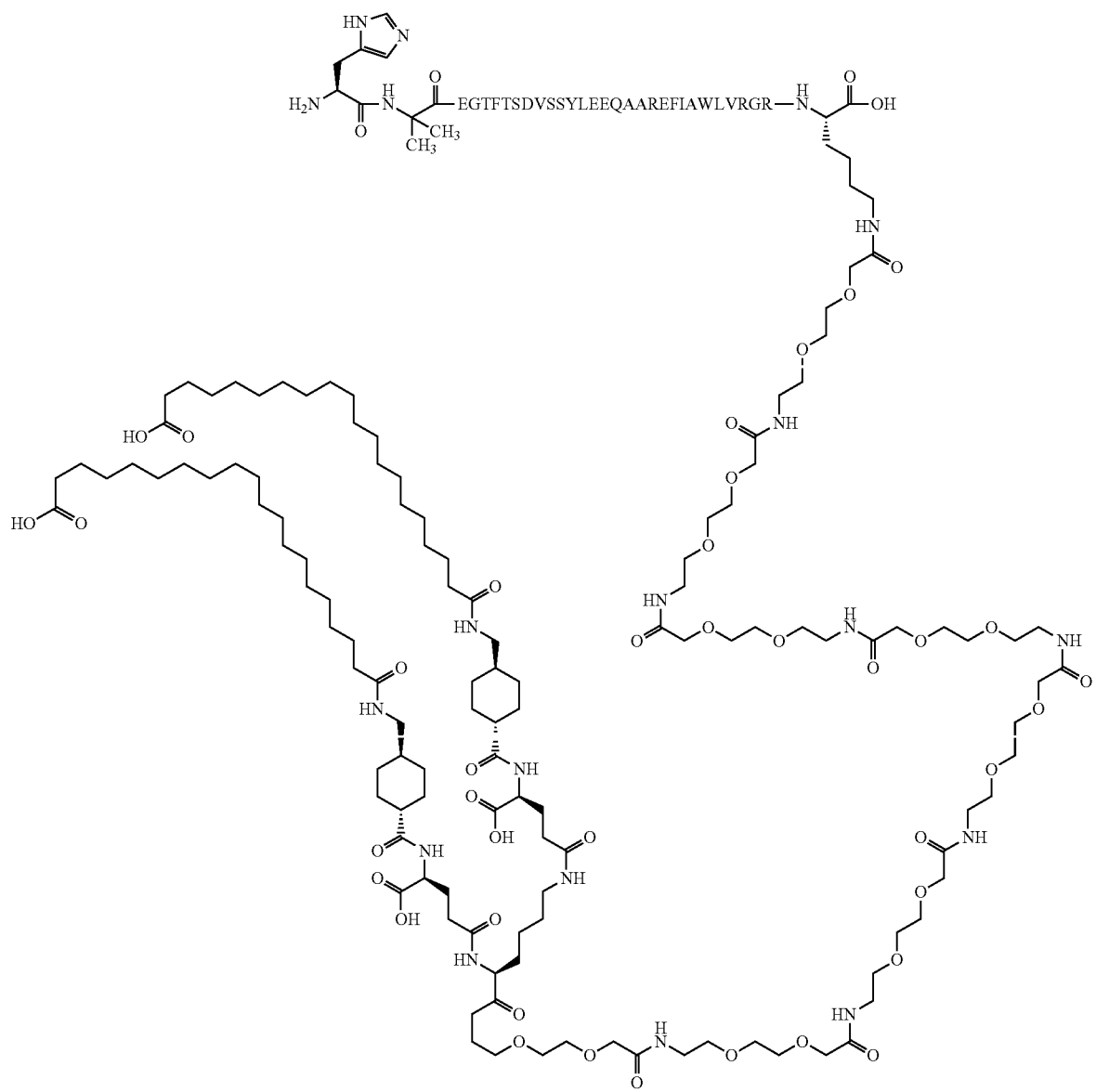

The peptide has SEQ ID NO: 2
Synthesis method: SPPS_P; SC_P; CP_M1
UPLC02: RT=12.0 min
LCMS01: RT=2.9 min, m/z: 1512 [M+4H]$^{4+}$, 1210 [M+5H]$^{5+}$

Example 14

N{Epsilon-37}-[2-[2-[2-[[2-[2-[2-[[(2S)-2,6-bis[[2-[2-[2-[[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]amino]hexanoyl]amino]ethoxy]ethoxy]acetyl]amino]ethoxy]ethoxy]acetyl]-[Aib8,Glu22,Arg26,Arg34,Lys37]-GLP-1-(7-37)-peptide Chem. 34

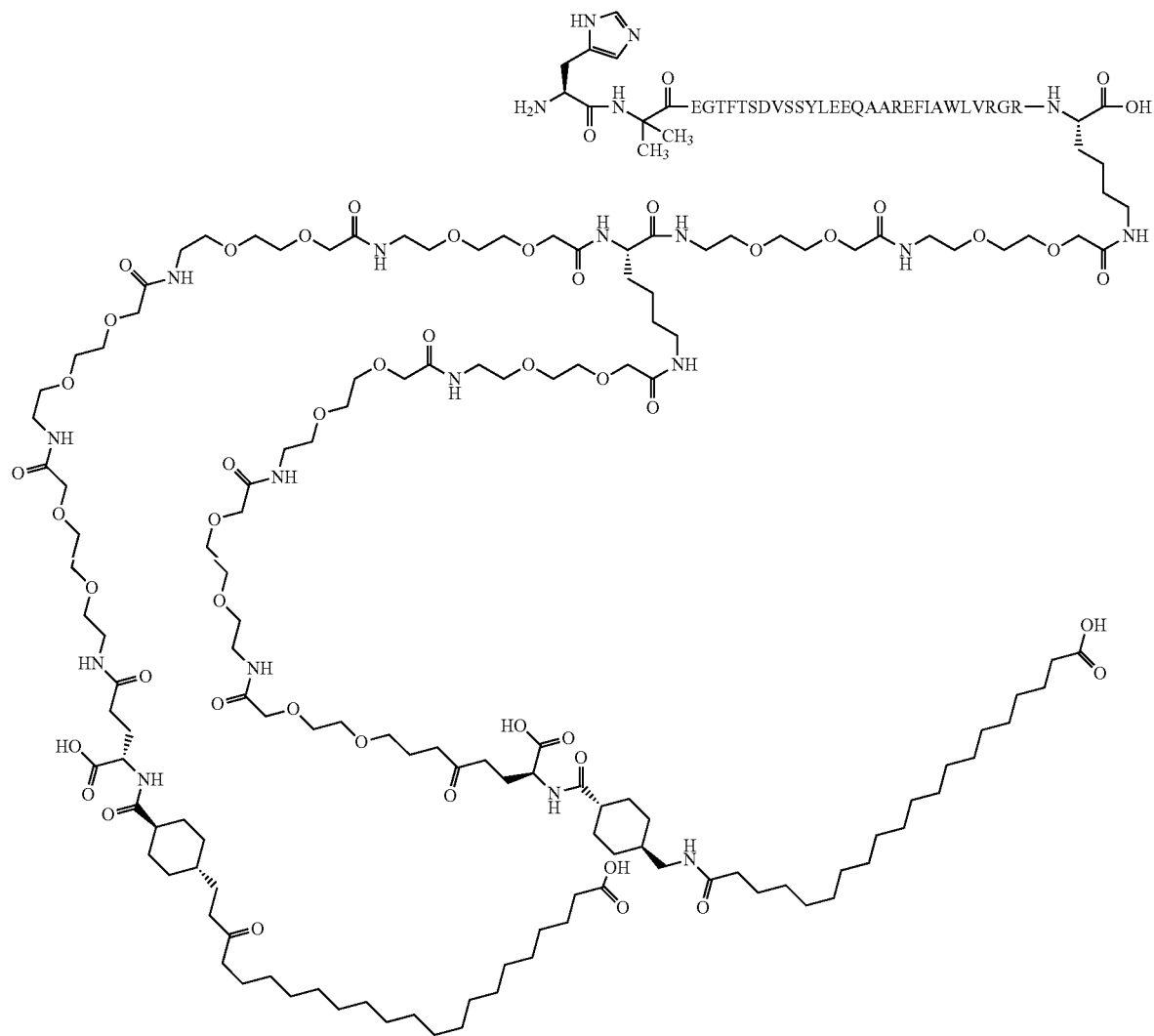

The peptide has SEQ ID NO: 2
Synthesis method: SPPS_P; SC_P; CP_M1
UPLC02: RT=10.9 min
LCMS01: RT=2.9 min, m/z: 1585 [M+4H]$^{4+}$, 1268 [M+5H]$^{5+}$

Example 15

N{Epsilon-37}-[2-[2-[2-[[2-[2-[2-[[2-[2-[2-[[2-[2-[2-[[(2S)-2,6-bis[[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]hexanoyl]amino]ethoxy]ethoxy]acetyl]amino]ethoxy]ethoxy]acetyl]amino]ethoxy]ethoxy]acetyl]-[Aib8,Glu22,Arg26,Arg34,Lys37]-GLP-1-(7-37)-peptide

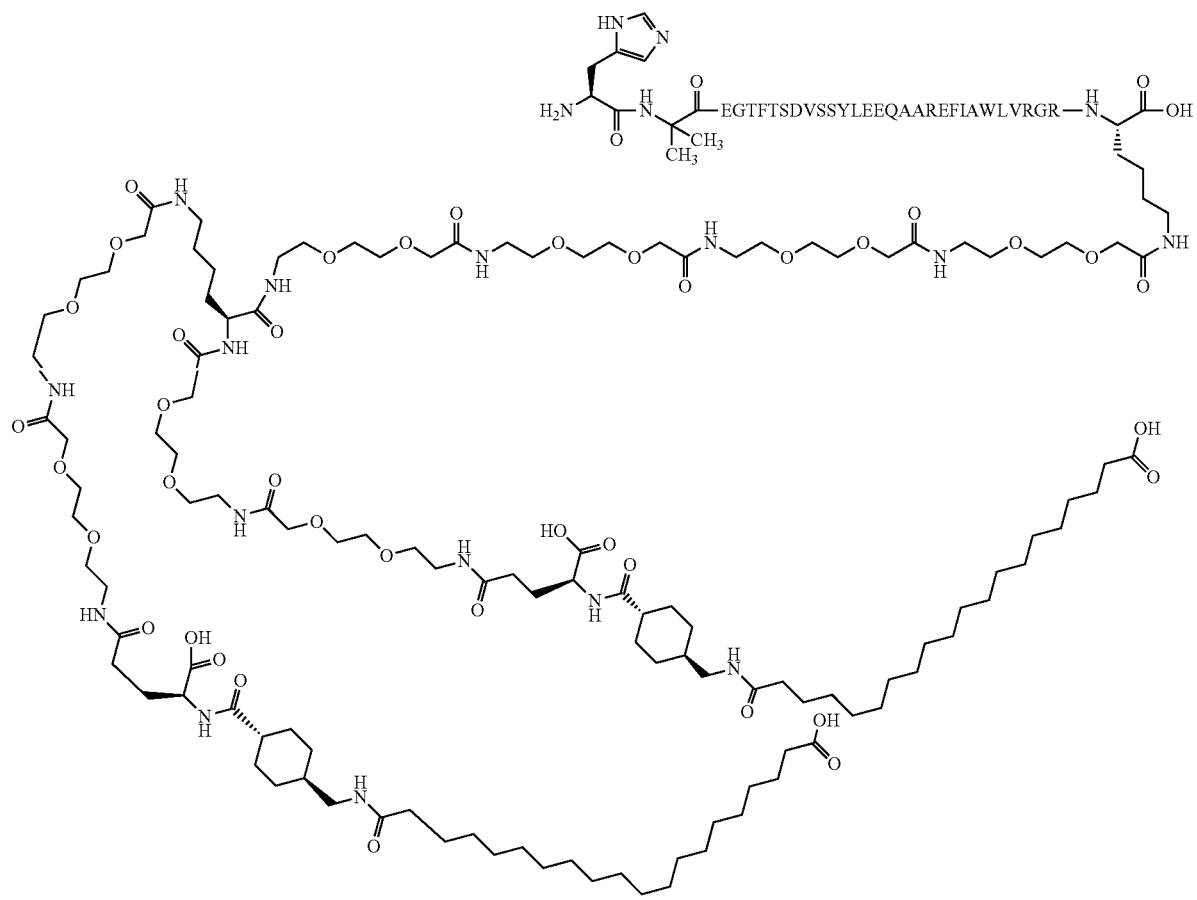

Chem. 35

The peptide has SEQ ID NO: 2
Synthesis method: SPPS_P; SC_P; CP_M1
UPLC02: RT=11.3 min
LCMS01: RT=3.0 min, m/z: 1512 $[M+4H]^{4+}$, 1210 $[M+5H]^{5+}$

Example 16

N{Epsilon-34}-[2-[2-[2-[[2-[2-[2-[[2-[2-[2-[[2-[2-[2-[[2-[2-[2-[[2-[2-[[(2S)-2,6-bis[[(4S)-4-carboxy-4-[[4-[(19-carboxynonadecanoylamino) methyl]cyclohexanecarbonyl]amino]butanoyl] amino]hexanoyl]amino]ethoxy]ethoxy]acetyl]amino] ethoxy]ethoxy]acetyl]amino]ethoxy]ethoxy]acetyl] amino]ethoxy]ethoxy]acetyl]amino]ethoxy]ethoxy] acetyl]amino]ethoxy]ethoxy]acetyl]-[Aib8,Glu22, Arg26]-GLP-1-(7-37)-peptide Chem. 36

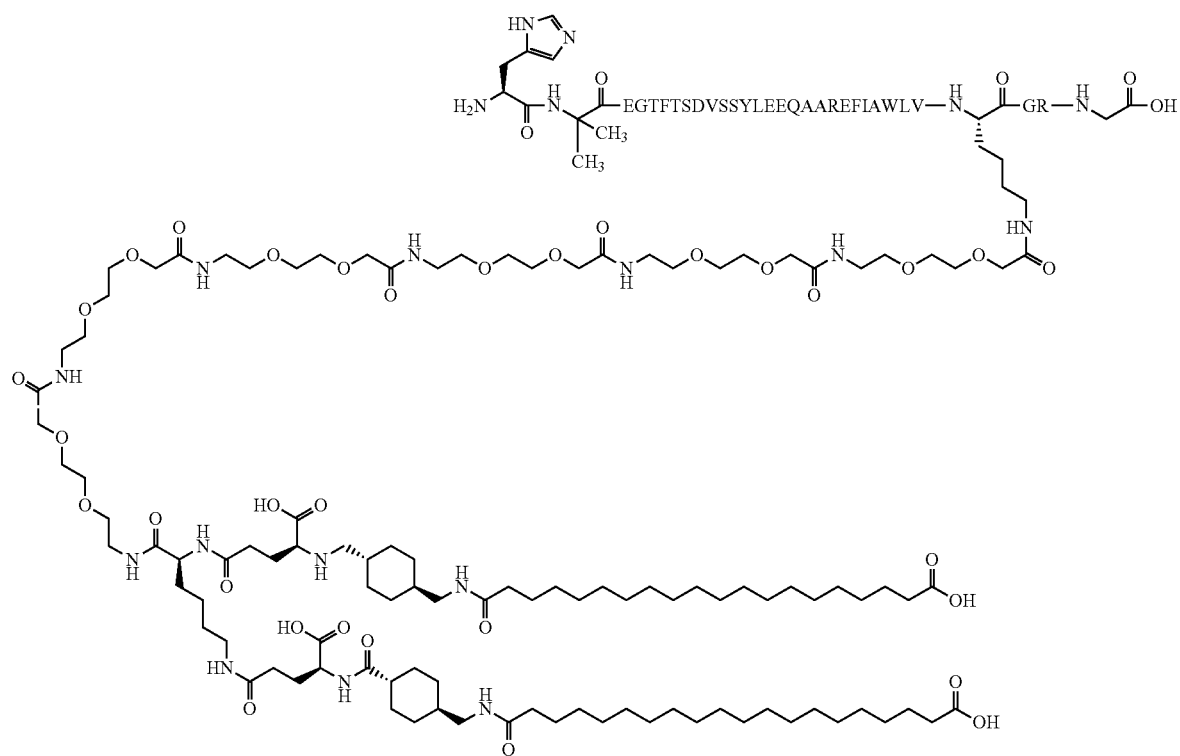

The peptide has SEQ ID NO: 5
Synthesis method: SPPS_P; SC_P; CP_M1
UPLC02: RT=11.9 min
LCMS27: RT=3.2 min, m/z: 2828 $[M+2H]^{2+}$, 1885 $[M+3H]^{3+}$, 1414 $[M+4H]^{4+}$, 1131 $[M+5H]^{5+}$

Example 17

N{Epsilon-35}-[2-[2-[2-[[2-[2-[2-[[2-[2-[2-[[2-[2-[2-[2-[2-[[2-[2-[2-[[(2S)-2,6-bis[[(4S)-4-carboxy-4-[[4-[(19-carboxynonadecanoylamino)methyl]cyclohexanecarbonyl]amino]butanoyl]amino]hexanoyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]-[Aib8,Glu22,Arg26,Arg34,Lys35]-GLP-1-(7-37)-peptide Chem. 37

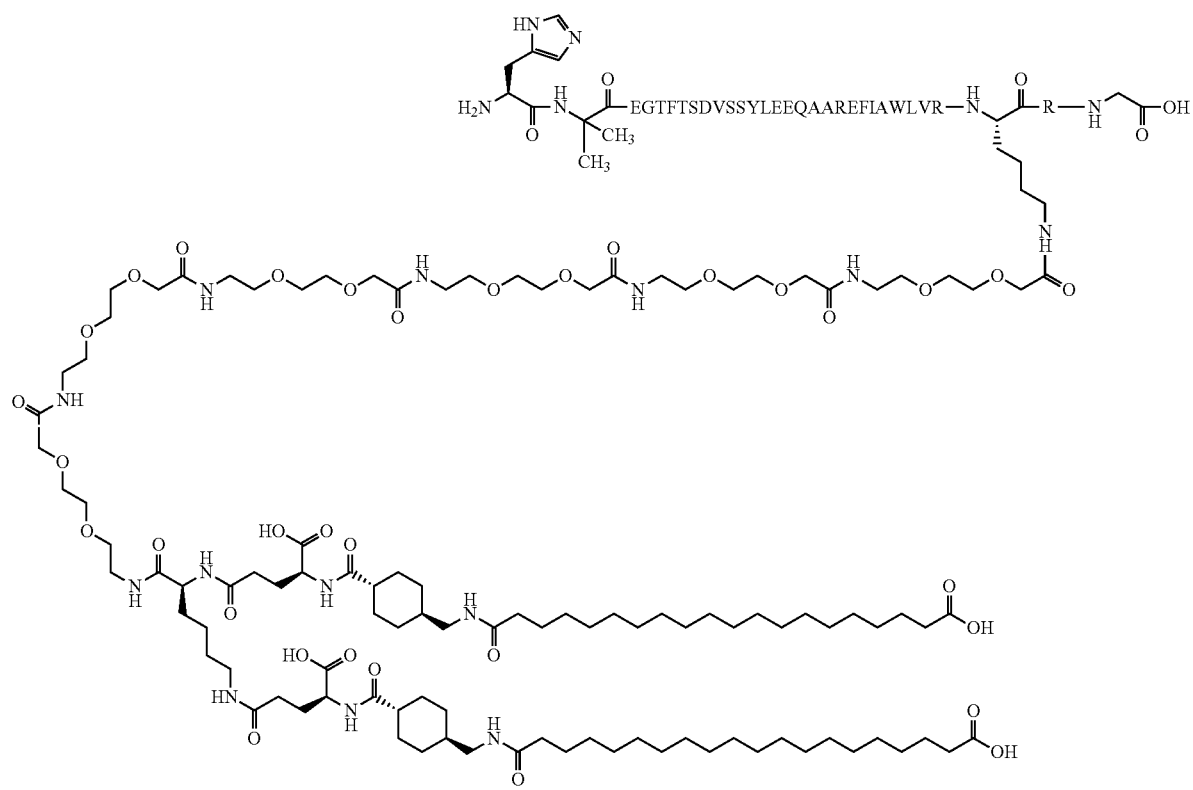

The peptide has SEQ ID NO: 6
Synthesis method: SPPS_P; SC_P; CP_M1
UPLC02: RT=11.1 min
LCMS27: RT=3.0 min, m/z: 1918 $[M+3H]^{3+}$, 1439 $[M+4H]^{4+}$, 1151 $[M+5H]^{5+}$

Example 18

N{Epsilon-36}-[2-[2-[2-[[2-[2-[2-[[2-[2-[2-[[2-[2-[2-[[2-[2-[2-[[2-[2-[[(2S)-2,6-bis[[(4S)-4-carboxy-4-[[4-[(19-carboxynonadecanoylamino)methyl]cyclohexanecarbonyl]amino]butanoyl]amino]hexanoyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]-[Aib8,Glu22,Arg26,Arg34,Lys36]-GLP-1-(7-37)-peptide

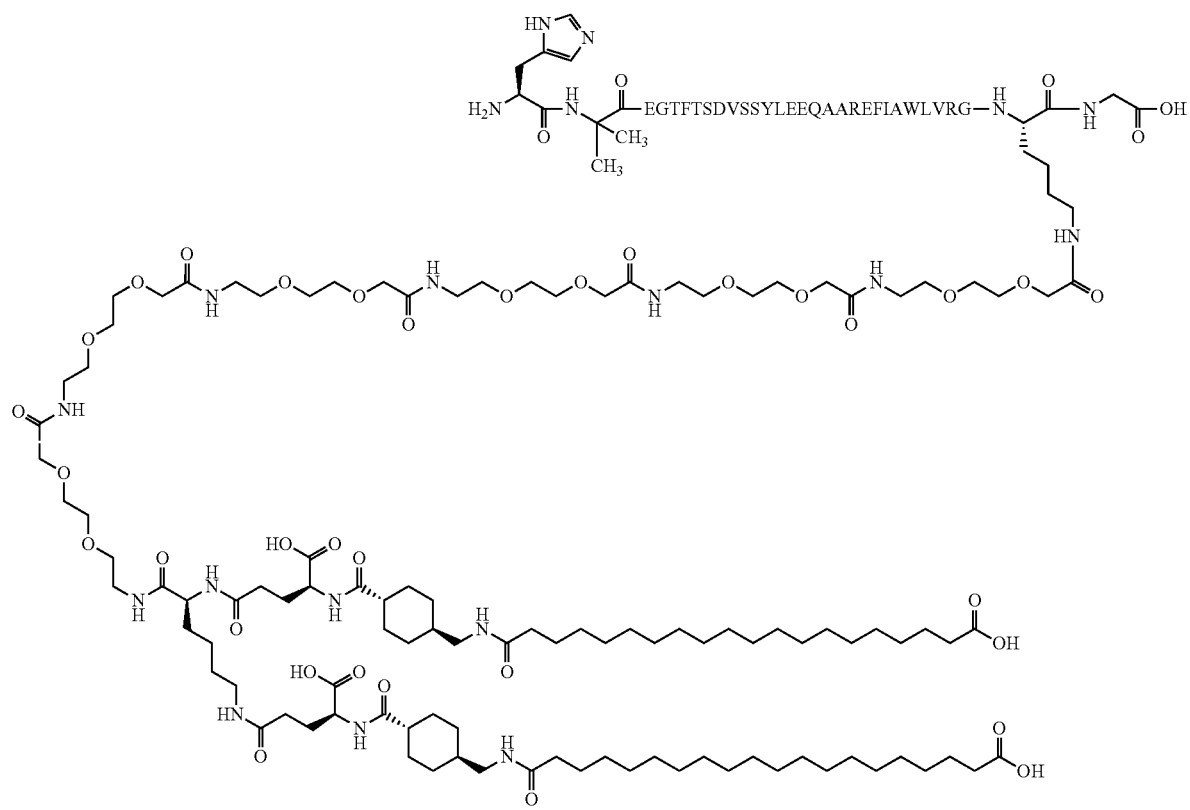

Chem. 38

The peptide has SEQ ID NO: 7
Synthesis method: SPPS_P; SC_P; CP_M1
UPLC02: RT=12.2 min
LCMS27: RT=3.2 min, m/z: 1885 [M+3H]$^{3+}$, 1414 [M+4H]$^{4+}$, 1131 [M+5H]$^{5+}$ Example 19

N{Alpha}([Aib8,Glu22,Arg26,Arg34]-GLP-1-(7-37)-peptidyl)-N{Epsilon}[2-[2-[2-[[2-[2-[2-[[2-[2-[2-[[2-[2-[2-[[2-[2-[2-[[2-[2-[2-[[(2S)-2,6-bis[[(4S)-4-carboxy-4-[[4-[(19-carboxynonadecanoylamino)methyl]cyclohexanecarbonyl]amino]butanoyl]amino]hexanoyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]Lys Chem. 39

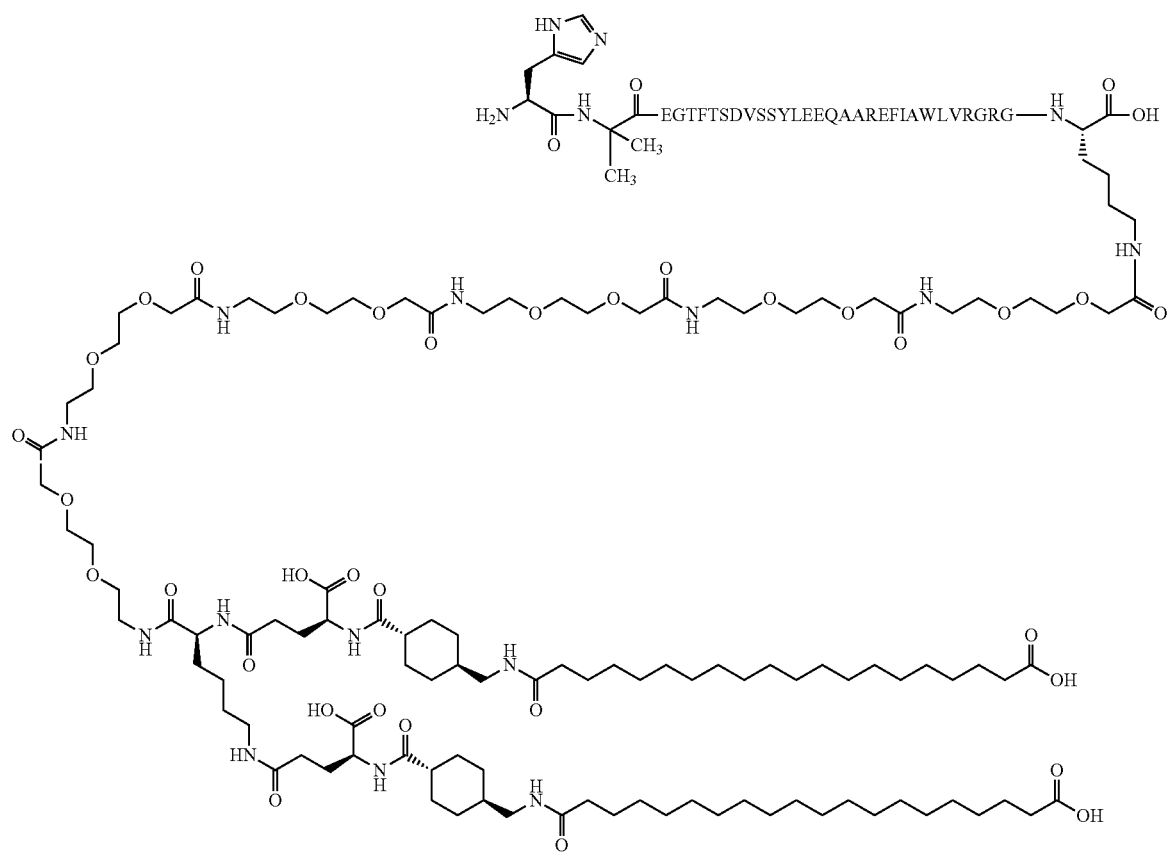

The peptide has SEQ ID NO: 8
Synthesis method: SPPS_P; SC_P; CP_M1
UPLC02: RT=11.2 min
LCMS27: RT=3.1 min, m/z: 1937 $[M+3H]^{3+}$, 1453 $[M+4H]^{4+}$, 1163 $[M+5H]^{5+}$

Example 20

N{Epsilon-34}-[2-[2-[2-[[2-[2-[2-[[2-[2-[2-[[2-[2-[2-[[2-[2-[2-[[2-[2-[[(2S)-2,6-bis[[(4S)-4-carboxy-4-[[4-[(19-carboxynonadecanoylamino)methyl]cyclohexanecarbonyl]amino]butanoyl]amino]hexanoyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]-[Aib8,Arg26]-GLP-1-(7-37)-peptide Chem. 40

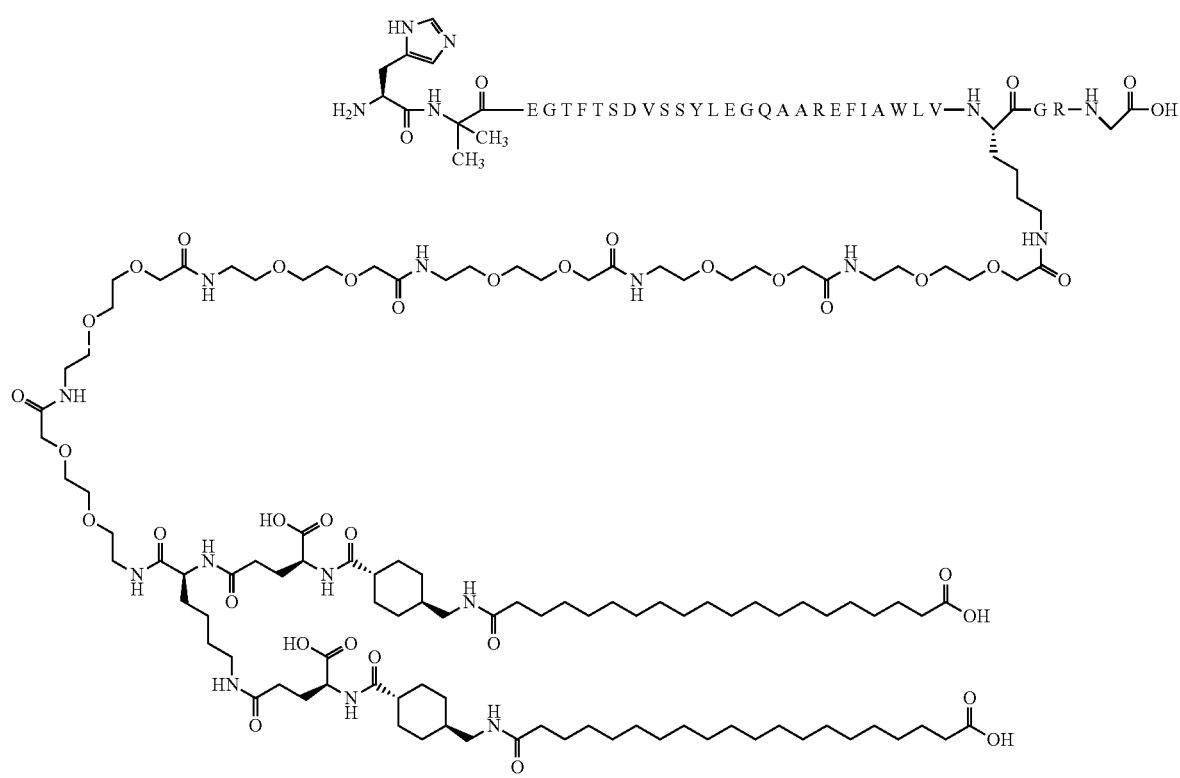

The peptide has SEQ ID NO: 9
Synthesis method: SPPS_P; SC_P; CP_M1
UPLC02: RT=12.4 min
LCMS27: RT=3.3 min, m/z: 2792 $[M+2H]^{2+}$, 1861 $[M+3H]^{3+}$, 1396 $[M+4H]^{4+}$, 1117 $[M+5H]^{5+}$ Example 21

N{Epsilon-37}-[2-[2-[2-[[2-[2-[2-[[2-[2-[2-[[2-[2-[2-[[(2S)-2,6-bis[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]hexanoyl]amino]ethoxy]ethoxy]acetyl]amino]ethoxy]ethoxy]acetyl]amino]ethoxy]ethoxy]acetyl]amino]ethoxy]ethoxy]acetyl]-[Aib8,Glu22,Arg26,Arg34,Lys37]-GLP-1-(7-37)-peptide Chem. 41

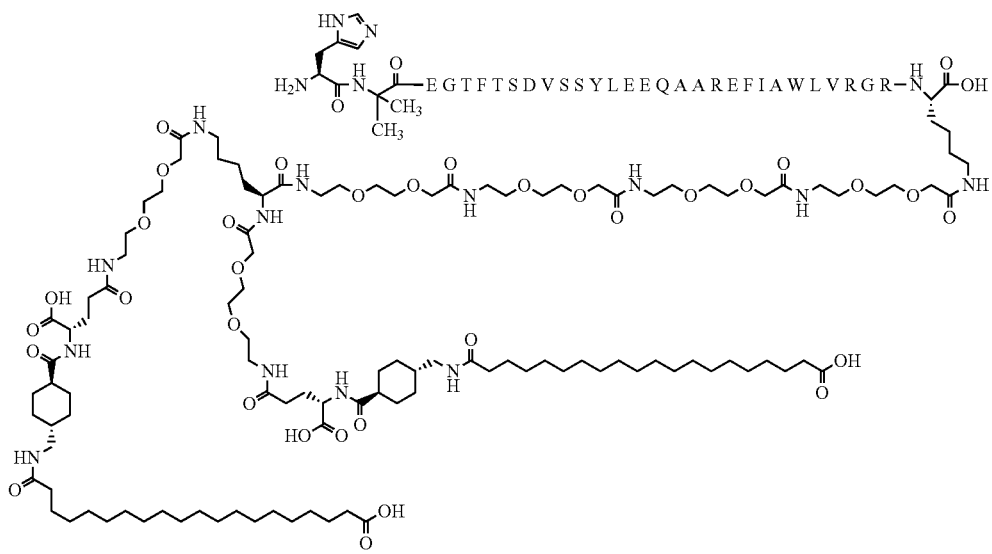

Synthesis method: SPPS_P; SC_P; CP_M1
UPLC02: RT=12.2 min
LCMS01: RT=2.5 min, m/z: 1440 [M+4H]$^{4+}$, 1152 [M+5H]$^{5+}$ Example 22

N{Epsilon-37}-[2-[2-[2-[[2-[2-[2-[[2-[2-[2-[[(2S)-2-[[2-[2-[2-[[2-[2-[2-[[2-[2-[2-[[(4R)-4-carboxy-4-[[4-[(19-carboxynonadecanoylamino)methyl]cyclo-hexanecarbonyl]amino]butanoyl]amino]ethoxy]ethoxy]acetyl]amino]ethoxy]ethoxy]acetyl]amino]ethoxy]ethoxy]acetyl]amino]-6-[[2-[2-[2-[[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]ethoxy]ethoxy]acetyl]amino]hexanoyl]amino]ethoxy]ethoxy]acetyl]amino]ethoxy]ethoxy]acetyl]amino]ethoxy]ethoxy]acetyl]-[Aib8,Glu22,Arg26,Arg34,Lys37]-GLP-1-(7-37)-peptide Chem. 42

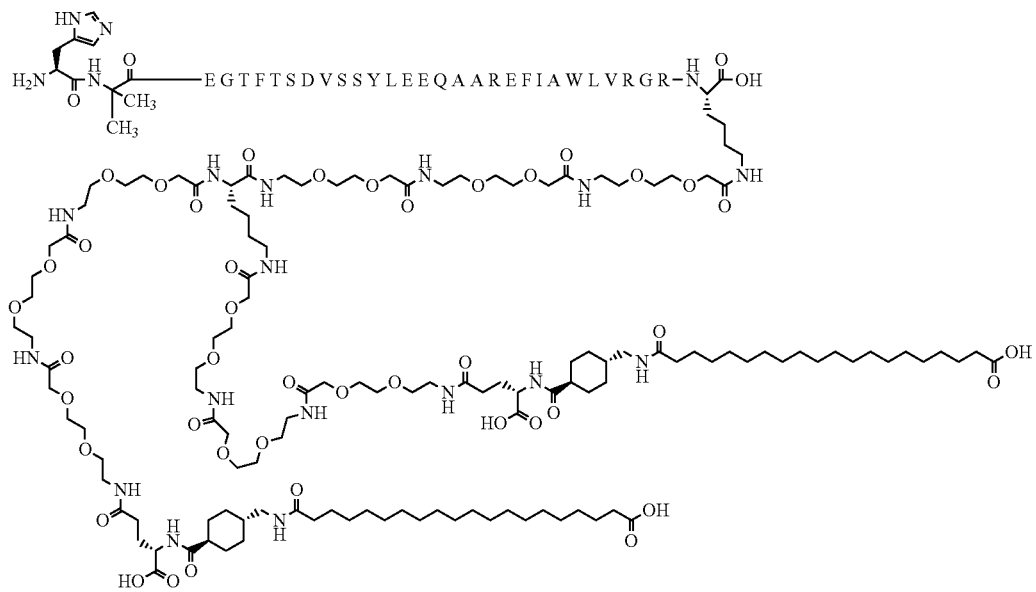

The peptide has SEQ ID NO: 2

Synthesis method: SPPS_P; SC_P; CP_M1

UPLC02: RT=11.7 min

LCMS01: RT=2.5 min, m/z: 1548 $[M+4H]^{4+}$, 1239 $[M+5H]^{5+}$

Comparative Example 1
N{Epsilon-37}-[2-[2-[2-[[(2S)-2,6-bis[[2-[2-[2-(dodecanoylamino)ethoxy]ethoxy]acetyl]amino]hexanoyl]amino]ethoxy]ethoxy]acetyl]-[Aib8,Aib22,Aib35,Lys37]-GLP-1-(7-37)-peptide Amide
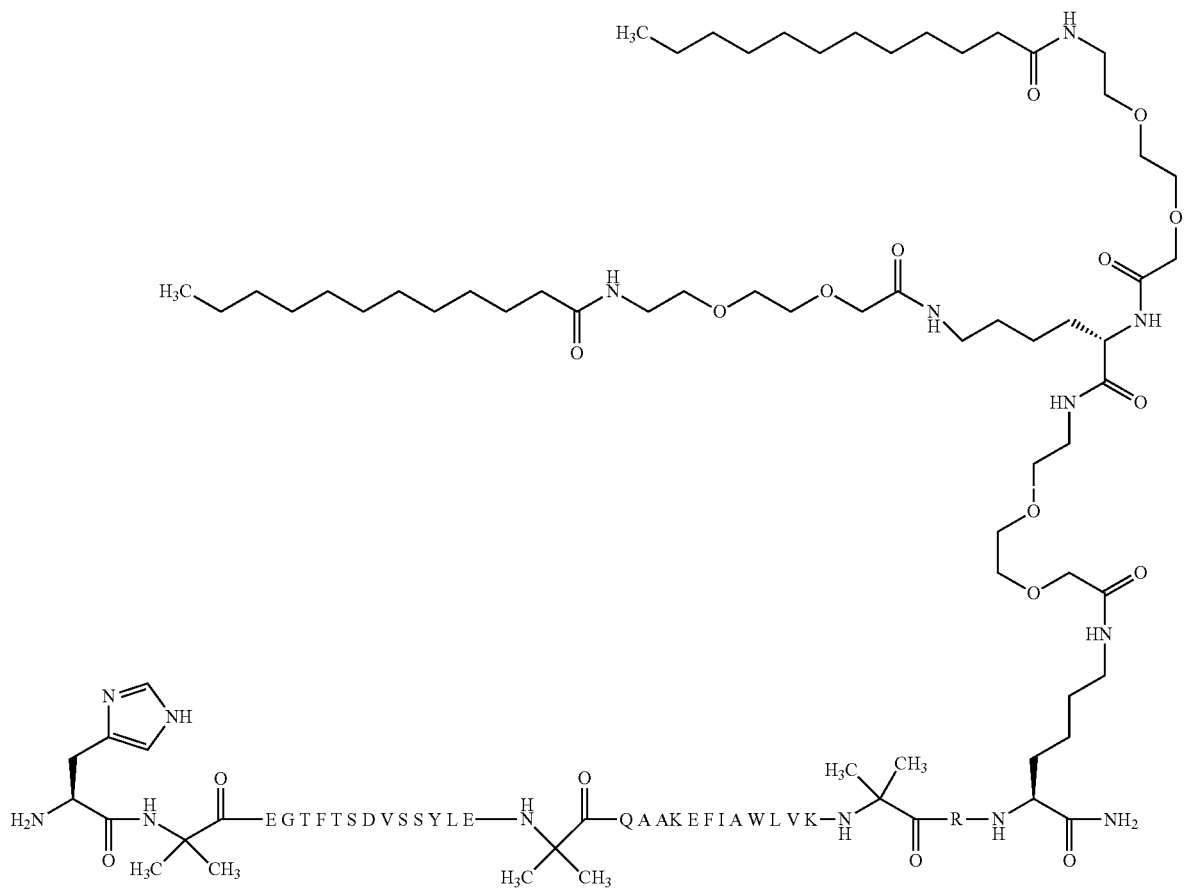
Chem. 43
The peptide has SEQ ID NO: 4
This is the compound of Example 8 of WO2005/027978 A2.
Synthesis method: SPPS_P; SC_P; CP_M1
UPLC02: Rt=11.4 min
LCMS01: Rt=2.7; m/4=1107; m/5=886

Comparative Example 2

N{Epsilon-37}-[2-[2-[2-[[(2S)-2,6-bis[[2-[2-[2-(tetradecanoylamino)ethoxy]ethoxy]acetyl]amino]hexanoyl]amino]ethoxy]ethoxy]acetyl]-[Aib8,Aib22,Aib35,Lys37]-GLP-1-(7-37)-peptide Amide

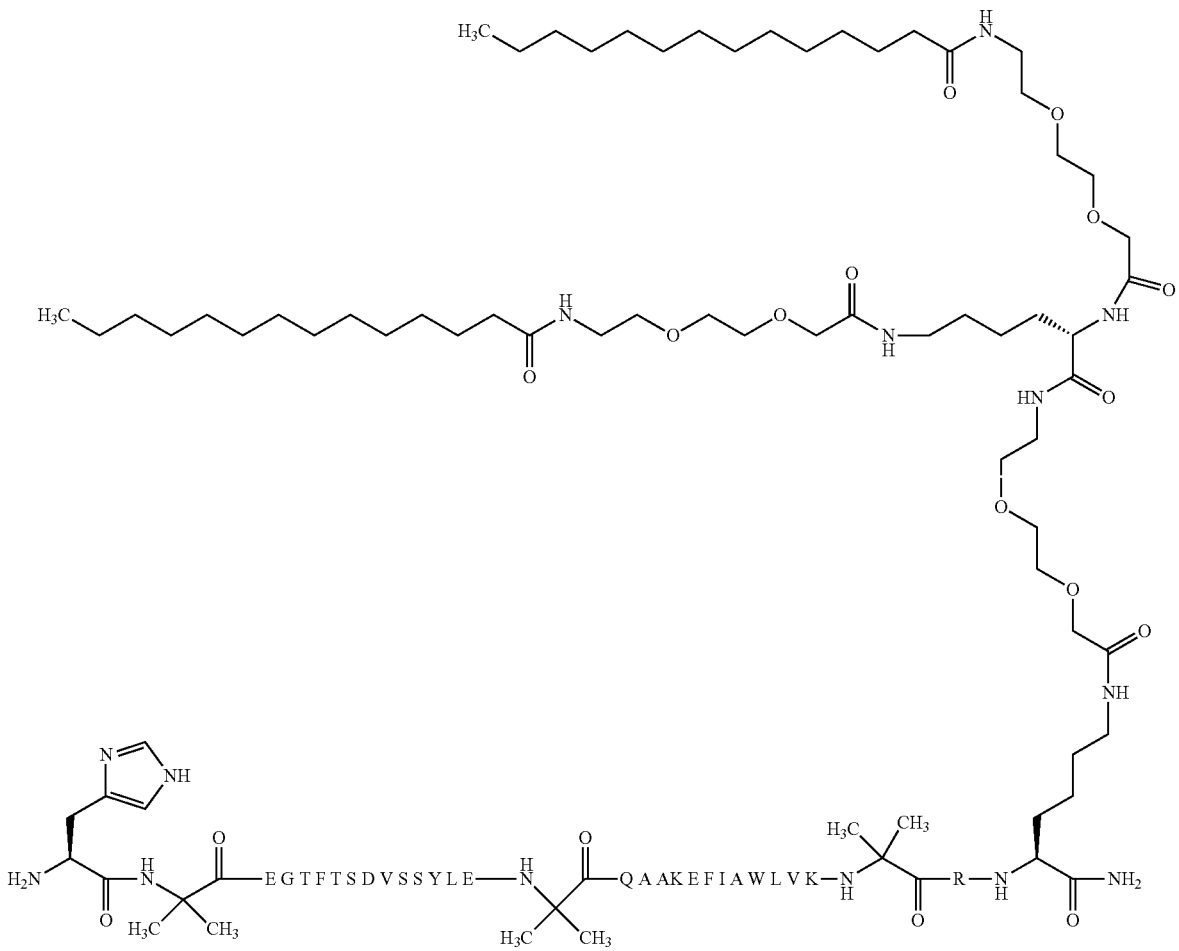

Chem. 44

The peptide has SEQ ID NO: 4
This is the compound of Example 9 of WO2005/027978 A2.
Synthesis method: SPPS_P; SC_P; CP_M1
UPLC02: Rt=12.9 min
LCMS01: Rt=2.9; m/3=1494; m/4=1121

Pharmacological Methods

Example 23: In Vitro Potency

The purpose of this example is to test the activity, or potency, of the GLP-1 derivatives in vitro. The in vitro potency is the measure of human GLP-1 receptor activation in a whole cell assay.

The potencies of the GLP-1 derivatives of Examples 1-22 and Comparative Examples 1-2 were determined as described below. Semaglutide was also included for comparison.

Principle

In vitro potency was determined by measuring the response of the human GLP-1 receptor in a reporter gene assay. The assay was performed in a stably transfected BHK cell line that expresses the human GLP-1 receptor and contains the DNA for the cAMP response element (CRE) coupled to a promoter and the gene for firefly luciferase (CRE luciferase). When the human GLP-1 receptor is activated it results in the production of cAMP, which in turn results in the luciferase protein being expressed. When assay incubation is completed the luciferase substrate (luciferin) is added and the enzyme converts luciferin to oxyluciferin to produce bioluminescence. The luminescence is measured as the readout for the assay.

Cell Culture and Preparation

The cells used in this assay (clone FCW467-12A/KZ10-1) were BHK cells with BHKTS13 as a parent cell line. The cells were derived from a clone (FCW467-12A) that expresses the human GLP-1 receptor and were established by further transfection with CRE luciferase to obtain the current clone.

The cells were cultured at 5% $CO_2$ in cell culture medium. They were aliquoted and stored in liquid nitrogen. Before each assay an aliquot was taken up and washed twice in PBS before being suspended at the desired concentration in the assay specific buffer. For 96-well plates the suspension was made to give a final concentration of $5 \times 10^3$ cells/well.

Materials

The following chemicals were used in the assay: Pluronic F-68 (10%) (Gibco 2404), human serum albumin (HSA) (Sigma A9511), ovalbumin (Sigma A5503), DMEM w/o phenol red (Gibco 11880-028), 1 M Hepes (Gibco 15630), Glutamax 100× (Gibco 35050) and steadylite plus (PerkinElmer 6016757).

Buffers

Cell culture medium consisted of DMEM medium with 10% FBS (Fetal Bovine Serum; Invitrogen 16140-071), 1 mg/ml G418 (Invitrogen 15140-122), 240 nM MTX (methotrexate; Sigma M9929) and 1% pen/strep (penicillin/streptomycin; Invitrogen 15140-122).

Assay medium consisted of DMEM w/o phenol red, 10 mM Hepes and 1χ Glutamax. The assay buffer consisted of 2% ovalbumin and 0.2% Pluronic F-68 in assay medium.

Procedure

1) Cell stocks were thawed in a 37° C. water bath.

2) Cells were washed three times in PBS.

3) Cells were counted and adjusted to $5 \times 10^3$ cells/50 μl ($1 \times 10^5$ cells/ml) in assay medium. A 50 μl aliquot of cells was transferred to each well in the assay plate.

4) Stocks of the test compounds and reference compounds were diluted to a concentration of 0.2 μM in assay buffer. Compounds were diluted 10-fold to give the following concentrations: $2 \times 10^{-7}$ M, $2 \times 10^{-8}$ M; $2 \times 10^{-9}$ M, $2 \times 10^{-10}$ M, $2 \times 10^{-11}$ M, $2 \times 10^{-12}$ M, $2 \times 10^{-13}$ M, and $2 \times 10^{-14}$ M.

5) A 50 μl aliquot of compound or blank was transferred from the dilution plate to the assay plate. Compounds were tested at the following final concentrations: $1 \times 10^{-7}$ M, $1 \times 10^{-8}$ M; $1 \times 10^{-9}$ M, $1 \times 10^{-10}$ M, $1 \times 10^{-11}$ M, $1 \times 10^{-12}$ M, $1 \times 10^{-13}$ M, and $1 \times 10^{-14}$ M.

6) The assay plate was incubated for 3 h in a 5% $CO_2$ incubator at 37° C.

7) The assay plate was removed from the incubator and allowed to stand at room temperature for 15 min.

8) A 100 μl aliquot of steadylite plus reagent was added to each well of the assay plate.

9) Each assay plate was covered with aluminum foil to protect it from light and shaken for 30 min at room temperature.

10) Each assay plate was read in a BioTek Synergy 2 Multi-Mode Reader.

Calculations and Results

The data from the BioTek Synergy 2 Multi-Mode Reader were transferred to GraphPad Prism software. The software performs a non-linear regression (log(agonist) vs. response (three parameters)). $EC_{50}$ values which were calculated by the software and reported in pM are shown in Table 1 below.

A minimum of two replicates was measured for each sample. The reported $EC_{50}$ values are averages of all of the measured values for each compound.

TABLE 1

| In vitro potency | |
|---|---|
| Example no. | $EC_{50}$ (pM) |
| 1 | 77 |
| 2 | 70 |
| 3 | 160 |
| 4 | 110 |
| 5 | 53 |
| 6 | 150 |
| 7 | 79 |
| 8 | 72 |
| 9 | 120 |
| 10 | 150 |
| 11 | 130 |
| 12 | 57 |
| 13 | 47 |
| 14 | 19 |
| 15 | 48 |
| 16 | 19 |
| 17 | 20 |
| 18 | 37 |
| 19 | 71 |
| 20 | 36 |
| 21 | 38 |
| 22 | 12 |
| Comparative Example 1 | 14 |
| Comparative Example 2 | 16 |
| semaglutide | 8.3 |

All compounds have potency data that confirms that they are GLP-1 receptor agonists.

Example 24: GLP-1 Receptor Binding

The purpose of this example is to test the receptor binding of the GLP-1 derivatives in vitro. The receptor binding is a measure of affinity of a derivative for the human GLP-1 receptor.

Principle

The receptor binding of the GLP-1 derivatives of Examples 1-22 and Comparative Examples 1-2 to the human GLP-1 receptor was measured in a competitive binding assay. In this type of assay a labelled ligand (in this case $^{125}$I-GLP-1) is bound to the receptor. Each derivative is added in a series of concentrations to isolated membranes containing the human GLP-1 receptor and displacement of the labelled ligand is monitored. The receptor binding is reported as the concentration at which half of the labelled ligand is displaced from the receptor, the $IC_{50}$ value. Semaglutide was included as comparative compound. In order to test the binding of the derivatives to albumin, the assay is performed in a low concentration of human serum albumin (HSA) (max. 0.001% final assay concentration as well as in the presence of a considerably higher concentration of HSA (2.0% final assay concentration). An increase of the $IC_{50}$ value in the presence of HSA indicates an affinity to serum albumin and represents a method to predict a protracted pharmacokinetic profile of the test substance in animal models. Semaglutide was included for comparison.

Materials

The following chemicals were used in the assay: Human serum albumin (HSA) (Sigma A1653), DMEM w/o phenol red (Gibco 11880-028), Pen/strep (Invitrogen 15140-122), G418 (Invitrogen 10131-027), 1 M Hepes (Gibco 15630), EDTA (Invitrogen 15575-038), PBS (Invitrogen 14190-094), fetal calf serum (Invitrogen 16140-071), EGTA, $MgCl_2$ (Merck 1.05832.1000), Tween 20 (Amresco 0850C335), SPA particles (wheat germ agglutinin (WGA)

SPA beads, Perkin Elmer RPNQ0001), [$^{125}$I]-GLP-1]-(7-36)NH$_2$ (produced in-house), OptiPlate™-96 (Packard 6005290).

Buffer 1 consisted of 20 mM Na-HEPES plus 10 mM EDTA and pH was adjusted to 7.4. Buffer 2 consisted of 20 mM Na-HEPES plus 0.1 mM EDTA and pH was adjusted to 7.4. Assay buffer consisted of 50 mM HEPES supplemented with 5 mM EGTA, 5 mM MgCl$_2$, 0.005% Tween 20 and pH was adjusted to 7.4. An 8% albumin stock consisted of HSA dissolved at 8% (w/v) in assay buffer. An 0.02% albumin stock consisted of HSA dissolved at 0.02% (w/v) in assay buffer.

Cell Culture and Membrane Preparation

The cells used in this assay (clone FCW467-12A) were BHK cells with BHKTS13 as a parent cell line. The cells express the human GLP-1 receptor.

The cells were grown at 5% CO$_2$ in DMEM, 10% fetal calf serum, 1% Pen/Strep (Penicillin/Streptomycin) and 1.0 mg/ml of the selection marker G418.

To make a membrane preparation the cells were grown to approximately 80% confluence. The cells were washed twice in phosphate-buffered saline and harvested. The cells were pelleted using a brief centrifugation and the cell pellet was kept on ice. The cell pellet was homogenised with ULTRA-THURRAX™ dispersing instrument for 20-30 seconds in a suitable amount of buffer 1 (e.g., 10 ml). The homogenate was centrifuged for 15 minutes. The pellet was re-suspended (homogenised) in 10 ml buffer 2 and centrifuged. This step was repeated once more. The resulting pellet was re-suspended in buffer 2 and the protein concentration was determined. The membranes were aliquoted and stored at minus 80° C.

Procedure

1. For the receptor binding assay in the presence of low HSA (0.005%) 50 µl of the assay buffer was added to each well of an assay plate. Assay continued with step 3.
2. For the receptor binding assay in the presence of high HSA (2%) 50 µl of the 8% albumin stock was added to each well of an assay plate. Assay continued with step 3.
3. Test compounds were serially diluted to give the following concentrations: 8×10$^{-7}$ M, 8×10$^{-8}$ M, 8×10$^{-9}$ M, 8×10$^{-10}$ M, 8×10$^{-11}$ M, 8×10$^{-12}$ M and 8×10$^{-13}$ M. Twenty-five µl were added to appropriate wells in the assay plate.
4. Cell membrane aliquots were thawed and diluted to their working concentration. Fifty µl were added to each well in the assay plate.
5. WGA SPA beads were suspended in assay buffer at 20 mg/ml. The suspension was diluted to 10 mg/ml in assay buffer just prior to addition to the assay plate. Fifty µl were added to each well in the assay plate.
6. The incubation was started by adding 25 µl of 480 pM solution of [$^{125}$I]-GLP-1]-(7-36)NH$_2$ to each well of the assay plate. A 25 µl aliquot was reserved for measuring total counts/well.
7. The assay plate was incubated for 2 h at 30° C.
8. The assay plate was centrifuged for 10 min.
9. The assay plate was read in a Packard TopCount NXT instrument.

Calculations

The data from the TopCount instrument were transferred to Graph Pad Prism software. Individual replicates were analysed using non-linear regression. IC$_{50}$ values were calculated by the software and reported in nM. The reported values are averages of all of the measured values for each compound.

Results

The following results were obtained:

TABLE 2

| | GLP-1 receptor binding | |
|---|---|---|
| Example no | Low HSA IC$_{50}$ (nM) | High HSA IC$_{50}$ (nM) |
| 1 | 1.2 | 140 |
| 2 | 0.56 | 49 |
| 3 | 1.2 | 180 |
| 4 | 0.78 | 51 |
| 5 | 0.91 | 9.7 |
| 6 | 1.0 | 140 |
| 7 | 0.57 | 54 |
| 8 | 1.1 | 45 |
| 9 | 1.8 | 150 |
| 10 | 19 | 120 |
| 11 | 1.5 | 150 |
| 12 | 0.63 | 17 |
| 13 | 0.17 | 32 |
| 14 | 0.42 | 27 |
| 15 | 0.87 | 48 |
| 16 | 0.72 | 88 |
| 17 | 0.64 | 77 |
| 18 | 0.68 | 24 |
| 19 | 0.69 | 34 |
| 20 | 1.6 | 74 |
| 21 | 1.5 | 19 |
| 22 | 1.4 | 63 |
| Comparative Example 1 | 0.27 | 0.13 |
| Comparative Example 2 | 1.2 | 0.52 |
| semaglutide | 0.59 | 420 |

All compounds show a very good binding to the GLP-1 receptor in the absence of albumin.

Example 25: Pharmacokinetic Study in Minipigs

The purpose of this study is to determine the protraction in vivo of the GLP-1 derivatives after i.v. administration to minipigs, i.e. the prolongation of their time in the body and thereby their time of action. This is done in a pharmacokinetic (PK) study, where the terminal half-life of the derivative in question is determined. By terminal half-life is meant the time it takes to halve a certain plasma concentration in the terminal elimination phase.

The derivatives of Examples 7, 8, and 13, and Comparative Examples 1 and 2 were dosed 5 nmol/kg. The derivatives of Examples 12, 14, and 15 were dosed 2 nmol/kg. The derivatives of Examples 1 and 2 were dosed 15 nmol/kg. Semaglutide was included for comparison (dosed 1.5 nmol/kg).

Male Göttingen minipigs were obtained from Ellegaard Göttingen Minipigs (Dalmose, Denmark) approximately 7-14 months of age and weighing approximately 16-35 kg were used in the studies. The minipigs were housed either individually (pigs with permanent catheters) or in a group and fed restrictedly once or twice daily with SDS minipig diet (Special Diets Services, Essex, UK).

After at least 2 weeks of acclimatisation two permanent central venous catheters were implanted in vena cava caudalis or cranialis in each animal. The animals were allowed 1 week recovery after the surgery, and were then used for repeated pharmacokinetic studies with a suitable wash-out period between successive GLP-1 derivative dosings.

The GLP-1 derivatives of Examples 1, 2, 7, 8, 12, and 14 were dissolved in 50 mM sodium phosphate, 70 mM sodium chloride, 0.05% polysorbate 80, pH 7.4. The GLP-1 derivative of Examples 13 and 15 were dissolved in 50 mM sodium phosphate, 70 mM sodium chloride, 0.05% polysorbate 80, pH 8.0. The derivative of Example 2 was dissolved in 50 mM sodium phosphate, 145 mM sodium chloride, 0.05% polysorbate 80, pH 7.4. The GLP-1 derivatives of Comparative Examples 1 and 2 were dissolved in 2 mM sodium acetate, 250 mM glycerol and 0.025% polysorbate 20, pH 4.0. All to a concentration of usually from 20-60 nmol/ml of the GLP-1 derivative in question, except for the compound of Example 2 which was formulated to a concentration of 160 nmol/ml. Semaglutide was dissolved to 15 nmol/ml in 50 mM sodium phosphate, 145 mM sodium chloride, 0.05% polysorbate 20, pH 7.4.

Intravenous injections (the volume corresponding to for example 0.050-0.125 ml/kg) of the compounds were given through one catheter or through the venflon, and blood was sampled at predefined time points for up till 25 days post dosing (preferably through the other catheter or by venipuncture). Blood samples (for example 0.8 ml) were collected in EDTA buffer (8 mM) and then centrifuged at 4° C. and 1942G for 10 minutes.

Plasma was pipetted into Micronic tubes on dry ice, and kept at −20° C. until analysed for plasma concentration of the respective GLP-1 compound using LOCI. Individual plasma concentration-time profiles were analyzed by a non-compartmental pharmacokinetic method in Phoenix v. 6.3 (Pharsight Inc., Mountain View, Calif., USA), or other relevant software for PK analysis, and the resulting terminal half-lives (harmonic mean) determined.

Results

TABLE 3

Pharmacokinetic study in minipigs (i.v.)

| Example no. | Terminal half-live (h) |
|---|---|
| 1 | 162 |
| 2 | 130 |
| 7 | 134 |
| 8 | 145 |
| 12 | 142 |
| 13 | 119 |
| 14 | 135 |
| 15 | 142 |
| Comparative Example 1 | 3 |
| Comparative Example 2 | 3 |
| semaglutide | 55 |

The tested derivatives of the invention have very long terminal half-lives (at least twice that of semaglutide, and at least thirty-five times that of the comparative example compounds).

Example 26: Pharmacodynamic Study in Rats

The purpose of the study is to verify the acute effect of the GLP-1 derivatives on food intake (FI) and body weight (BW) in lean rodents.

The GLP-1 derivatives of Examples 7-8, 12-19, and 21 were tested in a single-dose study in lean Sprague Dawley male rats as described in the following. The derivatives were tested at a dose of 50 nmol/kg (Examples 7-8, 15-19, and 21) or at 100 nmol/kg (Examples 12-14).

Six lean male Sprague Dawley rats (~300 g) per compound to be tested (from Taconic, Denmark), fed from birth with the diet NIH31 (NIH 31M Rodent Diet, commercially available from Taconic Farms, Inc., US, see www.taconic.com), were enrolled for the study at the age of approximately 10 weeks. Upon arrival the rats had a chip inserted in the dorsal neck region to be used for registration in the HM2 automatic food intake system (Ellegaard systems A/S, Denmark). The rats were given free access to standard chow (e.g. Altromin 1324, Brogaarden, Denmark) and tap water and kept at approximately 22° C. Rats were housed three per cage and after 1-2 weeks of acclimatisation, they were dosed according to BW. After dosing FI and BW were daily recorded for a duration of 144 hours. After the experiment the rats were euthanised.

The animals were grouped to receive s.c. treatment as follows: Vehicle or GLP-1 derivative, where vehicle was 50 mM sodium phosphate, 70 mM sodium chloride, 0.05% polysorbate 80, pH 7.4 (Examples 7-8, 12, 14-15), or 50 mM phosphate, 70 mM sodium chloride, 0.05% polysorbate 80, pH 8.0 (Example 13).

The GLP-1 derivatives were dissolved in the vehicle to a dosing concentration of 50 nmol/ml (Examples 7-8, 15-19, and 21) or 100 nmol/ml (Examples 12-14). Animals were dosed once, at the start of the experiment, s.c. with a dose-volume of 1 ml/kg (i.e. 300 μl per 300 g rat).

The day before dosing FI and BW was recorded in all groups and used as baseline. On the day of dosing the GLP-1 derivative was dosed at approximately 10 am (time 0). On the following days, FI was continuously recorded using an automatic food and water recording system (HM2, see above) and BW was determined once daily. Rats were weighed individually on a digital weighing scale (accuracy 0.1 g).

The data are presented as percent change in FI or BW measured at the 48 h time point. For example, the percent change in FI at 48 h for each individual is calculated as follows: [[(food intake at 48 h)−(baseline food intake)]/ (baseline food intake)]×100%], where baseline FI refers to the level before the administration of any treatment−and vice versa for the BW change. A negative value refers to a % reduction.

The following results were obtained (averages of all individual determinations corresponding to the respective treatment):

TABLE 4

Pharmacodynamic study in rats

| Example no. | % change in food intake | % change in body weight |
|---|---|---|
| 7 | −16 | +2 |
| 8 | −19 | −1 |
| 12 | −58 | −8 |
| 13 | −74 | −10 |
| 14 | −63 | −9 |
| 15 | −64 | −7 |
| 16 | −21 | 0 |
| 17 | +5 | +1 |
| 18 | −13 | 0 |
| 19 | −45 | −4 |
| 21 | −43 | −4 |

The results show that after a single s.c. injection of either 50 nmol/kg or 100 nmol/kg the tested derivatives are biologically active in vivo as they reduce food intake (except for the compound of Example 17) as well as body weight (except for the compounds of Examples 7, 16, 17 and 18). It is noted that the compounds of Examples 7, 16, 17 and 18 were tested in the lower dose. On an added note food intake is a much more direct measure of bioactivity than is body weight as this is a single dose experiment.

Example 27: Pharmacodynamic Study in db/db Mice

The purpose of the study is to verify the acute effect of the GLP-1 derivatives on blood glucose (BG) and body weight (BW) in a diabetic setting.

The GLP-1 derivatives of Examples 2-4 and 6-10 were tested in a single-dose study in an obese, diabetic mouse model (db/db mice) as described in the following. The derivatives were tested at a dose of 3 nmol/kg (Example 1), 10 nmol/kg (Examples 3-4 and 6-10), or 30 nmol/kg (Examples 2, 12, and 14).

Six db/db mice per compound to be tested (from Taconic, Denmark), fed from birth with the diet NIH31 (NIH 31M Rodent Diet, commercially available from Taconic Farms, Inc., US, see www.taconic.com), were enrolled for the study at the age of approximately 10 weeks. At arrival to the animal facility the mice were given free access to standard chow (e.g. Altromin 1324, Brogaarden, Denmark) and tap water and kept at 24° C. After 1-2 weeks of acclimatisation, the basal blood glucose was assessed twice on two consecutive days (i.e. at 9 am). The mice were allocated to treatment groups based on matching blood glucose levels and body weights. The mice were used in experiments with a duration of 96 hours (Examples 1, 3-4, and 6-10) or up to 240 hours (Examples 2, 12, and 14), and were re-used for up to 2 times. After the last experiment the mice were euthanised.

The animals were grouped to receive treatment as follows: Vehicle, s.c., or GLP-1 derivative, s.c. The vehicle was either 50 mM sodium phosphate, 70 mM sodium chloride, 0.05% polysorbate 80, pH 7.4 (Examples 1-4, 6-9, 12, and 14), or 2 mM sodium acetate, 250 mM glycerol, 0.025% polysorbate 20, pH 4.0 (Example 10). The GLP-1 derivative was dissolved in the vehicle, to a dosing concentration of 0.5-5 nmol/ml dependent on the respective dose. Animals were dosed once, at the start of the experiment, s.c. with a dose-volume of 6 ml/kg (i.e. 300 µl per 50 g mouse).

On the day of dosing, blood glucose was assessed at time −½ h (8.30 am), the mice were weighed after this. The GLP-1 derivative was dosed at approximately 9 am (time 0). On the day of dosing, blood glucose was assessed at times 1, 2, 4 and 8 h (10 am, 11 am, 1 pm and 5 pm) after dosing.

On the following days, the blood glucose was assessed at time 24 h, 48 h, 72 h, and 96 h (all Example compounds), and for the GLP-1 derivatives of Examples 2, 12, and 14 blood glucose was further assessed daily up to 240 h after dosing. On each day, the mice were weighed following blood glucose sampling.

The mice were weighed individually on a digital weighing scale.

Samples for the measurement of blood glucose were obtained from the tail tip capillary of conscious mice. Blood, 10 µl, was collected into heparinised capillaries and transferred to 500 µl glucose buffer (EKF system solution, Eppendorf, Germany). The glucose concentration was measured using the glucose oxidase method (glucose analyser Biosen 5040, EKF Diagnostic, GmbH, Germany). The samples were kept at room temperature for up to 1 h until analysis. If analysis had to be postponed, samples were kept at 4° C. for a maximum of 24 h.

The data are presented as percent change in blood glucose or body weight measured at the 48 h time points. For example, the percent change in blood glucose level at 48 h for each individual is calculated as follows: [[(blood glucose level at 48 h)−(basal blood glucose level)]/(basal blood glucose level)]×100%], where basal blood glucose level refers to the level before the administration of any treatment–and vice versa for the body weight change. A negative value refers to a % reduction.

The following results were obtained (averages of all individual determinations corresponding to the respective treatment):

TABLE 5

Effect on blood glucose and body weight in db/db mice

| Example no. | % change in blood glucose | % change in body weight |
| --- | --- | --- |
| 1 | −7 | −2 |
| 2 | −42 | −4 |
| 3 | −37 | −2 |
| 4 | −42 | −5 |
| 6 | −21 | −2 |
| 7 | −36 | −3 |
| 8 | −46 | −5 |
| 9 | −11 | −4 |
| 10 | −3 | −3 |
| 12 | −46 | −5 |
| 14 | −60 | −5 |

The results show that all derivatives tested have effect in vivo by decreasing BG as well as BW after 48 h, after a single s.c. injection of either 3 nmol/kg, 10 nmol/kg, or 30 nmol/kg. The effect on BG of the compounds of Examples 1 and 10 is not as pronounced, however these compounds were also tested in the lower doses of 3 and 10 nmol/kg, respectively.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A derivative of a GLP-1 analogue of Formula I:

Formula I:
(SEQ ID NO: 10)
Xaa$_7$-Xaa$_8$-Glu-Gly-Thr-Xaa$_{12}$-Thr-Ser-Asp-Xaa$_{16}$-Ser- Xaa$_{18}$-Xaa$_{19}$-Xaa$_{20}$-Glu-Xaa$_{22}$-Xaa$_{23}$-Ala-Xaa$_{25}$-Xaa$_{26}$-Xaa$_{27}$-

Phe-Ile-Xaa$_{30}$-Xaa$_{31}$-Leu-Xaa$_{33}$-Xaa$_{34}$-Xaa$_{35}$-Xaa$_{36}$-Xaa$_{37}$-

Xaa$_{38}$-Xaa$_{39}$, wherein
Xaa$_7$ is L-histidine, (S)-2-Hydroxy-3-(1H-imidazol-4-yl)-propionic acid, D-histidine, deamino-histidine, homo-histidine, N$^\alpha$-acetyl-histidine, N$^\alpha$-formyl-histidine, N$^\alpha$-methyl-histidine, 3-pyridylalanine, 2-pyridylalanine, or 4-pyridylalanine;

Xaa$_8$ is Ala, Gly, Ser, Aib, (1-aminocyclopropyl) carboxylic acid, or (1-aminocyclobutyl) carboxylic acid;
Xaa$_{12}$ is Phe or Leu;
Xaa$_{16}$ is Val or Leu;
Xaa$_{18}$ is Ser, Val, Arg, or Leu;
Xaa$_{19}$ is Tyr or Gln;
Xaa$_{20}$ is Leu or Met;
Xaa$_{22}$ is Gly or Glu;
Xaa$_{23}$ is Gln, Glu, or Arg;
Xaa$_{25}$ is Ala or Val;
Xaa$_{26}$ is Arg;
Xaa$_{27}$ is Glu or Leu;
Xaa$_{30}$ is Ala, Glu, or Arg;
Xaa$_{31}$ is Trp or His;
Xaa$_{33}$ is Val;
Xaa$_{34}$ is Lys, Arg, His, Asn, or Gln;
Xaa$_{35}$ is Lys, Gly, or Ala;

Xaa$_{36}$ is Lys, Arg, or Gly;
Xaa$_{37}$ is Gly, Pro, or Lys;
Xaa$_{38}$ is Lys, Gly, or absent;
Xaa$_{39}$ is Lys or absent;
  wherein at least one of Xaa$_{34}$, Xaa$_{35}$, Xaa$_{36}$, Xaa$_{37}$, Xaa$_{38}$, and Xaa$_{39}$ is Lys;
which derivative comprises a side chain that is attached to the Lys residue of Xaa$_{34}$, Xaa$_{35}$, Xaa$_{36}$, Xaa$_{37}$, Xaa$_{38}$, or Xaa$_{39}$,
which side chain comprises:
(i) a Branched linker of Chem. 11:

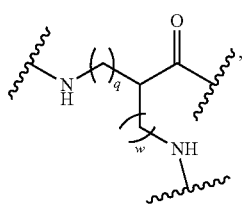

Chem. 11 wherein q is an integer in the range of 0-5, w is an integer in the range of 0-5, with the provisos that when w is 0 q is an integer in the range of 1-5, and when q is 0 w is an integer in the range of 1-5; and
(ii) a 1$^{st}$ and a 2$^{nd}$ Protractor of Chem. 12:

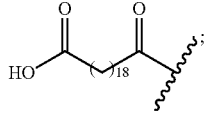

Chem. 12 wherein the Branched linker is connected
  a) at its —CO end to the epsilon amino group of the Lys residue of Xaa$_{34}$, Xaa$_{35}$, Xaa$_{36}$, Xaa$_{37}$, Xaa$_{38}$, or Xaa$_{39}$, via a Pre-linker, and
  b) at each of its two —NH ends to the —CO end of each of the 1$^{st}$ and 2$^{nd}$ Protractor, respectively, via a 1$^{st}$ and a 2$^{nd}$ Post-linker, respectively;
wherein each of the Pre-linker, the 1$^{st}$ Post-linker, and the 2$^{nd}$ Post-linker comprises a —CO group and an —NH group;
or a pharmaceutically acceptable salt, amide, or ester thereof.

2. The derivative of claim 1, wherein the GLP-1 analogue has a maximum of 10 amino acid changes as compared to the sequence of GLP-1(7-37) (SEQ ID NO: 1).

3. The derivative of claim 1, wherein the Pre-linker comprises at least one Linker element-1 of Chem. 1:

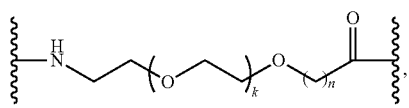

Chem. 1 wherein k is an integer in the range of 1-19, and n is an integer in the range of 1-5; and/or at least one Linker element-2 of Chem. 2b:

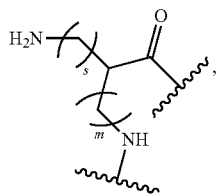

Chem. 2b wherein m is an integer in the range of 0-5, s is an integer in the range of 0-5, and with the provisos that when m is 0 s is an integer in the range of 1-5, and when s is 0 m is an integer in the range of 1-5.

4. The derivative of claim 1, wherein each of the 1$^{st}$ and the 2$^{nd}$ Post-linker comprises a Linker element-3 of Chem. 3:

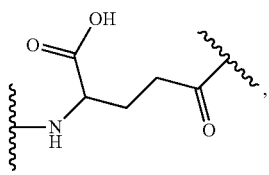

Chem. 3 and/or
a Linker element-4 of Chem. 4:

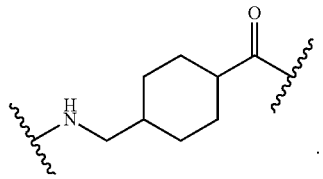

Chem 4

5. The derivative of claim 1, wherein each of the 1$^{st}$ and the 2$^{nd}$ Post-linker optionally comprises at least one Linker element-1 of Chem. 1:

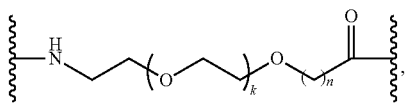

Chem. 1 wherein k is an integer in the range of 1-19, and n is an integer in the range of 1-5.

6. The derivative of claim 3, wherein Chem. 2b is represented by Chem. 2c:

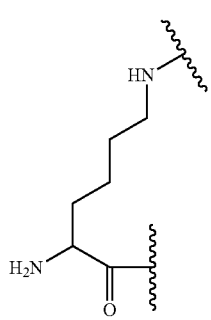

Chem. 2c

7. A GLP-1 derivative selected from
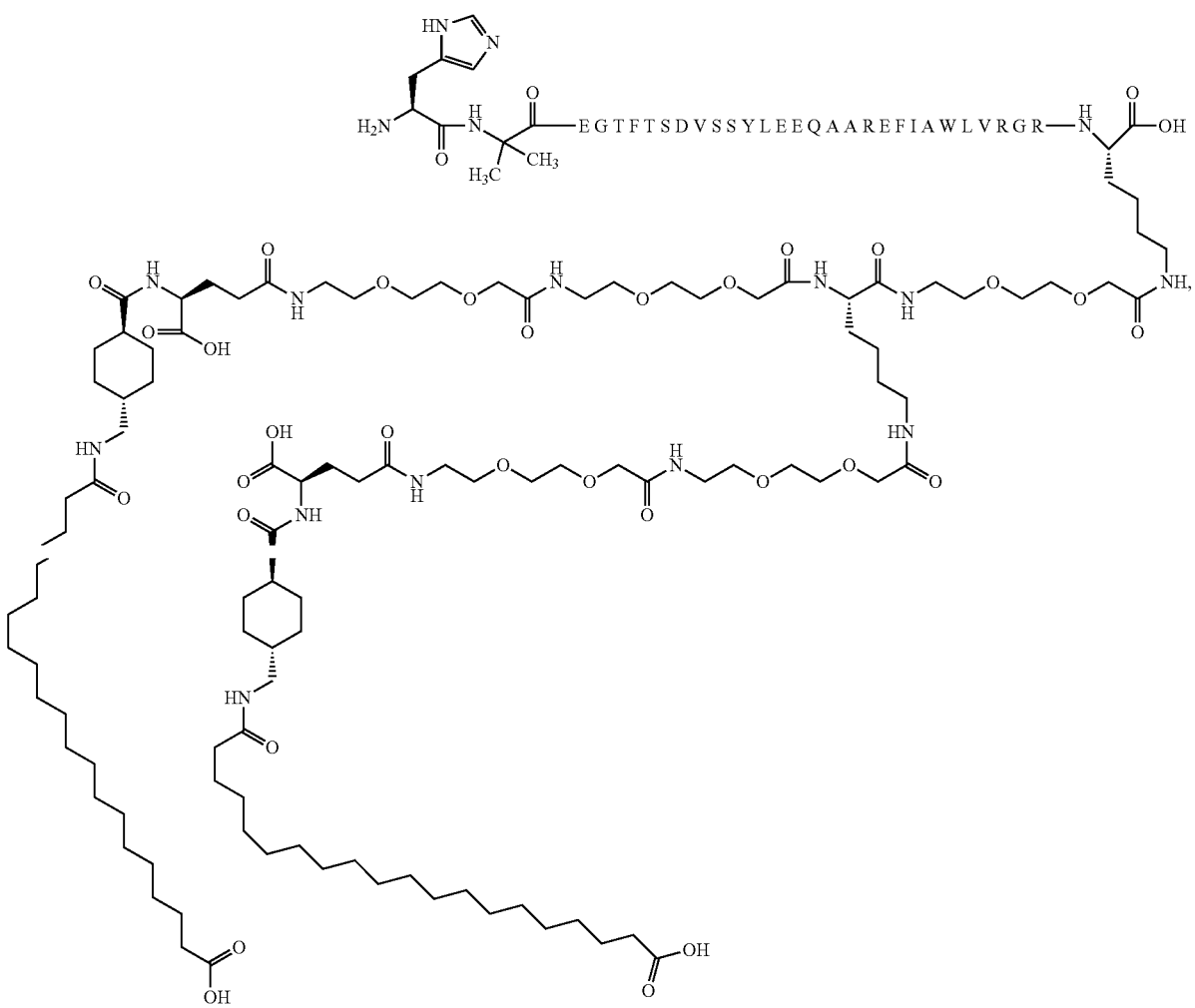
Chem. 21
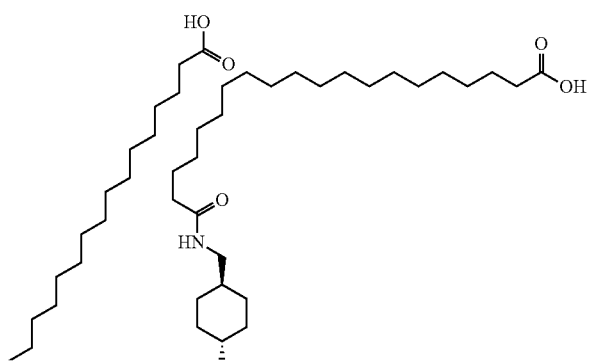
Chem. 22

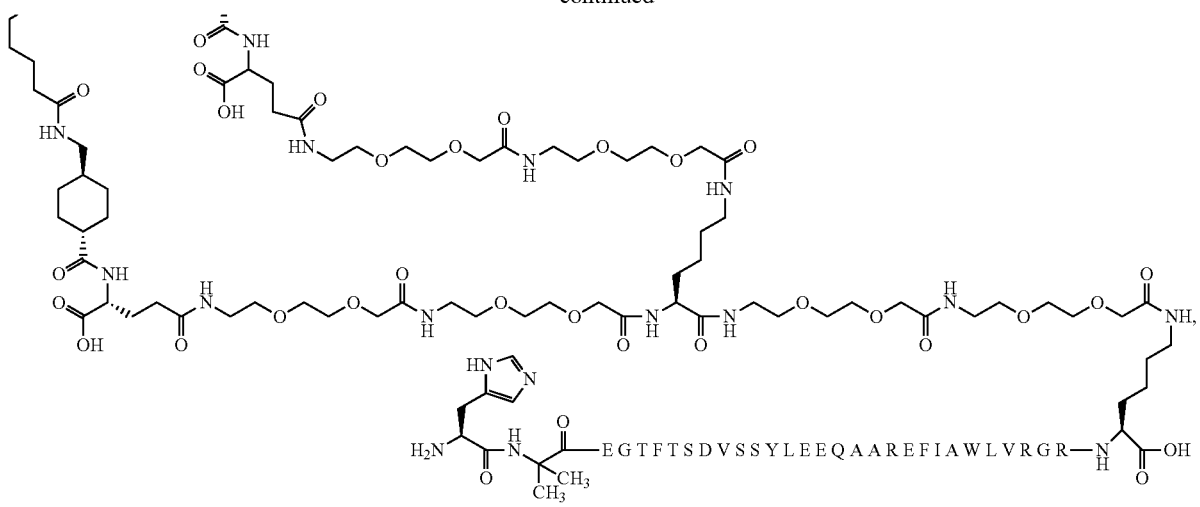
Chem. 23
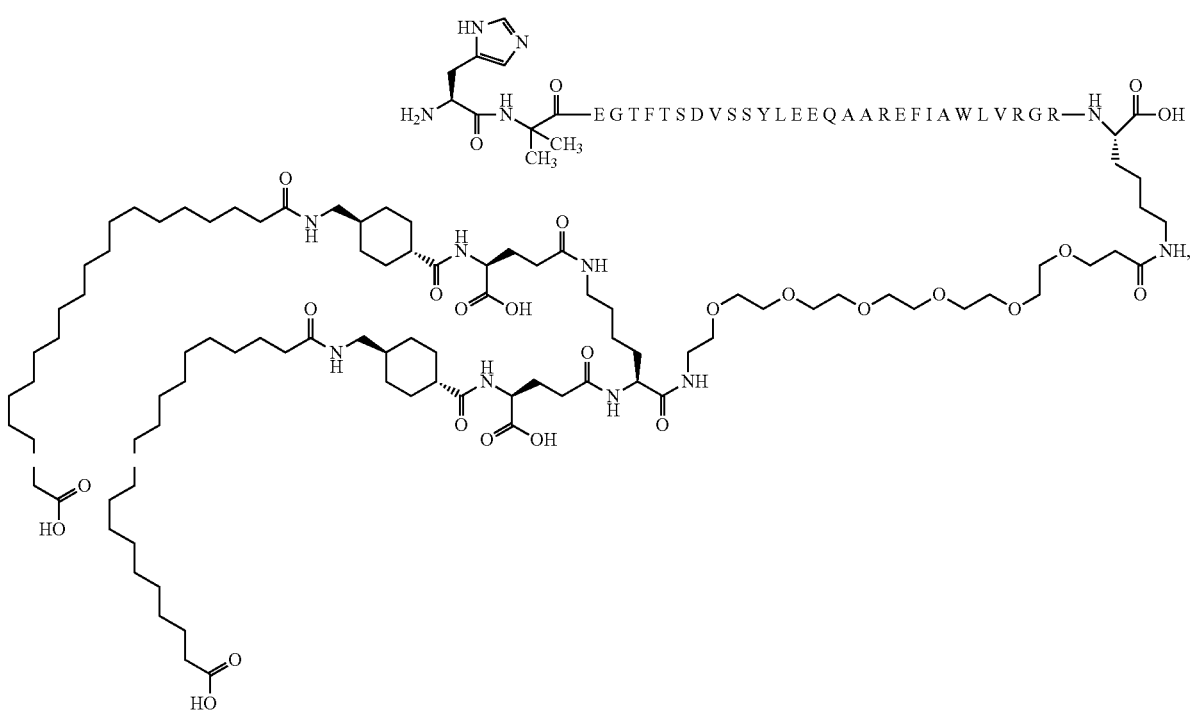
Chem. 24
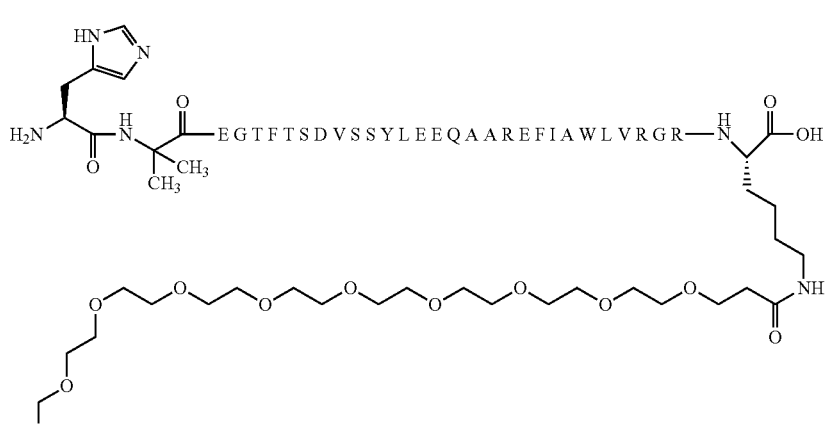

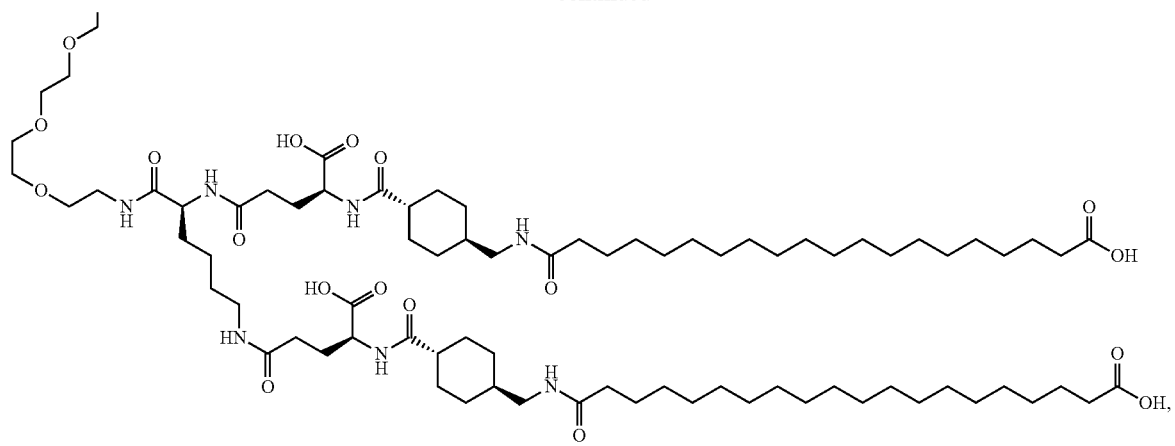
Chem. 25
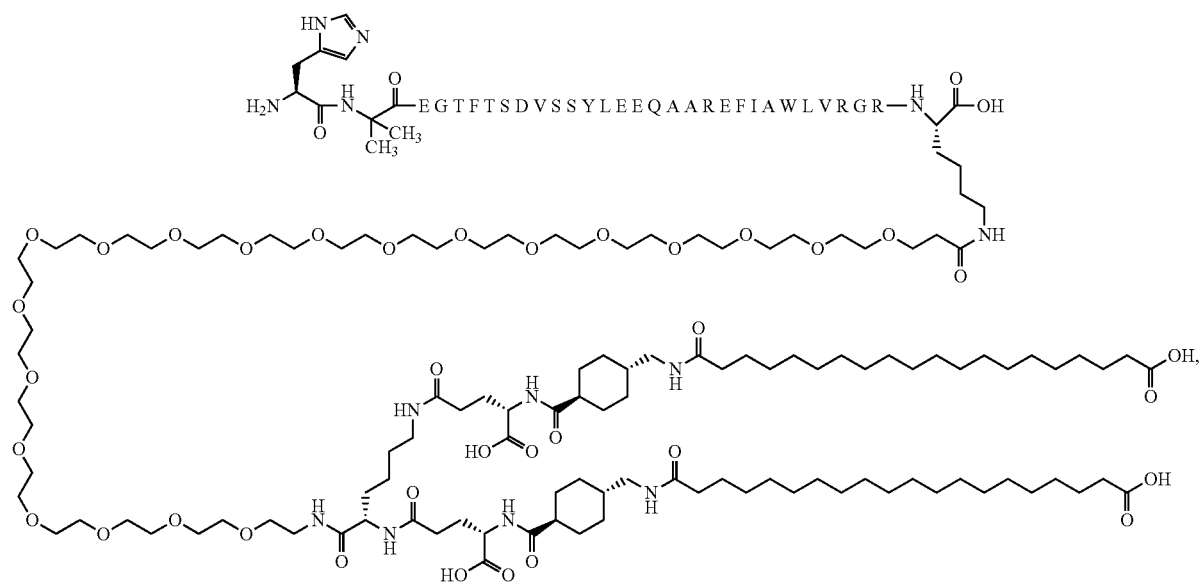
Chem. 26
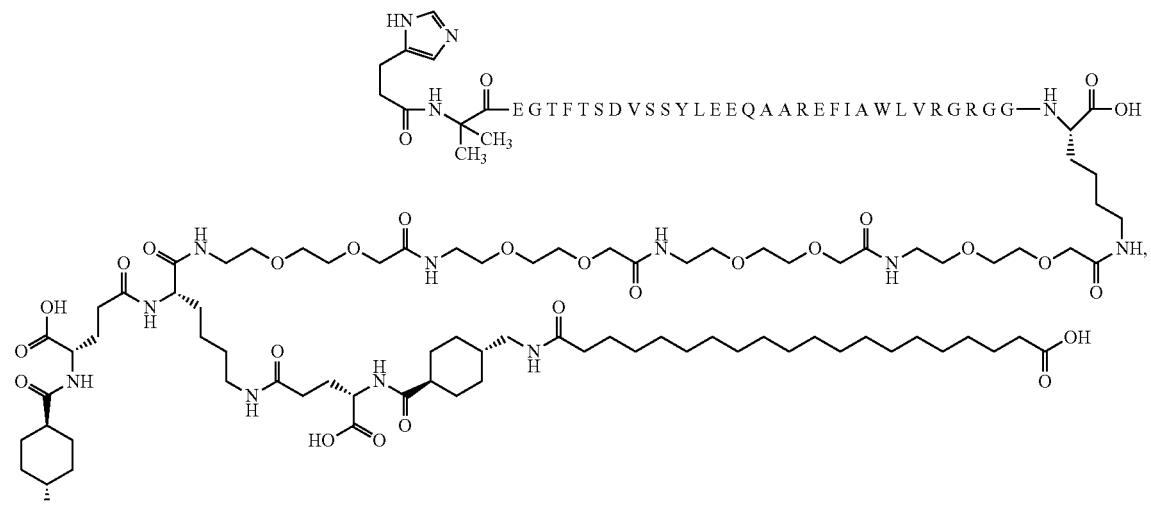

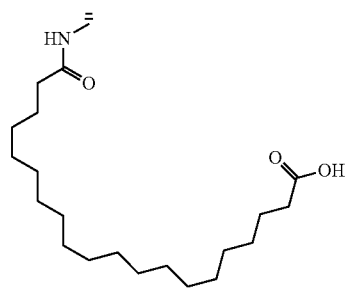
Chem. 27
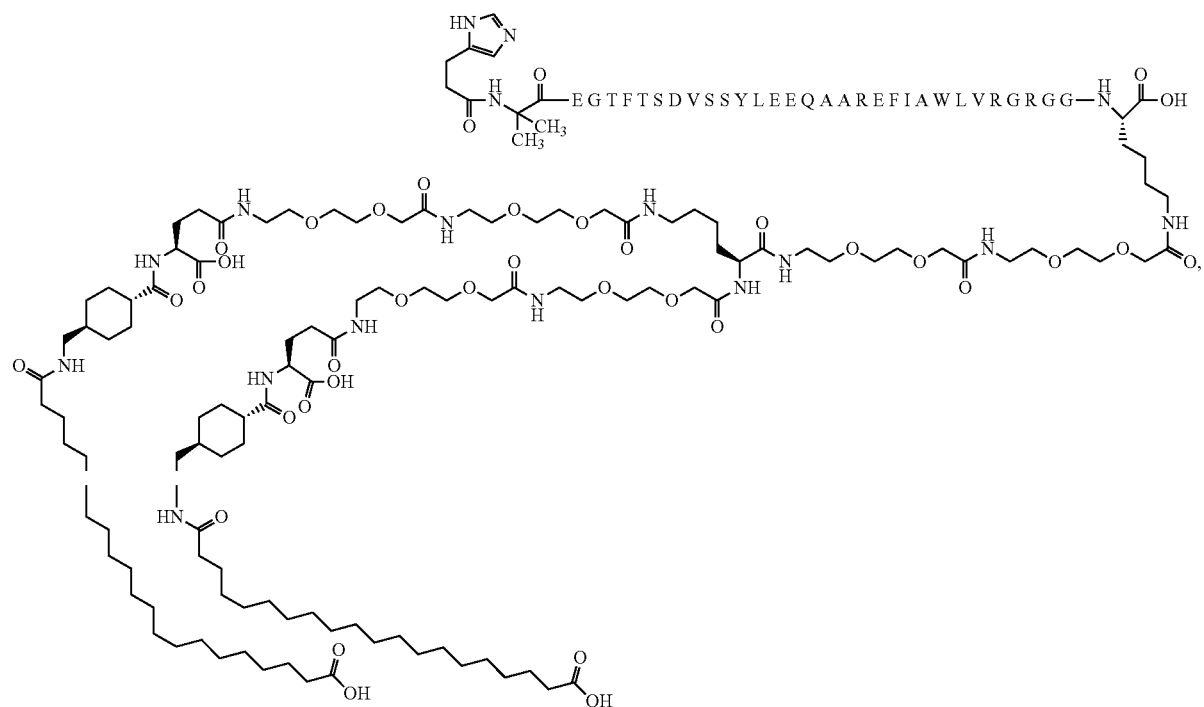
Chem. 28
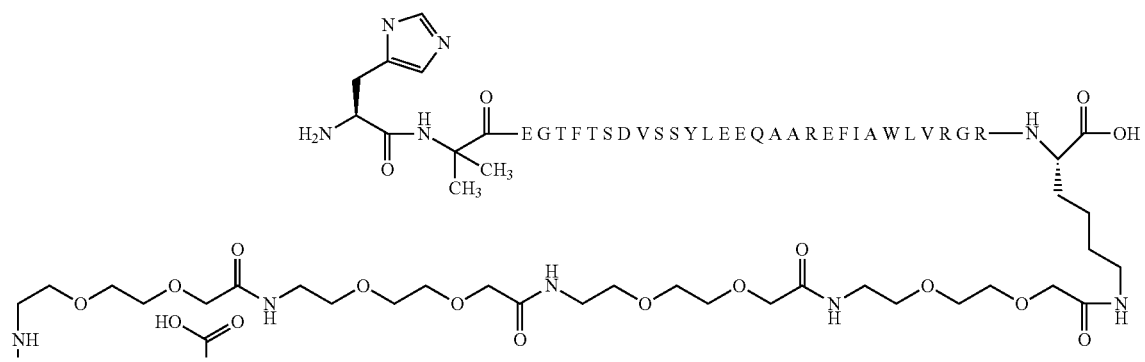

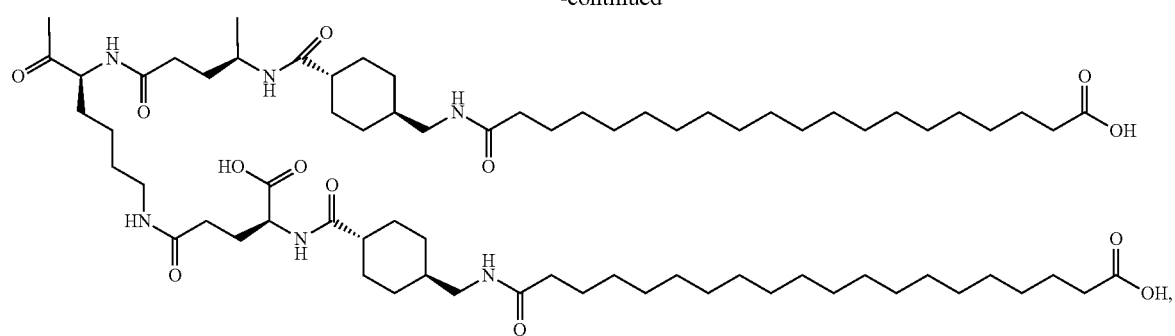
Chem. 29
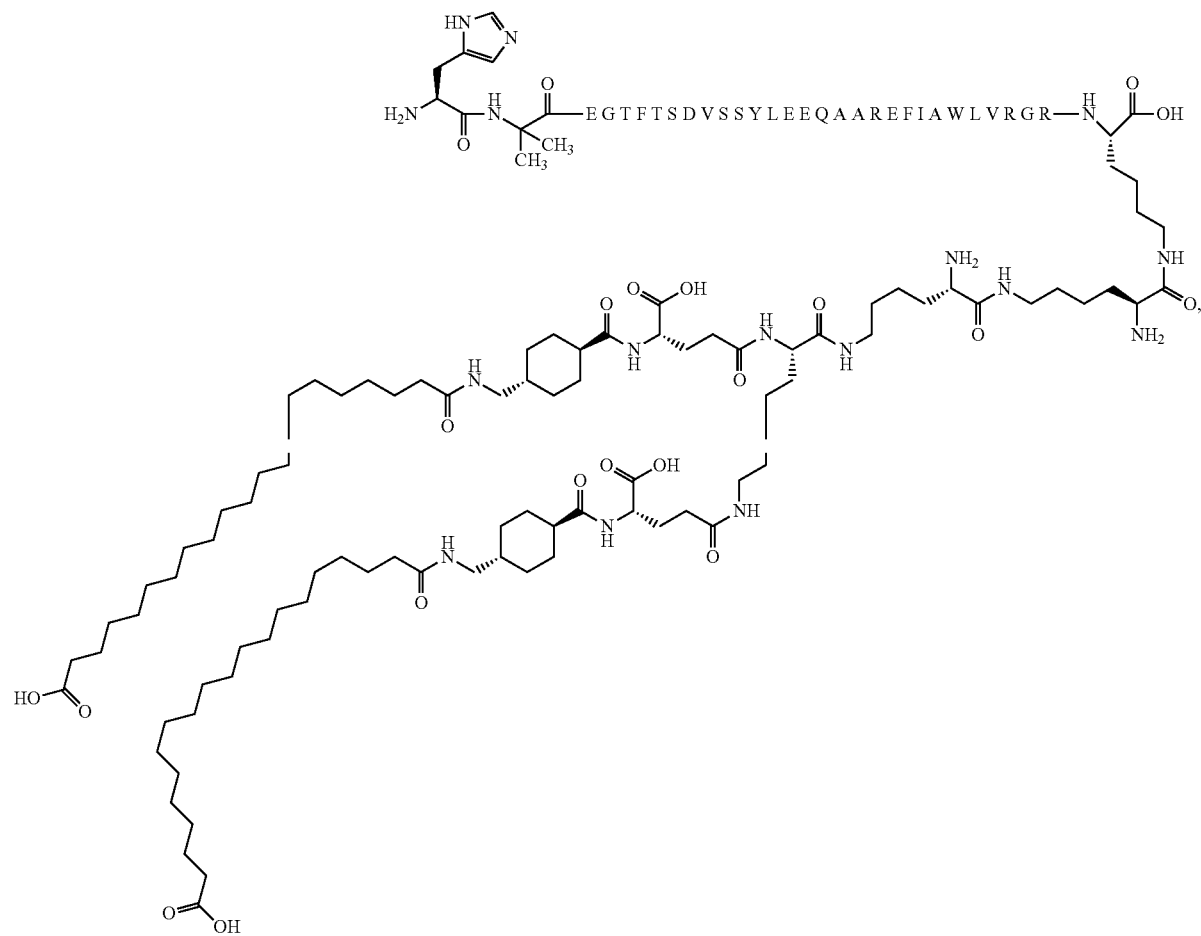

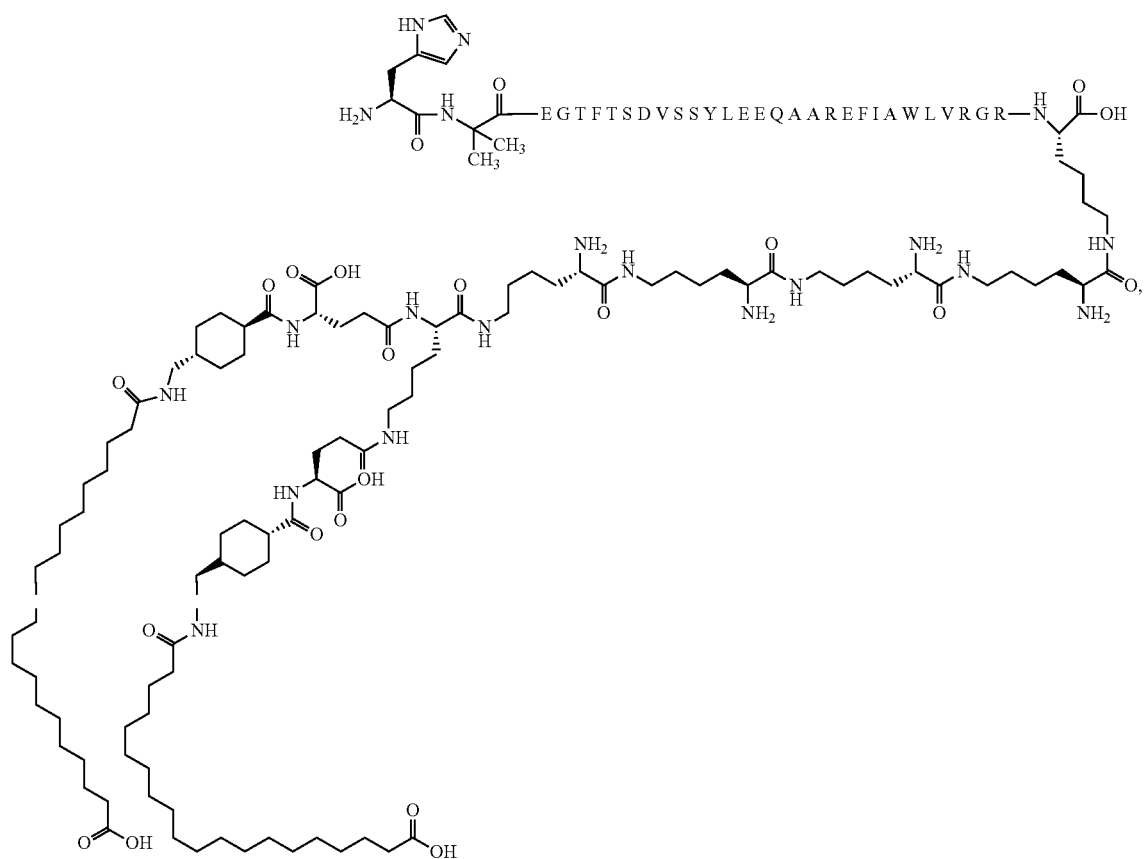
Chem. 30
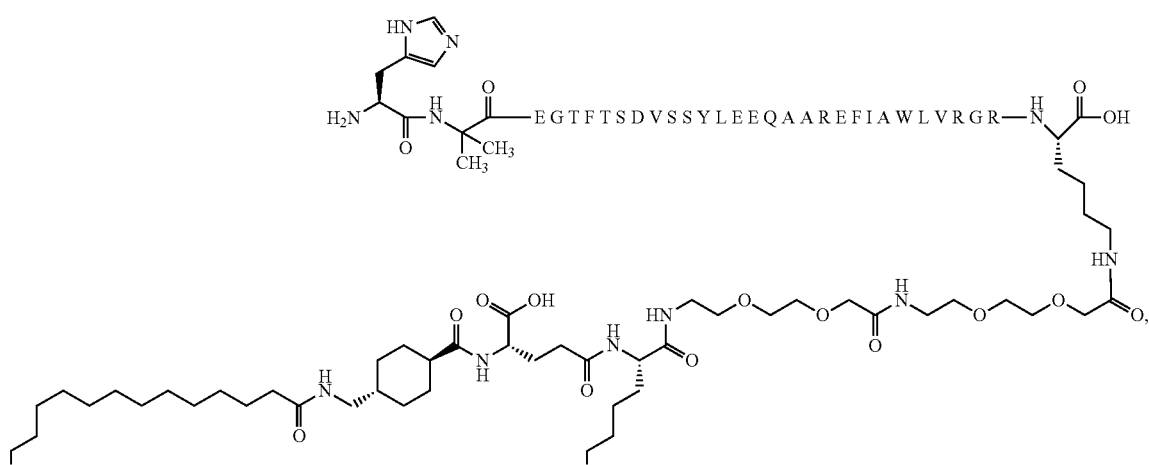
Chem. 31

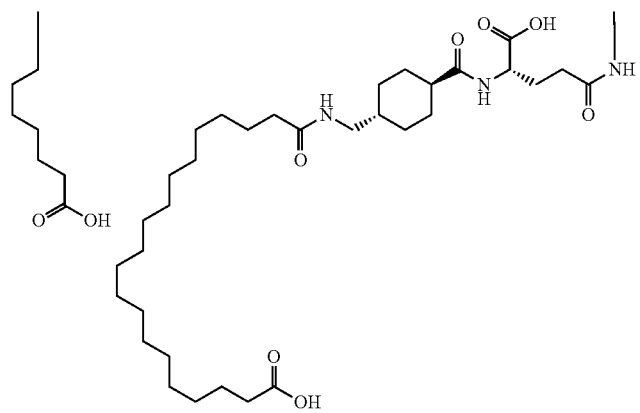
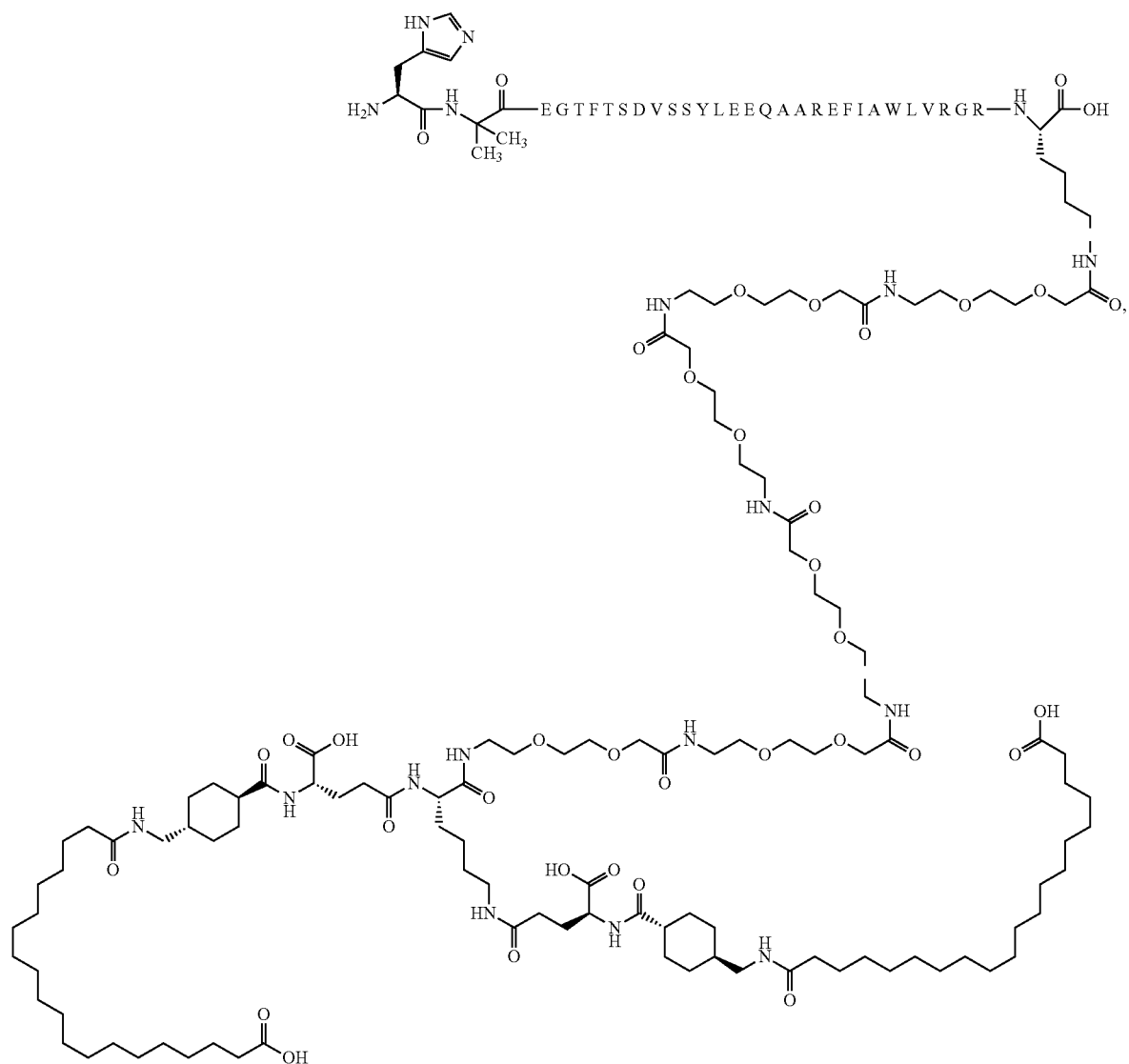
Chem. 32

Chem. 33
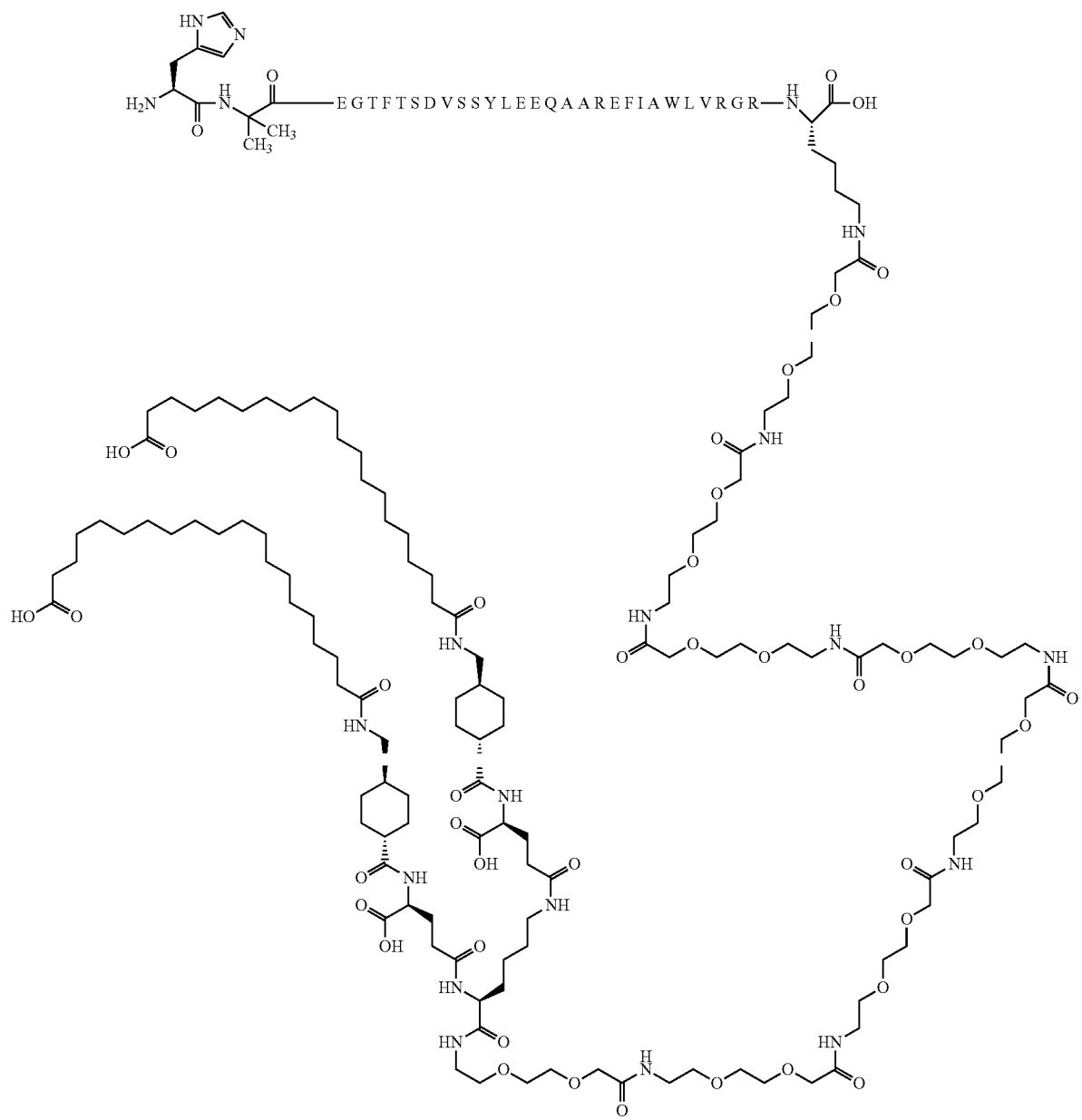

Chem. 34
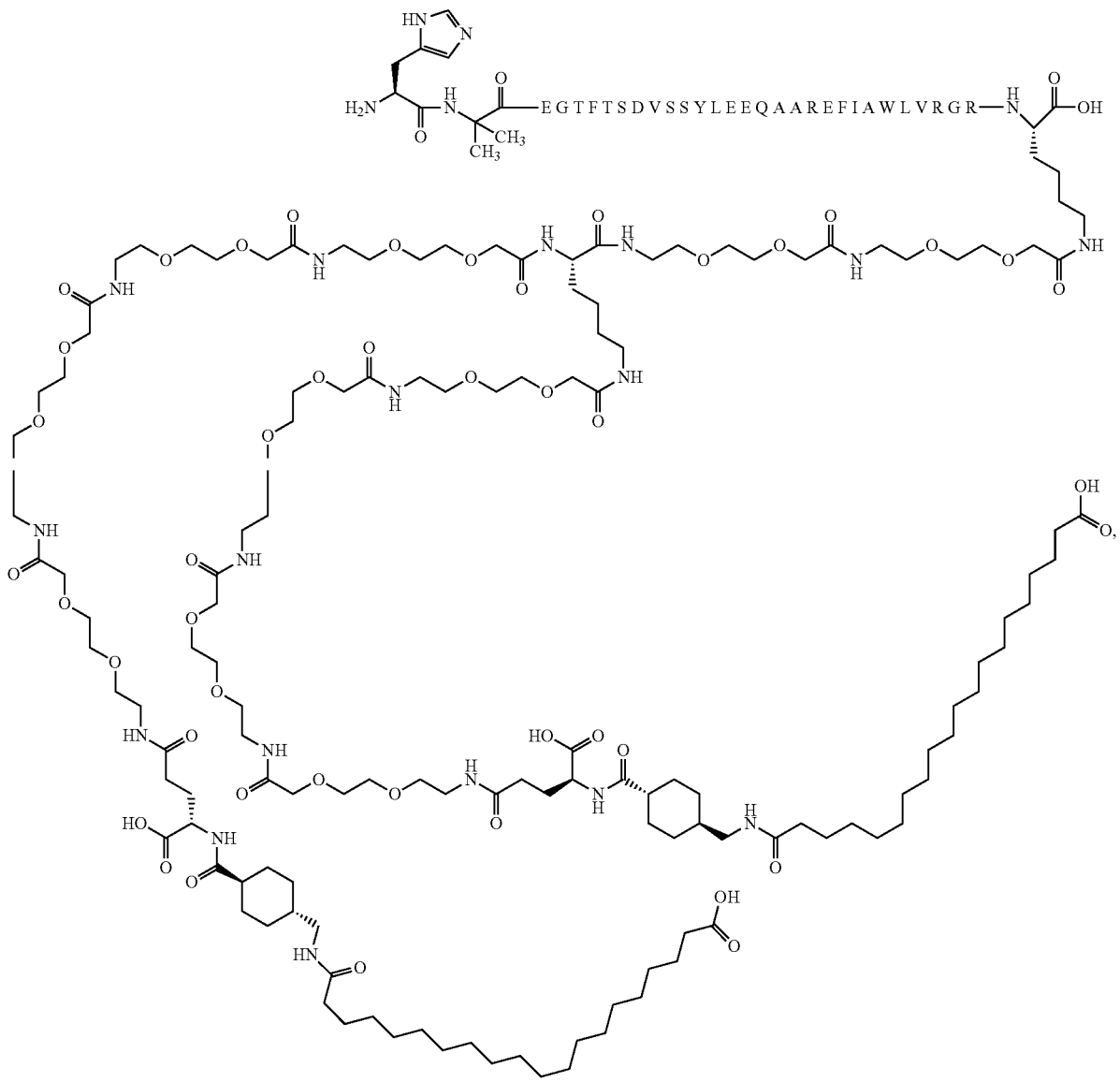
Chem. 35
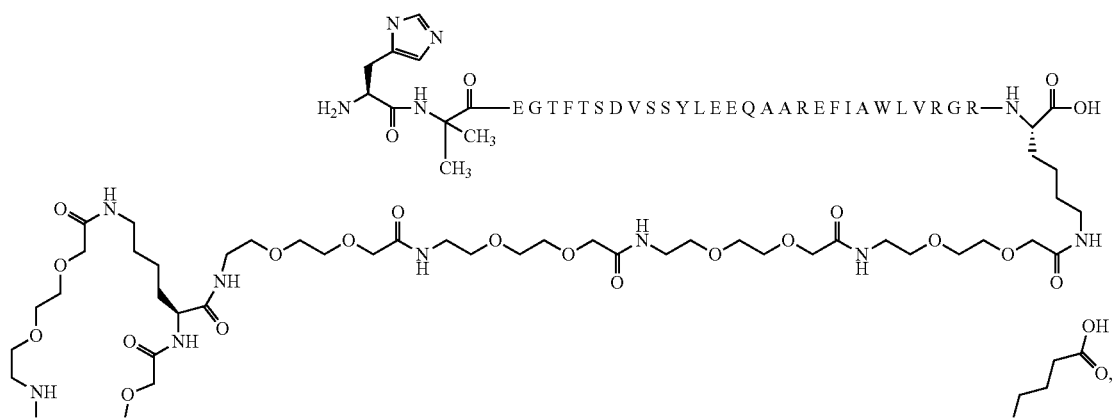

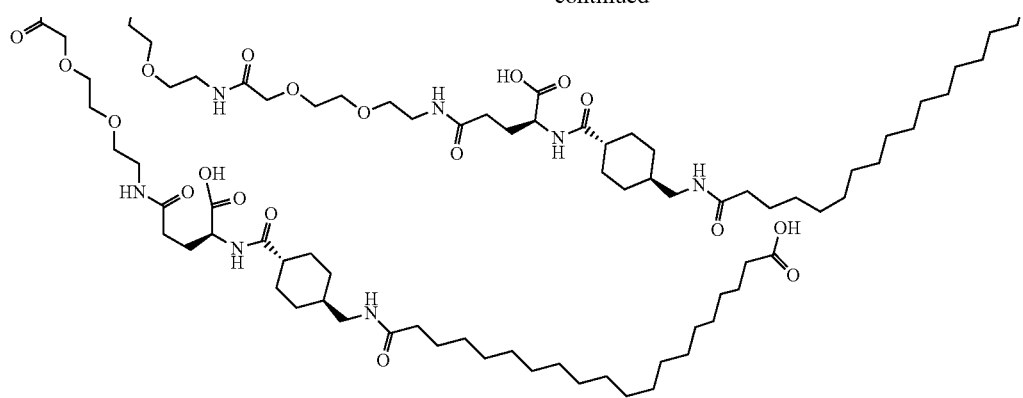
Chem. 36
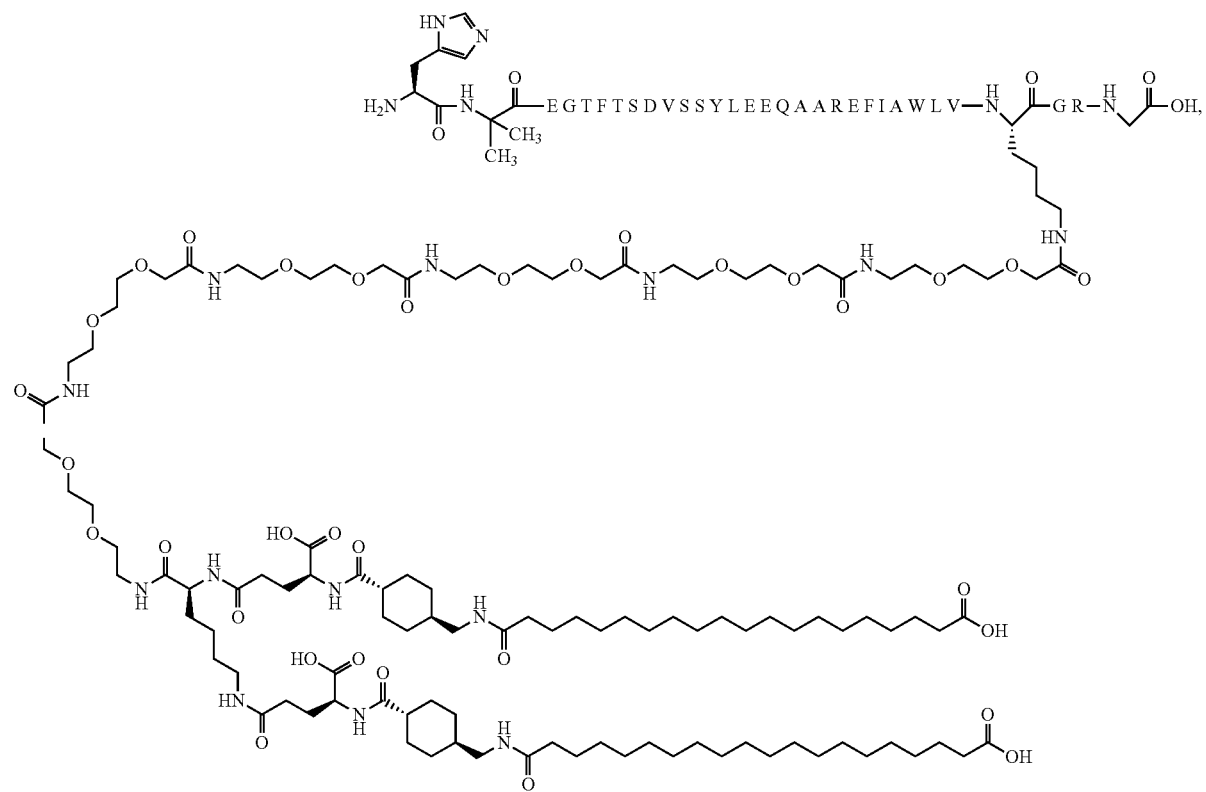
Chem. 37
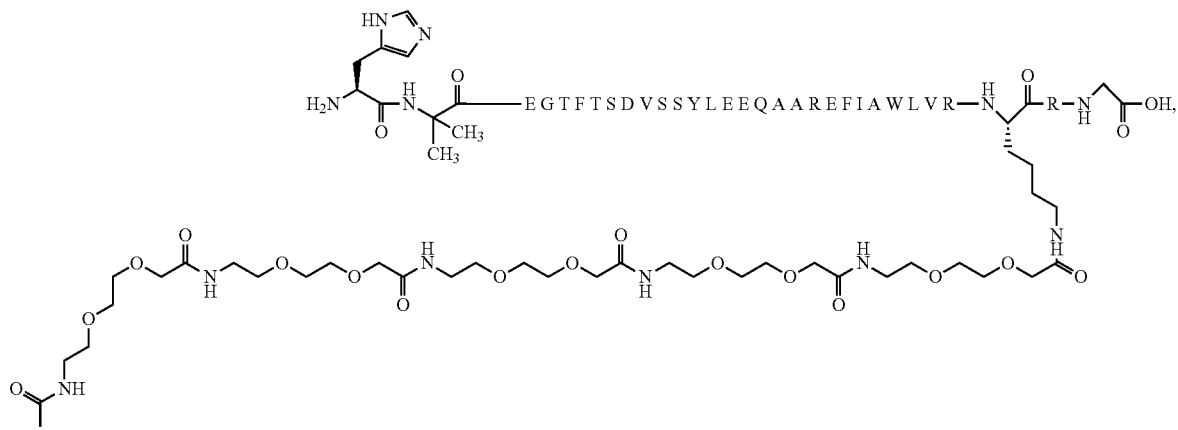

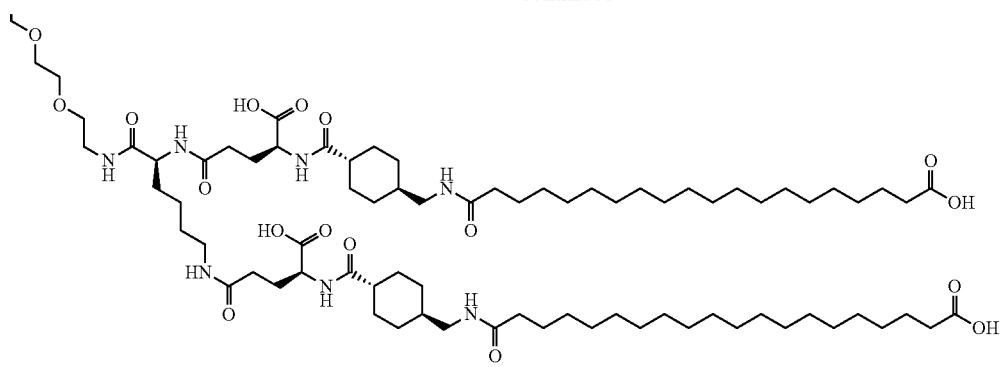
Chem. 38
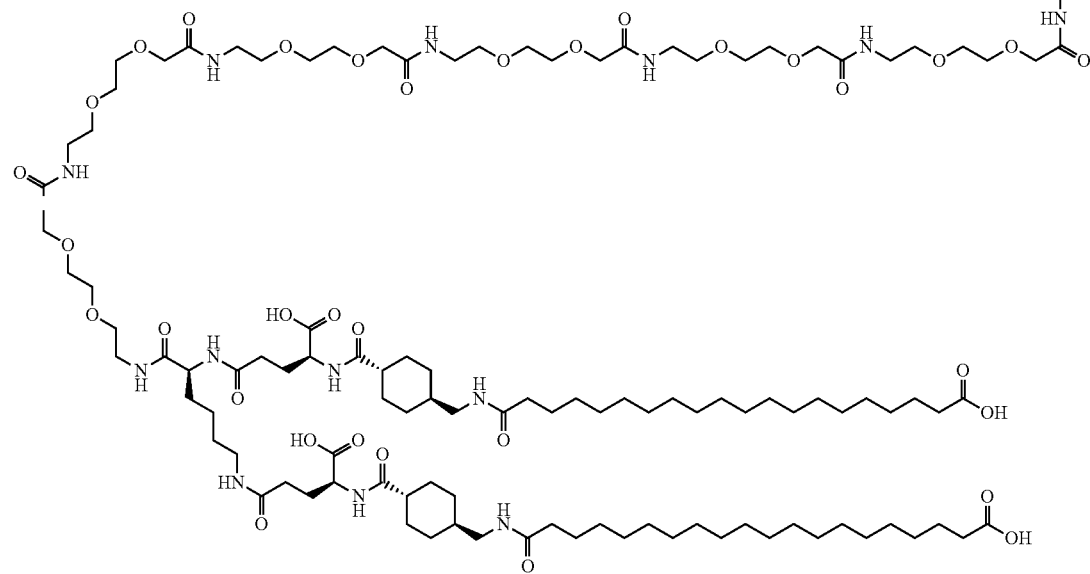
Chem. 39
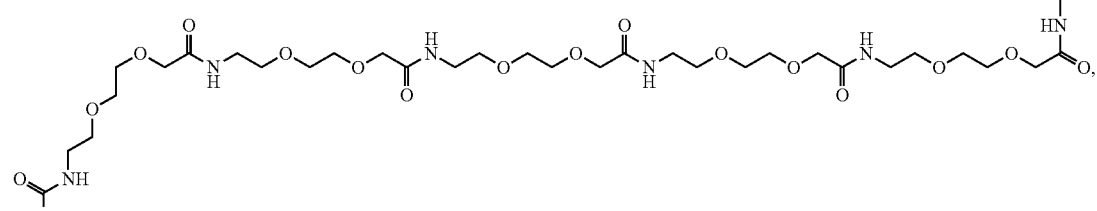

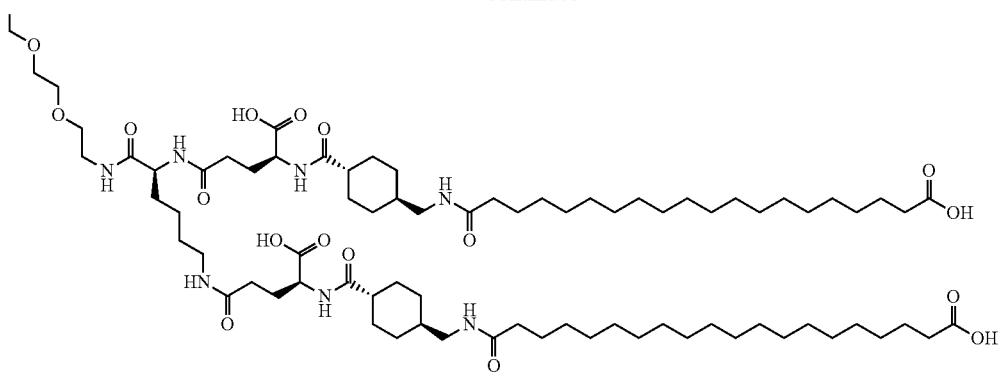
Chem. 40
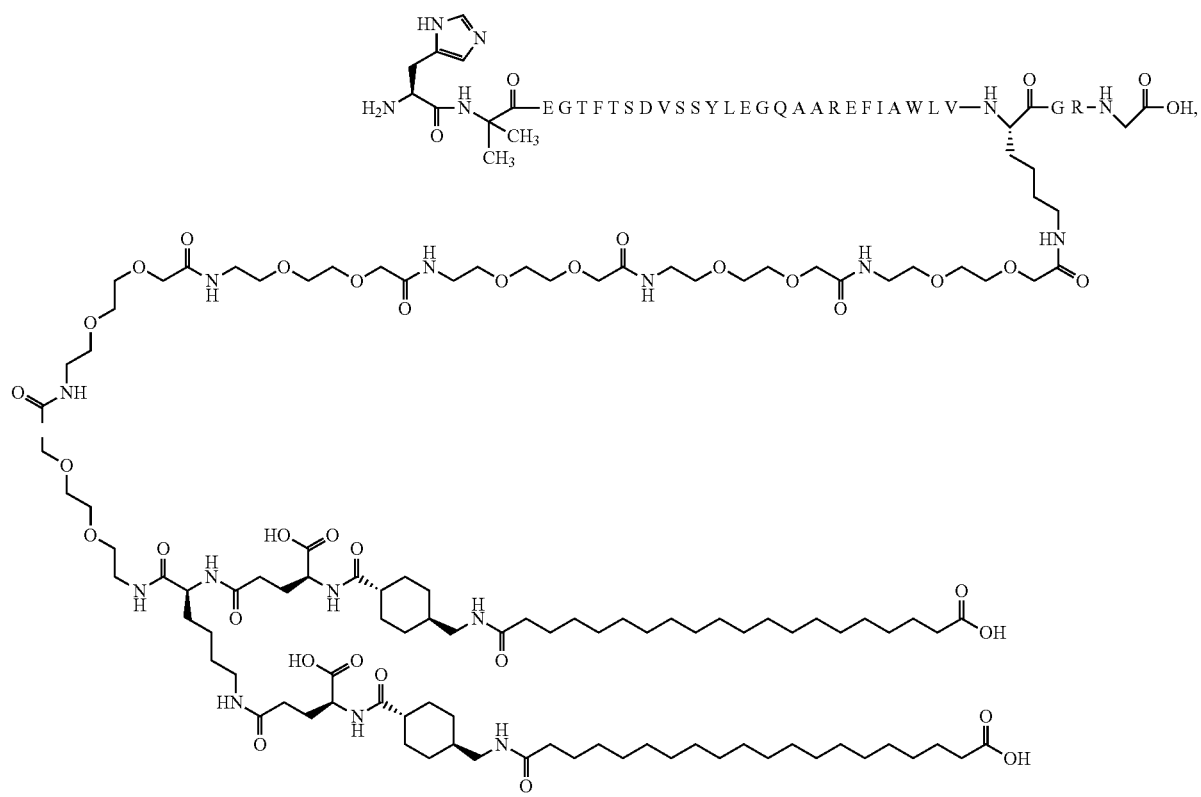
Chem. 41
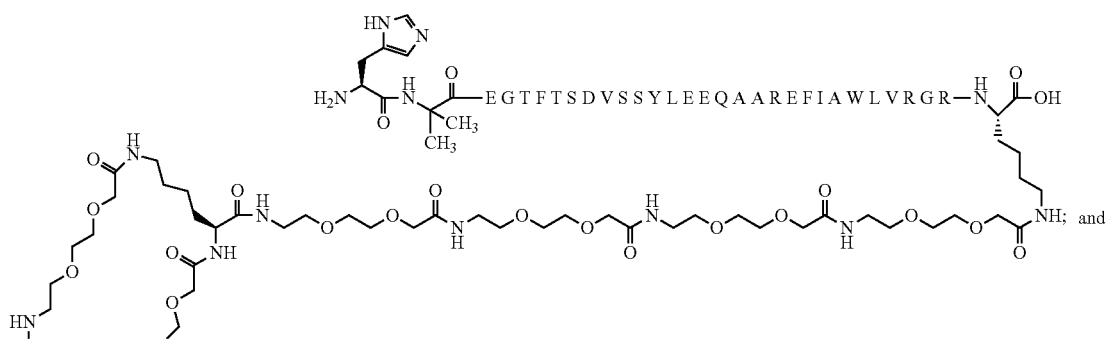
and

-continued

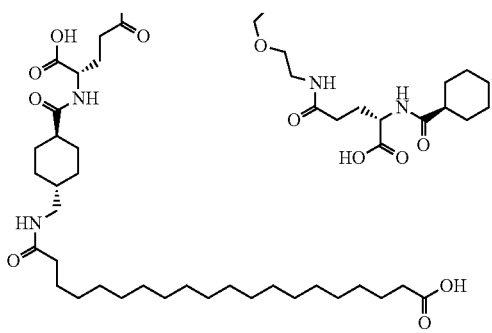
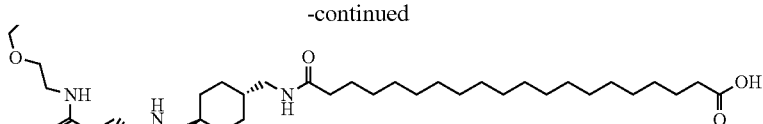

Chem. 42

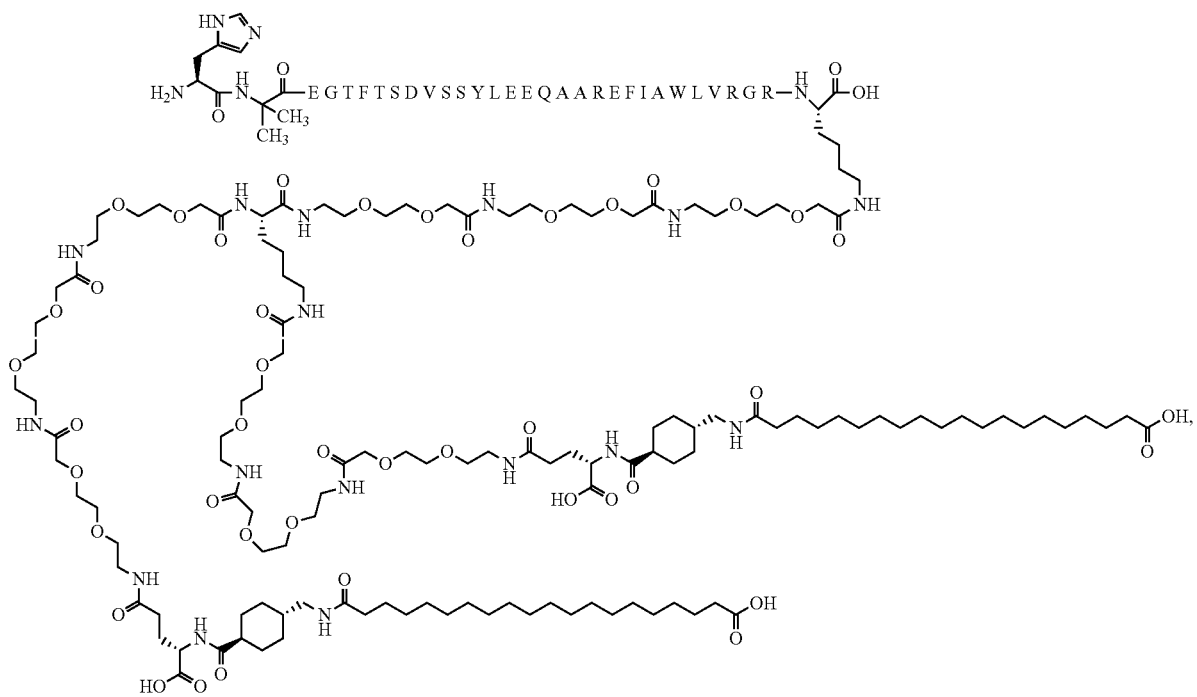

or a pharmaceutically acceptable salt, amide, or ester thereof.

8. A pharmaceutical composition comprising a derivative according to claim 1, and a pharmaceutically acceptable excipient.

9. A method for
treating all forms of diabetes, selected from the group consisting of hyperglycemia, type 2 diabetes, impaired glucose tolerance, type 1 diabetes, non-insulin dependent diabetes, MODY (maturity onset diabetes of the young), and gestational diabetes;
reduction of HbA1C;
delaying or preventing diabetic disease progression, selected from the group consisting of delaying or preventing progression in type 2 diabetes, delaying the progression of impaired glucose tolerance (IGT) to insulin requiring type 2 diabetes, delaying or preventing insulin resistance, and delaying the progression of non-insulin requiring type 2 diabetes to insulin requiring type 2 diabetes;
improving β-cell function selected from the group consisting of decreasing β-cell apoptosis, increasing β-cell function and/or β-cell mass, and for restoring glucose sensitivity to β-cells;
treating a cognitive disorder or a neurodegenerative disorder selected from the group consisting of Alzheimer's disease, Parkinson's disease, and/or multiple sclerosis;
prevention and/or treatment of an eating disorder;
treating obesity;
decreasing food intake, reducing body weight, suppressing appetite, or inducing satiety;
treating or preventing binge eating disorder, bulimia nervosa, or obesity induced by administration of an antipsychotic or a steroid;
reduction of gastric motility delaying gastric emptying, or increasing physical mobility;
prevention and/or treatment of comorbidities to obesity, selected from the group consisting of osteoarthritis and/or urine incontinence;

prevention and/or treatment of a diabetic complication, selected from the group consisting of angiopathy, neuropathy, nephropathy, and retinopathy;
improving a lipid parameter, selected from the group consisting of lowering total serum lipids, increasing HDL, lowering small, dense LDL, lowering VLDL, lowering triglycerides, lowering cholesterol, lowering plasma levels of lipoprotein a (Lp(a)) in a human, and inhibiting generation of apolipoprotein a (apo(a)) in vitro and/or in vivo;
treating dyslipidemia;
treatment of a cardiovascular disease, selected from the group consisting of syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atherosclerosis oblitterens), diastolic dysfunction, and systolic dysfunction;
reduction of blood pressure;
treatment of a gastrointestinal disease, selected from the group consisting of inflammatory bowel disease, short bowel syndrome, Crohn's disease or colitis, dyspepsia, and gastric ulcers;
treating an inflammation, selected from the group consisting of psoriasis, psoriactic arthritis, rheumatoid arthritis, and systemic lupus erythematosus;
treatment of a critically ill patient, a critical illness polynephropathy (CIPNP) patient, or a potential CIPNP patient;
prevention of development of critical illness or CIPNP;
prevention, treatment or cure of systemic inflammatory response syndrome (SIRS) in a patient;
prevention or reduction of the likelihood of a patient suffering from bacteraemia, septicaemia, or septic shock during hospitalisation;
stabilising blood glucose, insulin balance and optionally metabolism in intensive care unit patients with acute illness;
treatment of polycystic ovary syndrome (PCOS);
treatment of a cerebral disease, selected from the group consisting of cerebral ischemia, cerebral haemorrhage, and traumatic brain injury;
treatment of sleep apnoea; or
treatment of abuse, selected from the group consisting of alcohol abuse and drug abuse;
comprising administering to a subject in need thereof a pharmaceutically active amount of a derivative according to claim 1.

10. A pharmaceutical composition comprising a derivative according to claim 7, and a pharmaceutically acceptable excipient.

11. A method for
treating all forms of diabetes, selected from the group consisting of hyperglycemia, type 2 diabetes, impaired glucose tolerance, type 1 diabetes, non-insulin dependent diabetes, MODY (maturity onset diabetes of the young), and gestational diabetes;
reduction of HbA1C;
delaying or preventing diabetic disease progression, selected from the group consisting of delaying or preventing progression in type 2 diabetes, delaying the progression of impaired glucose tolerance (IGT) to insulin requiring type 2 diabetes, delaying or preventing insulin resistance, and delaying the progression of non-insulin requiring type 2 diabetes to insulin requiring type 2 diabetes;
improving β-cell function selected from the group consisting of decreasing β-cell apoptosis, increasing β-cell function and/or β-cell mass, and restoring glucose sensitivity to β-cells;
treating a cognitive disorder or a neurodegenerative disorder selected from the group consisting of Alzheimer's disease, Parkinson's disease, and multiple sclerosis;
prevention and/or treatment of an eating disorder;
treating obesity;
decreasing food intake, reducing body weight, suppressing appetite, or inducing satiety;
treating or preventing binge eating disorder, bulimia nervosa, or obesity induced by administration of an antipsychotic or a steroid;
reduction of gastric motility, delaying gastric emptying, or increasing physical mobility;
prevention and/or treatment of comorbidities to obesity, selected from the group consisting of osteoarthritis and urine incontinence;
prevention and/or treatment of a diabetic complication, selected from the group consisting of angiopathy, neuropathy, nephropathy, and retinopathy;
improving a lipid parameter, selected from the group consisting of lowering total serum lipids, increasing HDL, lowering small, dense LDL, lowering VLDL, lowering triglycerides, lowering cholesterol, lowering plasma levels of lipoprotein a (Lp(a)) in a human, and inhibiting generation of apolipoprotein a (apo(a)) in vitro and/or in vivo;
treating dyslipidemia;
treatment of a cardiovascular disease, selected from the group consisting of syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atherosclerosis oblitterens), diastolic dysfunction, and systolic dysfunction;
reduction of blood pressure;
treatment of a gastrointestinal disease, selected from the group consisting of inflammatory bowel disease, short bowel syndrome, Crohn's disease or colitis, dyspepsia, and gastric ulcers;
treating an inflammation, selected from the group consisting of psoriasis, psoriactic arthritis, rheumatoid arthritis, and systemic lupus erythematosus;
treatment of a critically ill patient, a critical illness polynephropathy (CIPNP) patient, or a potential CIPNP patient;
prevention of development of critical illness or CIPNP;
prevention, treatment or cure of systemic inflammatory response syndrome (SIRS) in a patient;
prevention or reduction of the likelihood of a patient suffering from bacteraemia, septicaemia, or septic shock during hospitalisation;
stabilising blood glucose, insulin balance and optionally metabolism in intensive care unit patients with acute illness;
treatment of polycystic ovary syndrome (PCOS);

treatment of a cerebral disease, selected from the group consisting of cerebral ischemia, cerebral haemorrhage, and traumatic brain injury;

treatment of sleep apnoea; or treatment of abuse, selected from the group consisting of alcohol abuse and drug abuse; comprising administering to a subject in need thereof a pharmaceutically active amount of a derivative according to claim 7.

* * * * *

SEQUENCE LISTING

<160> NUMBER OF SEQ ID NOS: 10

<210> SEQ ID NO 1
<211> LENGTH: 31
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly 20                  25                  30

<210> SEQ ID NO 2
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 2

His Xaa Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Arg Lys
                20                  25                  30

<210> SEQ ID NO 3
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Imp (3-(Imidazol-5-yl)propanoic acid)
<220> FEATURE:
<221> NAME/KEY: MOD_RES
<222> LOCATION: (2)..(2)
<223> OTHER INFORMATION: Aib

<400> SEQUENCE: 3

Xaa Xaa Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Arg Gly Gly
                20                  25                  30

Lys

<210> SEQ ID NO 4
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (16)..(16)
<223> OTHER INFORMATION: Aib
<220> FEATURE:
<221> NAME/KEY: MOD_RES
<222> LOCATION: (29)..(29)
<223> OTHER INFORMATION: Aib
<220> FEATURE:
<221> NAME/KEY: MOD_RES
<222> LOCATION: (31)..(31)
<223> OTHER INFORMATION: AMIDATION

<400> SEQUENCE: 4

His Xaa Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Xaa Arg Lys
                20                  25                  30

<210> SEQ ID NO 5
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 5

His Xaa Glu Gly Thr Phe Thr Ser Asp Val Ser Ser Tyr Leu Glu Glu
1               5                   10                  15

Gln Ala Ala Arg Glu Phe Ile Ala Trp Leu Val Lys Gly Arg Gly
            20                  25                  30

<210> SEQ ID NO 6
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 6

His Xaa Glu Gly Thr Phe Thr Ser Asp Val Ser Ser Tyr Leu Glu Glu
1               5                   10                  15

Gln Ala Ala Arg Glu Phe Ile Ala Trp Leu Val Arg Lys Arg Gly
            20                  25                  30

<210> SEQ ID NO 7
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 7

His Xaa Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Lys Gly
            20                  25                  30

<210> SEQ ID NO 8
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 8

His Xaa Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Arg Gly Lys

<210> SEQ ID NO 9
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Aib

<400> SEQUENCE: 9

His Xaa Glu Gly Thr Phe Thr Ser Asp Val Ser Ser Tyr Leu Glu Gly
1               5                   10                  15
Gln Ala Ala Arg Glu Phe Ile Ala Trp Leu Val Lys Gly Arg Gly
            20                  25                  30

<210> SEQ ID NO 10
<211> LENGTH: 33
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: L-histidine, (S)-2-Hydroxy-3-(1H-imidazol-4-
      yl)-propionic acid, D-histidine, deamino-histidine, homohistidine,
<220> FEATURE:
<221> NAME/KEY: MISC_FEATURE
<222> LOCATION: (1)..(1)
<223> OTHER INFORMATION: N alpha-acetyl-histidine, N alpha-formyl-
      histidine, N alpha-methyl-histidine, 3-pyridylalanine,
      2-pyridylalanine, or 4-pyridylalanine
<220> FEATURE:
<221> NAME/KEY: MISC_FEATURE
<222> LOCATION: (2)..(2)
<223> OTHER INFORMATION: Ala, Gly, Ser, Aib, (1-aminocyclopropyl)
      carboxylic acid, or (1-aminocyclobutyl) carboxylic acid
<220> FEATURE:
<221> NAME/KEY: MISC_FEATURE
<222> LOCATION: (6)..(6)
<223> OTHER INFORMATION: Phe or Leu
<220> FEATURE:
<221> NAME/KEY: MISC_FEATURE
<222> LOCATION: (10)..(10)
<223> OTHER INFORMATION: Val or Leu
<220> FEATURE:
<221> NAME/KEY: MISC_FEATURE
<222> LOCATION: (12)..(12)
<223> OTHER INFORMATION: Ser, Val, Arg, or Leu
<220> FEATURE:
<221> NAME/KEY: MISC_FEATURE
<222> LOCATION: (13)..(13)
<223> OTHER INFORMATION: Tyr or Gln
<220> FEATURE:
<221> NAME/KEY: MISC_FEATURE
<222> LOCATION: (14)..(14)
<223> OTHER INFORMATION: Leu or Met
<220> FEATURE:
<221> NAME/KEY: MISC_FEATURE
<222> LOCATION: (16)..(16)
<223> OTHER INFORMATION: Gly or Glu
<220> FEATURE:
<221> NAME/KEY: MISC_FEATURE
<222> LOCATION: (17)..(17)
<223> OTHER INFORMATION: Gln, Glu, or Arg
<220> FEATURE:
<221> NAME/KEY: MISC_FEATURE

```
<222> LOCATION: (19)..(19)
<223> OTHER INFORMATION: Ala or Val
<220> FEATURE:
<221> NAME/KEY: MISC_FEATURE
<222> LOCATION: (20)..(20)
<223> OTHER INFORMATION: Arg
<220> FEATURE:
<221> NAME/KEY: MISC_FEATURE
<222> LOCATION: (21)..(21)
<223> OTHER INFORMATION: Glu or Leu
<220> FEATURE:
<221> NAME/KEY: MISC_FEATURE
<222> LOCATION: (24)..(24)
<223> OTHER INFORMATION: Ala, Glu, or Arg
<220> FEATURE:
<221> NAME/KEY: MISC_FEATURE
<222> LOCATION: (25)..(25)
<223> OTHER INFORMATION: Trp or His
<220> FEATURE:
<221> NAME/KEY: MISC_FEATURE
<222> LOCATION: (27)..(27)
<223> OTHER INFORMATION: Val
<220> FEATURE:
<221> NAME/KEY: MISC_FEATURE
<222> LOCATION: (28)..(28)
<223> OTHER INFORMATION: Lys, Arg, His, Asn, or Gln
<220> FEATURE:
<221> NAME/KEY: MISC_FEATURE
<222> LOCATION: (29)..(29)
<223> OTHER INFORMATION: Lys, Gly, or Ala
<220> FEATURE:
<221> NAME/KEY: MISC_FEATURE
<222> LOCATION: (30)..(30)
<223> OTHER INFORMATION: Lys, Arg, or Gly
<220> FEATURE:
<221> NAME/KEY: MISC_FEATURE
<222> LOCATION: (31)..(31)
<223> OTHER INFORMATION: Gly, Pro, or Lys
<220> FEATURE:
<221> NAME/KEY: MISC_FEATURE
<222> LOCATION: (32)..(32)
<223> OTHER INFORMATION: Lys, Gly, or absent
<220> FEATURE:
<221> NAME/KEY: MISC_FEATURE
<222> LOCATION: (33)..(33)
<223> OTHER INFORMATION: Lys or absent

<400> SEQUENCE: 10

Xaa Xaa Glu Gly Thr Xaa Thr Ser Asp Xaa Ser Xaa Xaa Xaa Glu Xaa
1               5                   10                  15

Xaa Ala Xaa Xaa Xaa Phe Ile Xaa Xaa Leu Xaa Xaa Xaa Xaa Xaa Xaa
            20                  25                  30

Xaa
```